(12) United States Patent
Cali et al.

(10) Patent No.: US 6,806,082 B2
(45) Date of Patent: Oct. 19, 2004

(54) ISOLATED NUCLEIC ACID MOLECULE ENCODING A REGULATOR OF FUNGAL GENE EXPRESSION

(75) Inventors: Brian M. Cali, Arlington, MA (US); Douglas Holtzman, Jamaica Plain, MA (US); Kevin T. Madden, Charlestown, MA (US); G. Todd Milne, Brookline, MA (US); Amir Sherman, Jerusalem (IL); Jeffrey C. Silva, Beverly, MA (US); Joshua Trueheart, Concord, MA (US); Lixin Zhang, Lexington, MA (US)

(73) Assignee: Microbia, Inc., Cambridge, MA (US)

( * ) Notice: Subject to any disclaimer, the term of this patent is extended or adjusted under 35 U.S.C. 154(b) by 216 days.

(21) Appl. No.: 10/029,180

(22) Filed: Dec. 22, 2001

(65) Prior Publication Data

US 2002/0182708 A1 Dec. 5, 2002

Related U.S. Application Data

(60) Provisional application No. 60/257,431, filed on Dec. 22, 2000.

(51) Int. Cl.$^7$ ............................ C12N 5/10; C12N 1/00; C12N 15/31; C12N 15/63
(52) U.S. Cl. ...................... 435/325; 435/243; 435/419; 435/320.1; 536/23.74
(58) Field of Search ............................ 536/23.1, 23.74; 435/320.1, 69.1, 243, 325, 419

(56) References Cited

FOREIGN PATENT DOCUMENTS

| WO | WO 99/25735 | 5/1999 |
|---|---|---|
| WO | WO 99/25865 | 5/1999 |
| WO | WO 99/31244 | 6/1999 |
| WO | WO 01/29073 | 4/2001 |

OTHER PUBLICATIONS

Kupfer et al, GenBank, Accession No. AA785001, publically available Jul. 29, 1998.*
Bundgaard et al. (1972), "A new spectrophotometric method for the determination of penicillins," 24 *Journal of Pharm Pharmac* 790–794.
Alberts et al. (1980), "Mevinolin: A Highly Potent Competitive Inhibitor of Hydroxymethylglutaryl–Coenzyme A Reductase and a Cholesterol–Lowering Agent," 77 *Proc. Natl. Acad. Sci. USA* 3957–3961.
Borel (1986), "Ciclosporin and Its Future," 38 *Prog. Allergy* 9–18.
Demain (1992), "Microbial secondary metabolism: a new theoretical frontier for academia, a new opportunity for industry," 171 *Ciba Found Symp* 3–16.

Brakhage (1994), "Molecular Regulation of B–Lactam Biosynthesis in Filamentous Fungi," 62 *Microbiol. Mol. Biol. Rev.* 547–585.
(1994) *Fungal Physiology*, Griffin et al., 9:246–274.
Luengo et al. (1994), "Penicillin Biosynthesis," 29 *Prog. Ind. Microbiol.* 603–638.
Jensen et al. (1995), "Beta–Lactams," 28 *Biotechnology* 239–268.
Penalva et al. (1998), "The optimization of penicillin biosynthesis in fungi," 16 *Trends Biotechnol.* 483–489.
Weig et al. (1998), "Clinical aspects and pathogenesis of Candida infection," 6 *Trends in Microbiology* 468–470.
Baillie et al. (1999), "Candida Biofilms and Their Susceptibility to Antifungal Agents," 310 *Methods in Enzymology* 644–656.
Bentley (1999), "Secondary Metabolite Biosynthesis: The First Century," 19 *Crit. Rev. Biotechnol.* 1–40.
Casquiero et al. (1999), "Gene Targeting in Penicillium chrysogenum: Disruption of the lys2 Gene Leads to Penicillin Overproduction," 181 *J. Bacteriol* 1181–1188.
Ha et al. (1999), "Effects of Azole Antifungal Drugs on the Transition from Yeast Cells to Hyphae in Susceptible and Resistant Isolates of the Pathogenic Yeast *Candida albicans*," 43 *Antimicrobial Agents and Chemotherapy* 763–768.
Mingot et al. (1999), "Disruption of phacA, an *Asperigillus nidulans* Gene Encoding a Novel Cytochrome P450 Monooxygenase Catalyzing Phenylacetate 2–Hydroxylation, Results in Penicillin Overproduction" 274 *J. Biol. Chem.* 14545–14550.
Walker et al. (1999), "Pharmaceutical target discovery using Guilt–by–Association: schizophrenia and Parkinson's disease genes," ISMB 282–286.
Hasper et al. (2000), "The *Aspergillus niger* transcriptional activator XlnR, which is involved in the degradation of the polysaccharides xylan and cellulose, also regulates D–xylose reductase gene expression," 36 *Molecular Microbiology* 193–200.
Brakhage, A., "Molecular Regulation of Penicillin Biosynthesis in Aspergillus (Emericella) *nidulans*" FEMS Microbiology Letters 148:1–10, 1997.

* cited by examiner

*Primary Examiner*—Terry McKelvey
(74) *Attorney, Agent, or Firm*—Fish & Richardson P.C.

(57) ABSTRACT

The invention relates to regulators of fungal gene expression and their use in commercial and medical applications. More particularly, the invention relates to regulators of fungal genes involved in production of enzymes, secondary metabolites and other useful products, as well as to regulators of genes involved in fungal invasion. The invention provides novel regulators of fungal gene expression, and methods for using regulator genes in commercial and medical applications.

10 Claims, No Drawings

SEQUENCE LISTING

```
<160> NUMBER OF SEQ ID NOS: 138

<210> SEQ ID NO 1
<211> LENGTH: 1719
<212> TYPE: DNA
<213> ORGANISM: Artificial Sequence
<220> FEATURE:
<223> OTHER INFORMATION: fungal gene

<400> SEQUENCE: 1
atgggcacta ccctcgagtg catcatctgt cctggacagc cgcagttcag cgatgtctcc     60
cacctgttga cccatgctgc ctccaaggct catttggcca accacttcaa gctcaagctt    120
cgcaccgacg atcctaactc ggtcaagctt ctcgagcgat acgaccagtg gtttgataac    180
aatggcttcg cgaagctgct gtctgctcgc atggcaagca aagaaagtcg gaagaaaaga    240
aaggacgaag catcgacttc caacaccacc aaacgcacaa ggagccaagc atccatcgtg    300
gagaccgagg gctccagcac tcctgcaatg ccagccaccc ccaaccctga ttaccttgat    360
cctcgcctgg ccgattctca caatgacaac cagcaacatg cgggtacaac cctcgcagca    420
agcatcccaa accagttgcc tacggcgaac agcagtgcga aaactcgaac tggtccgacc    480
ctccgcttgt tgcgatcgtc taatggcaca aagtcgaatg ttttgccgcc tgttaatgct    540
tctgacctct acgatgaaag ccaatcattg gctttgccta agacaccgat acagcgccta    600
cacgaaccgg gacctttgga gacaacattg attaccaacg aagacactcc tgatcctttt    660
gtcgactctg gtgatcaaac ccaggcatcg gctgaggctg agatggacaa gactcgggct    720
gaagaaatct caagactcaa gggcgttcta tacccaggca tggatatttt tgattccgcc    780
actgtgcaga tgcgtcgtcg gcgcaaccag aagaaggaca gtggtgtact gaagaccatg    840
gaagaaactt ccttgctcgt ggagccttca gagcaggtct attcccctgg cggaactctg    900
ttgacggagc gtatgatcac gggcaatgtg gaggactaca gcccactgaa aggagagact    960
ccgattccca agggaggcct cactcgtacc aggagcacac gtctgaccaa ggctgatccc   1020
aacgtgtccc gtgccgcgga cagaaagcga cagaaaacgg acaaagaccg caagaacatg   1080
gcagatgaag gggccaacga agagcacacg tcttcccgcc gctcgcgccg cgcagcagct   1140
cactcttatg ttggtgacga tgaagagatt ggtcttactg tgaacacctt tggcaaacgg   1200
cccaggggtg gcttcgacgt tttttgttgat gagagaaagg aagaagagga cagcaaaaca   1260
acttatcagc aaccgggatt cagagcgcag tttgacacat tgacccccac tcgccttgtt   1320
ttgaacggaa agaccaacgc tggcattcat gccccgagaa ttggacacgc atcccttgcc   1380
aaagagaaca ttgagcctat tctgaacccc caaggtcgaa ttgcccccca cggttggaac   1440
tccccattcg ttaaataccc tgactccgat gactttggat tcggcccctc ataccttcct   1500
```

```
gatcttggtg atacatatga caccccttgac aaggctgggt atcgatccaa ccctctgcaa    1560
gctccctcga agcaccccctt ctatgagagc cagtatgaag aggagcatac tgcagcccag    1620
aatggctggc ttccagtgga ccagatagtt ccatccgacg taaccatccc cgaagacgac    1680
cagatctttc aacatacta cttttctacc gatgtgaac                             1719
```

<210> SEQ ID NO 2
<211> LENGTH: 573
<212> TYPE: PRT
<213> ORGANISM: Artificial Sequence
<220> FEATURE:
<223> OTHER INFORMATION: fungal gene

<400> SEQUENCE: 2

```
Met Gly Thr Thr Leu Glu Cys Ile Ile Cys Pro Gly Gln Pro Gln Phe
 1               5                  10                  15

Ser Asp Val Ser His Leu Leu Thr His Ala Ala Ser Lys Ala His Leu
            20                  25                  30

Ala Asn His Phe Lys Leu Lys Leu Arg Thr Asp Asp Pro Asn Ser Val
        35                  40                  45

Lys Leu Leu Glu Arg Tyr Asp Gln Trp Phe Asp Asn Asn Gly Phe Ala
    50                  55                  60

Lys Leu Leu Ser Ala Arg Met Ala Ser Lys Glu Ser Arg Lys Lys Arg
65                  70                  75                  80

Lys Asp Glu Ala Ser Thr Ser Asn Thr Thr Lys Arg Thr Arg Ser Gln
                85                  90                  95

Ala Ser Ile Val Glu Thr Glu Gly Ser Ser Thr Pro Ala Met Pro Ala
            100                 105                 110

Thr Pro Asn Pro Asp Tyr Leu Asp Pro Arg Leu Ala Asp Ser His Asn
        115                 120                 125

Asp Asn Gln Gln His Ala Gly Thr Thr Leu Ala Ala Ser Ile Pro Asn
    130                 135                 140

Gln Leu Pro Thr Ala Asn Ser Ser Ala Lys Thr Arg Thr Gly Pro Thr
145                 150                 155                 160

Leu Arg Leu Leu Arg Ser Ser Asn Gly Thr Lys Ser Asn Val Leu Pro
                165                 170                 175

Pro Val Asn Ala Ser Asp Leu Tyr Asp Glu Ser Gln Ser Leu Ala Leu
            180                 185                 190

Pro Lys Thr Pro Ile Gln Arg Leu His Glu Pro Gly Pro Leu Glu Thr
        195                 200                 205

Thr Leu Ile Thr Asn Glu Asp Thr Pro Asp Pro Phe Val Asp Ser Gly
    210                 215                 220

Asp Gln Thr Gln Ala Ser Ala Glu Ala Glu Met Asp Lys Thr Arg Ala
225                 230                 235                 240

Glu Glu Ile Ser Arg Leu Lys Gly Val Leu Tyr Pro Gly Met Asp Ile
                245                 250                 255

Phe Asp Ser Ala Thr Val Gln Met Arg Arg Arg Asn Gln Lys Lys
            260                 265                 270

Asp Ser Gly Val Leu Lys Thr Met Glu Glu Thr Ser Leu Leu Val Glu
        275                 280                 285

Pro Ser Glu Gln Val Tyr Ser Pro Gly Gly Thr Leu Leu Thr Glu Arg
    290                 295                 300

Met Ile Thr Gly Asn Val Glu Asp Tyr Ser Pro Leu Lys Gly Glu Thr
305                 310                 315                 320
```

```
Pro Ile Pro Lys Gly Gly Leu Thr Arg Thr Arg Ser Thr Arg Leu Thr
            325                 330                 335

Lys Ala Asp Pro Asn Val Ser Arg Ala Ala Asp Arg Lys Arg Gln Lys
                340                 345                 350

Thr Asp Lys Asp Arg Lys Asn Met Ala Asp Glu Gly Ala Asn Glu Glu
            355                 360                 365

His Thr Ser Ser Arg Arg Ser Arg Arg Ala Ala His Ser Tyr Val
        370                 375                 380

Gly Asp Asp Glu Glu Ile Gly Leu Thr Val Asn Thr Phe Gly Lys Arg
385                 390                 395                 400

Pro Arg Gly Gly Phe Asp Val Phe Val Asp Glu Arg Lys Glu Glu Glu
                405                 410                 415

Asp Ser Lys Thr Thr Tyr Gln Gln Pro Gly Phe Arg Ala Gln Phe Asp
            420                 425                 430

Thr Leu Thr Pro Thr Arg Leu Val Leu Asn Gly Lys Thr Asn Ala Gly
        435                 440                 445

Ile His Ala Pro Arg Ile Gly His Ala Ser Leu Ala Lys Glu Asn Ile
450                 455                 460

Glu Pro Ile Leu Asn Pro Gln Gly Arg Ile Ala Pro His Gly Trp Asn
465                 470                 475                 480

Ser Pro Phe Val Lys Tyr Pro Asp Ser Asp Phe Gly Phe Gly Pro
                485                 490                 495

Ser Tyr Leu Pro Asp Leu Gly Asp Thr Tyr Asp Thr Leu Asp Lys Ala
            500                 505                 510

Gly Tyr Arg Ser Asn Pro Leu Gln Ala Pro Ser Lys His Pro Phe Tyr
        515                 520                 525

Glu Ser Gln Tyr Glu Glu Glu His Thr Ala Ala Gln Asn Gly Trp Leu
            530                 535                 540

Pro Val Asp Gln Ile Val Pro Ser Asp Val Thr Ile Pro Glu Asp Asp
545                 550                 555                 560

Gln Ile Phe Pro Thr Tyr Tyr Phe Ser Thr Asp Val Asn
                565                 570

<210> SEQ ID NO 3
<211> LENGTH: 939
<212> TYPE: DNA
<213> ORGANISM: Artificial Sequence
<220> FEATURE:
<223> OTHER INFORMATION: fungal gene

<400> SEQUENCE: 3
atggcactaa tcactcgcaa atacggcgag atccgccaga tcacaggcct gagcgaccac      60
gctgtgatcc tccagtcgca taaagtccag tactcccgc cgctggatcg ctactatgcc     120
atcaaggtct ttcgccgcag tcccggtcag agcacggacg agtacacaaa acaagtcaat     180
gcggagttcg ccgtcgtcgc caatctgcac accagcacg tcgtctcgac cttcgaactc     240
ctccccatcg gcggaggaaa tctagccgct tgcatggagt actgtgcggg tgggatcttc     300
cactccctga tcacggctgg tccctcgcac agattaccct cggaagaggc agactgtctt     360
ttcaagcagc ttcttcgtgg catctcctac cttcacaaat caggcatcgc ccaccgcgac     420
ctgaagccgg agaacctcct cctgacacac agggcttgcc tcaagatctc agactttgcg     480
aatgccgagc gcgtccgttt cgatggtgat gattctcagc atgccaatga cctggcggaa     540
actgaacgcc gcagcttaga accgacaccg tatcttgccc cggagcgata ccttgacgag     600
ggcgacaggt acatgtccag atccgacccc agagccctcg atatctgggc cgcggctgtt     660
```

```
atatacgtcg ctatgaggac aggaaggaac ctgtggaaag cggcaacgga gaaggacgag    720
ggcttcaggg cgtatgtcga agagcgtaag gccgagaaga cgaatactgt tatccaggat    780
tcgtgccatg aacggggccg caaagtgata tacgccatgt taagcactga tcctgggaag    840
cgacctatcg cgactgagat tctttcctca gagtggcttc agaacattga ctgctgtatc    900
tttgatcatt cccaagcaga gtctaatgga ttttcggcc                          939
```

<210> SEQ ID NO 4
<211> LENGTH: 313
<212> TYPE: PRT
<213> ORGANISM: Artificial Sequence
<220> FEATURE:
<223> OTHER INFORMATION: fungal gene

<400> SEQUENCE: 4

```
Met Ala Leu Ile Thr Arg Lys Tyr Gly Glu Ile Arg Gln Ile Thr Gly
  1               5                  10                  15

Leu Ser Asp His Ala Val Ile Leu Gln Ser His Lys Val Gln Tyr Cys
                 20                  25                  30

Pro Pro Leu Asp Arg Tyr Tyr Ala Ile Lys Val Phe Arg Arg Ser Pro
             35                  40                  45

Gly Gln Ser Thr Asp Glu Tyr Thr Lys Gln Val Asn Ala Glu Phe Ala
         50                  55                  60

Val Val Ala Asn Leu His His Gln His Val Val Ser Thr Phe Glu Leu
 65                  70                  75                  80

Leu Pro Ile Gly Gly Gly Asn Leu Ala Ala Cys Met Glu Tyr Cys Ala
                 85                  90                  95

Gly Gly Asp Leu His Ser Leu Ile Thr Ala Gly Pro Ser His Arg Leu
            100                 105                 110

Pro Ser Glu Glu Ala Asp Cys Leu Phe Lys Gln Leu Leu Arg Gly Ile
        115                 120                 125

Ser Tyr Leu His Lys Ser Gly Ile Ala His Arg Asp Leu Lys Pro Glu
130                 135                 140

Asn Leu Leu Leu Thr His Arg Ala Cys Leu Lys Ile Ser Asp Phe Ala
145                 150                 155                 160

Asn Ala Glu Arg Val Arg Phe Asp Gly Asp Ser Gln His Ala Asn
                165                 170                 175

Asp Leu Ala Glu Thr Glu Arg Arg Ser Leu Glu Pro Thr Pro Tyr Leu
            180                 185                 190

Ala Pro Glu Arg Tyr Leu Asp Glu Gly Asp Arg Tyr Met Ser Arg Ser
        195                 200                 205

Asp Pro Arg Ala Leu Asp Ile Trp Ala Ala Ala Val Ile Tyr Val Ala
    210                 215                 220

Met Arg Thr Gly Arg Asn Leu Trp Lys Ala Ala Thr Glu Lys Asp Glu
225                 230                 235                 240

Gly Phe Arg Ala Tyr Val Glu Glu Arg Lys Ala Glu Lys Thr Asn Thr
                245                 250                 255

Val Ile Gln Asp Ser Cys His Glu Arg Gly Arg Lys Val Ile Tyr Ala
            260                 265                 270

Met Leu Ser Thr Asp Pro Gly Lys Arg Pro Ile Ala Thr Glu Ile Leu
        275                 280                 285

Ser Ser Glu Trp Leu Gln Asn Ile Asp Cys Cys Ile Phe Asp His Ser
    290                 295                 300

Gln Ala Glu Ser Asn Gly Phe Ser Ala
```

<210> SEQ ID NO 5
<211> LENGTH: 1512
<212> TYPE: DNA
<213> ORGANISM: Artificial Sequence
<220> FEATURE:
<223> OTHER INFORMATION: fungal gene

<400> SEQUENCE: 5

```
atgactgagc gctcagttca gatctggttt caaaacaggc gcgcaaagat caagatgctt      60
gcgaagaaga gcatcgagac cggcgagggc tgtgattcaa ttcccgagtc aatgcgccag     120
tacttagcca tgcagttcga tcccagcaaa cccggtgctc agacccctt tggccgaact      180
ggcggatacg gagcaaatgg tgcatacct aatgagccaa caccttcagg caaagttgtg      240
atccatcact ttacctgtcg atccctgaca attggcagct ggaggcggat cggacaaaat    300
gccatggacc tggttgtttt ctactccccc gagaaggcgt gcatgaccta ctatatcaac    360
aacgacgcag ccggatacaa aatcgaatat cccttctcct acatcaagaa cattacactt    420
gagtcgggcg atcaaggacc gcagcccaac ggtgcgcctc cacggcctac tggtctggtc    480
gttgaattga accgaccgcc cctcttttac atggattcct ccaactcggg tggtttctac    540
cagtgcggcg actttacgga agaccaacaa gctagctcgg taatgattca tcgccttggc    600
ggacacccca aggttctgag cgttcaactt gcaaaattgg tgtctctgga gtctttccag    660
aaccgtctcg cgtatggcaa cttcccggca acaactcta tgtcgccgcc tttcattcaa      720
cgcccagctt cgcagccaaa tcaattcgcc cctgctttta tgagtatgta tgcggagaat    780
ccggccgtga tgaacctcca agctgcccgt ggacacaagc gtcaaagaag ccgctccgtt    840
cccgtggcta tcgatttctc cgcactagga gcgccaatga cccagttcag catgccacaa    900
gctcaacaat tcagccaggc tgattcggga atatacgcgc ctataccca gtcgacacac      960
tcacttgctg cgaacctccg cattgatacc tcttctggat atgccttcga cccgcgtgca   1020
caccccatgt cggctactac aactgcgtct ccgtccgatt tgctagccc tgccctgttt    1080
agcgcaggac cccaagggga ttcgactccg gtagggagtg taggagctca gtttactttg   1140
ccctatgttt cgcccgctgt ggactcaggc gtatccactc aagcagcttc cccatactcg   1200
aatgtaagcc atgttgatcc tatgatcgcg aaccattcgc ctcctttgac aaatatgtcg   1260
catactccgc atgacgtgta cggcatggga agcgaacacc aacccagtta cacagaggaa   1320
ggtatgccaa tgggcggcgg gatgtacaaa cacataaact tctcgtcggt gcctaccaca   1380
gtgggcctcg aaggcaatgc atttgacttg ccgatgcact ccatgtctgg gcatgcttcg   1440
cccgcgtcc agggtgacta tcaaggaata gcactggaaa atgtcgatcc gaatgttttg   1500
actcccggct ct                                                       1512
```

<210> SEQ ID NO 6
<211> LENGTH: 504
<212> TYPE: PRT
<213> ORGANISM: Artificial Sequence
<220> FEATURE:
<223> OTHER INFORMATION: fungal gene

<400> SEQUENCE: 6

```
Met Thr Glu Arg Ser Val Gln Ile Trp Phe Gln Asn Arg Arg Ala Lys
 1               5                  10                  15

Ile Lys Met Leu Ala Lys Lys Ser Ile Glu Thr Gly Glu Gly Cys Asp
            20                  25                  30
```

```
Ser Ile Pro Glu Ser Met Arg Gln Tyr Leu Ala Met Gln Phe Asp Pro
         35                  40                  45

Ser Lys Pro Gly Ala Arg Asp Pro Phe Gly Arg Thr Gly Gly Tyr Gly
 50                  55                  60

Ala Asn Gly Ala Tyr Pro Asn Glu Pro Thr Pro Ser Gly Lys Val Val
 65                  70                  75                  80

Ile His His Phe Thr Cys Arg Ser Leu Thr Ile Gly Ser Trp Arg Arg
                 85                  90                  95

Ile Gly Gln Asn Ala Met Asp Leu Val Val Phe Tyr Ser Pro Glu Lys
             100                 105                 110

Ala Cys Met Thr Tyr Tyr Ile Asn Asn Asp Ala Ala Gly Tyr Lys Ile
             115                 120                 125

Glu Tyr Pro Phe Ser Tyr Ile Lys Asn Ile Thr Leu Glu Ser Gly Asp
             130                 135                 140

Gln Gly Pro Gln Pro Asn Gly Ala Pro Pro Arg Pro Thr Gly Leu Val
145                 150                 155                 160

Val Glu Leu Asn Arg Pro Pro Leu Phe Tyr Met Asp Ser Ser Asn Ser
                 165                 170                 175

Gly Gly Phe Tyr Gln Cys Gly Asp Phe Thr Glu Asp Gln Gln Ala Ser
                 180                 185                 190

Ser Val Met Ile His Arg Leu Gly Gly His Pro Lys Val Leu Ser Val
             195                 200                 205

Gln Leu Ala Lys Leu Val Ser Leu Glu Ser Phe Gln Asn Arg Leu Ala
    210                 215                 220

Tyr Gly Asn Phe Pro Ala Asn Asn Ser Met Ser Pro Pro Phe Ile Gln
225                 230                 235                 240

Arg Pro Ala Ser Gln Pro Asn Gln Phe Ala Pro Ala Phe Met Ser Met
                 245                 250                 255

Tyr Ala Glu Asn Pro Ala Val Met Asn Leu Gln Ala Ala Arg Gly His
                 260                 265                 270

Lys Arg Gln Arg Ser Arg Ser Val Pro Val Ala Ile Asp Phe Ser Ala
    275                 280                 285

Leu Gly Ala Pro Met Thr Gln Phe Ser Met Pro Gln Ala Gln Gln Phe
    290                 295                 300

Ser Gln Ala Asp Ser Gly Ile Tyr Ala Pro Ile Pro Gln Ser Thr His
305                 310                 315                 320

Ser Leu Ala Ala Asn Leu Arg Ile Asp Thr Ser Ser Gly Tyr Ala Phe
                 325                 330                 335

Asp Pro Arg Ala His Pro Met Ser Ala Thr Thr Ala Ser Pro Ser
                 340                 345                 350

Asp Phe Ala Ser Pro Ala Leu Phe Ser Ala Gly Pro Gln Gly Asp Ser
    355                 360                 365

Thr Pro Val Gly Ser Val Gly Ala Gln Phe Thr Leu Pro Tyr Val Ser
    370                 375                 380

Pro Ala Val Asp Ser Gly Val Ser Thr Gln Ala Ala Ser Pro Tyr Ser
385                 390                 395                 400

Asn Val Ser His Val Asp Pro Met Ile Ala Asn His Ser Pro Pro Leu
             405                 410                 415

Thr Asn Met Ser His Thr Pro His Asp Val Tyr Gly Met Gly Ser Glu
             420                 425                 430

His Gln Pro Ser Tyr Thr Glu Glu Gly Met Pro Met Gly Gly Gly Met
    435                 440                 445
```

-continued

```
Tyr Lys His Ile Asn Phe Ser Ser Val Pro Thr Thr Val Gly Leu Glu
        450                 455                 460

Gly Asn Ala Phe Asp Leu Pro Met His Ser Met Ser Gly His Ala Ser
465                 470                 475                 480

Pro Gly Val Gln Gly Asp Tyr Gln Gly Ile Ala Leu Glu Asn Val Asp
                485                 490                 495

Pro Asn Val Leu Thr Pro Gly Ser
            500
```

<210> SEQ ID NO 7
<211> LENGTH: 1557
<212> TYPE: DNA
<213> ORGANISM: Artificial Sequence
<220> FEATURE:
<223> OTHER INFORMATION: fungal gene

<400> SEQUENCE: 7

| | |
|---|---:|
| atggatccta gaaaccatcc ctctcggcct ccgtctacca gtctgcctca aggatcggcg | 60 |
| cctcttcctt ctgctcccat ctcgagcatg ccaatgcctc agtacacgat gcagcctcag | 120 |
| tacccagtct ctcagccgca caccctgcct cctctgcaac cccatcatag ccagtcgccc | 180 |
| gctcctcact cgtacatggg gcagccgccg taccggcctg atctgaacag gtaccccgca | 240 |
| tcaagtcacg atgtttacgc gtcttctgct gcgccgataa tgccccacac taccgtgggc | 300 |
| agcttgcctc cgacatcttt cctttctcat cccaatccgc aggcgcaggc acaggcgcag | 360 |
| caatcgccgc actatcctcc tcctcatagc gtgctcccgc ccgcttccag cgctcagtcg | 420 |
| tacccgcagc caattgcgcc ggcgcctccc cgggaccgtc gtgctgactt caacaatgga | 480 |
| cttccttcag gagcattcag ttattcggac ggaaagcctc aaggttggga ccccgttgct | 540 |
| gcgaatggtg ctgcgccgta tcccgggaag gactcccccc gaacccaggt tgttggttct | 600 |
| caggggcgac gcggtatcct tccgagtgtt ccgggacgcg caactccggt cacaaatggt | 660 |
| gttaacggca ccggcaagaa cactactatc ccggccaagg atgccgatgg aaagttccct | 720 |
| tgcccgaact gtaacaagac ttatcttcat gccaagcatc tcaagcgcca tctgctacgc | 780 |
| cacactggtg accgcccgta catgtgtgtt ctttgcaaag acaccttctc tcgcagtgat | 840 |
| atcctgaaac gtcatttcca aaaatgctca atcaggcgtg gtaacccccac cggagcaacg | 900 |
| cacttgtcgc accccaatgc gcatgtgaag aggtcccaac agcaggctgc ggcgaatcct | 960 |
| gtaaaacctg tccaggatga agtcagtagt accgtcccgc ctcccaatgg catcccgggc | 1020 |
| acgacttacg gcgagggagc cgtcaacggc aatggactag ctccggcccg gccagggtac | 1080 |
| gcggatcacc agactatggg cttcccaatg tcatccgtca acgggatggg ccgtggtcag | 1140 |
| cctgaagacg cgtttcccgg cggccggccg catcaaggag ccccttggcc acaagctccc | 1200 |
| aagcagagcc cgtatctcgt gcagccgggt gctgacccct ctggccacca gttgaatatt | 1260 |
| gaccgaaaca tcgagcaggt aaaacaaccg gttgttcaag accccaagcg ccctgtgatg | 1320 |
| ccaggacatc ccggccaccc cggtgagctt gactggacgt ctatgttcca acctcaagct | 1380 |
| cccgagggct acatgttctc ccagtctatg cctggtggtc aagagcccat ccacgctcat | 1440 |
| gtcgagaccg agcgaaagta ttaccccacc actaccgctg gtcaagagag tggaatgaac | 1500 |
| ggtctctatc tggcttcgac tatgagtggc gacggcaccg ttcagcccgc cagacaa | 1557 |

<210> SEQ ID NO 8
<211> LENGTH: 519
<212> TYPE: PRT
<213> ORGANISM: Artificial Sequence -continued

```
<220> FEATURE:
<223> OTHER INFORMATION: fungal gene

<400> SEQUENCE: 8

Met Asp Pro Arg Asn His Pro Ser Arg Pro Ser Thr Ser Leu Pro
 1               5                  10                  15

Gln Gly Ser Ala Pro Leu Pro Ser Ala Pro Ile Ser Ser Met Pro Met
            20                  25                  30

Pro Gln Tyr Thr Met Gln Pro Gln Tyr Pro Val Ser Gln Pro His Thr
        35                  40                  45

Leu Pro Pro Leu Gln Pro His His Ser Gln Ser Pro Ala Pro His Ser
 50                  55                  60

Tyr Met Gly Gln Pro Pro Tyr Arg Pro Asp Leu Asn Arg Tyr Pro Ala
 65                  70                  75                  80

Ser Ser His Asp Val Tyr Ala Ser Ser Ala Pro Ile Met Pro His
                85                  90                  95

Thr Thr Val Gly Ser Leu Pro Pro Thr Ser Phe Leu Ser His Pro Asn
                100                 105                 110

Pro Gln Ala Gln Ala Gln Ala Gln Gln Ser Pro His Tyr Pro Pro Pro
            115                 120                 125

His Ser Val Leu Pro Pro Ala Ser Ser Ala Gln Ser Tyr Pro Gln Pro
        130                 135                 140

Ile Ala Pro Ala Pro Pro Arg Asp Arg Arg Ala Asp Phe Asn Asn Gly
145                 150                 155                 160

Leu Pro Ser Gly Ala Phe Ser Tyr Ser Asp Gly Lys Pro Gln Gly Trp
                165                 170                 175

Asp Pro Val Ala Ala Asn Gly Ala Ala Pro Tyr Pro Gly Lys Asp Ser
                180                 185                 190

Pro Arg Thr Gln Val Val Gly Ser Gln Gly Arg Arg Gly Ile Leu Pro
            195                 200                 205

Ser Val Pro Gly Arg Ala Thr Pro Val Thr Asn Gly Val Asn Gly Thr
        210                 215                 220

Gly Lys Asn Thr Thr Ile Pro Ala Lys Asp Ala Asp Gly Lys Phe Pro
225                 230                 235                 240

Cys Pro Asn Cys Asn Lys Thr Tyr Leu His Ala Lys His Leu Lys Arg
                245                 250                 255

His Leu Leu Arg His Thr Gly Asp Arg Pro Tyr Met Cys Val Leu Cys
                260                 265                 270

Lys Asp Thr Phe Ser Arg Ser Asp Ile Leu Lys Arg His Phe Gln Lys
            275                 280                 285

Cys Ser Ile Arg Arg Gly Asn Pro Thr Gly Ala Thr His Leu Ser His
        290                 295                 300

Pro Asn Ala His Val Lys Arg Ser Gln Gln Gln Ala Ala Asn Pro
305                 310                 315                 320

Val Lys Pro Val Gln Asp Glu Val Ser Ser Thr Val Pro Pro Asn
                325                 330                 335

Gly Ile Pro Gly Thr Thr Tyr Gly Glu Gly Ala Val Asn Gly Asn Gly
            340                 345                 350

Leu Ala Pro Ala Arg Pro Gly Tyr Ala Asp His Gln Thr Met Gly Phe
        355                 360                 365

Pro Met Ser Ser Val Asn Gly Met Gly Arg Gly Gln Pro Glu Asp Ala
    370                 375                 380

Phe Pro Gly Gly Arg Pro His Gln Gly Ala Pro Trp Pro Gln Ala Pro
385                 390                 395                 400
```

```
Lys Gln Ser Pro Tyr Leu Val Gln Pro Gly Ala Asp Pro Ser Gly His
                405                 410                 415
Gln Leu Asn Ile Asp Arg Asn Ile Glu Gln Val Lys Gln Pro Val Val
            420                 425                 430
Gln Asp Pro Lys Arg Pro Val Met Pro Gly His Pro Gly His Pro Gly
        435                 440                 445
Glu Leu Asp Trp Thr Ser Met Phe Gln Pro Gln Ala Pro Glu Gly Tyr
    450                 455                 460
Met Phe Ser Gln Ser Met Pro Gly Gly Gln Glu Pro Ile His Ala His
465                 470                 475                 480
Val Glu Thr Glu Arg Lys Tyr Tyr Pro Thr Thr Thr Ala Gly Gln Glu
                485                 490                 495
Ser Gly Met Asn Gly Leu Tyr Leu Ala Ser Thr Met Ser Gly Asp Gly
            500                 505                 510
Thr Val Gln Pro Ala Arg Gln
        515
```

<210> SEQ ID NO 9
<211> LENGTH: 1116
<212> TYPE: DNA
<213> ORGANISM: Artificial Sequence
<220> FEATURE:
<223> OTHER INFORMATION: fungal gene

<400> SEQUENCE: 9

```
atgattaatg agacgcagga gattcactcc gagaacgaca tcgacagagc gccgatgcga      60
tcgtcgattg agctgccttc tctccgtgat cacttcaaac gggactcgtt gcctccattt     120
tcgtcccctc aacctagatc gctcctaccc tcgattctca accactctcc tcccggtcgc     180
tcttcgaccc ttccgccgat ccagcggacg aacaagcttc ccgacctcg caaaggatcg      240
ataaccgggg cgcggaaagc caagcatgaa cggtcgaggt cgaaagagtt tggtaggcgc     300
ccgagcatag gcgataggaa ggctctatca gcagaaccgc aaaccgctgc ctgggcgcag     360
ggcaagcgtt ggaggatctc attgaggcg ccacatcag caaccgaggt tgatgacgac       420
agacagtcag agttggggcg ttcaccaacc attccaccaa ccattccgaa tatcgcttcg     480
atcacatcgg caccatcaat caaaagccga tcatccatgc cgcctgcctt ccaatcccct     540
gggctacccc cacctgcatc gcatcgcccg ttcccaccca catcatatgc agcgtcgccc     600
ttgcacaaat ctttgacccc gccgccttat gaattctccc gcaaccgtga cgccgaccta     660
gaacctttcc cctccattga atcgtctttg gactcagcat cgacaacatc tggaaagcac     720
ttttactcca accacttgaa ccccgccaga atccagatt cgagtccagt gttaaactta      780
tttccatctt ccgcagccca gcgacaacac caccgcttct ctaatcccac cccggcgtct     840
ttccgtagca gggagataca gatcttctgc gccagctgca agcaggcatg gcctctcaat     900
gaatgctatg cctgtactga atgtatctgc ggggtatgcc gcgattgcgt cggaagtttc     960
atgagcagtc cgcctgcgac gttcaagaac gtgacatcca gccctgggag cgcaatgtca    1020
cacggcccga caagctatcc gagtccgaac ccacgtggtt gcccacgctg ccacaccgtg    1080
ggagggaagt ggaaagcatt ccaactggac atcaaa                              1116
```

<210> SEQ ID NO 10
<211> LENGTH: 372
<212> TYPE: PRT
<213> ORGANISM: Artificial Sequence
<220> FEATURE:

<223> OTHER INFORMATION: fungal gene

<400> SEQUENCE: 10

```
Met Ile Asn Glu Thr Gln Glu Ile His Ser Glu Asn Asp Ile Asp Arg
  1               5                  10                  15

Ala Pro Met Arg Ser Ser Ile Glu Leu Pro Ser Leu Arg Asp His Phe
             20                  25                  30

Lys Arg Asp Ser Leu Pro Pro Phe Ser Ser Pro Gln Pro Arg Ser Leu
         35                  40                  45

Leu Pro Ser Ile Leu Asn His Ser Pro Pro Gly Arg Ser Ser Thr Leu
     50                  55                  60

Pro Pro Ile Gln Arg Thr Asn Lys Leu Pro Arg Pro Arg Lys Gly Ser
 65                  70                  75                  80

Ile Thr Gly Ala Arg Lys Ala Lys His Glu Arg Ser Arg Ser Lys Glu
                 85                  90                  95

Phe Gly Arg Arg Pro Ser Ile Gly Asp Arg Lys Ala Leu Ser Ala Glu
            100                 105                 110

Pro Gln Thr Ala Ala Trp Ala Gln Gly Lys Arg Trp Glu Asp Leu Ile
        115                 120                 125

Glu Ala Ala Thr Ser Ala Thr Glu Val Asp Asp Arg Gln Ser Glu
    130                 135                 140

Leu Gly Arg Ser Pro Thr Ile Pro Pro Thr Ile Pro Asn Ile Ala Ser
145                 150                 155                 160

Ile Thr Ser Ala Pro Ser Ile Lys Ser Arg Ser Ser Met Pro Pro Ala
                165                 170                 175

Phe Gln Ser Pro Gly Leu Pro Pro Ala Ser His Arg Pro Phe Pro
            180                 185                 190

Pro Thr Ser Tyr Ala Ala Ser Pro Leu His Lys Ser Leu Thr Pro Pro
        195                 200                 205

Pro Tyr Glu Phe Ser Arg Asn Arg Asp Ala Asp Leu Glu Pro Phe Pro
    210                 215                 220

Ser Ile Glu Ser Ser Leu Asp Ser Ala Ser Thr Thr Ser Gly Lys His
225                 230                 235                 240

Phe Tyr Ser Asn His Leu Asn Pro Ala Arg Asn Pro Asp Ser Ser Pro
                245                 250                 255

Val Leu Asn Leu Phe Pro Ser Ser Ala Ala Gln Arg Gln His His Arg
            260                 265                 270

Phe Ser Asn Pro Thr Pro Ala Ser Phe Arg Ser Arg Glu Ile Gln Ile
        275                 280                 285

Phe Cys Ala Ser Cys Lys Gln Ala Trp Pro Leu Asn Glu Cys Tyr Ala
    290                 295                 300

Cys Thr Glu Cys Ile Cys Gly Val Cys Arg Asp Cys Val Gly Ser Phe
305                 310                 315                 320

Met Ser Ser Pro Pro Ala Thr Phe Lys Asn Val Thr Ser Ser Pro Gly
                325                 330                 335

Ser Ala Met Ser His Gly Pro Thr Ser Tyr Pro Ser Pro Asn Pro Arg
            340                 345                 350

Gly Cys Pro Arg Cys His Thr Val Gly Gly Lys Trp Lys Ala Phe Gln
        355                 360                 365

Leu Asp Ile Lys
    370
```

<210> SEQ ID NO 11
<211> LENGTH: 933

<212> TYPE: DNA
<213> ORGANISM: Artificial Sequence
<220> FEATURE:
<223> OTHER INFORMATION: fungal gene

<400> SEQUENCE: 11

```
atgacggcgc gccaatcaac accgtcctcc gacaactcgc actcagacag cggcgtccgc      60
aagcgagtat gcaaggcttg cgatcgttgc gactgaaaaa agtccaagtg tgacggagcc     120
aaaccatgcg gtcgctgtcg agcagacaac acgctctgtg ttttcggcga gaggaagaaa     180
gctcatgaca aagtgtaccc taaggggtat gttgagatgc tggaacaaca acaaacttgg     240
ctagtcaatg gcctgcaaga actgtatcgc cgccttcttg agggtgatgg atggccgggc     300
gagccgctga aatgcgaagc gaacgggcag cccttgacac acgatctctt gacgcagctc     360
ggcgctctcg acacaagcaa gcacgagcgg ttcgaagaac acgccgaggt catgcagcag     420
gaattatgga agcgaaatgc cggacacatg cagcgccagg actcatcaga taccagctcc     480
gagagcccac agtcgcccgt catgccgtct caattctcag atccctttc tgtgcgcaca      540
gtaccacaaa ctccgacaac gatcagcccg aacacgacgc tgcgaataga cgtcccgcaa     600
tcagcgacga agagtgaacc gcagatgaca tcgccaaact ccatatacac cacagccgtg     660
tccatgccgc gagtggtcga cccgtctgag ctgcagagcg cccaaatagc aaacccgcag     720
tggcccagcc ctggctttgg aggctacgac gaaatggacc tgatgtctgg caatacaat      780
ggtctgccat acgaagatgc gatctcctcg ccaatgttca atcgtccaat gccaatgggg     840
tgcctgatac agggtcata cgggaacttg gataacaaga cgactttga ggatatcaac       900
caatttctga acacacagtt ggagattacg tcg                                    933
```

<210> SEQ ID NO 12
<211> LENGTH: 311
<212> TYPE: PRT
<213> ORGANISM: Artificial Sequence
<220> FEATURE:
<223> OTHER INFORMATION: fungal gene

<400> SEQUENCE: 12

```
Met Thr Ala Arg Gln Ser Thr Pro Ser Ser Asp Asn Ser His Ser Asp
  1               5                  10                  15

Ser Gly Val Arg Lys Arg Val Cys Lys Ala Cys Asp Arg Cys Arg Leu
             20                  25                  30

Lys Lys Ser Lys Cys Asp Gly Ala Lys Pro Cys Gly Arg Cys Arg Ala
         35                  40                  45

Asp Asn Thr Leu Cys Val Phe Gly Glu Arg Lys Lys Ala His Asp Lys
     50                  55                  60

Val Tyr Pro Lys Gly Tyr Val Glu Met Leu Glu Gln Gln Gln Thr Trp
 65                  70                  75                  80

Leu Val Asn Gly Leu Gln Glu Leu Tyr Arg Arg Leu Leu Glu Gly Asp
                 85                  90                  95

Gly Trp Pro Gly Glu Pro Leu Lys Cys Glu Ala Asn Gly Gln Pro Leu
            100                 105                 110

Thr His Asp Leu Leu Thr Gln Leu Gly Ala Leu Asp Thr Ser Lys His
        115                 120                 125

Glu Arg Phe Glu Glu His Ala Glu Val Met Gln Gln Glu Leu Trp Lys
    130                 135                 140

Arg Asn Ala Gly His Met Gln Arg Gln Asp Ser Ser Asp Thr Ser Ser
145                 150                 155                 160
```

-continued

```
Glu Ser Pro Gln Ser Pro Val Met Pro Ser Gln Phe Ser Asp Pro Phe
                165                 170                 175

Ser Val Arg Thr Val Pro Gln Thr Pro Thr Thr Ile Ser Pro Asn Thr
            180                 185                 190

Thr Leu Arg Ile Asp Val Pro Gln Ser Ala Thr Lys Ser Glu Pro Gln
        195                 200                 205

Met Thr Ser Pro Asn Ser Ile Tyr Thr Thr Ala Val Ser Met Pro Arg
    210                 215                 220

Val Val Asp Pro Ser Glu Leu Gln Ser Ala Gln Ile Ala Asn Pro Gln
225                 230                 235                 240

Trp Pro Ser Pro Gly Phe Gly Gly Tyr Asp Glu Met Asp Leu Met Ser
                245                 250                 255

Gly Gln Tyr Asn Gly Leu Pro Tyr Glu Asp Ala Ile Ser Ser Pro Met
                260                 265                 270

Phe Asn Arg Pro Met Pro Met Gly Cys Leu Ile Pro Gly Ser Tyr Gly
            275                 280                 285

Asn Leu Asp Asn Lys Asn Asp Phe Glu Asp Ile Asn Gln Phe Leu Asn
    290                 295                 300

Thr Gln Leu Glu Ile Thr Ser
305                 310
```

<210> SEQ ID NO 13
<211> LENGTH: 660
<212> TYPE: DNA
<213> ORGANISM: Artificial Sequence
<220> FEATURE:
<223> OTHER INFORMATION: fungal gene

<400> SEQUENCE: 13

```
atgtcgcagc ccatcgcctg ccctccaatg gagcactcgc cctcctcctt gtcctcctac      60
tcctcttact cccccagttc gtcctactcc gccgtgagcg acgactcggg catgagcatg     120
ttggacatgt acttcctgca cggtggccgt ggacacggcg ccagccccgg cacaagcacg     180
ggtcccggca gcgtcgtcga tttcccgttc agccagcaat cgttcgattt cgagccttcg     240
tcgctggaca gcaatggccc ctacttcgag ttcaacccga ctttcgtata cacacccgag     300
gcgtttcccg tcatggacgc cccgacctcc tacccggcga gctcgaaccc ggcctggtcg     360
ccaacctcca tgcttgtcga gcagtcgata tttcctctcg acgggcttag ccaagaacca     420
gtcaagccag ccaaaccta cagctgcgaa gattgcggca aggccttcac ccgcccagcg      480
gacctaaagc gccaccatag cactgtacac taccggtttt ccagaactg ccctgtaccg      540
gactgctcgc gcaaggacaa ccatggcttt ccgcggcgcg accacctcgt cgagcacctg     600
cgctcgtacc accacatgga tgtgccgaag cggcgcgcag caaagcgatt gagaactgtt     660
```

<210> SEQ ID NO 14
<211> LENGTH: 220
<212> TYPE: PRT
<213> ORGANISM: Artificial Sequence
<220> FEATURE:
<223> OTHER INFORMATION: fungal gene

<400> SEQUENCE: 14

```
Met Ser Gln Pro Ile Ala Cys Pro Pro Met Glu His Ser Pro Ser Ser
  1               5                  10                  15

Leu Ser Ser Tyr Ser Ser Tyr Ser Pro Ser Ser Tyr Ser Ala Val
            20                  25                  30

Ser Asp Asp Ser Gly Met Ser Met Leu Asp Met Tyr Phe Leu His Gly
```

35                  40                  45
Gly Arg Gly His Gly Ala Ser Pro Gly Thr Ser Thr Gly Pro Gly Ser
        50                  55                  60

Val Val Asp Phe Pro Phe Ser Gln Gln Ser Phe Asp Phe Glu Pro Ser
65                  70                  75                  80

Ser Leu Asp Ser Asn Gly Pro Tyr Phe Glu Phe Asn Pro Thr Phe Val
                85                  90                  95

Tyr Thr Pro Glu Ala Phe Pro Val Met Asp Ala Pro Thr Ser Tyr Pro
            100                 105                 110

Ala Ser Ser Asn Pro Ala Trp Ser Pro Thr Ser Met Leu Val Glu Gln
        115                 120                 125

Ser Ile Phe Pro Leu Asp Gly Leu Ser Gln Glu Pro Val Lys Pro Ala
    130                 135                 140

Lys Pro Tyr Ser Cys Glu Asp Cys Gly Lys Ala Phe Thr Arg Pro Ala
145                 150                 155                 160

Asp Leu Lys Arg His His Ser Thr Val His Tyr Pro Val Phe Gln Asn
                165                 170                 175

Cys Pro Val Pro Asp Cys Ser Arg Lys Asp Asn His Gly Phe Pro Arg
            180                 185                 190

Arg Asp His Leu Val Glu His Leu Arg Ser Tyr His His Met Asp Val
        195                 200                 205

Pro Lys Arg Arg Ala Ala Lys Arg Leu Arg Thr Val
    210                 215                 220

<210> SEQ ID NO 15
<211> LENGTH: 684
<212> TYPE: DNA
<213> ORGANISM: Artificial Sequence
<220> FEATURE:
<223> OTHER INFORMATION: fungal gene

<400> SEQUENCE: 15
atgcttgcgc agaataacat ccagaaccag cagcagcagc agatgatgca gcagcagcag      60
cagcaacaac aacaacaaca acaacaacaa atcaccagaa tcaacaacaa gaagtttgcc     120
aatccccagg cataccaggc tcagatgatg cgcgcgcaac tcatgcagat gcagctcgcc     180
caacagcagc agcaacaaag gcaacagcaa tcaacagcag cagcaacaag c gcagccgcaa   240 ggccagcaac agccacagca tcaacaagga caaatgcttc aaaacagccc tcagctcaac     300
gcccagcaac agcagatgtt gatggcagcg gcacaagcta acggcggcca actcccgcaa     360
aacatgcagg gcatgggtat gcagccgcga atgagtactc cagcgcggta caaccagctc     420
tatcagcagc ggcttttgag actacggcaa gacatggcta cgcgtctgat gccacagtac     480
ggaccaccca cgcaatatcc gccacaggtt gcgcaggagt acagtgttgg ccttgaaaac     540
gctgctaagg gcttcgtgca agacctcatt cgcagggagc gtgtcgagtt tgctgctgct     600
caacagcgac aagcccaggc tgctgcccac gcccaggcag tgcagcaaca gcagcacaac     660
atgatgcaga atggaatggg caag                                            684

<210> SEQ ID NO 16
<211> LENGTH: 228
<212> TYPE: PRT
<213> ORGANISM: Artificial Sequence
<220> FEATURE:
<223> OTHER INFORMATION: fungal gene

<400> SEQUENCE: 16

```
Met Leu Ala Gln Asn Asn Ile Gln Asn Gln Gln Gln Gln Met Met
 1               5                  10                  15

Gln Gln Gln Gln Gln Gln Gln Gln Gln Gln Gln Gln Gln Asn His
            20                  25                  30

Gln Asn Gln Gln Gln Lys Phe Ala Asn Pro Gln Ala Tyr Gln Ala Gln
        35                  40                  45

Met Met Arg Ala Gln Leu Met Gln Met Gln Leu Ala Gln Gln Gln Gln
50                  55                  60

Gln Gln Arg Gln Gln Ser Gln Gln Gln Gln Ala Gln Pro Gln
65                  70                  75                  80

Gly Gln Gln Gln Pro Gln His Gln Gln Gly Gln Met Leu Gln Asn Ser
                85                  90                  95

Pro Gln Leu Asn Ala Gln Gln Gln Met Leu Met Ala Ala Gln
            100                 105                 110

Ala Asn Gly Gly Gln Leu Pro Gln Asn Met Gln Gly Met Gly Met Gln
            115                 120                 125

Pro Arg Met Ser Thr Pro Ala Arg Tyr Asn Gln Leu Tyr Gln Gln Arg
        130                 135                 140

Leu Leu Arg Leu Arg Gln Asp Met Ala Thr Arg Leu Met Pro Gln Tyr
145                 150                 155                 160

Gly Pro Pro Thr Gln Tyr Pro Pro Gln Val Ala Gln Glu Tyr Ser Val
            165                 170                 175

Gly Leu Glu Asn Ala Ala Lys Gly Phe Val Gln Asp Leu Ile Arg Arg
            180                 185                 190

Glu Arg Val Glu Phe Ala Ala Ala Gln Gln Arg Gln Ala Gln Ala Ala
        195                 200                 205

Ala His Ala Gln Ala Val Gln Gln Gln Gln His Asn Met Met Gln Asn
    210                 215                 220

Gly Met Gly Lys
225
```

<210> SEQ ID NO 17
<211> LENGTH: 906
<212> TYPE: DNA
<213> ORGANISM: Artificial Sequence
<220> FEATURE:
<223> OTHER INFORMATION: fungal gene

<400> SEQUENCE: 17

```
atgaacaacg acttcatgca aaacaacatt cgcagcgccc aggatgtgga acagattatt      60
tccaacatcc gattctccgg catgacgcct ctaggttccg ctctgagatc caaggtactt     120
gatcccatga tagtgggtcc agccagagca ggccgcctgc aaaagccggt tctcgtcatc     180
actatcaccg atggtcagcc cgctggagaa cctctggact ccgtcgctca gggaattcgc     240
tacgctgttg atgaggtttc gagatcccca tttggacgtg gtgcggttgc cttccagttc     300
tcgcaagtcg gaaacgacac caaggctcgg gacttcctcg gcagtctcga caacgaccct     360
agcattggtg gcctgatcga ctgcaccctc aactttgaag tagaacagga tgagatgtcc     420
cgtgctaacc cacctgtgca tctgactcgt gagctgtggt gcgcgaaact catgctcggc     480
tctatcgatt cctcgtacga taccaaggac gagaggggta gtggcccatc tggtgctcct     540
cctgggcctc ctcctggcca gtacggcggc tatggtcagt caggaccggg atacggctca     600
tccgcaccat acaatcccgg ccagcaacag ccgtacagcc tgcttaccc cccgcacagc     660
caagcgcctg gaggctatgc acagccacct ccccaaggcc agtacggcgg ctatagccaa     720
```

```
ccgggcccgg gatatggctc acccgcgcct tacagctccg gacaacaaca ggggtatggc    780 tctgctccttt acccaccgag cagccaagcg tctgggagct atggccagca acaatatgga    840
caacggcccg gatctcagcc tggttatccc ggtcaacagc ctccgtacgg acagcagccg    900
aggtat                                                                906
```

<210> SEQ ID NO 18
<211> LENGTH: 302
<212> TYPE: PRT
<213> ORGANISM: Artificial Sequence
<220> FEATURE:
<223> OTHER INFORMATION: fungal gene

<400> SEQUENCE: 18

```
Met Asn Asp Phe Met Gln Asn Asn Ile Arg Ser Ala Gln Asp Val
  1               5                  10                  15

Glu Gln Ile Ile Ser Asn Ile Arg Phe Ser Gly Met Thr Pro Leu Gly
             20                  25                  30

Ser Ala Leu Arg Ser Lys Val Leu Asp Pro Met Ile Val Gly Pro Ala
             35                  40                  45

Arg Ala Gly Arg Leu Gln Lys Pro Val Leu Val Ile Thr Ile Thr Asp
 50                  55                  60

Gly Gln Pro Ala Gly Glu Pro Leu Asp Ser Val Ala Gln Gly Ile Arg
 65                  70                  75                  80

Tyr Ala Val Asp Glu Val Ser Arg Ser Pro Phe Gly Arg Gly Ala Val
                 85                  90                  95

Ala Phe Gln Phe Ser Gln Val Gly Asn Asp Thr Lys Ala Arg Asp Phe
            100                 105                 110

Leu Gly Ser Leu Asp Asn Asp Pro Ser Ile Gly Gly Leu Ile Asp Cys
            115                 120                 125

Thr Ser Asn Phe Glu Val Glu Gln Asp Glu Met Ser Arg Ala Asn Pro
            130                 135                 140

Pro Val His Leu Thr Arg Glu Leu Trp Cys Ala Lys Leu Met Leu Gly
145                 150                 155                 160

Ser Ile Asp Ser Ser Tyr Asp Thr Lys Asp Glu Arg Gly Ser Gly Pro
                165                 170                 175

Ser Gly Ala Pro Pro Gly Pro Pro Gly Gln Tyr Gly Gly Tyr Gly
            180                 185                 190

Gln Ser Gly Pro Gly Tyr Gly Ser Ser Ala Pro Tyr Asn Pro Gly Gln
            195                 200                 205

Gln Gln Pro Tyr Ser Pro Ala Tyr Pro Pro His Ser Gln Ala Pro Gly
            210                 215                 220

Gly Tyr Ala Gln Pro Pro Gln Gly Gln Tyr Gly Tyr Ser Gln
225                 230                 235                 240

Pro Gly Pro Gly Tyr Gly Ser Pro Ala Pro Tyr Ser Ser Gly Gln Gln
                245                 250                 255

Gln Gly Tyr Gly Ser Ala Pro Tyr Pro Pro Ser Ser Gln Ala Ser Gly
            260                 265                 270

Ser Tyr Gly Gln Gln Gln Tyr Gly Gln Arg Pro Gly Ser Gln Pro Gly
            275                 280                 285

Tyr Pro Gly Gln Gln Pro Pro Tyr Gly Gln Gln Pro Arg Tyr
            290                 295                 300
```

<210> SEQ ID NO 19
<211> LENGTH: 810
<212> TYPE: DNA

<213> ORGANISM: Artificial Sequence
<220> FEATURE:
<223> OTHER INFORMATION: fungal gene

<400> SEQUENCE: 19

```
atgactagcc gtcagaatga atacttcatc cccggagatg gtattagccg agaagtaatt     60
caggccgaca tctgccgtta ccttggaaat gatgctttag taagacctgg aaaccacaat    120
ggtcgcgcgg gattcttcat tcgcgcttat cgaaacctca catcagaaat gattgctgat    180
ctcaaggcgg actccgcccg ctgggaagca gacgtcagaa gtcgtgctga ccaaggttat    240
cccgggggca gctacatcca ggactacagc tactctcaac tagccgggc tacaccaacc     300
tactcaaccct ctatgggaag ttccatgcac cctgaaatgt cccatggtca aggcccttct    360
cctcctacaa cctacgctgc tccgccgcag cagtattctg agcagtatca ccaatctggc    420
tacccagcaa cttcaagtcc gtcatactca atgctccgt catatccttc aaaccactcg     480
ggctttggat ctggtcagcc cccatacact caacatatcc cctacagtgc tccaacccag    540
cctcctgtga cttctgaggt ccaccttca tatacttacg ccagctctgg ctatggtttc     600
gagaatgggc gaaacaatgc ccctcggtac cctggtcctg gatatgatgc cgattctgat    660
tattctcctg ttactaccgg aatggcttat cctgctacca ctgcccctga tccacggata    720
ggaatggagc ccagatacac accggagtcc acatatgacc gcagtaggcc gcagccagca    780
agagaaagag aggctccccg ccgaacgcgg                                     810
```

<210> SEQ ID NO 20
<211> LENGTH: 270
<212> TYPE: PRT
<213> ORGANISM: Artificial Sequence
<220> FEATURE:
<223> OTHER INFORMATION: fungal gene

<400> SEQUENCE: 20

```
Met Thr Ser Arg Gln Asn Glu Tyr Phe Ile Pro Gly Asp Gly Ile Ser
  1               5                  10                  15

Arg Glu Val Ile Gln Ala Asp Ile Cys Arg Tyr Leu Gly Asn Asp Ala
             20                  25                  30

Leu Val Arg Pro Gly Asn His Asn Gly Arg Ala Gly Phe Phe Ile Arg
         35                  40                  45

Ala Tyr Arg Asn Leu Thr Ser Glu Met Ile Ala Asp Leu Lys Ala Asp
     50                  55                  60

Ser Ala Arg Trp Glu Ala Asp Val Arg Ser Arg Ala Asp Gln Gly Tyr
 65                  70                  75                  80

Pro Arg Gly Ser Tyr Ile Gln Asp Tyr Ser Tyr Ser Gln Pro Ser Arg
                 85                  90                  95

Ala Thr Pro Thr Tyr Ser Thr Ser Met Gly Ser Ser Met His Pro Glu
            100                 105                 110

Met Ser His Gly Gln Gly Pro Ser Pro Thr Thr Tyr Ala Ala Pro
        115                 120                 125

Pro Gln Gln Tyr Ser Glu Gln Tyr His Gln Ser Gly Tyr Pro Ala Thr
    130                 135                 140

Ser Ser Pro Ser Tyr Ser Asn Ala Pro Ser Tyr Pro Asn Asn His Ser
145                 150                 155                 160

Gly Phe Gly Ser Gly Gln Pro Pro Tyr Pro Gln His Ile Pro Tyr Ser
                165                 170                 175

Ala Pro Thr Gln Pro Pro Val Ser Glu Val His Pro Ser Tyr Thr
            180                 185                 190
```

| Tyr | Ala | Ser | Ser | Gly | Tyr | Gly | Phe | Glu | Asn | Gly | Arg | Asn | Asn | Ala | Pro |
|     |     | 195 |     |     |     | 200 |     |     |     |     | 205 |     |     |     |     |

| Arg | Tyr | Pro | Gly | Pro | Gly | Tyr | Asp | Ala | Asp | Ser | Asp | Tyr | Ser | Pro | Val |
|     | 210 |     |     |     |     | 215 |     |     |     |     | 220 |     |     |     |     |

| Thr | Thr | Gly | Met | Ala | Tyr | Pro | Ala | Thr | Thr | Ala | Pro | Asp | Pro | Arg | Ile |
| 225 |     |     |     |     | 230 |     |     |     |     | 235 |     |     |     |     | 240 |

| Gly | Met | Glu | Pro | Arg | Tyr | Thr | Pro | Glu | Ser | Thr | Tyr | Asp | Arg | Ser | Arg |
|     |     |     |     | 245 |     |     |     |     | 250 |     |     |     |     | 255 |     |

| Pro | Gln | Pro | Ala | Arg | Glu | Arg | Glu | Ala | Pro | Arg | Arg | Thr | Arg |
|     |     |     |     | 260 |     |     |     |     | 265 |     |     |     | 270 |

<210> SEQ ID NO 21
<211> LENGTH: 2082
<212> TYPE: DNA
<213> ORGANISM: Artificial Sequence
<220> FEATURE:
<223> OTHER INFORMATION: fungal gene

<400> SEQUENCE: 21

| atgacacacc gagattccga cttccgtcat caactgggca agtttcgact cgatacccctg | 60 |
| ccgtcgcccg ctgtcgctgc tgctgctgca ccccgctca tctcctccac ctccatcctc | 120 |
| tccagcccca acacgaccac caccaccacc accacaacaa cttcctcctc gggccccgtc | 180 |
| cgaagcaaaa gagtctccac cgcctgcgat ttctgtcgca aacgcaagaa gaaatgtgac | 240 |
| tttcgttatc ccaattgttc cgcctgtacg cgcgccggcg tgcgatgtac cattccacca | 300 |
| cccggccctc aggtcgccag cgcctccgtc cctcgtgatc agctggaaac tctgcaaaat | 360 |
| cgcgtccgat ggctggaaga cgtggtgcgc cggaagacgg gcatctctgt cgccgatcgg | 420 |
| cccacgggga cgccgctcga tggcgagggc gacccggact ggtggtacca ggtgccggcc | 480 |
| ttgatgatga cccgggacaa cctctcccgc acggcgccgg ggacgaccgc gggaggcgtc | 540 |
| acctccagcc cgtctacctc gtctccatcc gccgtgggac ccgaattgcc caatgtcggc | 600 |
| gaaatcttcc gcgaccagct ggagcatcgt cgaccgtccg tggctcgtcc cgtcgcctcg | 660 |
| gccccgcgcg tgctgcgact cgcctcgctg gcggaggcgg aacgcgtagc cgcacagtac | 720 |
| ttcgatagca tgggctatca atatcccttt ctccatcgcg gggatttcct cgcgcagttg | 780 |
| cgatcgcttt ataccctccga cagcgtcgtt gccccggagg tccactatac ctaccacatt | 840 |
| actatcgcca tctcgctcat catcgggtcg gccgacggcg cacaggccat cgagttctat | 900 |
| cgggccagtc aggagacgtt ttcgatggca ttgcagaatg aggacctggc ggccgtccgc | 960 |
| gcgctgctaa gtatggcctt gtatacaatg tttgcaacaa gcggtccgag cgtgtggcat | 1020 |
| gtgttgggta ccgcactgcg gctggccacc agtctgggc tgcacaaagc gcgacccgct | 1080 |
| gccagcttgg tggaagagga gatggctaaa cgggccttct ggagtctgta caatctggac | 1140 |
| cgactgatcg ccagcacgtt aggacgacct cttggcttag cggacgagga catcaccgtg | 1200 |
| gggttgccac gcgagttcaa cgaggactgg accgaggcgc ccgggtcgag tgccatgacc | 1260 |
| attccagtgc aggtggtgcg actacgtcgg atcttttcgc gcatctaccg atatctgtac | 1320 |
| aacaatcagc ccccaccccct ttcatccgaa gtcaccgcca cgctgcgcca tttccgacag | 1380 |
| gagctggacg attggcgacg cgcggctccc gtataccctc ccgccctcct ctactccaca | 1440 |
| agctactacg actatctatt tgcgacgaca gtactgctca tgtaccgacc gagtccacgg | 1500 |
| aacccgacgc cagatactct gagcattatc agctgtggcg acgcgagcat ccaggtgatt | 1560 |
| cggtcgtact gggacagcta ctcggtaggc aaattgaagt ggatctggtt gacactgagc | 1620 |

-continued

```
cagatctact tcgccggcat cacgatcctg tggtgtctgc atcagaactt gcgcgcgata    1680
caggacggtc aagcgccacc ctggcaaccg gatgaccaga ccatgcgccg ggggatccaa    1740
gcggttgtcg tcctgatgga ggagtttggc aaacggcggc cggggggtgga acgtctggcg   1800 gagacattcc gtcaacaaag cacgacgatc ttcagccatc tggtggcata tcagccccaa    1860
cctccaccgc agagccaacc cccggcacct ccaccattat cgcagtcaca atcgcagccc    1920
catatgctgg tggcgccgcc ggtcccgctg cccccggtgc tggacgacgt gctgctggtg    1980
gacgggtcag gcaatattcc cgtgatggat ccgtccatgg ccgaacaatt gttctattcg    2040
tacgattggt ttcaggagga gatggcgacg ttttataccc tc                      2082
```

<210> SEQ ID NO 22
<211> LENGTH: 694
<212> TYPE: PRT
<213> ORGANISM: Artificial Sequence
<220> FEATURE:
<223> OTHER INFORMATION: fungal gene

<400> SEQUENCE: 22

```
Met Thr His Arg Asp Ser Asp Phe Arg His Gln Leu Gly Lys Phe Arg
 1               5                  10                  15

Leu Asp Thr Leu Pro Ser Pro Ala Val Ala Ala Ala Ala Pro Pro
            20                  25                  30

Leu Ile Ser Ser Thr Ser Ile Leu Ser Ser Pro Asn Thr Thr Thr Thr
        35                  40                  45

Thr Thr Thr Thr Thr Thr Ser Ser Ser Gly Pro Val Arg Ser Lys Arg
    50                  55                  60

Val Ser Thr Ala Cys Asp Phe Cys Arg Lys Arg Lys Lys Cys Asp
65                  70                  75                  80

Phe Arg Tyr Pro Asn Cys Ser Ala Cys Thr Arg Ala Gly Val Arg Cys
                85                  90                  95

Thr Ile Pro Pro Gly Pro Gln Val Ala Ser Ala Ser Val Pro Arg
            100                 105                 110

Asp Gln Leu Glu Thr Leu Gln Asn Arg Val Arg Trp Leu Glu Asp Val
        115                 120                 125

Val Arg Arg Lys Thr Gly Ile Ser Val Ala Asp Arg Pro Thr Gly Thr
    130                 135                 140

Pro Leu Asp Gly Glu Gly Asp Pro Asp Trp Trp Tyr Gln Val Pro Ala
145                 150                 155                 160

Leu Met Met Thr Arg Asp Asn Leu Ser Arg Thr Ala Pro Gly Thr Thr
                165                 170                 175

Ala Gly Gly Val Thr Ser Ser Pro Ser Thr Ser Ser Pro Ser Ala Val
            180                 185                 190

Gly Pro Glu Leu Pro Asn Val Gly Glu Ile Phe Arg Asp Gln Leu Glu
        195                 200                 205

His Arg Arg Pro Ser Val Ala Arg Pro Val Ala Ser Ala Pro Arg Val
    210                 215                 220

Leu Arg Leu Ala Ser Leu Ala Glu Ala Glu Val Ala Gln Tyr
225                 230                 235                 240

Phe Asp Ser Met Gly Tyr Gln Tyr Pro Phe Leu His Arg Gly Asp Phe
                245                 250                 255

Leu Ala Gln Leu Arg Ser Leu Tyr Thr Ser Asp Ser Val Val Ala Pro
            260                 265                 270

Glu Val His Tyr Thr Tyr His Ile Thr Ile Ala Ile Ser Leu Ile Ile
```

```
                275                 280                 285
Gly Ser Ala Asp Gly Ala Gln Ala Ile Glu Phe Tyr Arg Ala Ser Gln
        290                 295                 300
Glu Thr Phe Ser Met Ala Leu Gln Asn Glu Asp Leu Ala Ala Val Arg
305                 310                 315                 320
Ala Leu Leu Ser Met Ala Leu Tyr Thr Met Phe Ala Thr Ser Gly Pro
                325                 330                 335
Ser Val Trp His Val Leu Gly Thr Ala Leu Arg Leu Ala Thr Ser Leu
            340                 345                 350
Gly Leu His Lys Ala Arg Pro Ala Ala Ser Leu Val Glu Glu Glu Met
                355                 360                 365
Ala Lys Arg Ala Phe Trp Ser Leu Tyr Asn Leu Asp Arg Leu Ile Ala
370                 375                 380
Ser Thr Leu Gly Arg Pro Leu Gly Leu Ala Asp Glu Asp Ile Thr Val
385                 390                 395                 400
Gly Leu Pro Arg Glu Phe Asn Glu Asp Trp Thr Glu Ala Pro Gly Ser
                405                 410                 415
Ser Ala Met Thr Ile Pro Val Gln Val Val Arg Leu Arg Arg Ile Phe
                420                 425                 430
Ser Arg Ile Tyr Arg Tyr Leu Tyr Asn Asn Gln Pro Pro Leu Ser
                435                 440                 445
Ser Glu Val Thr Ala Thr Leu Arg His Phe Arg Gln Glu Leu Asp Asp
            450                 455                 460
Trp Arg Arg Ala Ala Pro Val Tyr Pro Pro Ala Leu Leu Tyr Ser Thr
465                 470                 475                 480
Ser Tyr Tyr Asp Tyr Leu Phe Ala Thr Thr Val Leu Leu Met Tyr Arg
                485                 490                 495
Pro Ser Pro Arg Asn Pro Thr Pro Asp Thr Leu Ser Ile Ile Ser Cys
            500                 505                 510
Gly Asp Ala Ser Ile Gln Val Ile Arg Ser Tyr Trp Asp Ser Tyr Ser
            515                 520                 525
Val Gly Lys Leu Lys Trp Ile Trp Leu Thr Leu Ser Gln Ile Tyr Phe
530                 535                 540
Ala Gly Ile Thr Ile Leu Trp Cys Leu His Gln Asn Leu Arg Ala Ile
545                 550                 555                 560
Gln Asp Gly Gln Ala Pro Pro Trp Gln Pro Asp Gln Thr Met Arg
                565                 570                 575
Arg Gly Ile Gln Ala Val Val Leu Met Glu Glu Phe Gly Lys Arg
            580                 585                 590
Arg Pro Gly Val Glu Arg Leu Ala Glu Thr Phe Arg Gln Gln Ser Thr
            595                 600                 605
Thr Ile Phe Ser His Leu Val Ala Tyr Gln Pro Gln Pro Pro Gln
610                 615                 620
Ser Gln Pro Pro Ala Pro Pro Leu Ser Gln Ser Gln Ser Gln Pro
625                 630                 635                 640
His Met Leu Val Ala Pro Pro Val Pro Leu Ala Pro Val Leu Asp Asp
                645                 650                 655
Val Leu Leu Val Asp Gly Ser Gly Asn Ile Pro Val Met Asp Pro Ser
            660                 665                 670
Met Ala Glu Gln Leu Phe Tyr Ser Tyr Asp Trp Phe Gln Glu Glu Met
        675                 680                 685
Ala Thr Phe Tyr Thr Leu
        690
```

<210> SEQ ID NO 23
<211> LENGTH: 1371
<212> TYPE: DNA
<213> ORGANISM: Artificial Sequence
<220> FEATURE:
<223> OTHER INFORMATION: fungal gene

<400> SEQUENCE: 23

```
atgtcgccca ctctgcaccc ccaggccttc tacggcacgt tgatccattc actcaaccca      60
tcgacaatcg aatacctccc caacacattg atcataatcg accaacatgg aaaaatagag     120
ggactccatc cgcaaatccc cgcatcctcc atccaatctc tcctggccac gcacaaccac     180
actaccacca gctgcccaac caccatcctt tcgcccgccg agttcctcat tcccggattc     240
atcgacaccc acattcacgc tccccaatgg agtcaacgcg gcgtggggcg gggcatccca     300
ctgctcaact ggctggaggg gatcacgttc gcgcatgaag cgcgctgcag cgacgacgcc     360
tacgcgcggc ggctcttcca ctcgtgcgtg agcggcggcc tcaaacaagg cgtcacgaca     420
gcctgctact acagttcgcg gcacgcctcg gcaacggtca tcctggccga cgcgtgtctc     480
gcgctgggac agcgcgccct gctgggcaaa tgcaacatgg accggcacgc ggtcgactgg     540
tacgtcgacg agtcggcggc ggcctcggtc tccgacacgg agcacgtcat ccgggcggtg     600
cgcgcgctgg acgccgagca cggcctcgtc acaccggtga tcacgccgcg gttcgcgatc     660
agctgctcgg acgggctgct ccgggcgctg gcgagctcg cggcgcgggc cgagtaccgc     720
gcgctgccca tccagacgca cttcaacgag tcgcggcagg agatggcgtt cacgcgcagc     780
ctgttccccg gggtgcagga cgagacggcg ctgtacgagt cgtttgggct gctcaactcg     840
cggtgcgtgc tggcgcatgc gatctacctg tcgccgcggg agatggaccg cgtgcaggcg     900
ctggactgtg ggatcgcgca ttgtcccgtg ccgaatacta ccatggacga gttcatggtg     960
gcgcctgtgc gggagtatct ggcgcggggg atgaaggtgg gtctggggac ggactgtggg    1020
ggtgggtttt cgtcgtcgat gctggatgtc atgcgcatgg cgtttatggt gagtgtggca    1080
cgggagacgc agacggacgg ccgcgacaag ccgctgtctc ttgcggaggg gttctatctg    1140
gcgacggcgg gcggggcgag ggtgtgtggg ctggcggaga aggttgggcg gtttgcggtg    1200
ggcatggagt ttgatgcggt gctggtgagg acgggcgatg aggtcgatgg ggtcatgacg    1260
ccagtggagg aggaggattc gctcgagacg gtgtttgaga agttcttgat gacgggggat    1320
gatcgcaaca tggtgcgagt ttttgtcaag gggagggagg tgagggggtt g            1371
```

<210> SEQ ID NO 24
<211> LENGTH: 457
<212> TYPE: PRT
<213> ORGANISM: Artificial Sequence
<220> FEATURE:
<223> OTHER INFORMATION: fungal gene

<400> SEQUENCE: 24

```
Met Ser Pro Thr Leu His Pro Gln Ala Phe Tyr Gly Thr Leu Ile His
 1               5                  10                  15

Ser Leu Asn Pro Ser Thr Ile Glu Tyr Leu Pro Asn Thr Leu Ile Ile
             20                  25                  30

Ile Asp Gln His Gly Lys Ile Glu Gly Leu His Pro Gln Ile Pro Ala
         35                  40                  45

Ser Ser Ile Gln Ser Leu Leu Ala Thr His Asn His Thr Thr Thr Ser
     50                  55                  60
```

```
Cys Pro Thr Thr Ile Leu Ser Pro Ala Glu Phe Leu Ile Pro Gly Phe
 65                  70                  75                  80

Ile Asp Thr His Ile His Ala Pro Gln Trp Ser Gln Arg Gly Val Gly
                 85                  90                  95

Arg Gly Ile Pro Leu Leu Asn Trp Leu Glu Gly Ile Thr Phe Ala His
            100                 105                 110

Glu Ala Arg Cys Ser Asp Asp Ala Tyr Ala Arg Arg Leu Phe His Ser
        115                 120                 125

Cys Val Ser Gly Gly Leu Lys Gln Gly Val Thr Thr Ala Cys Tyr Tyr
130                 135                 140

Ser Ser Arg His Ala Ser Ala Thr Val Ile Leu Ala Glu Thr Cys Leu
145                 150                 155                 160

Ala Leu Gly Gln Arg Ala Leu Leu Gly Lys Cys Asn Met Asp Arg His
                165                 170                 175

Ala Val Asp Trp Tyr Val Asp Glu Ser Ala Ala Ser Val Ser Asp
                180                 185                 190

Thr Glu His Val Ile Arg Ala Val Arg Ala Leu Asp Ala Glu His Gly
            195                 200                 205

Leu Val Thr Pro Val Ile Thr Pro Arg Phe Ala Ile Ser Cys Ser Asp
        210                 215                 220

Gly Leu Leu Arg Ala Leu Gly Glu Leu Ala Ala Arg Ala Glu Tyr Arg
225                 230                 235                 240

Ala Leu Pro Ile Gln Thr His Phe Asn Glu Ser Arg Gln Glu Met Ala
                245                 250                 255

Phe Thr Arg Ser Leu Phe Pro Gly Val Gln Asp Glu Thr Ala Leu Tyr
            260                 265                 270

Glu Ser Phe Gly Leu Leu Asn Ser Arg Cys Val Leu Ala His Ala Ile
        275                 280                 285

Tyr Leu Ser Pro Arg Glu Met Asp Arg Val Gln Ala Leu Asp Cys Gly
290                 295                 300

Ile Ala His Cys Pro Val Pro Asn Thr Thr Met Asp Glu Phe Met Val
305                 310                 315                 320

Ala Pro Val Arg Glu Tyr Leu Ala Arg Gly Met Lys Val Gly Leu Gly
                325                 330                 335

Thr Asp Cys Gly Gly Gly Phe Ser Ser Ser Met Leu Asp Val Met Arg
            340                 345                 350

Met Ala Phe Met Val Ser Val Ala Arg Glu Thr Gln Thr Asp Gly Arg
        355                 360                 365

Asp Lys Pro Leu Ser Leu Ala Glu Gly Phe Tyr Leu Ala Thr Ala Gly
370                 375                 380

Gly Ala Arg Val Cys Gly Leu Ala Glu Lys Val Gly Arg Phe Ala Val
385                 390                 395                 400

Gly Met Glu Phe Asp Ala Val Leu Val Arg Thr Gly Asp Glu Val Asp
                405                 410                 415

Gly Val Met Thr Pro Val Glu Glu Asp Ser Leu Glu Thr Val Phe
            420                 425                 430

Glu Lys Phe Leu Met Thr Gly Asp Asp Arg Asn Met Val Arg Val Phe
        435                 440                 445

Val Lys Gly Arg Glu Val Arg Gly Leu
450                 455

<210> SEQ ID NO 25
<211> LENGTH: 2832
<212> TYPE: DNA
```

<213> ORGANISM: Artificial Sequence
<220> FEATURE:
<223> OTHER INFORMATION: fungal gene

<400> SEQUENCE: 25

| | | | | | |
|---|---|---|---|---|---|
| atgcccggtg | tcgacaagat | ggccacggcc | atttcccaac | ccacttccca | tcccccgaag | 60 |
| atgaagcgac | cgcccccgcc | ttttgtccag | accggggtca | atggagtcaa | ggctcagcaa | 120 |
| tcctcatcct | ccccgcaatc | cgcgtcgaag | cgtctcccgg | gcgccggcca | aacttcttcg | 180 |
| gctacctcga | tggctggaac | accgcaaat | ggcatcaatg | gcacgacaga | cgcgaagggt | 240 |
| cccctgaatc | gtccgaagag | ggatgcgccg | aagccagggg | aggctgctgg | ccggttacaa | 300 |
| aagctgcagt | cgcggaccac | gtccacggat | ttgggccagc | gctccagcaa | acaatgcgca | 360 |
| gaaccctatg | tgaaaacgac | aaattacatc | ctcaagaaat | actccaaatg | tcctccatcg | 420 |
| cttgtcctcc | accttcaccc | cacacatttc | cgcttcgaac | aacaagatgg | gagttttccg | 480 |
| tataactccg | aaatgaaggt | tgtcatcgaa | catcttcgcg | ccggcactgt | gcctcacgag | 540 |
| ataatagaag | agctcctgcg | tgccaacatc | cggttctatg | aaggctgtct | catcgtacgg | 600 |
| gtgattgacc | acaagtctgt | gtccgcgcag | gcgcgaaaga | cgacagcaca | ttcatccaat | 660 |
| gaaaataaca | ccccttctc | gatccacaac | tataacgaac | acataacacc | atctgcctat | 720 |
| gtcccgtatc | ctaaacagaa | tcaattaacc | tccgagaaag | acgacacgaa | ttctacagct | 780 |
| gggaatcagg | cggatgctcc | caacggcgag | caatccgcca | gcgccaagga | tcaaggcgat | 840 |
| tctggatcct | ctcaacaaaa | cgaagctcct | tcaaaaccgc | gggttttac | gactgtcctc | 900 |
| catcctactc | cccgttcact | gcaagcggaa | ctcacgttgc | ttgcaaccac | ccctgcgaga | 960 |
| acatcacctg | caaactcgac | tactcgtaca | cagggtgctt | ccatggcccc | tccgtcgccc | 1020 |
| gggggctcta | acactcaact | cgatcgaggc | catgttgcca | agaagcagaa | aatgatggtt | 1080 |
| gaacccgcgg | atttgcctga | atgtgaatca | cgactgacgc | gagccctcgc | accacctctc | 1140 |
| ttcctggatc | cggttgatag | cttcgatgct | gcacaagacc | ttctcaggca | catggaaagc | 1200 |
| cctctccata | tggatcctcc | accgtcgccg | aagagaagga | agcgcacggt | ggcagagctt | 1260 |
| gctgccgacg | aagcattggc | cgccgaggag | gagcggttca | tgcttattat | ggacgaaaga | 1320 |
| ctcgagccaa | acggacctgg | aggcgctgga | gggcctaagg | ctgcagcagt | ggacgatact | 1380 |
| ggtggaggcg | ctcccttcga | gcctcgtttc | tcgagattca | agaccctcga | aacattcga | 1440 |
| atgcaacacg | aagagaaggc | caaacgaaa | catgagatca | gctcaaaaca | ggagctggcc | 1500 |
| aagaggcagc | aacaggagca | ggagagagaa | agacgacggg | ccctggaaca | gcgacaggca | 1560 |
| gaagagcacg | ccaaggatga | agcacgaagg | cagcaccttg | ctgcgcagca | gcaagcccaa | 1620 |
| gcgcaactgg | cggcgcaaca | acagaatagg | catgtcatgg | cccaggcgaa | tggagtcagt | 1680 |
| caggcaccac | agtcatcgcc | tgtggtccgc | aatcagaccc | cgcataatac | ctcgtctcct | 1740 |
| ctggtcggca | atgctatggg | aacacaagcc | ggtgttccca | tgagcatgac | gtcttctatg | 1800 |
| cagggtgctg | gaagccctca | gaggcctcca | tcagcgctac | agcacgccca | ccccaaccct | 1860 |
| atgagccatc | cgatggcggc | atcacgaagc | caacaaggcc | cgagccgtca | tggaacgccg | 1920 |
| cagatgaccc | agggaacgcc | cgcaatgtct | catgccacgc | caataatgcg | caacgtgacc | 1980 |
| cccacccaac | gtatgagcca | cgccagccca | ggtcggtcaa | cgatggctcc | tacaccggtg | 2040 |
| atgaatcaag | ctatgatggg | aactccacag | atggctggcg | gcatgggcct | cacccctcag | 2100 |
| cagcagcaac | aaatgttgat | gcagcaaaga | cagcaactcc | tggcgcagca | aggacatctc | 2160 |
| ggtcatggcc | agcttactcc | gcaacagtac | gctcagttgc | aagcgaatgc | tcatgcacag | 2220 |

-continued

```
cagagtatcc agtcgcaccc acagcacatg atgcaagcgc aacagcagaa ccagcaacag      2280
ccaaagatac cgaatcaaca ggcctatcaa agccagatga tgcgtgcgca gctcgcgcag      2340
ttgcagatgg tccagcaaca acaacagcag cagcagcagc agcagcagca acagcaacag      2400
caacagtccc agggccagca ggctcatgta caccagggca gtccgcagat gaacccccaa      2460
cagcagatga tgatggcagc cgcccaagcc aacagcggac atccaccgca gaacatgcag      2520
ggagtaagca tggcacaagg tgctatggcg cagcgctaca ataacatgta ccaacagcgc      2580
ttgctacggt tgaggcaaga aatggcgtcc aagttgatgc cccagtacgg gcccccgggg      2640
cagtacccac cgcaccttt tgcagcaatac catgctgggc tcgaacggaa cgctaaggcc      2700
tgggtgagcg atatcatccg ccgagagcgt gaggccgcac agcaacaacg agcgaaccag      2760
gtcgctgccg tgcaagcgca agtcttgcag cagcaacagc agcagaacat gatgcagaac      2820
ggcatgggca aa                                                         2832
```

<210> SEQ ID NO 26
<211> LENGTH: 944
<212> TYPE: PRT
<213> ORGANISM: Artificial Sequence
<220> FEATURE:
<223> OTHER INFORMATION: fungal gene

<400> SEQUENCE: 26

```
Met Pro Gly Val Asp Lys Met Ala Thr Ala Ile Ser Gln Pro Thr Ser
 1               5                  10                  15

His Pro Pro Lys Met Lys Arg Pro Pro Pro Phe Val Gln Thr Gly
             20                  25                  30

Val Asn Gly Val Lys Ala Gln Gln Ser Ser Ser Pro Gln Ser Ala
         35                  40                  45

Ser Lys Arg Leu Pro Gly Ala Gly Gln Thr Ser Ser Ala Thr Ser Met
     50                  55                  60

Ala Gly Thr Thr Ala Asn Gly Ile Asn Gly Thr Thr Asp Ala Lys Gly
 65                  70                  75                  80

Pro Leu Asn Arg Pro Lys Arg Asp Ala Pro Lys Pro Gly Glu Ala Ala
                 85                  90                  95

Gly Arg Leu Gln Lys Leu Gln Ser Arg Thr Thr Ser Thr Asp Leu Gly
            100                 105                 110

Gln Arg Ser Ser Lys Gln Cys Ala Glu Pro Tyr Val Lys Thr Thr Asn
        115                 120                 125

Tyr Ile Leu Lys Lys Tyr Ser Lys Cys Pro Pro Ser Leu Val Leu His
    130                 135                 140

Leu His Pro Thr His Phe Arg Phe Glu Gln Gln Asp Gly Ser Phe Pro
145                 150                 155                 160

Tyr Asn Ser Glu Met Lys Val Val Ile Glu His Leu Arg Ala Gly Thr
                165                 170                 175

Val Pro His Glu Ile Ile Glu Glu Leu Leu Arg Ala Asn Ile Arg Phe
            180                 185                 190

Tyr Glu Gly Cys Leu Ile Val Arg Val Ile Asp His Lys Ser Val Ser
        195                 200                 205

Ala Gln Ala Arg Lys Thr Thr Ala His Ser Ser Asn Glu Asn Asn Thr
    210                 215                 220

Pro Phe Ser Ile His Asn Tyr Asn Glu His Ile Thr Pro Ser Ala Tyr
225                 230                 235                 240

Val Pro Tyr Pro Lys Gln Asn Gln Leu Thr Ser Glu Lys Asp Asp Thr
```

-continued

```
                245                 250                 255
Asn Ser Thr Ala Gly Asn Gln Ala Asp Ala Pro Asn Gly Glu Gln Ser
            260                 265                 270
Ala Ser Ala Lys Asp Gln Gly Asp Ser Gly Ser Gln Gln Asn Glu
        275                 280                 285
Ala Pro Ser Lys Pro Arg Val Phe Thr Thr Val Leu His Pro Thr Pro
        290                 295                 300
Arg Ser Leu Gln Ala Glu Leu Thr Leu Leu Ala Thr Thr Pro Ala Arg
305                 310                 315                 320
Thr Ser Pro Ala Asn Ser Thr Thr Arg Thr Gln Gly Ala Ser Met Ala
                325                 330                 335
Pro Pro Ser Pro Gly Gly Ser Asn Thr Gln Leu Asp Arg Gly His Val
            340                 345                 350
Ala Lys Lys Gln Lys Met Met Val Glu Pro Ala Asp Leu Pro Glu Cys
        355                 360                 365
Glu Ser Arg Leu Thr Arg Leu Ala Pro Pro Leu Phe Leu Asp Pro
        370                 375                 380
Val Asp Ser Phe Asp Ala Ala Gln Asp Leu Leu Arg His Met Glu Ser
385                 390                 395                 400
Pro Leu His Met Asp Pro Pro Ser Pro Lys Arg Arg Lys Arg Thr
                405                 410                 415
Val Ala Glu Leu Ala Ala Asp Glu Ala Leu Ala Ala Glu Glu Arg
            420                 425                 430
Phe Met Leu Ile Met Asp Glu Arg Leu Glu Pro Asn Gly Pro Gly Gly
            435                 440                 445
Ala Gly Gly Pro Lys Ala Ala Val Asp Asp Thr Gly Gly Gly Ala
        450                 455                 460
Pro Phe Glu Pro Arg Phe Ser Arg Phe Lys Thr Leu Glu Asn Ile Arg
465                 470                 475                 480
Met Gln His Glu Glu Lys Ala Lys Arg Glu His Glu Ile Lys Leu Lys
                485                 490                 495
Gln Glu Leu Ala Lys Arg Gln Gln Glu Gln Glu Arg Glu Arg Arg
            500                 505                 510
Arg Ala Leu Glu Gln Arg Gln Ala Glu Glu His Ala Lys Asp Glu Ala
        515                 520                 525
Arg Arg Gln His Leu Ala Ala Gln Gln Ala Gln Ala Gln Leu Ala
        530                 535                 540
Ala Gln Gln Gln Asn Arg His Val Met Ala Gln Ala Asn Gly Val Ser
545                 550                 555                 560
Gln Ala Pro Gln Ser Ser Pro Val Val Arg Asn Gln Thr Pro His Asn
                565                 570                 575
Thr Ser Ser Pro Leu Val Gly Asn Ala Met Gly Thr Gln Ala Gly Val
            580                 585                 590
Pro Met Ser Met Thr Ser Ser Met Gln Gly Ala Gly Ser Pro Gln Arg
            595                 600                 605
Pro Pro Ser Ala Leu Gln His Ala His Pro Asn Leu Met Ser His Pro
        610                 615                 620
Met Ala Ala Ser Arg Ser Gln Gln Gly Pro Ser Arg His Gly Thr Pro
625                 630                 635                 640
Gln Met Thr Gln Gly Thr Pro Ala Met Ser His Ala Thr Pro Ile Met
                645                 650                 655
Arg Asn Val Thr Pro Thr Gln Arg Met Ser His Ala Ser Pro Gly Arg
            660                 665                 670
```

```
Ser Thr Met Ala Pro Thr Pro Val Met Asn Gln Ala Met Met Gly Thr
            675                 680                 685

Pro Gln Met Ala Gly Gly Met Gly Leu Thr Pro Gln Gln Gln Gln Gln
    690                 695                 700

Met Leu Met Gln Gln Arg Gln Gln Leu Leu Ala Gln Gln Gly His Leu
705                 710                 715                 720

Gly His Gly Gln Leu Thr Pro Gln Tyr Ala Gln Leu Gln Ala Asn
                725                 730                 735

Ala His Ala Gln Gln Ser Ile Gln Ser His Pro Gln His Met Met Gln
            740                 745                 750

Ala Gln Gln Gln Asn Gln Gln Gln Pro Lys Ile Pro Asn Gln Gln Ala
            755                 760                 765

Tyr Gln Ser Gln Met Met Arg Ala Gln Leu Ala Gln Leu Gln Met Val
    770                 775                 780

Gln Gln Gln Gln Gln Gln Gln Gln Gln Gln Gln Gln Gln Gln Gln Gln
785                 790                 795                 800

Gln Gln Ser Gln Gly Gln Gln Ala His Val His Gln Gly Ser Pro Gln
            805                 810                 815

Met Asn Pro Gln Gln Met Met Met Ala Ala Gln Ala Asn Ser
            820                 825                 830

Gly His Pro Pro Gln Asn Met Gln Gly Val Ser Met Ala Gln Gly Ala
            835                 840                 845

Met Ala Gln Arg Tyr Asn Asn Met Tyr Gln Gln Arg Leu Leu Arg Leu
    850                 855                 860

Arg Gln Glu Met Ala Ser Lys Leu Met Pro Gln Tyr Gly Pro Pro Gly
865                 870                 875                 880

Gln Tyr Pro Pro His Leu Leu Gln Gln Tyr His Ala Gly Leu Glu Arg
                885                 890                 895

Asn Ala Lys Ala Trp Val Ser Asp Ile Ile Arg Arg Glu Arg Glu Ala
            900                 905                 910

Ala Gln Gln Gln Arg Ala Asn Gln Val Ala Ala Val Gln Ala Gln Val
            915                 920                 925

Leu Gln Gln Gln Gln Gln Asn Met Met Gln Asn Gly Met Gly Lys
    930                 935                 940

<210> SEQ ID NO 27
<211> LENGTH: 2043
<212> TYPE: DNA
<213> ORGANISM: Artificial Sequence
<220> FEATURE:
<223> OTHER INFORMATION: fungal gene

<400> SEQUENCE: 27
atgaactacc tacaccagcc gtaccaatat gtcgcccatc caggcatccc aatggaccag    60
cctatgtcct cgacccgac  catgggtcat ccggccatga tgcacccat  ggacggcggt   120
tatctctacc aacatccgcc gttcgacatg gtcgacttct accccatcat ggactacgag   180
gaatacgcag agaacctgtc ccgtccgata ttgaccaaag aacaagtcga gactctcgag   240
gcccaattcc aggctcatcc gaagcccagt agcaacgtca gcgccaattg gccgctcaa    300
acaaatctca gtcttccccg agtcgcgaac tggttccaaa acagacgggc caaagcgaag   360
cagcagaaac gtcaggaaga attcgagcgc atgcagaagg cgaaagcgga ggccgaggaa   420
gccgccggg  gcaaatcaga gaacgaaccc aacgcggaat ccacctcgga ctccaaacct   480
tccacagaca acaagaccga caaggtcacg cctcagcaat cttccagcac ggacacgacg   540
```

```
gaggaccaat ccaagaccgc ggcgtctgca tcgtccagtc gatccaagca caagaaaaca    600
cgcagtgagt ccgctcgcga ggccactttt gcttcgctgc aacgagcgtt gaacgccgcg    660
gttgcagctc gcgaccacaa tagccctgac aatgaacatc gtccagctgg aaatcccaac    720
gccgagggct ccatctcccc cgcaaccccc ttcctcgaca cacacactcc gggtcaccat    780
tacgccgacg tccagagtgc ccagagtgcg ctcaataccc cctatcccga gtgggatcac    840
tcgaagcatt gggctccgtc tcagagtcct gcagaatctc ttggctcaca acatactcac    900
aatgtcatgc cgagcgtaca attcccctca tcacagagtg aagaatgggc tggccaagta    960
cagccaacgg acaactcatt ccacacgatg cagtatcctg tacagccgga gatggcactt   1020
tcgaagcgag gctcatcgga agagctggca agcacgcttg aaggcatcgg catccacacc   1080
accgggtcga acggcctgtc acacctctcc acgggaccgg agcgtcccac ctggagggaa   1140
accggcaagg agctcgacct tgctgcgcgc cgtaagcgcc cacgaccggc ggcgattggt   1200
acttccagat cttcctcgat gctcgcggga tcgtcttcca tgtctcccac gacaagagtg   1260
ccgagctatg gcgccagtca cggagtgaga cagtcgaagt caacacaatg cctcaactcc   1320
aggtatgccg gtgtacgcaa ggcgtcagct gctcagcgtt caccattgaa cctgtccaac   1380
ttcgcagagg ctgggctttt ggttcgaag gcggaaatgt cgtcgatgtt gcaacccgct   1440
gtcacgacgg gtgcattggc accaccaaca cccctgacgc ctgaagatct gcatcacctg   1500
ctcccgaata ctcccaccga tggggatac tgcctgtcag cccaaccgac gagtgggttg   1560
ttccctacca cacaacccat gcagatcaac atcgcgtctc cgcccgcgac accgttgggg   1620
gttgacctga tgtcgtctta cccgtacaac aacgtcgcgc cccgatgtc tgcccctgcc   1680
cattacacgt cgttcccaga gtacgtacac tgtgactcgg caaccatgac ggggcggagc   1740
tggacagatg caacatcgat gccttctccg gaagcttcgt tccaaagtcg ctgtcccatg   1800
ccgcagcagg cggatgggtc tatgtcgtat gagcgctctg tcgacacggt ccctatctca   1860
gagtctccct ctttggtgta ttcaactagc gagggcgacc tgtcggtgca cgctgactcc   1920
aaaggcatga gttctgcat ccaggaattc cctgaacagc aagaagctca tcgattcgtt   1980
gcccagcaaa tgtcccagaa acccaaggcg tacacattca ataaccagac gcccaatgat   2040
ttc                                                                2043
```

<210> SEQ ID NO 28
<211> LENGTH: 681
<212> TYPE: PRT
<213> ORGANISM: Artificial Sequence
<220> FEATURE:
<223> OTHER INFORMATION: fungal gene

<400> SEQUENCE: 28

```
Met Asn Tyr Leu His Gln Pro Tyr Gln Tyr Val Ala His Pro Gly Ile
  1               5                  10                  15

Pro Met Asp Gln Pro Met Ser Phe Asp Pro Thr Met Gly His Pro Ala
             20                  25                  30

Met Met His Pro Met Asp Gly Gly Tyr Leu Tyr Gln His Pro Pro Phe
         35                  40                  45

Asp Met Val Asp Phe Tyr Pro Ile Met Asp Tyr Glu Glu Tyr Ala Glu
     50                  55                  60

Asn Leu Ser Arg Pro Ile Leu Thr Lys Glu Gln Val Glu Thr Leu Glu
 65                  70                  75                  80

Ala Gln Phe Gln Ala His Pro Lys Pro Ser Ser Asn Val Lys Arg Gln
```

-continued

```
                85                  90                  95
Leu Ala Ala Gln Thr Asn Leu Ser Leu Pro Arg Val Ala Asn Trp Phe
            100                 105                 110
Gln Asn Arg Arg Ala Lys Ala Lys Gln Gln Lys Arg Gln Glu Glu Phe
            115                 120                 125
Glu Arg Met Gln Lys Ala Lys Ala Glu Ala Glu Ala Ala Arg Gly
    130                 135                 140
Lys Ser Glu Asn Glu Pro Asn Ala Glu Ser Thr Ser Asp Ser Lys Pro
145                 150                 155                 160
Ser Thr Asp Asn Lys Thr Asp Lys Val Thr Pro Gln Gln Ser Ser Ser
                165                 170                 175
Thr Asp Thr Thr Glu Asp Gln Ser Lys Thr Ala Ala Ser Ala Ser Ser
            180                 185                 190
Ser Arg Ser Lys His Lys Lys Thr Arg Ser Glu Ser Ala Arg Glu Ala
    195                 200                 205
Thr Phe Ala Ser Leu Gln Arg Ala Leu Asn Ala Ala Val Ala Ala Arg
    210                 215                 220
Asp His Asn Ser Pro Asp Asn Glu His Arg Pro Ala Gly Asn Pro Asn
225                 230                 235                 240
Ala Glu Gly Ser Ile Ser Pro Ala Thr Pro Phe Leu Asp Thr His Thr
                245                 250                 255
Pro Gly His His Tyr Ala Asp Val Gln Ser Ala Gln Ser Ala Leu Asn
            260                 265                 270
Thr Pro Tyr Pro Glu Trp Asp His Ser Lys His Trp Ala Pro Ser Gln
            275                 280                 285
Ser Pro Ala Glu Ser Leu Gly Ser Gln His Thr His Asn Val Met Pro
    290                 295                 300
Ser Val Gln Phe Pro Ser Ser Gln Ser Glu Glu Trp Ala Gly Gln Val
305                 310                 315                 320
Gln Pro Thr Asp Asn Ser Phe His Thr Met Gln Tyr Pro Val Gln Pro
                325                 330                 335
Glu Met Ala Leu Ser Lys Arg Gly Ser Ser Glu Glu Leu Ala Ser Thr
            340                 345                 350
Leu Glu Gly Ile Gly Ile His Thr Thr Gly Ser Asn Gly Leu Ser His
            355                 360                 365
Leu Ser Thr Gly Pro Glu Arg Pro Thr Trp Arg Glu Thr Gly Lys Glu
    370                 375                 380
Leu Asp Leu Ala Ala Arg Arg Lys Arg Pro Arg Pro Ala Ala Ile Gly
385                 390                 395                 400
Thr Ser Arg Ser Ser Ser Met Leu Ala Gly Ser Ser Ser Met Ser Pro
                405                 410                 415
Thr Thr Arg Val Pro Ser Tyr Gly Ala Ser His Gly Val Arg Gln Ser
            420                 425                 430
Lys Ser Thr Gln Cys Leu Asn Ser Arg Tyr Ala Gly Val Arg Lys Ala
            435                 440                 445
Ser Ala Ala Gln Arg Ser Pro Leu Asn Leu Ser Asn Phe Ala Glu Ala
    450                 455                 460
Gly Ala Phe Gly Ser Lys Ala Glu Met Ser Ser Met Leu Gln Pro Ala
465                 470                 475                 480
Val Thr Thr Gly Ala Leu Ala Pro Thr Pro Leu Thr Pro Glu Asp
                485                 490                 495
Leu His His Leu Leu Pro Asn Thr Pro Thr Asp Gly Gly Tyr Cys Leu
            500                 505                 510
```

```
Ser Ala Gln Pro Thr Ser Gly Leu Phe Pro Thr Thr Gln Pro Met Gln
        515                 520                 525

Ile Asn Ile Ala Ser Pro Pro Ala Thr Pro Leu Gly Val Asp Leu Met
    530                 535                 540

Ser Ser Tyr Pro Tyr Asn Asn Val Ala Pro Pro Met Ser Ala Pro Ala
545                 550                 555                 560

His Tyr Thr Ser Phe Pro Glu Tyr Val His Cys Asp Ser Ala Thr Met
                565                 570                 575

Thr Gly Arg Ser Trp Thr Asp Ala Thr Ser Met Pro Ser Pro Glu Ala
            580                 585                 590

Ser Phe Gln Ser Arg Cys Pro Met Pro Gln Gln Ala Asp Gly Ser Met
        595                 600                 605

Ser Tyr Glu Arg Ser Val Asp Thr Val Pro Ile Ser Glu Ser Pro Ser
    610                 615                 620

Leu Val Tyr Ser Thr Ser Glu Gly Asp Leu Ser Val His Ala Asp Ser
625                 630                 635                 640

Lys Gly Met Glu Phe Cys Ile Gln Glu Phe Pro Glu Gln Gln Glu Ala
                645                 650                 655

His Arg Phe Val Ala Gln Gln Met Ser Gln Lys Pro Lys Ala Tyr Thr
            660                 665                 670

Phe Asn Asn Gln Thr Pro Asn Asp Phe
        675                 680

<210> SEQ ID NO 29
<211> LENGTH: 792
<212> TYPE: DNA
<213> ORGANISM: Artificial Sequence
<220> FEATURE:
<223> OTHER INFORMATION: fungal gene

<400> SEQUENCE: 29
atgaatcaag ctatgatggg aactccacag atggctggcg gcatgggcct cacccctcag      60
cagcagcaac aaatgttgat gcagcaaaga cagcaactcc tggcgcagca aggacatctc     120
ggtcatggcc agcttactcc gcaacagtac gctcagttgc aagcgaatgc tcatgcacag     180
cagagtatcc agtcgcaccc acagcacatg atgcaagcgc aacagcagaa ccagcaacag     240
ccaaagatac cgaatcaaca ggcctatcaa gccagatga tgcgtgcgca gctcgcgcag      300
ttgcagatgg tccagcaaca acaacagcag cagcagcagc agcagcagca acagcaacag     360
caacagtccc agggccagca ggctcatgta caccagggca gtccgcagat gaacccccaa     420
cagcagatga tgatggcagc cgcccaagcc aacagcggac atccaccgca gaacatgcag     480
ggagtaagca tggcacaagg tgctatggcg cagcgctaca ataacatgta ccaacagcgc     540
ttgctacggt tgaggcaaga aatggcgtcc aagttgatgc cccagtacgg gccccgcggg     600
cagtacccac cgcacctttt gcagcaatac catgctgggc tcgaacgaa cgctaaggcc      660 tgggtgagcg atatcatccg ccgagagcgt gaggccgcac agcaacaacg agcgaaccag     720
gtcgctgccg tgcaagcgca agtcttgcag cagcaacagc agcagaacat gatgcagaac     780
ggcatgggca aa                                                          792

<210> SEQ ID NO 30
<211> LENGTH: 264
<212> TYPE: PRT
<213> ORGANISM: Artificial Sequence
<220> FEATURE:
<223> OTHER INFORMATION: fungal gene
```

-continued

```
<400> SEQUENCE: 30

Met Asn Gln Ala Met Met Gly Thr Pro Gln Met Ala Gly Gly Met Gly
  1               5                  10                  15

Leu Thr Pro Gln Gln Gln Gln Met Leu Met Gln Gln Arg Gln Gln
             20                  25                  30

Leu Leu Ala Gln Gln Gly His Leu Gly His Gly Gln Leu Thr Pro Gln
         35                  40                  45

Gln Tyr Ala Gln Leu Gln Ala Asn Ala His Ala Gln Gln Ser Ile Gln
     50                  55                  60

Ser His Pro Gln His Met Met Gln Ala Gln Gln Gln Asn Gln Gln Gln
 65                  70                  75                  80

Pro Lys Ile Pro Asn Gln Gln Ala Tyr Gln Ser Gln Met Met Arg Ala
                 85                  90                  95

Gln Leu Ala Gln Leu Gln Met Val Gln Gln Gln Gln Gln Gln Gln Gln
            100                 105                 110

Gln Gln Gln Gln Gln Gln Gln Gln Gln Ser Gln Gly Gln Gln Ala
            115                 120                 125

His Val His Gln Gly Ser Pro Gln Met Asn Pro Gln Gln Met Met
        130                 135                 140

Met Ala Ala Gln Ala Asn Ser Gly His Pro Pro Gln Asn Met Gln
145                 150                 155                 160

Gly Val Ser Met Ala Gln Gly Ala Met Ala Gln Arg Tyr Asn Asn Met
                165                 170                 175

Tyr Gln Gln Arg Leu Leu Arg Leu Arg Gln Glu Met Ala Ser Lys Leu
            180                 185                 190

Met Pro Gln Tyr Gly Pro Pro Gly Gln Tyr Pro Pro His Leu Leu Gln
            195                 200                 205

Gln Tyr His Ala Gly Leu Glu Arg Asn Ala Lys Ala Trp Val Ser Asp
        210                 215                 220

Ile Ile Arg Arg Glu Arg Glu Ala Ala Gln Gln Arg Ala Asn Gln
225                 230                 235                 240

Val Ala Ala Val Gln Ala Gln Val Leu Gln Gln Gln Gln Gln Asn
                245                 250                 255

Met Met Gln Asn Gly Met Gly Lys
            260

<210> SEQ ID NO 31
<211> LENGTH: 1290
<212> TYPE: DNA
<213> ORGANISM: Artificial Sequence
<220> FEATURE:
<223> OTHER INFORMATION: fungal gene

<400> SEQUENCE: 31
atgccgccac cagcctctgc agtggatttc tcgaatctac tgaaccccca aggcaacgcc      60
acctcttcca ctccttcgac tcccgtggac agctccaagg cgccgtccac tcctaccagt     120
gctcagtcta acacgagtat ggcctcatcg gtgagcctcc tcccacctct catgaaagga     180
gcgcgccccg ccaacgaaga agtccgccag gatcttcctc gcccttacaa gtgccccctc     240
tgtgaccgtg ccttccaccg cttggaacac cagaccagac acatccgcac ccatacgggt     300
gaaaagccgc acgcatgcca gttccccgga tgcacgaagc gcttcagtcg ctccgatgag     360
ctgacgcgcc actcccggat ccacaacaac cccaactccc gacgcagtaa caaggcgcaa     420
catctggccg ccgctgctgc tgccgccgcc gcgggtcagg acaatgcgat ggtcggcgcc     480
```

-continued

```
ccggcagggg ccatgatgcc tcctcccagc aagcccatca cgcggtccgc ccccgtctcg      540
caggtgggat ccccggacgt gtccccgcct cattcgtact ccaactacgc cggtcacatg      600
cggtcgaact tgggaccgta tgcccggcac ggcgagcggg cgtcttcggg catggatatc      660
aacctcctcg cgaccgctgc ctcgcaagtc gagcgcgatg agcactacgg cttccacggt      720
ccccgtggtc acccgttctt tgcgccccgt catcacggcg gcaccggtcg tctcccgtcg      780
ctgtcggcct acgcgatctc gcacagcatg agtcgctcgc attcccacga ggatgacgat      840
gcttacacgc agcatcgcgt gaagcgctcc cgccccaact cccccaactc gaccgccccc      900
tcctctccca ccttctcgca cgattcgctt tctcccacgc ccgaccacac tccgctggcg      960 accccctgccc attcgccgcg gctgcggcct ctgggtgcca gtgaactgca tctgccttcg     1020
attcgccacc tgtcgctcca tcacacgccg gcgctcgcgc ccatggagcc ccagccggag     1080
ggccccaact actacagccc tgcccagggt cacgtgggtc ccagcatcag cgacatcatg     1140
tcgcggcccg acggcaccca gcgcaaactc cccgtccctc aggtgcccaa agtggccgtg     1200
caggacatgc tgaatccggc gacgggattt tcgtcggtgt cctcgtcgac gaacaactcc     1260
gtcgcgggtg gcgatctggc agaccgtttc                                      1290
```

<210> SEQ ID NO 32
<211> LENGTH: 430
<212> TYPE: PRT
<213> ORGANISM: Artificial Sequence
<220> FEATURE:
<223> OTHER INFORMATION: fungal gene

<400> SEQUENCE: 32

```
Met Pro Pro Pro Ala Ser Ala Val Asp Phe Ser Asn Leu Leu Asn Pro
  1               5                  10                  15

Gln Gly Asn Ala Thr Ser Ser Thr Pro Ser Thr Pro Val Asp Ser Ser
             20                  25                  30

Lys Ala Pro Ser Thr Pro Thr Ser Ala Gln Ser Asn Thr Ser Met Ala
         35                  40                  45

Ser Ser Val Ser Leu Leu Pro Pro Leu Met Lys Gly Ala Arg Pro Ala
     50                  55                  60

Asn Glu Glu Val Arg Gln Asp Leu Pro Arg Pro Tyr Lys Cys Pro Leu
 65                  70                  75                  80

Cys Asp Arg Ala Phe His Arg Leu Glu His Gln Thr Arg His Ile Arg
                 85                  90                  95

Thr His Thr Gly Glu Lys Pro His Ala Cys Gln Phe Pro Gly Cys Thr
            100                 105                 110

Lys Arg Phe Ser Arg Ser Asp Glu Leu Thr Arg His Ser Arg Ile His
        115                 120                 125

Asn Asn Pro Asn Ser Arg Arg Ser Asn Lys Ala Gln His Leu Ala Ala
    130                 135                 140

Ala Ala Ala Ala Ala Ala Gly Gln Asp Asn Ala Met Val Gly Ala
145                 150                 155                 160

Pro Ala Gly Ala Met Met Pro Pro Ser Lys Pro Ile Thr Arg Ser
                165                 170                 175

Ala Pro Val Ser Gln Val Gly Ser Pro Asp Val Ser Pro His Ser
            180                 185                 190

Tyr Ser Asn Tyr Ala Gly His Met Arg Ser Asn Leu Gly Pro Tyr Ala
        195                 200                 205

Arg His Gly Glu Arg Ala Ser Ser Gly Met Asp Ile Asn Leu Leu Ala
```

-continued

```
             210                 215                 220
Thr Ala Ala Ser Gln Val Glu Arg Asp Glu His Tyr Gly Phe His Gly
225                 230                 235                 240

Pro Arg Gly His Pro Phe Phe Ala Pro Arg His His Gly Gly Thr Gly
                245                 250                 255

Arg Leu Pro Ser Leu Ser Ala Tyr Ala Ile Ser His Ser Met Ser Arg
                260                 265                 270

Ser His Ser His Glu Asp Asp Ala Tyr Thr Gln His Arg Val Lys
            275                 280                 285

Arg Ser Arg Pro Asn Ser Pro Asn Ser Thr Ala Pro Ser Ser Pro Thr
290                 295                 300

Phe Ser His Asp Ser Leu Ser Pro Thr Pro Asp His Thr Pro Leu Ala
305                 310                 315                 320

Thr Pro Ala His Ser Pro Arg Leu Arg Pro Leu Gly Ala Ser Glu Leu
                325                 330                 335

His Leu Pro Ser Ile Arg His Leu Ser Leu His His Thr Pro Ala Leu
                340                 345                 350

Ala Pro Met Glu Pro Gln Pro Glu Gly Pro Asn Tyr Tyr Ser Pro Ala
                355                 360                 365

Gln Gly His Val Gly Pro Ser Ile Ser Asp Ile Met Ser Arg Pro Asp
370                 375                 380

Gly Thr Gln Arg Lys Leu Pro Val Pro Gln Val Pro Lys Val Ala Val
385                 390                 395                 400

Gln Asp Met Leu Asn Pro Ala Thr Gly Phe Ser Ser Val Ser Ser Ser
                405                 410                 415

Thr Asn Asn Ser Val Ala Gly Gly Asp Leu Ala Asp Arg Phe
                420                 425                 430
```

<210> SEQ ID NO 33
<211> LENGTH: 3645
<212> TYPE: DNA
<213> ORGANISM: Artificial Sequence
<220> FEATURE:
<223> OTHER INFORMATION: fungal gene

<400> SEQUENCE: 33

```
atgaatcccg caaacttcaa cgtgggcggc tccatgcccg ccgcgcccac cccccagatg      60
ccgagactcg acaataacca ggtcatgatg aactatgtcg cccaggcttt acatgcacaa     120
ggcacctata ccggttggcg cgccgaagtg cccatgaaag agcgcgtggt tcgagtgtat     180
caaatgttca cctcccttcg ccttatccaa ccccaagcag atctgcaaca cctggcccaa     240
gctgccctca gctttgagca gaaggccttc aaagacgctc agcagaaagt cgattacgac     300
aaagaatgta acgacaaatt attgcatatt cgagatactc gagcgagaca ggccgccgtc     360
atgcagaatg gcatgattcc cccgggcgct cccaaagccg gcggcatgcg tggcgtcgga     420
caaccctcct tcccgcaaca gatgaatcga gccatgcaat ccaatcccat ggccggtcaa     480
caagccatgg ccatggggat gaccgatccg aatcaacagg ccgccatgcc gcagcgatcg     540
caacagcagc aagccatgat gcagcagcag cagcaacaac agcaacaaca gcaacagcag     600
cagcagcagc agcagccacg cgctcaacaa cgctccgcca ataccctcgc cctggtcgac     660
gagctgaata acctgactcc gcaagagtac gagaacgtca atcgcgtcgc tcaccagatc     720
atgaccaaga cctcgccggt ggatgcggag aaaatcaaac gcaacctgca gaacatgaat     780
cctgtacaac gccggtacct gactgaaaga acatcgacc cggtcgcgta tttctttcgc     840
```

```
tcgcaggccc tcgcccacct caagcggcag atgaaggccc gtgtggacat gtctcacccc    900
cagaataccg gcgtcgaccc gaacaatgtg atgatgggcg ccgatccgac gatgaacccc    960
cagatgttcc cgaacatgat gaacctacag cgcaattcgg ccttcgccat gggcaaccag   1020
ccaaacatgg accccctcttc cttcattggc aacgtggaga acatccaagg acagcaggcg   1080
gatggcctcc gttcgcagga agctggtcag ctggtcgtcc ccgcgagctc ctcccagatg   1140
aaccaacaac cgttcaacaa cgcccagaac accttcccga tgggccaaca gctcgcgcag   1200
ggaggacagg ctaatctggg cgctgccggc atcaaccccc agatgttcgc caacaacac    1260
atgcaaaaca ccccgaatat gccgccggat cggcccccagc cggccgcccc tttccagccc   1320
cagactcaag cacagaacca ggctcaggcc caggcccgcg cccaggcagc tcaaaaagcc   1380
cagatggcga tttcccaggc cggccaagct aattcgcacc tgcaacagcc catgccgcag   1440
caaagccctg ccatgcccat gttgaaccga cccatgcctc cgggccagat gtctcccgcg   1500
cagatggcag cgcaagtccg tcctccgtcg cgggcacccg ccatgggcca gcagccttcc   1560
atgggaggcc agcagcctat gcagggtcga ccgcaaatcc ccccgggtct cccccccggcc  1620
attcaagaac aactggcgca aatgtctcca gagcagctga accgggtctt ggcccagcgg   1680
cgcgccatgg cgaataatcc ggccctggcg agagccaacg cggcccggca atccgtgccc   1740
atgcagcaga gcgtgtccca gtccgcgcag gcccagtcga tggcgaacaa ccagaacatg   1800
cgagcgatga atgtacaagc gcagctagct gggatgggcg gggcgcaaca aatgatgcct   1860
ggtcaacaaa tgtccctcca acagcagcag cagcaacagc agcagcagca gcgtcaagag   1920
ctatataaga tgcagctact ccaacagtca ggcggtaatc tagagctctc gaatgagcaa   1980
agcaaggaga tggaccggtt acacttccca ccctcactcc tgggaaataa cccgaacata   2040
gtttcgctgg tgcccaagaa tatcaagacg tggggtcagc tcaaacagtg ggccgcgaca   2100
aatccacaac tcccaggagg gctgaatctg cagaagttga tggccctcca gaaattccac   2160
tttacgcaaa tactcaacca gagcaaagaa cgcagtcgca acccagacca ggcggggcag   2220
ggtccctgga tgtcgggccc gacacaagcc cccagcaac cgccgatgat gaaccctcag    2280
cagtttccgc cggggcaaca gcaagctgcg atcaacatgg ctgcgatccg tcccgtcacc   2340
gcacaagaca tccaagcggc tcgtcagcgg caccccggcca tggcacaaaa cttcacggat   2400
gaccaaattc gggaaagcct caacaaagcc cgacaacggc agttgatgct cttggctcag   2460
caacgcgcgg ctcaagcgca ggagttggcc gcccaacaac agcaaaccca ggcacttcag   2520
cagacccccg tgggcggacc agctcctggc ccccatctcc gcccagaggg ccctgggcag   2580
cccgcaacgc aaccgcagca acaaagcccg gcgacaaagg ccccctcgac cgtaccagga   2640
aagaaggccc ctccggcgaa gcaacaaccc gcgaagagga gttgccgag cgacgagacc    2700
gcagacgcgc aaaatcccga caatcaagtg gcgcagaagc ccactcaagc tggtgccccg   2760
caaggggtgg cggctcctgc accctccaag cccaatatgc cattcaccag agagcagttg   2820
gccgccatga cgccgcagca acgtgctcag attgaagcac atatgcgacg ccagcaaggc   2880
cagactcgta ccaaggctgc agccgaagag gcttggaaca atctgccgga gaagatccgt   2940
caagcttatc atgataccttt gaaacaagcg ccccccgatga aattcgcagc catcacgccc   3000
gagcagcatg cggccatgaa ccagcaactt cgggactgta ctgatatgct gggccggatg   3060
gataccctgg tccagtggtt tgcaaaaatc cccggccaag agaagaatgt gcgcagtttg   3120
ctggcaatgc gaatccaatt gatgaggcag ttcaagaata gtccggactg ggttcttaac   3180
gacagcctga ccatctctcc cgaaaattta accgccacca taaattatat taagaagctc   3240
```

-continued

```
ttccatgcga tgatcacccg cgtcagtcag catcaaaatc aagctcctgg acaacgaccc    3300
ggcggtcccc agccacccct tgacacaagca agccaaaacg ccatgccagc cctgaatgcc    3360
acgaacctgc aacagctcca gcaacaagag gaagctctcc aacgggcgcg gcgagcgtcg    3420
agccagaccg ccgtgtctgc aacatcggct gtcccacccg ccccatttgg cgcgccgtcc    3480
cctcagggcg ttcctcatgc gtacgggccg ggaagcatgc cgccggagca gttgaagttg    3540
cctccgccga agaagagaaa gcagtcccat ccagggggcta cccccaccgt cggcacgcct    3600
gctaccaagc cgccaaccac ccggcccgcc gacgtcaaaa tgccc                    3645
```

<210> SEQ ID NO 34
<211> LENGTH: 1215
<212> TYPE: PRT
<213> ORGANISM: Artificial Sequence
<220> FEATURE:
<223> OTHER INFORMATION: fungal gene

<400> SEQUENCE: 34

```
Met Asn Pro Ala Asn Phe Asn Val Gly Gly Ser Met Pro Ala Ala Pro
  1               5                  10                  15

Thr Pro Gln Met Pro Arg Leu Asp Asn Asn Gln Val Met Met Asn Tyr
             20                  25                  30

Val Ala Gln Ala Leu His Ala Gln Gly Thr Tyr Thr Gly Trp Arg Ala
         35                  40                  45

Glu Val Pro Met Lys Glu Arg Val Val Arg Val Tyr Gln Met Phe Thr
     50                  55                  60

Ser Leu Arg Leu Ile Gln Pro Gln Ala Asp Leu Gln His Leu Ala Gln
 65                  70                  75                  80

Ala Ala Leu Ser Phe Glu Gln Lys Ala Phe Lys Asp Ala Gln Gln Lys
                 85                  90                  95

Val Asp Tyr Asp Lys Glu Cys Asn Asp Lys Leu Leu His Ile Arg Asp
            100                 105                 110

Thr Arg Ala Arg Gln Ala Ala Val Met Gln Asn Gly Met Ile Pro Pro
        115                 120                 125

Gly Ala Pro Lys Ala Gly Gly Met Arg Gly Val Gly Gln Pro Ser Phe
    130                 135                 140

Pro Gln Gln Met Asn Arg Ala Met Gln Ser Asn Pro Met Ala Gly Gln
145                 150                 155                 160

Gln Ala Met Ala Met Gly Met Thr Asp Pro Asn Gln Gln Ala Ala Met
                165                 170                 175

Pro Gln Arg Ser Gln Gln Gln Ala Met Met Gln Gln Gln Gln
            180                 185                 190

Gln Gln Gln Gln Gln Gln Gln Gln Gln Gln Gln Pro Arg Ala
        195                 200                 205

Gln Gln Arg Ser Ala Asn Thr Leu Ala Leu Val Asp Glu Leu Asn Asn
    210                 215                 220

Leu Thr Pro Gln Glu Tyr Glu Asn Val Asn Arg Val Ala His Gln Ile
225                 230                 235                 240

Met Thr Lys Thr Ser Pro Val Asp Ala Glu Lys Ile Lys Arg Asn Leu
                245                 250                 255

Gln Asn Met Asn Pro Val Gln Arg Arg Tyr Leu Thr Glu Arg Asn Ile
            260                 265                 270

Asp Pro Val Ala Tyr Phe Phe Arg Ser Gln Ala Leu Ala His Leu Lys
        275                 280                 285
```

-continued

```
Arg Gln Met Lys Ala Arg Val Asp Met Ser His Pro Gln Asn Thr Gly
    290                 295                 300

Val Asp Pro Asn Asn Val Met Met Gly Ala Asp Pro Thr Met Asn Pro
305                 310                 315                 320

Gln Met Phe Pro Asn Met Met Asn Leu Gln Arg Asn Ser Ala Phe Ala
                325                 330                 335

Met Gly Asn Gln Pro Asn Met Asp Pro Ser Ser Phe Ile Gly Asn Val
                340                 345                 350

Glu Asn Ile Gln Gly Gln Gln Ala Asp Gly Leu Arg Ser Gln Glu Ala
            355                 360                 365

Gly Gln Leu Val Val Pro Ala Ser Ser Ser Gln Met Asn Gln Gln Pro
    370                 375                 380

Phe Asn Asn Ala Gln Asn Thr Phe Pro Met Gly Gln Gln Leu Ala Gln
385                 390                 395                 400

Gly Gly Gln Ala Asn Leu Gly Ala Ala Gly Ile Asn Pro Gln Met Phe
                405                 410                 415

Ala Gln Gln His Met Gln Asn Thr Pro Asn Met Pro Pro Asp Arg Pro
                420                 425                 430

Gln Pro Ala Ala Pro Phe Gln Pro Gln Thr Gln Ala Gln Asn Gln Ala
            435                 440                 445

Gln Ala Gln Ala Arg Ala Gln Ala Ala Gln Lys Ala Gln Met Ala Ile
    450                 455                 460

Ser Gln Ala Gly Gln Ala Asn Ser His Leu Gln Gln Pro Met Pro Gln
465                 470                 475                 480

Gln Ser Pro Ala Met Pro Met Leu Asn Arg Pro Met Pro Pro Gly Gln
                485                 490                 495

Met Ser Pro Ala Gln Met Ala Ala Gln Val Arg Pro Pro Ser Arg Ala
                500                 505                 510

Pro Ala Met Gly Gln Gln Pro Ser Met Gly Gly Gln Gln Pro Met Gln
            515                 520                 525

Gly Arg Pro Gln Ile Pro Pro Gly Leu Pro Pro Ala Ile Gln Glu Gln
    530                 535                 540

Leu Ala Gln Met Ser Pro Glu Gln Leu Asn Arg Val Leu Ala Gln Arg
545                 550                 555                 560

Arg Ala Met Ala Asn Asn Pro Ala Leu Ala Arg Ala Asn Ala Ala Arg
                565                 570                 575

Gln Ser Val Pro Met Gln Gln Ser Val Ser Gln Ser Ala Gln Ala Gln
            580                 585                 590

Ser Met Ala Asn Asn Gln Asn Met Arg Ala Met Asn Val Gln Ala Gln
    595                 600                 605

Leu Ala Gly Met Gly Gly Ala Gln Gln Met Met Pro Gly Gln Gln Met
    610                 615                 620

Ser Leu Gln Gln Gln Gln Gln Gln Gln Gln Gln Gln Arg Gln Glu
625                 630                 635                 640

Leu Tyr Lys Met Gln Leu Leu Gln Gln Ser Gly Gly Asn Leu Glu Leu
                645                 650                 655

Ser Asn Glu Gln Ser Lys Glu Met Asp Arg Leu His Phe Pro Pro Ser
                660                 665                 670

Leu Leu Gly Asn Asn Pro Asn Ile Val Ser Leu Val Pro Lys Asn Ile
            675                 680                 685

Lys Thr Trp Gly Gln Leu Lys Gln Trp Ala Ala Thr Asn Pro Gln Leu
    690                 695                 700

Pro Gly Gly Leu Asn Leu Gln Lys Leu Met Ala Leu Gln Lys Phe His
```

-continued

```
         705                 710                 715                 720
    Phe Thr Gln Ile Leu Asn Gln Ser Lys Glu Arg Ser Arg Asn Pro Asp
                    725                 730                 735
    Gln Ala Gly Gln Gly Pro Trp Met Ser Gly Pro Thr Gln Ala Pro Gln
                    740                 745                 750
    Gln Pro Pro Met Met Asn Pro Gln Gln Phe Pro Pro Gly Gln Gln Gln
                    755                 760                 765
    Ala Ala Ile Asn Met Ala Ala Ile Arg Pro Val Thr Ala Gln Asp Ile
                    770                 775                 780
    Gln Ala Ala Arg Gln Arg His Pro Ala Met Ala Gln Asn Phe Thr Asp
    785                 790                 795                 800
    Asp Gln Ile Arg Glu Ser Leu Asn Lys Ala Arg Gln Arg Gln Leu Met
                    805                 810                 815
    Leu Leu Ala Gln Gln Arg Ala Ala Gln Ala Gln Glu Leu Ala Ala Gln
                    820                 825                 830
    Gln Gln Gln Thr Gln Ala Leu Gln Gln Thr Pro Val Gly Gly Pro Ala
                    835                 840                 845
    Pro Gly Pro His Leu Arg Pro Glu Gly Pro Gly Gln Pro Ala Thr Gln
                    850                 855                 860
    Pro Gln Gln Gln Ser Pro Ala Thr Lys Ala Pro Ser Thr Val Pro Gly
    865                 870                 875                 880
    Lys Lys Ala Pro Pro Ala Lys Gln Gln Pro Ala Lys Arg Lys Leu Pro
                    885                 890                 895
    Ser Asp Glu Thr Ala Asp Ala Gln Asn Pro Asp Asn Gln Val Ala Gln
                    900                 905                 910
    Lys Pro Thr Gln Ala Gly Ala Pro Gln Gly Val Ala Ala Pro Ala Pro
                    915                 920                 925
    Ser Lys Pro Asn Met Pro Phe Thr Arg Glu Gln Leu Ala Ala Met Thr
                    930                 935                 940
    Pro Gln Gln Arg Ala Gln Ile Glu Ala His Met Arg Arg Gln Gln Gly
    945                 950                 955                 960
    Gln Thr Arg Thr Lys Ala Ala Ala Glu Glu Ala Trp Asn Asn Leu Pro
                    965                 970                 975
    Glu Lys Ile Arg Gln Ala Tyr His Asp Thr Leu Lys Gln Ala Pro Pro
                    980                 985                 990
    Met Lys Phe Ala Ala Ile Thr Pro Glu Gln His Ala Ala Met Asn Gln
                    995                 1000                1005
    Gln Leu Arg Asp Cys Thr Asp Met Leu Gly Arg Met Asp Thr Leu Val
                    1010                1015                1020
    Gln Trp Phe Ala Lys Ile Pro Gly Gln Glu Lys Asn Val Arg Ser Leu
    1025                1030                1035                1040
    Leu Ala Met Arg Ile Gln Leu Met Arg Gln Phe Lys Asn Ser Pro Asp
                    1045                1050                1055
    Trp Val Leu Asn Asp Ser Leu Thr Ile Ser Pro Glu Asn Leu Thr Ala
                    1060                1065                1070
    Thr Ile Asn Tyr Ile Lys Lys Leu Phe His Ala Met Ile Thr Arg Val
                    1075                1080                1085
    Ser Gln His Gln Asn Gln Ala Pro Gly Gln Arg Pro Gly Gly Pro Gln
                    1090                1095                1100
    Pro Pro Leu Thr Gln Ala Ser Gln Asn Ala Met Pro Ala Leu Asn Ala
    1105                1110                1115                1120
    Thr Asn Leu Gln Gln Leu Gln Gln Gln Glu Glu Ala Leu Gln Arg Ala
                    1125                1130                1135
```

Arg Arg Ala Ser Ser Gln Thr Ala Val Ser Ala Thr Ser Ala Val Pro
            1140                1145                1150

Pro Ala Pro Phe Gly Ala Pro Ser Pro Gln Gly Val Pro His Ala Tyr
        1155                1160                1165

Gly Pro Gly Ser Met Pro Pro Glu Gln Leu Lys Leu Pro Pro Pro Lys
    1170                1175                1180

Lys Arg Lys Gln Ser His Pro Gly Ala Thr Pro Thr Val Gly Thr Pro
1185                1190                1195                1200

Ala Thr Lys Pro Pro Thr Thr Arg Pro Ala Asp Val Lys Met Pro
            1205                1210                1215

<210> SEQ ID NO 35
<211> LENGTH: 1146
<212> TYPE: DNA
<213> ORGANISM: Artificial Sequence
<220> FEATURE:
<223> OTHER INFORMATION: fungal gene

<400> SEQUENCE: 35

| | |
|---|---|
| atgctcctac agttcgacgg ccggtctcca tatggctgcg tggagtgtca tccccagctg | 60 |
| atccagtgtg tcgacaagcc gtctcgttgc ccgtgccttt gcggcgccag catgacctgc | 120 |
| gactacatgg cgaccacccc agcgaactgg tccacgacta ccgagtccgc gtcttcaccg | 180 |
| gcgatgacct ccattgcgga ccccatgaac cacccgctcg cccacttcgc gcctgcgggg | 240 |
| gagctgaacc acaccgagct cgagctgatg gtgcaatggt gcaccgacac ctaccgttcc | 300 |
| gtcgcgcacc agcccagcgt cgaatggatc tggcatgccg ccgtgcctcg ggaggccttg | 360 |
| caacggcccct ttctcctcca cggcatcctg gccgtctccg ccctgcacct cttcttccgc | 420 |
| accaccggcg acacgcaggc acactacttg cgtaccgccc acgcccatcg acaacacgcc | 480 |
| gaggaaggcc tctcccaagc gctccgcgca ctggacgcct ccaactgcaa cgccgcgttc | 540 |
| gccgtctgca gcatgctcac cgtcttctcc tttgccctgc cgctggccgc cgccgcacc | 600 |
| ccgacagccg cacacagtcc gctggacgag ctgtgtcaca tcatgcggca cacgcaccag | 660 |
| tccatgagct ccctgtgcga gatcgtctac tgggtcggcc gcggcgacct ccacgcgctc | 720 |
| atcgagtgcg acgaaaccgc accccggatg ccggacacgt cgcggctcgc catcatggcg | 780 |
| ttggcgcgcc tgaacgatac cctggcgacg caatccccgc agcacgagaa gcgcgtattc | 840 |
| gaccgcgccc tcgacgccct gggccactca ctcgaccagc tcgcccgcgg cggcgagctt | 900 |
| ctcctctcgg ccttccggtg gattgtgcag atcccaccgc ggttcatcga gctcctccac | 960 |
| gagcggcatc cgtttgcgct ggtgatcctg cgcactatg cggtcgtcct gcatctgctg | 1020 |
| cgggagcgtt ggtgggtggg tgactgggc gcacgggtga ttcaagcggt gggacggagt | 1080 |
| ttagaatggg agtggagaaa ggccctggga tgggtgttgg atgcgacggg atgtattctg | 1140 |
| ccgcaa | 1146 |

<210> SEQ ID NO 36
<211> LENGTH: 382
<212> TYPE: PRT
<213> ORGANISM: Artificial Sequence
<220> FEATURE:
<223> OTHER INFORMATION: fungal gene

<400> SEQUENCE: 36

Met Leu Leu Gln Phe Asp Gly Arg Ser Pro Tyr Gly Cys Val Glu Cys
1               5                   10                  15

-continued

```
His Pro Gln Leu Ile Gln Cys Val Asp Lys Pro Ser Arg Cys Pro Cys
             20                  25                  30

Leu Cys Gly Ala Ser Met Thr Cys Asp Tyr Met Ala Thr Pro Ala
         35                  40                  45

Asn Trp Ser Thr Thr Glu Ser Ala Ser Pro Ala Met Thr Ser
 50                  55                  60

Ile Ala Asp Pro Met Asn His Pro Leu Ala His Phe Ala Pro Ala Gly
 65                  70                  75                  80

Glu Leu Asn His Thr Glu Leu Glu Leu Met Val Gln Trp Cys Thr Asp
                 85                  90                  95

Thr Tyr Arg Ser Val Ala His Gln Pro Ser Val Glu Trp Ile Trp His
            100                 105                 110

Ala Ala Val Pro Arg Glu Ala Leu Gln Arg Pro Phe Leu Leu His Gly
            115                 120                 125

Ile Leu Ala Val Ser Ala Leu His Leu Phe Phe Arg Thr Thr Gly Asp
130                 135                 140

Thr Gln Ala His Tyr Leu Arg Thr Ala His Ala His Arg Gln His Ala
145                 150                 155                 160

Glu Glu Gly Leu Ser Gln Ala Leu Arg Ala Leu Asp Ala Ser Asn Cys
                165                 170                 175

Asn Ala Ala Phe Ala Val Cys Ser Met Leu Thr Val Phe Ser Phe Ala
            180                 185                 190

Leu Pro Leu Ala Ala Arg Arg Thr Pro Thr Ala Ala His Ser Pro Leu
            195                 200                 205

Asp Glu Leu Cys His Ile Met Arg His Thr His Gln Ser Met Ser Ser
            210                 215                 220

Leu Cys Glu Ile Val Tyr Trp Val Gly Arg Gly Asp Leu His Ala Leu
225                 230                 235                 240

Ile Glu Cys Asp Glu Thr Ala Pro Arg Met Pro Asp Thr Ser Arg Leu
                245                 250                 255

Ala Ile Met Ala Leu Ala Arg Leu Asn Asp Thr Leu Ala Thr Gln Ser
            260                 265                 270

Pro Gln His Glu Lys Arg Val Phe Asp Arg Ala Leu Asp Ala Leu Gly
            275                 280                 285

His Ser Leu Asp Gln Leu Ala Arg Gly Gly Glu Leu Leu Ser Ala
            290                 295                 300

Phe Arg Trp Ile Val Gln Ile Pro Pro Arg Phe Ile Glu Leu Leu His
305                 310                 315                 320

Glu Arg His Pro Phe Ala Leu Val Ile Leu Ala His Tyr Ala Val Val
                325                 330                 335

Leu His Leu Leu Arg Glu Arg Trp Trp Val Gly Asp Trp Gly Ala Arg
            340                 345                 350

Val Ile Gln Ala Val Gly Arg Ser Leu Glu Trp Glu Trp Arg Lys Ala
            355                 360                 365

Leu Gly Trp Val Leu Asp Ala Thr Gly Cys Ile Leu Pro Gln
370                 375                 380
```

<210> SEQ ID NO 37
<211> LENGTH: 540
<212> TYPE: DNA
<213> ORGANISM: Artificial Sequence
<220> FEATURE:
<223> OTHER INFORMATION: fungal gene

<400> SEQUENCE: 37

```
atgtccggct acaacaacca gtacaaccag ggctacggct acaaccaggg tggttatccc    60
ccgcagggtg gttactccca gggtggctat ggtcagtccc aggtggtag cgccaacgat    120 tactacggcg gacagcagcc tcagcatcac cagcagcacg gatacaacca gtatgaccag   180
agccagcagg gttatggtca gcagcagcag tatggtcagc agcaatacgg tcagcaaggt   240
catgatcaac aggctcccgg tgaagcccag gagggcgagc gtggactgat gggcgctctg   300
gccggtggtg cagcgggtgg tttcgccggt cacaaggcca ccacggcttc ctcggaacc   360 atcggcggtg ccatcatggg aagcatcgcg gaagatgcca tcaagaagca caagaacaag   420
aacgagggtc cccccgagta cggcagcaac tatggcggca gccagtatgg cggccctcct   480
ccctcccacg gaggctctaa caacggcatg atggaccagc tgggcagctt cttcaagaaa   540
```

```
<210> SEQ ID NO 38
<211> LENGTH: 180
<212> TYPE: PRT
<213> ORGANISM: Artificial Sequence
<220> FEATURE:
<223> OTHER INFORMATION: fungal gene

<400> SEQUENCE: 38

Met Ser Gly Tyr Asn Asn Gln Tyr Asn Gln Gly Tyr Gly Tyr Asn Gln
 1               5                  10                  15
Gly Gly Tyr Pro Pro Gln Gly Gly Tyr Ser Gln Gly Tyr Gly Gln
            20                  25                  30
Ser Gln Gly Gly Ser Ala Asn Asp Tyr Tyr Gly Gly Gln Gln Pro Gln
        35                  40                  45
His His Gln Gln His Gly Tyr Asn Gln Tyr Asp Gln Ser Gln Gln Gly
    50                  55                  60
Tyr Gly Gln Gln Gln Gln Tyr Gly Gln Gln Tyr Gly Gln Gln Gly
65                  70                  75                  80
His Asp Gln Gln Ala Pro Gly Glu Ala Gln Glu Gly Glu Arg Gly Leu
                85                  90                  95
Met Gly Ala Leu Ala Gly Gly Ala Ala Gly Gly Phe Ala Gly His Lys
            100                 105                 110
Ala Asn His Gly Phe Leu Gly Thr Ile Gly Gly Ala Ile Met Gly Ser
        115                 120                 125
Ile Ala Glu Asp Ala Ile Lys Lys His Lys Asn Lys Asn Glu Gly Pro
    130                 135                 140
Pro Glu Tyr Gly Ser Asn Tyr Gly Gly Ser Gln Tyr Gly Gly Pro Pro
145                 150                 155                 160
Pro Ser His Gly Gly Ser Asn Asn Gly Met Met Asp Gln Leu Gly Ser
                165                 170                 175
Phe Phe Lys Lys
            180
```

```
<210> SEQ ID NO 39
<211> LENGTH: 1191
<212> TYPE: DNA
<213> ORGANISM: Artificial Sequence
<220> FEATURE:
<223> OTHER INFORMATION: fungal gene

<400> SEQUENCE: 39
atgttcgcag aatcccaacc ccccagcagc ggtggcgaca cccccaagct ccgggcggct    60
tgtgagaact gccgtcagtc gaaagtgaaa tgcaacctgg agggaagaa cacctgcatc   120 cgctgtcttc gccatggcct tccttgtcga taccgggtcg ccaaccgatc cggcaagccg   180
```

```
aagggagca agaaccgagc tacgctgcga aagctgggcc agctccagga cgagaagccg      240
gtgcagggct cgcacagcgc gcgggagccg aagaaggccg tggagccggt gtgtccgccg      300
gagtatgagg tcgaccgcag attcgagtac cagacaagcg agccgagtca gccgcggctg      360
tctgagagtc cacatatgca cgactcccac ccgacaatcg acgcctgcat gctagtgaat      420
gagacgccca tcgactacac ggctacctat ggcggcccgt tctcccccgc catgccgatg      480
tgcacgccgg cgtcgatgtc gccgacatcg cccaccttcc tgcaaaagga gttcatcacg      540
aaaggcctga ccagcttccc gctggccgtg cacgtccccg cgccttaccg ccgcgctgc       600 gagtgcgacg aggcgctcgg cttccacttg aacggactgc gacatatggt ggtcgacccg      660
gcgcggctgc gcttcgacca gggcctgcag gcgatcaaga cggcgctcgc cgtatgtcag      720
gggttcctgc ggtgcgcgcg ctgtccaaag gcaacacga acttcctggt ctcgctgtcg       780
acgctggacc tcgtgctgca gctcttcgac ttctgggtga gttgcgagtt cgcagcccac      840
ggccacggcc acgggccgcc ggcgtcgtcg ctggaggccg agcccatggc ttacggcgag      900
tacgagacag cgcccgagga ggcgcggcac atgcggcggg tggtgctgcg cgggcgcctg      960
ctgcagtgca aggaggtgct gggcctgctg cacgaggccg tggagctggc cgagggccag     1020
ggcctgagca gtagcagcag cagtagcgag gcgctggacg ggagctggct gcagcagatc     1080
atccgcgggt atgcgagcgc gacggagtcc ctcctccagc cgctggggtg tatttgcgga     1140
ggcagcgcgg tgcaactagc gcatagaccg agtaccgggt tagataggct g             1191
```

<210> SEQ ID NO 40
<211> LENGTH: 397
<212> TYPE: PRT
<213> ORGANISM: Artificial Sequence
<220> FEATURE:
<223> OTHER INFORMATION: fungal gene

<400> SEQUENCE: 40

```
Met Phe Ala Glu Ser Gln Pro Ser Ser Gly Gly Asp Thr Pro Lys
  1               5                  10                  15

Leu Arg Ala Ala Cys Glu Asn Cys Arg Gln Ser Lys Val Lys Cys Asn
                 20                  25                  30

Leu Gly Gly Lys Asn Thr Cys Ile Arg Cys Leu Arg His Gly Leu Pro
         35                  40                  45

Cys Arg Tyr Arg Val Ala Asn Arg Ser Gly Lys Pro Lys Gly Ser Lys
     50                  55                  60

Asn Arg Ala Thr Leu Arg Lys Leu Gly Gln Leu Gln Asp Glu Lys Pro
 65                  70                  75                  80

Val Gln Gly Ser His Ser Ala Arg Glu Pro Lys Lys Ala Val Glu Pro
                 85                  90                  95

Val Cys Pro Pro Glu Tyr Glu Val Asp Arg Arg Phe Glu Tyr Gln Thr
                100                 105                 110

Ser Glu Pro Ser Gln Pro Arg Leu Ser Glu Ser Pro His Met His Asp
            115                 120                 125

Ser His Pro Thr Ile Asp Ala Cys Met Leu Val Asn Glu Thr Pro Ile
        130                 135                 140

Asp Tyr Thr Ala Thr Tyr Gly Gly Pro Phe Ser Pro Ala Met Pro Met
145                 150                 155                 160

Cys Thr Pro Ala Ser Met Ser Pro Thr Ser Pro Thr Phe Leu Gln Lys
                165                 170                 175

Glu Phe Ile Thr Lys Gly Leu Thr Ser Phe Pro Leu Ala Val His Val
```

```
                      180                 185                 190
Pro Gly Ala Leu Pro Pro Arg Cys Glu Cys Asp Glu Ala Leu Gly Phe
        195                 200                 205

His Leu Asn Gly Leu Arg His Met Val Val Asp Pro Ala Arg Leu Arg
    210                 215                 220

Phe Asp Gln Gly Leu Gln Ala Ile Lys Thr Ala Leu Ala Val Cys Gln
225                 230                 235                 240

Gly Phe Leu Arg Cys Ala Arg Cys Pro Lys Gly Asn Thr Asn Phe Leu
                245                 250                 255

Val Ser Leu Ser Thr Leu Asp Leu Val Leu Gln Leu Phe Asp Phe Trp
            260                 265                 270

Val Ser Cys Glu Phe Ala Ala His Gly His Gly His Gly Pro Pro Ala
        275                 280                 285

Ser Ser Leu Glu Ala Glu Pro Met Ala Tyr Gly Glu Tyr Glu Thr Ala
    290                 295                 300

Pro Glu Glu Ala Arg His Met Arg Arg Val Val Leu Arg Gly Arg Leu
305                 310                 315                 320

Leu Gln Cys Lys Glu Val Leu Gly Leu Leu His Glu Ala Val Glu Leu
                325                 330                 335

Ala Glu Gly Gln Gly Leu Ser Ser Ser Ser Ser Ser Glu Ala Leu
            340                 345                 350

Asp Gly Ser Trp Leu Gln Gln Ile Ile Arg Gly Tyr Ala Ser Ala Thr
        355                 360                 365

Glu Ser Leu Leu Gln Pro Leu Gly Cys Ile Cys Gly Gly Ser Ala Val
    370                 375                 380

Gln Leu Ala His Arg Pro Ser Thr Gly Leu Asp Arg Leu
385                 390                 395

<210> SEQ ID NO 41
<211> LENGTH: 1155
<212> TYPE: DNA
<213> ORGANISM: Artificial Sequence
<220> FEATURE:
<223> OTHER INFORMATION: fungal gene

<400> SEQUENCE: 41
atggacgata cccaccccgc cgccgccacc gccgccgttg ccctggccca attacaccac      60
aatcgcttgg tctccgactg ggagacggac atggaatccc actccgacaa tgacatcagc     120
cgcgaccgca tgcgatcctc catcgagctc ccctctctgc gcgaccactt caagcaggac     180
tccctcccac ccttctcccc gcgaccgcgc gaactgctcc cctccatcct caaccactcg     240
cccccaggtc gctcctccac tcttcccccc atccagcaaa agaagtggcc gcgcccgcgc     300
aaatcctcca tctccggcgc tcgcaagccc aaacatgaac gctccaagtc caaggagtac     360
ggtcgccgcc ccagcttagg cgatcgcaaa gccctgtccg ccgaacccca gaccgccgcc     420
tgggctcagg gcaagcgctg ggaggatctg atcgaagccg cgacttcggc gaccgaggcc     480
gacgacgaac gccattctga ggtcggtcgg tcgcccacca tccctccggt gtccagcttc     540
acctccgccc ccatggggaa gaatcgctcg tcgcttcccc gggattccaa aggactacca     600 cccccccacct cgcatcgtcc gttccgcgcct catccctacg ccgcgtcgcc gttgaacaag     660
tccctgaccc caccgccgta cgacctcgcg cgcagccggg acaatgacct ggagcccttc     720
ccctcgatag agtcgtccct cgactccgcc tcgaccgcgt ccggaaagac cctccactat     780
aatcacgtcg gtccggccaa cgactccagt ccggtgctga acatgttccc gtcgtcggcc     840
```

```
gtgcagcgcc aacaccatcg cttttccaac cccaccccg cctccatgcg gagccgcgag    900
atccagatct attgcgccca ctgcaagcga ccgtgggcgc tcaacgaatg ctacgcctgc    960
accgagtgca tctgcggcgt ctgtcgcgaa tgtgtcggaa tgttcatcgg cagcccgccc   1020
acctccttcc gcaacgtcac ctccagcccg ggcagtgcct tgcccacgg cccgaccagc   1080 tatcctagcg cccgaggttg tccccgctgt cgcaccgtcg gcggcaagtg gaaggctttt   1140
cagctggatt tcaag                                                    1155
```

<210> SEQ ID NO 42
<211> LENGTH: 385
<212> TYPE: PRT
<213> ORGANISM: Artificial Sequence
<220> FEATURE:
<223> OTHER INFORMATION: fungal gene

<400> SEQUENCE: 42

```
Met Asp Asp Thr His Pro Ala Ala Thr Ala Val Ala Leu Ala
 1               5                  10                  15

Gln Leu His His Asn Arg Leu Val Ser Asp Trp Glu Thr Asp Met Glu
                20                  25                  30

Ser His Ser Asp Asn Asp Ile Ser Arg Asp Arg Met Arg Ser Ser Ile
            35                  40                  45

Glu Leu Pro Ser Leu Arg Asp His Phe Lys Gln Asp Ser Leu Pro Pro
     50                  55                  60

Phe Ser Pro Arg Pro Arg Glu Leu Leu Pro Ser Ile Leu Asn His Ser
 65                  70                  75                  80

Pro Pro Gly Arg Ser Ser Thr Leu Pro Pro Ile Gln Gln Lys Lys Trp
                 85                  90                  95

Pro Arg Pro Arg Lys Ser Ser Ile Ser Gly Ala Arg Lys Pro Lys His
                100                 105                 110

Glu Arg Ser Lys Ser Lys Glu Tyr Gly Arg Arg Pro Ser Leu Gly Asp
            115                 120                 125

Arg Lys Ala Leu Ser Ala Glu Pro Gln Thr Ala Ala Trp Ala Gln Gly
    130                 135                 140

Lys Arg Trp Glu Asp Leu Ile Glu Ala Ala Thr Ser Ala Thr Glu Ala
145                 150                 155                 160

Asp Asp Glu Arg His Ser Glu Val Gly Arg Ser Pro Thr Ile Pro Pro
                165                 170                 175

Val Ser Ser Phe Thr Ser Ala Pro Met Gly Lys Asn Arg Ser Ser Leu
            180                 185                 190

Pro Pro Gly Phe Gln Gly Leu Pro Pro Thr Ser His Arg Pro Phe
        195                 200                 205

Pro Pro His Pro Tyr Ala Ala Ser Pro Leu Asn Lys Ser Leu Thr Pro
    210                 215                 220

Pro Pro Tyr Asp Leu Ala Arg Ser Arg Asp Asn Asp Leu Glu Pro Phe
225                 230                 235                 240

Pro Ser Ile Glu Ser Ser Leu Asp Ser Ala Ser Thr Ala Ser Gly Lys
                245                 250                 255

Thr Leu His Tyr Asn His Val Gly Pro Ala Asn Asp Ser Ser Pro Val
            260                 265                 270

Leu Asn Met Phe Pro Ser Ser Ala Val Gln Arg Gln His His Arg Phe
        275                 280                 285

Ser Asn Pro Thr Pro Ala Ser Met Arg Ser Arg Glu Ile Gln Ile Tyr
    290                 295                 300
```

| | | | | | | | | | | | | | | |
|---|---|---|---|---|---|---|---|---|---|---|---|---|---|---|
| Cys | Ala | His | Cys | Lys | Arg | Pro | Trp | Ala | Leu | Asn | Glu | Cys | Tyr | Ala | Cys |
| 305 | | | | 310 | | | | | 315 | | | | | 320 |

| Thr | Glu | Cys | Ile | Cys | Gly | Val | Cys | Arg | Glu | Cys | Val | Gly | Met | Phe | Ile |
| | | | 325 | | | | | 330 | | | | | 335 | | |

| Gly | Ser | Pro | Pro | Thr | Ser | Phe | Arg | Asn | Val | Thr | Ser | Ser | Pro | Gly | Ser |
| | | | 340 | | | | | 345 | | | | | 350 | | |

| Ala | Leu | Pro | His | Gly | Pro | Thr | Ser | Tyr | Pro | Ser | Ala | Arg | Gly | Cys | Pro |
| | | 355 | | | | | 360 | | | | | 365 | | | |

| Arg | Cys | Arg | Thr | Val | Gly | Gly | Lys | Trp | Lys | Ala | Phe | Gln | Leu | Asp | Phe |
| | 370 | | | | | 375 | | | | | 380 | | | | |

| Lys |
| 385 |

<210> SEQ ID NO 43
<211> LENGTH: 1395
<212> TYPE: DNA
<213> ORGANISM: Artificial Sequence
<220> FEATURE:
<223> OTHER INFORMATION: fungal gene

<400> SEQUENCE: 43

```
atgccacctc ctgtcggcag atacggcatg ggcgccgccc ccttcgctca tttgcaacag      60
gcccatctcc agcagcaaca gccccagcat catccccatg cccagtcggc caacacagct     120
cttccgccgc cctcgcttgg cggccatccc ggcttcgccg ccagcaccaa caccaacatg     180
aaccccttca cgttatccgg cacggggatc gcgaatggca tgtcggtcgc tgcgtttggc     240
ggcgacggtg gaggcacggg ccttgccagt catgccgcgc agatggggtt cgcgagaggg     300
gcacagatgc agcaacagca gttacatcag gcccacgacg gccgactagc cctcgagacc     360
aaagccggtg gcgtcaaaac gcggatacga gacgtatgga agcataatct tgctcaggaa     420
atggcgatcc tcagacaact ggtggagaag tatccctaca tcagcatgga taccgagttt     480
cccggcatcg tcgctcgtcc cattggcgcc tttacgaata agcggactac ccactaccaa     540
acccttcgat gtaacgtcga cctgttgaag atgatccagc tgggaatcac cctttttttct    600
tccgaaggag aagttcctcc ccccaatgcc accgatgcga atggacagcc gctcggaaac     660
ggtctggtac ctgcgcccctg cacctggcag ttcaacttcc ggttttcgtt ggaggatgac     720
atgtacgccc aagagtcaac ggcgatgttg gcgaaggccg tatcgatttt cgccatgcac     780
gacaagaatg gaatcgatcc ctttgagttc ggcgccctct tgatcagctc aggcctcgtc     840
ctcctcgatg acgtccactg ggtttcgttc cactccggct acgatttcgg ctatttgatg     900
aagattatgc tctgcaaacc tctcccggag aacgaagagg aatttcacag gcttctcaac     960
atcttcttcc cgtcattata cgatattaaa tacctgatga agcatgcggg tcgcaatcaa    1020
gccaagtcgg gattgcaaga tattgcggac gagctgggcg tcaagcgtgt cgggattgct    1080
catcaggccg gtcggactc gctcgtcacg ggcgagatct actggaagat gcgccagttg    1140
gtcttcaacg gaaacatcga cgaagcgaaa tactccggtc agatctgggg gctgaacggc    1200
caaatgccag cgctgctgta ttctatgcag cccatcaga cccccaatct caacggggct     1260
accatctatt cggccactgg cacccccagt acgcccaatg ctgttcattc tgtcacgggc    1320
agccacacac cccagcatgc actgacaccc ggtgccaccg gcggggtgtt gggacagttc    1380
cagatggcaa agtca                                                     1395
```

<210> SEQ ID NO 44
<211> LENGTH: 465

```
<212> TYPE: PRT
<213> ORGANISM: Artificial Sequence
<220> FEATURE:
<223> OTHER INFORMATION: fungal gene

<400> SEQUENCE: 44
```

| | | | | | | | | | | | | | | | |
|---|---|---|---|---|---|---|---|---|---|---|---|---|---|---|---|
| Met | Pro | Pro | Pro | Val | Gly | Arg | Tyr | Gly | Met | Gly | Ala | Ala | Pro | Phe | Ala |
| 1 | | | | 5 | | | | | 10 | | | | | 15 | |
| His | Leu | Gln | Gln | Ala | His | Leu | Gln | Gln | Gln | Pro | Gln | His | His | Pro | |
| | | | 20 | | | | | 25 | | | | | 30 | | |
| His | Ala | Gln | Ser | Ala | Asn | Thr | Ala | Leu | Pro | Pro | Ser | Leu | Gly | Gly | |
| | | | 35 | | | | | 40 | | | | | 45 | | |
| His | Pro | Gly | Phe | Ala | Ala | Ser | Thr | Asn | Thr | Asn | Met | Asn | Pro | Phe | Thr |
| | | 50 | | | | | 55 | | | | | 60 | | | |
| Leu | Ser | Gly | Thr | Gly | Ile | Ala | Asn | Gly | Met | Ser | Val | Ala | Ala | Phe | Gly |
| 65 | | | | | 70 | | | | | 75 | | | | | 80 |
| Gly | Asp | Gly | Gly | Gly | Thr | Gly | Leu | Ala | Ser | His | Ala | Ala | Gln | Met | Gly |
| | | | | 85 | | | | | 90 | | | | | 95 | |
| Phe | Ala | Arg | Gly | Ala | Gln | Met | Gln | Gln | Gln | Gln | Leu | His | Gln | Ala | His |
| | | | | 100 | | | | | 105 | | | | | 110 | |
| Asp | Gly | Arg | Leu | Ala | Leu | Glu | Thr | Lys | Ala | Gly | Gly | Val | Lys | Thr | Arg |
| | | | 115 | | | | | 120 | | | | | 125 | | |
| Ile | Arg | Asp | Val | Trp | Lys | His | Asn | Leu | Ala | Gln | Glu | Met | Ala | Ile | Leu |
| | | 130 | | | | | 135 | | | | | 140 | | | |
| Arg | Gln | Leu | Val | Glu | Lys | Tyr | Pro | Tyr | Ile | Ser | Met | Asp | Thr | Glu | Phe |
| 145 | | | | | 150 | | | | | 155 | | | | | 160 |
| Pro | Gly | Ile | Val | Ala | Arg | Pro | Ile | Gly | Ala | Phe | Thr | Asn | Lys | Ala | Asp |
| | | | | 165 | | | | | 170 | | | | | 175 | |
| Tyr | His | Tyr | Gln | Thr | Leu | Arg | Cys | Asn | Val | Asp | Leu | Leu | Lys | Met | Ile |
| | | | 180 | | | | | 185 | | | | | 190 | | |
| Gln | Leu | Gly | Ile | Thr | Leu | Phe | Ser | Ser | Glu | Gly | Glu | Val | Pro | Pro | Pro |
| | | | 195 | | | | | 200 | | | | | 205 | | |
| Asn | Ala | Thr | Asp | Ala | Asn | Gly | Gln | Pro | Leu | Gly | Asn | Gly | Leu | Val | Pro |
| | | 210 | | | | | 215 | | | | | 220 | | | |
| Ala | Pro | Cys | Thr | Trp | Gln | Phe | Asn | Phe | Arg | Phe | Ser | Leu | Glu | Asp | Asp |
| 225 | | | | | 230 | | | | | 235 | | | | | 240 |
| Met | Tyr | Ala | Gln | Glu | Ser | Thr | Ala | Met | Leu | Ala | Lys | Ala | Gly | Ile | Asp |
| | | | | 245 | | | | | 250 | | | | | 255 | |
| Phe | Ala | Met | His | Asp | Lys | Asn | Gly | Ile | Asp | Pro | Phe | Glu | Phe | Gly | Ala |
| | | | 260 | | | | | 265 | | | | | 270 | | |
| Leu | Leu | Ile | Ser | Ser | Gly | Leu | Val | Leu | Asp | Asp | Val | His | Trp | Val | |
| | | | 275 | | | | | 280 | | | | | 285 | | |
| Ser | Phe | His | Ser | Gly | Tyr | Asp | Phe | Gly | Tyr | Leu | Met | Lys | Ile | Met | Leu |
| | | | 290 | | | | | 295 | | | | | 300 | | |
| Cys | Lys | Pro | Leu | Pro | Glu | Asn | Glu | Glu | Phe | His | Arg | Leu | Leu | Asn | |
| 305 | | | | | 310 | | | | | 315 | | | | | 320 |
| Ile | Phe | Phe | Pro | Ser | Leu | Tyr | Asp | Ile | Lys | Tyr | Leu | Met | Lys | His | Ala |
| | | | | 325 | | | | | 330 | | | | | 335 | |
| Gly | Arg | Asn | Gln | Ala | Lys | Ser | Gly | Leu | Gln | Asp | Ile | Ala | Asp | Glu | Leu |
| | | | 340 | | | | | 345 | | | | | 350 | | |
| Gly | Val | Lys | Arg | Val | Gly | Ile | Ala | His | Gln | Ala | Gly | Ser | Asp | Ser | Leu |
| | | | 355 | | | | | 360 | | | | | 365 | | |
| Val | Thr | Gly | Glu | Ile | Tyr | Trp | Lys | Met | Arg | Gln | Leu | Val | Phe | Asn | Gly |
| | | 370 | | | | | 375 | | | | | 380 | | | |

```
Asn Ile Asp Glu Ala Lys Tyr Ser Gly Gln Ile Trp Gly Leu Asn Gly
385                 390                 395                 400
Gln Met Pro Ala Leu Leu Tyr Ser Met Gln Pro His Gln Thr Pro Asn
                405                 410                 415
Leu Asn Gly Ala Thr Ile Tyr Ser Ala Thr Gly Thr Pro Ser Thr Pro
            420                 425                 430
Asn Ala Val His Ser Val Thr Gly Ser His Thr Pro Gln His Ala Leu
        435                 440                 445
Thr Pro Gly Ala Thr Gly Gly Val Leu Gly Gln Phe Gln Met Ala Lys
    450                 455                 460
Ser
465

<210> SEQ ID NO 45
<211> LENGTH: 1518
<212> TYPE: DNA
<213> ORGANISM: Artificial Sequence
<220> FEATURE:
<223> OTHER INFORMATION: fungal gene

<400> SEQUENCE: 45
atgaccgagc gctccgtgca gatctggttc cagaacaggc gcgccaagat caagatgctc      60
gcgaagaaaa gcatcgagac cggtgaaggc tgcgactcca ttcccgagtc gatgcgccag     120
tatctggcca tgcaattcga tccgaataaa cccggcgcac gagacccgtt tggtcgcacg     180
ggggctttcg gtcccaatgg cgggtatccc acgactcgg ccccctctgg caaagttgtg      240
attcaccatt tcacctgccg ctctttgacc atcggtagct ggcgccgcat tggacagaac     300
gcgatggact tggtggtttt ctactccccc gagaaggctt gcatgaccta ctatatcaac     360
aacgactcgg ccggctacaa aatcgagtac ccttttgcct acattaaaaa catcacgctg     420
gaatcgggcg atcagacagc gcagcccaac ggagcgcccc cgcgcccggg cggtctcatt     480
gttgaattga accgcccgcc gctcttctac atggattcct ccaactccgg tggcttctac     540
cagtgcggcg acttcaccga ggaccagcag gccagccagc tgttggtgca ccatctcggc     600
ggccacccca aagtcctgag cgtccagctg gccaagctgg tctcgttgga gtcgttccag     660
aaccgtctgg cctacaacaa cttcgccatg agtgcgccca tgtccccgcc ttttatccag     720
cggcccgcct cccagccgaa tcagtttgcc ccggcgtttg tgggcatgta tgcggagaac     780
cccgcgacgc tgagcctgca gcaggcggcg cgcggacaca agcgccaacg cagccgttcg     840
gtgcccgtag ccgtcgactt ctcggccatg cagaccccca tgtcgtacca gatgcagaac     900
ccgtcgcagt tcaaccagcc agattcgagt atctttgccc ccgttccgca gtcgacccat     960
ccactggcgg tgaacctgcg catcgatacg tcggcccct acggcttcga cccgcgcggc    1020
catcccatgt cggcggccac cacgaactca ccctcggact tgccagtcc ctcgctattc     1080 tcgacgggc ctccgggcga atccacgccg gtcgccacga gcatccaccc gcaattcaac     1140
atgccatttg tgtccccgcc ggtggactcg tctacgctcg ccacccaggc cgcgtcgccg    1200
tactccacgg tcagccacgc ggaccccatg attgccgacc agtcccctcc catgaccaac    1260
atgcatgcgt cgcaggagat gtacggcctg agcaacgagc atcaacccca ttttgcggac    1320
gagaacatgt ccatgagcgg catgttcccc aagcacaaca tgaatttctc ggtaccccac    1380
acgatggacg tcggaggcaa cacctttgat cttcccattc agaccctgtc caaccacccg    1440 tccccgggg ttcagggtga ctaccaaagc atgactccgc tggagaatgt cgatcccaac    1500
acgctggctc ctggggcg                                                 1518
```

<210> SEQ ID NO 46
<211> LENGTH: 506
<212> TYPE: PRT
<213> ORGANISM: Artificial Sequence
<220> FEATURE:
<223> OTHER INFORMATION: fungal gene

<400> SEQUENCE: 46

```
Met Thr Glu Arg Ser Val Gln Ile Trp Phe Gln Asn Arg Arg Ala Lys
 1               5                  10                  15

Ile Lys Met Leu Ala Lys Lys Ser Ile Glu Thr Gly Glu Gly Cys Asp
             20                  25                  30

Ser Ile Pro Glu Ser Met Arg Gln Tyr Leu Ala Met Gln Phe Asp Pro
         35                  40                  45

Asn Lys Pro Gly Ala Arg Asp Pro Phe Gly Arg Thr Gly Ala Phe Gly
     50                  55                  60

Pro Asn Gly Gly Tyr Pro His Asp Ser Ala Pro Ser Gly Lys Val Val
 65                  70                  75                  80

Ile His His Phe Thr Cys Arg Ser Leu Thr Ile Gly Ser Trp Arg Arg
                 85                  90                  95

Ile Gly Gln Asn Ala Met Asp Leu Val Val Phe Tyr Ser Pro Glu Lys
            100                 105                 110

Ala Cys Met Thr Tyr Tyr Ile Asn Asn Asp Ser Ala Gly Tyr Lys Ile
        115                 120                 125

Glu Tyr Pro Phe Ala Tyr Ile Lys Asn Ile Thr Leu Glu Ser Gly Asp
    130                 135                 140

Gln Thr Ala Gln Pro Asn Gly Ala Pro Pro Arg Pro Gly Gly Leu Ile
145                 150                 155                 160

Val Glu Leu Asn Arg Pro Leu Phe Tyr Met Asp Ser Ser Asn Ser
                165                 170                 175

Gly Gly Phe Tyr Gln Cys Gly Asp Phe Thr Glu Asp Gln Gln Ala Ser
            180                 185                 190

Gln Leu Leu Val His His Leu Gly Gly His Pro Lys Val Leu Ser Val
        195                 200                 205

Gln Leu Ala Lys Leu Val Ser Leu Glu Ser Phe Gln Asn Arg Leu Ala
    210                 215                 220

Tyr Asn Asn Phe Ala Met Ser Ala Pro Met Ser Pro Pro Phe Ile Gln
225                 230                 235                 240

Arg Pro Ala Ser Gln Pro Asn Gln Phe Ala Pro Ala Phe Val Gly Met
                245                 250                 255

Tyr Ala Glu Asn Pro Ala Thr Leu Ser Leu Gln Gln Ala Ala Arg Gly
            260                 265                 270

His Lys Arg Gln Arg Ser Arg Ser Val Pro Val Ala Val Asp Phe Ser
        275                 280                 285

Ala Met Gln Thr Pro Met Ser Tyr Gln Met Gln Asn Pro Ser Gln Phe
    290                 295                 300

Asn Gln Pro Asp Ser Ser Ile Phe Ala Pro Val Pro Gln Ser Thr His
305                 310                 315                 320

Pro Leu Ala Val Asn Leu Arg Ile Asp Thr Ser Ala Pro Tyr Gly Phe
                325                 330                 335

Asp Pro Arg Gly His Pro Met Ser Ala Ala Thr Thr Asn Ser Pro Ser
            340                 345                 350

Asp Phe Ala Ser Pro Ser Leu Phe Ser Thr Gly Pro Pro Gly Glu Ser
        355                 360                 365
```

-continued

```
Thr Pro Val Ala Thr Ser Ile His Pro Gln Phe Asn Met Pro Phe Val
    370                 375                 380

Ser Pro Pro Val Asp Ser Ser Thr Leu Ala Thr Gln Ala Ala Ser Pro
385                 390                 395                 400

Tyr Ser Thr Val Ser His Ala Asp Pro Met Ile Ala Asp Gln Ser Pro
                405                 410                 415

Pro Met Thr Asn Met His Ala Ser Gln Glu Met Tyr Gly Leu Ser Asn
            420                 425                 430

Glu His Gln Pro His Phe Ala Asp Glu Asn Met Ser Met Ser Gly Met
                435                 440                 445

Phe Pro Lys His Asn Met Asn Phe Ser Val Pro Thr Thr Met Asp Val
        450                 455                 460

Gly Gly Asn Thr Phe Asp Leu Pro Ile Gln Thr Leu Ser Asn His Pro
465                 470                 475                 480

Ser Pro Gly Val Gln Gly Asp Tyr Gln Ser Met Thr Pro Leu Glu Asn
                485                 490                 495

Val Asp Pro Asn Thr Leu Ala Pro Gly Ala
            500                 505
```

<210> SEQ ID NO 47
<211> LENGTH: 1731
<212> TYPE: DNA
<213> ORGANISM: Artificial Sequence
<220> FEATURE:
<223> OTHER INFORMATION: fungal gene

<400> SEQUENCE: 47

```
atgatgccag cgcaaatgcg gcagcttaac atgagaggaa atgcaatggt tcctcccaac      60
cttcagaaga gtgtgctgca gaacaatacc tctggcctct ctcaacaaca aatcgcccaa     120
ctccagaaga accacatttt gcagatgatg cagatgcaaa gagatcagtc cgagatggac     180
atgaatggtc accgtcccca gtcccctgcg tctgccgaga acgccccttc cccatccaag     240
cggccccgtc tggaaggcgg accgatgaac ggacaacagt tagcgcctaa cggacgtggt     300
caagcacagg gaatgcccgg tcaaccgaat ccgcaggccc tttttatgca gaatgggggt     360
ctcaacccac gaggaatgaa cccggcccaa cttcaggctt ccagcagggt ccgggcgcg      420
cagcagaaat caatccaggg catgccgaat ggcattatga atcccggtgt gatgccaaac     480
cagacggatc tgatgcccat gccagaaggt cagggtatgt acccgatgaa cggtgactac     540
tatgcgcga atggtcaaat ggcccaggtt cgggctggga tgcagacgcc tggcaatcag     600
ggaaaccatg ctcttcagga ttatcagatg cagcttatgt tgctggaaca gcagaataag     660
cgacgtttga tgatggctcg ccaagagcag gatagcatgc tcgtcctga cggccagccc      720
ccaatgcctg gcagcagca gttgccgcca ggcacctctc cccaaggcag cagggcgggc      780
gcctctccga accccaacga tcagatgaag agggtacac gaagatgcc gcagaccggt       840
cttccaggct ctccgaatcc tggcgatgtc gctcaaggtc gtggatcccc ggcttccatg     900
aatttcaaca gcgcccagat gccacccgac atgacgaacc cattcttcgc cgctccgaac     960
ggtatgcgac ccccgagctc gaacccggca tttaccaccg gtccgccgat gggccagcaa    1020
attcctgcag gtgcccagat gccgaatcgc gcttggcagc gcagcaggg cgctcagggc     1080
caacctatgc ccccacagca gtcccctgcg gcgcagccgg ccacgggaac tccccaggaa    1140
cgcaaccaaa tgccgccgcc ccaggctcct ccgctgctg ggcctaattc cggacgcacg     1200
cagccgccgt ctcctcagac cggagccgct gcccctccca cgccccagca atccaacaag    1260
```

-continued

```
gccgcaccca aggggaagaa agacacgaag gacactaatc ggaagcggcc gaagaaggca    1320
gctggccctg cagcggctgc agctgcctcg aatactgccg cgaccccctc gtccgaggct    1380
gagcatgcga cgacgccgtc gacgccgatc acgcctcagc atccgaactc gttcaacaag    1440
ccggggccca ataccacgac gagtgcgccc cagcaaccca catcggcgcc tgccgcaccg    1500
acgctggtgc agccgccgcc acccgaccag aaccagccgt tcaatgacct tagcatgcca    1560
gacgcgtctg ctttcaacct ggacttcagc gccctggaga atccggacat tttggagaac    1620
ttcgacttcg atacctttct caacactgac gcggatacgg cggggtttgg gtttgatccc    1680
aacatgccat atcctgggga cggcgttgag actggtgccg agaaggtct g              1731
```

<210> SEQ ID NO 48
<211> LENGTH: 577
<212> TYPE: PRT
<213> ORGANISM: Artificial Sequence
<220> FEATURE:
<223> OTHER INFORMATION: fungal gene

<400> SEQUENCE: 48

```
Met Met Pro Ala Gln Met Arg Gln Leu Asn Met Arg Gly Asn Ala Met
 1               5                  10                  15

Val Pro Pro Asn Leu Gln Lys Ser Val Leu Gln Asn Asn Thr Ser Gly
            20                  25                  30

Leu Ser Gln Gln Gln Ile Ala Gln Leu Gln Lys Asn Gln His Leu Gln
        35                  40                  45

Met Met Gln Met Gln Arg Asp Gln Ser Glu Met Asp Met Asn Gly His
    50                  55                  60

Arg Pro Gln Ser Pro Ala Ser Ala Glu Asn Ala Pro Ser Pro Ser Lys
65                  70                  75                  80

Arg Pro Arg Leu Glu Gly Gly Pro Met Asn Gly Gln Gln Leu Ala Pro
                85                  90                  95

Asn Gly Arg Gly Gln Ala Gln Gly Met Pro Gly Gln Pro Asn Pro Gln
            100                 105                 110

Ala Leu Phe Met Gln Asn Gly Gly Leu Asn Pro Arg Gly Met Asn Pro
        115                 120                 125

Ala Gln Leu Gln Ala Phe Gln Gln Gly Pro Gly Ala Gln Gln Lys Ser
    130                 135                 140

Ile Gln Gly Met Pro Asn Gly Ile Met Asn Pro Gly Val Met Pro Asn
145                 150                 155                 160

Gln Thr Asp Leu Met Pro Met Pro Glu Gly Gln Gly Met Tyr Pro Met
                165                 170                 175

Asn Gly Asp Tyr Tyr Gly Ala Asn Gly Gln Met Ala Gln Val Arg Ala
            180                 185                 190

Gly Met Gln Thr Pro Gly Asn Gln Gly Asn His Ala Leu Gln Asp Tyr
        195                 200                 205

Gln Met Gln Leu Met Leu Glu Gln Gln Asn Lys Arg Arg Leu Met
    210                 215                 220

Met Ala Arg Gln Glu Gln Asp Ser Met Ala Arg Pro Asp Gly Gln Pro
225                 230                 235                 240

Pro Met Pro Gly Gln Gln Gln Leu Pro Pro Gly Thr Ser Pro Gln Gly
                245                 250                 255

Ser Arg Ala Gly Ala Ser Pro Asn Pro Asn Asp Gln Met Lys Arg Gly
            260                 265                 270

Thr Pro Lys Met Pro Gln Thr Gly Leu Pro Gly Ser Pro Asn Pro Gly
```

-continued

```
                275                 280                 285
Asp Val Ala Gln Gly Arg Gly Ser Pro Ala Ser Met Asn Phe Asn Ser
    290                 295                 300

Ala Gln Met Pro Pro Asp Met Thr Asn Pro Phe Phe Ala Ala Pro Asn
305                 310                 315                 320

Gly Met Arg Pro Pro Ser Ser Asn Pro Ala Phe Thr Thr Gly Pro Pro
                325                 330                 335

Met Gly Gln Gln Ile Pro Ala Gly Ala Gln Met Pro Asn Arg Ala Trp
            340                 345                 350

Gln Pro Gln Gln Gly Ala Gln Gly Gln Pro Met Pro Pro Gln Gln Ser
        355                 360                 365

Pro Ala Ala Gln Pro Ala Thr Gly Thr Pro Gln Glu Arg Asn Gln Met
    370                 375                 380

Pro Pro Pro Gln Ala Pro Pro Ala Ala Gly Pro Asn Ser Gly Arg Thr
385                 390                 395                 400

Gln Pro Pro Ser Pro Gln Thr Gly Ala Ala Ala Pro Pro Thr Pro Gln
                405                 410                 415

Gln Ser Asn Lys Ala Ala Pro Lys Gly Lys Lys Asp Thr Lys Asp Thr
            420                 425                 430

Asn Arg Lys Arg Pro Lys Lys Ala Ala Gly Pro Ala Ala Ala Ala Ala
        435                 440                 445

Ala Ser Asn Thr Ala Ala Thr Pro Ser Ser Glu Ala Glu His Ala Thr
    450                 455                 460

Thr Pro Ser Thr Pro Ile Thr Pro Gln His Pro Asn Ser Phe Asn Lys
465                 470                 475                 480

Pro Gly Pro Asn Thr Thr Thr Ser Ala Pro Gln Gln Pro Thr Ser Ala
                485                 490                 495

Pro Ala Ala Pro Thr Leu Val Gln Pro Pro Pro Asp Gln Asn Gln
            500                 505                 510

Pro Phe Asn Asp Leu Ser Met Pro Asp Ala Ser Ala Phe Asn Leu Asp
        515                 520                 525

Phe Ser Ala Leu Glu Asn Pro Asp Ile Leu Glu Asn Phe Asp Phe Asp
    530                 535                 540

Thr Phe Leu Asn Thr Asp Ala Asp Thr Ala Gly Phe Gly Phe Asp Pro
545                 550                 555                 560

Asn Met Pro Tyr Pro Gly Asp Gly Val Glu Thr Gly Ala Gly Glu Gly
                565                 570                 575

Leu
```

<210> SEQ ID NO 49
<211> LENGTH: 1152
<212> TYPE: DNA
<213> ORGANISM: Artificial Sequence
<220> FEATURE:
<223> OTHER INFORMATION: fungal gene

<400> SEQUENCE: 49

| | | | | | |
|---|---|---|---|---|---|
| atggagtatt | ccggggcaga | tcccaccttt | gttgcgaaaa | ccagcgcctt | ggcagtcacg | 60 |
| catcccttct | gccgcattat | gaagcgggac | ggtaactgcg | gctggcgagc | ggctgccttt | 120 |
| gggtatttcg | aaagcctttt | caatctccac | aatctcatcc | atgcgcagtc | cgagttggtc | 180 |
| cgcatcaagg | gtctcaattc | gcttcttgac | caagtaggtc | accaggagca | tttgtacgag | 240 |
| atctttgtag | atgcaaccga | gagtgtcttt | gagcaagtgt | gtgaggcgat | tcaggccggg | 300 |
| gtacgggacg | attcgttcct | gaaggatctc | ttcaatgagg | agttcaactc | cagtgcggtc | 360 |

```
atcacgcatt tcaggcttct taccagcgcc tggatgaaat tgaatcctca tcggtaccag    420
gccttcctgc cgctcccct cgatcagtac tgcacgacgc ggatcgagac cgtcaaaacg    480
gaaattgatg aagtgggcct ccaagctctg gtggacggcg tcatcgagcc gtccggcgtt    540
gctgtcgaga tcctgtacct ggaccggagt cagggcgaag cagtcactcc ccatctcttg    600
accccgagtc ggcctagcgc ttcgacaatc cgtttgctgt atcgccctgg ccactacgat    660
attgcgtacc aagcggaacc taccgtgaca atggaaccca tcgtcaatta tcagtacggc    720
atgaccacca actactcgcc ctgggaccaa ggcgccctct cgtttgatgt gaactcgagt    780
ctcatgtcca ttcccaacct gatgatggac ccctcctttg cgctctcccc ttcccccatg    840
actcccgctc cgagcccgta ccgcgtctcg ccccctcagg aagtgttcca acctccgatg    900
cacacgcctc cgccaccggt ccccgtcgca tcgccgccac caccccgcat gtcagccccg    960
cccccgatga cttcgttacc taaccggtcc tcagacgggc cgcagattcg actgaatccg    1020
ttggtgatga agcagaactt gagccactcg ctccccgtca cgactccatt caagaattcg    1080
ccgtacaacc aggcccattt ccaaaaccag gactttgagc caatccactg ggaacccagt    1140
gattcccgca aa                                                       1152
```

<210> SEQ ID NO 50
<211> LENGTH: 384
<212> TYPE: PRT
<213> ORGANISM: Artificial Sequence
<220> FEATURE:
<223> OTHER INFORMATION: fungal gene

<400> SEQUENCE: 50

```
Met Glu Tyr Ser Gly Ala Asp Pro Thr Phe Val Ala Lys Thr Ser Ala
 1               5                  10                  15

Leu Ala Val Thr His Pro Phe Cys Arg Ile Met Lys Arg Asp Gly Asn
                20                  25                  30

Cys Gly Trp Arg Ala Ala Phe Gly Tyr Phe Glu Ser Leu Phe Asn
        35                  40                  45

Leu His Asn Leu Ile His Ala Gln Ser Glu Leu Val Arg Ile Lys Gly
    50                  55                  60

Leu Asn Ser Leu Leu Asp Gln Val Gly His Gln Glu His Leu Tyr Glu
65                  70                  75                  80

Ile Phe Val Asp Ala Thr Glu Ser Val Phe Glu Gln Val Cys Glu Ala
                85                  90                  95

Ile Gln Ala Gly Val Arg Asp Asp Ser Phe Leu Lys Asp Leu Phe Asn
            100                 105                 110

Glu Glu Phe Asn Ser Ser Ala Val Ile Thr His Phe Arg Leu Leu Thr
        115                 120                 125

Ser Ala Trp Met Lys Leu Asn Pro His Arg Tyr Gln Ala Phe Leu Pro
    130                 135                 140

Leu Pro Leu Asp Gln Tyr Cys Thr Thr Arg Ile Glu Thr Val Lys Thr
145                 150                 155                 160

Glu Ile Asp Glu Val Gly Leu Gln Ala Leu Val Asp Gly Val Ile Glu
                165                 170                 175

Pro Ser Gly Val Ala Val Glu Ile Leu Tyr Leu Asp Arg Ser Gln Gly
            180                 185                 190

Glu Ala Val Thr Pro His Leu Leu Thr Pro Ser Arg Pro Ser Ala Ser
        195                 200                 205

Thr Ile Arg Leu Leu Tyr Arg Pro Gly His Tyr Asp Ile Ala Tyr Gln
```

```
    210                 215                 220
Ala Glu Pro Thr Val Thr Met Glu Pro Ile Val Asn Tyr Gln Tyr Gly
225                 230                 235                 240

Met Thr Thr Asn Tyr Ser Pro Trp Asp Gln Gly Ala Leu Ser Phe Asp
                245                 250                 255

Val Asn Ser Ser Leu Met Ser Ile Pro Asn Leu Met Met Asp Pro Ser
            260                 265                 270

Phe Ala Leu Ser Pro Ser Pro Met Thr Pro Ala Pro Ser Pro Tyr Arg
        275                 280                 285

Val Ser Pro Pro Gln Glu Val Phe Gln Pro Pro Met His Thr Pro Pro
    290                 295                 300

Pro Pro Val Pro Val Ala Ser Pro Pro Pro Arg Met Ser Ala Pro
305                 310                 315                 320

Pro Pro Met Thr Ser Leu Pro Asn Arg Ser Ser Asp Gly Pro Gln Ile
                325                 330                 335

Arg Leu Asn Pro Leu Val Met Lys Gln Asn Leu Ser His Ser Leu Pro
            340                 345                 350

Val Thr Thr Pro Phe Lys Asn Ser Pro Tyr Asn Gln Ala His Phe Gln
        355                 360                 365

Asn Gln Asp Phe Glu Pro Ile His Trp Glu Pro Ser Asp Ser Arg Lys
    370                 375                 380

<210> SEQ ID NO 51
<211> LENGTH: 2388
<212> TYPE: DNA
<213> ORGANISM: Artificial Sequence
<220> FEATURE:
<223> OTHER INFORMATION: fungal gene

<400> SEQUENCE: 51
atggctacta ctgactggca gcccgacttt gtacctccga acccaccggc cctagagagt      60
gtaggagctc atacggaccg ggctcttcag aatacctctg gaacgtgca gtcctattca     120
gacaatctcg cccccaacga cacgacgggg cgagatagtg acatctgca gccgtatgct     180
cccaagtatc ctcctccgct cccaatccct gcccatcctg tcccttcggc tgcggccagc     240
ctgcaccatc aacacatcct agccaaccga tggcagcaga agaagctccg tcgacttcag     300
tccctggggc caaccagct ggttggtccc cgtcggggaa gaagctatct caagtcccag     360
aagtacctgg agtatcgagc gcggcctcga cgggacacgg gcaaggatgg ggagcctgtc     420
tggtcggatg agctggagga tgccttccaa caagcactcg aggcaaaccc tcccatgggc     480
cggagaaagt ggtccgaacg gggcaaatcc tatggtcgaa cgagctgat tgccgagttt     540
atctacaagg ctacgggcaa gaggagaact aggaaacaag tgtccagtca cctgcaggtg     600
ctcgactcgt tcctcaaggg ggaccctgac tgggaaagac tggtacggga cagccgaca     660
gaccgctctg cagcccagcc tcaagcagct ggcccaaggt ggcggacctc catgaacac     720
cccctgtcaa gtcactacaa tcatctccac gctccttacc atgatcctct gcgacctgtg     780
cagccttacg tggggagct gcctccccct tcctttgccc caacccaa cgtccatgat     840
gccaacatca cacccgtcca gggcctcaat tttgacatgt gggtcagtgc accgaaccag     900
ccggaccgca ttgagaatgc tttccatgta cacccgct tgcagggcga ccaacgccat     960
cccgtggccc cttcaatgcc gttggagaac atcgtcgggt ggcggaccta cttcccttat    1020
ctgaattccc tgatggcgga cccaactgct tccctgaact gcgagatcat cctcctcgaa    1080
gccaacctcg agttgatgga cgactttcct ccgtccggtt cgcggctggg gatccagctg    1140
```

```
gagctggact tgcccattc cgctgtgggc gatgcaccag tcagtcagat ggacaactgg    1200
tcttgcagca cctacatgta tgaggagagc cagaagatcc tggaggtcaa ccacagcctt    1260
tcaaagccgg cttcgacgaa agtcaagcca ccgttcgaat cgctctggtg ggccaaactc    1320
ttcacacagc tcacgcagga gaagcagatg gccgagaagg cgggtcagca tcatgcggcg    1380
gacgagcaca cgcggcactt cttccggacc atgtctgcgg tgcaggagat ccgtgctacg    1440
tctcccaact cccgtcgact ctccagccac tacggcggct cctcgtgcga cgagagtaag    1500
cgggtcgcga tcttgctctg gaagttccgc cagacgcggc ctggggaggt tggcaccacg    1560
acctggcgga gactctttcc gccgccggac cgcacgtcca ccaatagccc tcgtccggcg    1620
acgggcatcg acctccccc  gctgtcactg gactcgatcc tgctcaacaa gcccgcaccc    1680
aacgtctacc aagcgcctcc gccgcagcca cacgaattga tgcaccacca cggcgcgtcg    1740
cagcctcctt ggcagatgta cccaccccg  catgatcaca tgtacccac  ggggagcttt    1800 gatcttctca actcgatctc gaaaccggag gacggcctgg gtgacaagac ggcggtctcg    1860
tcggtgatcg accccttccc caatatgcag cagcatgaga ccagccagcc gcccaacctc    1920
aatggcagca acggcggtcc gatcatgctc aacgtgccgg acatgtcgtt gtcgcaccac    1980
aacctggggg gatacacaat gggccacgag agccaccact acgtgccgcc accgcagcaa    2040
cacggggtgc atgtccccga caacaacagc gttctgaata acatctttgc ctccggaccg    2100
cagtcgttcg aggagctggg ccataacagc cacgcggcgt ggtcgggacc gtccacgacc    2160
ctcccgtcgg acgtgggatc caacagctac ggccatcttt cctatcagtc cgaccagcac    2220
ccgccggcga cgcgcgagcc ccatcagtct aacggcttcg agggcctgat ggggacggat    2280
ctgatggaca agctcgtggg caacatgccg ggcgaccctg gcttgaatgg ggcaggcccc    2340
gatcacgcca catccgcgta ccctgagaac agcacggttg aggcggtt                 2388
```

<210> SEQ ID NO 52
<211> LENGTH: 796
<212> TYPE: PRT
<213> ORGANISM: Artificial Sequence
<220> FEATURE:
<223> OTHER INFORMATION: fungal gene

<400> SEQUENCE: 52

```
Met Ala Thr Thr Asp Trp Gln Pro Asp Phe Val Pro Pro Asn Pro Pro
 1               5                  10                  15

Ala Leu Glu Ser Val Gly Ala His Thr Asp Arg Ala Leu Gln Asn Thr
             20                  25                  30

Ser Gly Asn Val Gln Ser Tyr Ser Asp Asn Leu Ala Pro Asn Asp Thr
         35                  40                  45

Thr Gly Arg Asp Ser Gly His Leu Gln Pro Tyr Ala Pro Lys Tyr Pro
     50                  55                  60

Pro Pro Leu Pro Ile Pro Ala His Pro Val Pro Ser Ala Ala Ala Ser
 65                  70                  75                  80

Leu His His Gln His Ile Leu Ala Asn Arg Trp Gln Gln Lys Lys Leu
                 85                  90                  95

Arg Arg Leu Gln Ser Leu Gly Pro Asn Gln Leu Val Gly Pro Arg Arg
            100                 105                 110

Gly Arg Ser Tyr Leu Lys Ser Gln Lys Tyr Leu Glu Tyr Arg Ala Arg
        115                 120                 125

Pro Arg Arg Asp Thr Gly Lys Asp Gly Glu Pro Val Trp Ser Asp Glu
    130                 135                 140
```

```
Leu Glu Asp Ala Phe Gln Gln Ala Leu Glu Ala Asn Pro Pro Met Gly
145                 150                 155                 160

Arg Arg Lys Trp Ser Glu Arg Gly Lys Ser Tyr Gly Arg Asn Glu Leu
            165                 170                 175

Ile Ala Glu Phe Ile Tyr Lys Ala Thr Gly Lys Arg Thr Arg Lys
                180                 185                 190

Gln Val Ser Ser His Leu Gln Val Leu Asp Ser Phe Leu Lys Gly Asp
            195                 200                 205

Pro Asp Trp Glu Arg Leu Val Arg Glu Gln Pro Thr Asp Arg Ser Ala
            210                 215                 220

Ala Gln Pro Gln Ala Ala Gly Pro Arg Trp Arg Thr Ser Met Glu His
225                 230                 235                 240

Pro Leu Ser Ser His Tyr Asn His Leu His Ala Pro Tyr His Asp Pro
                245                 250                 255

Leu Arg Pro Val Gln Pro Tyr Val Gly Glu Leu Pro Pro Ser Phe
            260                 265                 270

Ala Pro Asn Pro Asn Val His Asp Ala Asn Ile Asn Thr Val Gln Gly
            275                 280                 285

Leu Asn Phe Asp Met Trp Val Ser Ala Pro Asn Gln Pro Asp Arg Ile
290                 295                 300

Glu Asn Ala Phe His Val Tyr Thr Arg Leu Gln Gly Asp Gln Arg His
305                 310                 315                 320

Pro Val Ala Pro Ser Met Pro Leu Glu Asn Ile Val Gly Trp Arg Thr
                325                 330                 335

Tyr Phe Pro Tyr Leu Asn Ser Leu Met Ala Asp Pro Thr Ala Ser Leu
                340                 345                 350

Asn Cys Glu Ile Ile Leu Leu Glu Ala Asn Leu Glu Leu Met Asp Asp
            355                 360                 365

Phe Pro Pro Ser Gly Ser Arg Leu Gly Ile Gln Leu Glu Leu Asp Phe
370                 375                 380

Ala His Ser Ala Val Gly Asp Ala Pro Val Ser Gln Met Asp Asn Trp
385                 390                 395                 400

Ser Cys Ser Thr Tyr Met Tyr Glu Glu Ser Gln Lys Ile Leu Glu Val
                405                 410                 415

Asn His Ser Leu Ser Lys Pro Ala Ser Thr Lys Val Lys Pro Pro Phe
            420                 425                 430

Glu Ser Leu Trp Trp Ala Lys Leu Phe Thr Gln Leu Thr Gln Glu Lys
            435                 440                 445

Gln Met Ala Glu Lys Ala Gly Gln His His Ala Ala Asp Glu His Thr
450                 455                 460

Arg His Phe Phe Arg Thr Met Ser Ala Val Gln Glu Ile Arg Ala Thr
465                 470                 475                 480

Ser Pro Asn Ser Arg Arg Leu Ser His Tyr Gly Gly Ser Ser Cys
                485                 490                 495

Asp Glu Ser Lys Arg Val Ala Ile Leu Leu Trp Lys Phe Arg Gln Thr
            500                 505                 510

Arg Pro Gly Glu Val Gly Thr Thr Thr Trp Arg Arg Leu Phe Pro Pro
            515                 520                 525

Pro Asp Arg Thr Ser Thr Asn Ser Pro Arg Pro Ala Thr Gly Ile Asp
            530                 535                 540

Leu Pro Pro Leu Ser Leu Asp Ser Ile Leu Leu Asn Lys Pro Ala Pro
545                 550                 555                 560
```

```
Asn Val Tyr Gln Ala Pro Pro Gln Pro His Glu Leu Met His His
            565                 570                 575
His Gly Ala Ser Gln Pro Pro Trp Gln Met Tyr Pro Pro His Asp
        580                 585                 590
His Met Tyr Pro Thr Gly Ser Phe Asp Leu Leu Asn Ser Ile Ser Lys
    595                 600                 605
Pro Glu Asp Gly Leu Gly Asp Lys Thr Ala Val Ser Ser Val Ile Asp
610                 615                 620
Pro Phe Pro Asn Met Gln Gln His Glu Thr Ser Gln Pro Pro Asn Leu
625                 630                 635                 640
Asn Gly Ser Asn Gly Gly Pro Ile Met Leu Asn Val Pro Asp Met Ser
                645                 650                 655
Leu Ser His His Asn Leu Gly Gly Tyr Thr Met Gly His Glu Ser His
                660                 665                 670
His Tyr Val Pro Pro Gln Gln His Gly Val His Val Pro Asp Asn
    675                 680                 685
Asn Ser Val Leu Asn Asn Ile Phe Ala Ser Gly Pro Gln Ser Phe Glu
690                 695                 700
Glu Leu Gly His Asn Ser His Ala Ala Trp Ser Gly Pro Ser Thr Thr
705                 710                 715                 720
Leu Pro Ser Asp Val Gly Ser Asn Ser Tyr Gly His Leu Ser Tyr Gln
                725                 730                 735
Ser Asp Gln His Pro Pro Ala Thr Arg Glu Pro His Gln Ser Asn Gly
                740                 745                 750
Phe Glu Gly Leu Met Gly Thr Asp Leu Met Asp Lys Leu Val Gly Asn
            755                 760                 765
Met Pro Gly Asp Pro Gly Leu Asn Gly Ala Gly Pro Asp His Ala Thr
    770                 775                 780
Ser Ala Tyr Pro Glu Asn Ser Thr Val Glu Ala Val
785                 790                 795
```

<210> SEQ ID NO 53
<211> LENGTH: 1431
<212> TYPE: DNA
<213> ORGANISM: Artificial Sequence
<220> FEATURE:
<223> OTHER INFORMATION: fungal gene

<400> SEQUENCE: 53

```
atgccacctc ccgtcggcag atatgcgcca tctggcttaa acgctccata caacatacaa    60
caagctcacc ttcaatctca acatcccgca cacgcacagt ccggaaacac actccctccc   120
ccttcgcttg gtcatcctgg tttcgcgggc aatccgaata ccaacatcaa ccctttttaca  180
ctatccggcg gaattgcaaa tggtatggcg gtagccggct cccgggagc tggtgcaggt    240
gatggcggcg gcaccggtct ggctagtcat gcggcacaga tgggattcgc gcgcggtgcg   300
caaatgcaac aacagcaact acaccagggt cacgacggtc ggttagcgct cgaagcaaag   360
ggcggtgcag tgaagtcaag aattagagat gtctggaagc acaacctggc ccatgagatg   420
gcggtgctga ggcagttggt cgacaagtac ccttacatca gcatggacac cgagttccct   480
ggtattgttg ctcggccgat agggtctttt tcgaacaaag ccgattacca ttatcagacc   540
ctccgatgca atgttgatct tctgaagatg atacaactag gcatcacgtt attcaatgac   600
gaaggagagg tcccccccagc ctcaggcact gatgccaatg acaagcgta tggtgtgccc   660
gctccctgca catggcagtt caacttccga ttttcacttg aaggcgacat gtacgcccag   720
```

-continued

```
gagtcaacag ccatgcttgc caaatctgga attgacttcg ccatgcatga aaagaacggc      780
attgatcctt tcgaattcgg tgctcttttg attagctctg gattggtgct actggatgac      840
gttcactggg tgtctttcca ctccgggtac gactttggct acttgatgaa gatcatgctc      900
tgctcccagc ttccagaaaa cgaagaggag ttccacaagc ttcttaccat cttcttcccg      960
tcactttacg acatcaaata cctcatgaag cacgccggtc gcaaccaagc cgtcaacggt     1020
tcccctctca gtcaggctgc agcccagatt ctcaccaatc taggccagaa atctggtttg     1080
caagacattg ccgatgaact tggcgtgaag cgcgtcggaa tcgctcacca ggctggctca     1140
gactccctag tcaccggcga gatctactgg aagacgcgcc aactcatttt cggaggggca     1200
attgacgaca gcaaatattc tggccaaatc tggggtctca acggacaaat gcctgcagtg     1260
gcctacaaca tggctcagca acgcccaac cttaatggcg cgaccattta ctcgggcggc      1320 accccccagca ctcccaatac tgggtctcac ggggctggcg cccacacacc tcagcactac    1380
ggagctggct acaatgcccc gactcccgga gcctatcaaa tgggccgggt a              1431
```

<210> SEQ ID NO 54
<211> LENGTH: 477
<212> TYPE: PRT
<213> ORGANISM: Artificial Sequence
<220> FEATURE:
<223> OTHER INFORMATION: fungal gene

<400> SEQUENCE: 54

```
Met Pro Pro Pro Val Gly Arg Tyr Ala Pro Ser Gly Leu Asn Ala Pro
 1               5                  10                  15

Tyr Asn Ile Gln Gln Ala His Leu Gln Ser Gln His Pro Ala His Ala
            20                  25                  30

Gln Ser Gly Asn Thr Leu Pro Pro Ser Leu Gly His Pro Gly Phe
        35                  40                  45

Ala Gly Asn Pro Asn Thr Asn Ile Asn Pro Phe Thr Leu Ser Gly Gly
    50                  55                  60

Ile Ala Asn Gly Met Ala Val Ala Gly Phe Pro Gly Ala Gly Ala Gly
65                  70                  75                  80

Asp Gly Gly Thr Gly Leu Ala Ser His Ala Ala Gln Met Gly Phe
                85                  90                  95

Ala Arg Gly Ala Gln Met Gln Gln Gln Leu His Gln Gly His Asp
            100                 105                 110

Gly Arg Leu Ala Leu Glu Ala Lys Gly Gly Ala Val Lys Ser Arg Ile
        115                 120                 125

Arg Asp Val Trp Lys His Asn Leu Ala His Glu Met Ala Val Leu Arg
    130                 135                 140

Gln Leu Val Asp Lys Tyr Pro Tyr Ile Ser Met Asp Thr Glu Phe Pro
145                 150                 155                 160

Gly Ile Val Ala Arg Pro Ile Gly Ser Phe Ser Asn Lys Ala Asp Tyr
                165                 170                 175

His Tyr Gln Thr Leu Arg Cys Asn Val Asp Leu Leu Lys Met Ile Gln
            180                 185                 190

Leu Gly Ile Thr Leu Phe Asn Asp Glu Gly Glu Val Pro Pro Ala Ser
        195                 200                 205

Gly Thr Asp Ala Asn Gly Gln Ala Tyr Gly Val Pro Ala Pro Cys Thr
    210                 215                 220

Trp Gln Phe Asn Phe Arg Phe Ser Leu Glu Gly Asp Met Tyr Ala Gln
225                 230                 235                 240
```

```
Glu Ser Thr Ala Met Leu Ala Lys Ser Gly Ile Asp Phe Ala Met His
                245                 250                 255
Glu Lys Asn Gly Ile Asp Pro Phe Glu Phe Gly Ala Leu Leu Ile Ser
            260                 265                 270
Ser Gly Leu Val Leu Leu Asp Asp Val His Trp Val Ser Phe His Ser
        275                 280                 285
Gly Tyr Asp Phe Gly Tyr Leu Met Lys Ile Met Leu Cys Ser Gln Leu
    290                 295                 300
Pro Glu Asn Glu Glu Glu Phe His Lys Leu Leu Thr Ile Phe Phe Pro
305                 310                 315                 320
Ser Leu Tyr Asp Ile Lys Tyr Leu Met Lys His Ala Gly Arg Asn Gln
                325                 330                 335
Ala Val Asn Gly Ser Pro Leu Ser Gln Ala Ala Gln Ile Leu Thr
            340                 345                 350
Asn Leu Gly Gln Lys Ser Gly Leu Gln Asp Ile Ala Asp Glu Leu Gly
        355                 360                 365
Val Lys Arg Val Gly Ile Ala His Gln Ala Gly Ser Asp Ser Leu Val
    370                 375                 380
Thr Gly Glu Ile Tyr Trp Lys Thr Arg Gln Leu Ile Phe Gly Gly Ala
385                 390                 395                 400
Ile Asp Asp Ser Lys Tyr Ser Gly Gln Ile Trp Gly Leu Asn Gly Gln
                405                 410                 415
Met Pro Ala Val Ala Tyr Asn Met Ala Gln Gln Thr Pro Asn Leu Asn
            420                 425                 430
Gly Ala Thr Ile Tyr Ser Gly Gly Thr Pro Ser Thr Pro Asn Thr Gly
        435                 440                 445
Ser His Gly Ala Gly Ala His Thr Pro Gln His Tyr Gly Ala Gly Tyr
    450                 455                 460
Asn Ala Pro Thr Pro Gly Ala Tyr Gln Met Gly Arg Val
465                 470                 475

<210> SEQ ID NO 55
<211> LENGTH: 1146
<212> TYPE: DNA
<213> ORGANISM: Artificial Sequence
<220> FEATURE:
<223> OTHER INFORMATION: fungal gene

<400> SEQUENCE: 55
atgtttgctg ctggtggaag ccctcaattt gcttcgccca tgtctggtac aacacatggg      60
ttctgggaag gaaagacggc cgcccgtcgt ctttctgtgc aacgagtag  caacccttc      120
ctcgcacagc atgcaacgc atatcctcca ggatatcaca accccgtcgg tgcaccttat      180
caaaatgctg ctgggtatt cgcaagcccc actagcacac actactctgt atctcgtgat      240
gagggtacct aagcgcggc cgaggcggag atgcggagga gaacgtggca cccttcgtca      300
tacacaggt ttccacgccc tggaactagt ggcctgaacc aatatcatac acccgacaat      360
gtcccagcct cattcggtgc gaacgggtcg accgagcatc cgccccggct tcccggcatt      420
gagagttttg acaaggttgt ccaacggccg atgaccccgc ccaccaggaa accagccca      480
atgcagcttg atggccagca tcgtccaccc cctaacccag ctttggatc agggttcaat      540
tatacacagc cagcccaccg tccaccacct cccatctccg ccctggtca ccgacgaggc      600
catgtatcct gggatatgtc tttgcatcat aacctgaccg gctcgatat ccgagaccga      660
cgtccttcta ccgcatctgc ttctcaatgg agccaacaaa ccctcgcaga actccagaat      720
```

-continued

```
gtctcttccc gcccgtcatc atcttaccag cctgcattcg gcccaacggc cgagagaagc    780
cctgaagagt atcggggaca tcgcccaagc ctctcaacgg gaagccgcac gcgaacttcc    840
cccgaagatt cgagtagcag cgaggtgtc cataccccat ccaccgcatc gcttgagtat     900
catcccgcga ttgtgcacag cagcggatat atcgaatctg atgattcctc cttgccttcc    960
gatcaccctc aaccgatctg tggccgtcag tcctcccacg cggatggcta tgaaccccac   1020
aatgaccggg agcccaggcc cgacgtcttc ccagactctc ctgcccgaaa ttcgggcatg   1080
ggtcgcctgg aggctcttgt cgccgtcgcc acaagcgaga acaaggagc cgccaagcta    1140 tttctg                                                              1146
```

<210> SEQ ID NO 56
<211> LENGTH: 382
<212> TYPE: PRT
<213> ORGANISM: Artificial Sequence
<220> FEATURE:
<223> OTHER INFORMATION: fungal gene

<400> SEQUENCE: 56

```
Met Phe Ala Ala Gly Gly Ser Pro Gln Phe Ala Ser Pro Met Ser Gly
  1               5                  10                  15

Thr Thr His Gly Phe Trp Glu Gly Lys Thr Ala Ala Arg Arg Leu Ser
             20                  25                  30

Val Pro Thr Ser Ser Asn Pro Phe Leu Ala Gln His Gly Asn Ala Tyr
         35                  40                  45

Pro Pro Gly Tyr His Asn Pro Val Gly Ala Pro Tyr Gln Asn Ala Ala
     50                  55                  60

Gly Val Phe Ala Ser Pro Thr Ser Thr His Tyr Ser Val Ser Arg Asp
 65                  70                  75                  80

Glu Gly Thr Leu Ser Ala Ala Glu Ala Glu Met Arg Arg Arg Thr Trp
                 85                  90                  95

His Pro Ser Ser Tyr Thr Gly Phe Pro Arg Pro Gly Thr Ser Gly Leu
            100                 105                 110

Asn Gln Tyr His Thr Pro Asp Asn Val Pro Ala Ser Phe Gly Ala Asn
        115                 120                 125

Gly Ser Thr Glu His Pro Pro Arg Leu Pro Gly Ile Glu Ser Phe Asp
    130                 135                 140

Lys Val Val Gln Arg Pro Met Thr Pro Thr Arg Lys Thr Ser Pro
145                 150                 155                 160

Met Gln Leu Asp Gly Gln His Arg Pro Pro Asn Pro Gly Phe Gly
                165                 170                 175

Ser Gly Phe Asn Tyr Thr Gln Pro Ala His Arg Pro Pro Pro Ile
            180                 185                 190

Ser Gly Pro Gly His Arg Arg Gly His Val Ser Trp Asp Met Ser Leu
    195                 200                 205

His His Asn Leu Thr Gly Leu Asp Ile Arg Asp Arg Arg Pro Ser Thr
        210                 215                 220

Ala Ser Ala Ser Gln Trp Ser Gln Gln Thr Leu Ala Glu Leu Gln Asn
225                 230                 235                 240

Val Ser Ser Arg Pro Ser Ser Tyr Gln Pro Ala Phe Gly Pro Thr
                245                 250                 255

Ala Glu Arg Ser Pro Glu Glu Tyr Arg Gly His Arg Pro Ser Leu Ser
            260                 265                 270

Thr Gly Ser Arg Thr Arg Thr Ser Pro Glu Asp Ser Ser Ser Ser Glu
        275                 280                 285
```

```
Gly Val His Thr Pro Ser Thr Ala Ser Leu Glu Tyr His Pro Ala Ile
        290                 295                 300

Val His Ser Ser Gly Tyr Ile Glu Ser Asp Ser Ser Leu Pro Ser
305                 310                 315                 320

Asp His Pro Gln Pro Ile Cys Gly Arg Gln Ser Ser His Ala Asp Gly
                325                 330                 335

Tyr Glu Pro His Asn Asp Arg Glu Pro Arg Pro Asp Val Phe Pro Asp
            340                 345                 350

Ser Pro Ala Arg Asn Ser Gly Met Gly Arg Leu Glu Ala Leu Val Ala
        355                 360                 365

Val Ala Thr Ser Glu Asn Lys Gly Ala Ala Lys Leu Phe Leu
    370                 375                 380

<210> SEQ ID NO 57
<211> LENGTH: 909
<212> TYPE: DNA
<213> ORGANISM: Artificial Sequence
<220> FEATURE:
<223> OTHER INFORMATION: fungal gene

<400> SEQUENCE: 57
aagacgatga gcgtgacggt tttgggcgtg acccaccatt tggtctcata ctacagtgtg    60
gaggacgtga tgcgcggcat cctcaaccca ccctcgatgg tggattccct acgctttatc   120
cgaccccgca ccgaactcac ccagaaacaa agcttccgtt ccccgatcga cgagctcgag   180
gccaacgccg tggaaaacca ggagccctcc cacgctgctc tataccggata tcgcccgcag   240 atgatggccc ctcccacgta cgccatgcca acccttcaa cgacttcta catgcacccc      300 agtccctacg ccgccacaca tccccgcag caaggcccga tccagggata ctcgatgggc    360
gccccgatgg cagcccaaac cgcgccaaac ccatacctgc aagcccagg ccaaaccgcc    420 atcccaccga agcaggaaga ctaccacgca ttccgcgcag ggccttatgg cggcagcatg    480
gactccatga gcgcacacag catggcctcc atcccgggca gcatcaacgc ggggctgtcc    540
agctcactca cgaacgaaa cagatccacc tcggatcaca gccttccgc ttaccgcaat      600 tcttccatct cttcgcgcag ccaggccact gacgctactt cccccatgga tccatcaaca    660
ccggccacct actcccgcgg cagcttcagc atgtccggtc aactggagaa cccacatcca    720
gcactcgatc gcaacatgcc tggtctggat gctagcgttc gtcgcgagtc aaatcctatt    780
catccgtcct actacactgc ggatcgctcc cagtactatg tacccgcgcc ttacgctgcc    840
acgcaaccta tgtcgacatg gacgactacg gcggcgacgc aaccacagat ggcgcaacct    900
caaatctaa                                                           909

<210> SEQ ID NO 58
<211> LENGTH: 302
<212> TYPE: PRT
<213> ORGANISM: Artificial Sequence
<220> FEATURE:
<223> OTHER INFORMATION: fungal gene

<400> SEQUENCE: 58

Lys Thr Met Ser Val Thr Val Leu Gly Val Thr His His Leu Val Ser
1               5                   10                  15

Tyr Tyr Ser Val Glu Asp Val Met Arg Gly Ile Leu Asn Pro Pro Ser
            20                  25                  30

Met Val Asp Ser Leu Arg Phe Ile Arg Pro Arg Thr Glu Leu Thr Gln
        35                  40                  45
```

```
Lys Gln Ser Phe Arg Ser Pro Ile Asp Glu Leu Glu Ala Asn Ala Val
 50                  55                  60

Glu Asn Gln Glu Pro Ser His Ala Ala Leu Tyr Gly Tyr Arg Pro Gln
 65                  70                  75                  80

Met Met Ala Pro Pro Thr Tyr Ala Met Pro Thr Pro Ser Asn Asp Phe
                 85                  90                  95

Tyr Met His Pro Ser Pro Tyr Ala Ala Thr His Pro Pro Gln Gln Gly
                100                 105                 110

Pro Ile Gln Gly Tyr Ser Met Gly Ala Pro Met Ala Ala Gln Thr Ala
                115                 120                 125

Pro Asn Pro Tyr Leu Pro Ser Pro Gly Gln Thr Ala Ile Pro Pro Lys
130                 135                 140

Gln Glu Asp Tyr His Ala Phe Arg Ala Gly Pro Tyr Gly Gly Ser Met
145                 150                 155                 160

Asp Ser Met Ser Ala His Ser Met Ala Ser Ile Pro Gly Ser Ile Asn
                165                 170                 175

Ala Gly Leu Ser Ser Ser Leu Asn Glu Arg Asn Arg Ser Thr Ser Asp
                180                 185                 190

His Ser Pro Ser Ala Tyr Arg Asn Ser Ser Ile Ser Ser Arg Ser Gln
                195                 200                 205

Ala Thr Asp Ala Thr Ser Pro Met Asp Pro Ser Thr Pro Ala Thr Tyr
210                 215                 220

Ser Arg Gly Ser Phe Ser Met Ser Gly Gln Leu Glu Asn Pro His Pro
225                 230                 235                 240

Ala Leu Asp Arg Asn Met Pro Gly Leu Asp Ala Ser Val Arg Arg Glu
                245                 250                 255

Ser Asn Pro Ile His Pro Ser Tyr Tyr Thr Ala Asp Arg Ser Gln Tyr
                260                 265                 270

Tyr Val Pro Ala Pro Tyr Ala Ala Thr Gln Pro Met Ser Thr Trp Thr
                275                 280                 285

Thr Thr Ala Ala Thr Gln Pro Gln Met Ala Gln Pro Gln Ile
290                 295                 300
```

<210> SEQ ID NO 59
<211> LENGTH: 918
<212> TYPE: DNA
<213> ORGANISM: Artificial Sequence
<220> FEATURE:
<223> OTHER INFORMATION: fungal gene

<400> SEQUENCE: 59

```
atggctccag gcagtgggcg cgactttaac tgctcatggg agcattgtgg aaagtctttc      60
aatcgcaagt cggatctctg tcgccattat cgcatccata ccaatgagcg cccgtatcat     120
tgcaccgtaa aggactgcaa taagagcttc attcagcgga gtgccttgac cgtacactcg     180
aggacccaca ctggcgaaaa gccccatgtt tgtgaccatg aaggctgtca gaaggcattc     240
tccgactcat cgagtctagc tcgccatcgc gaatccaca ccgggaagcg gccatacata     300
tgccacgagc ctacatgcga acggagtttt tgtcgcaaga ccaccctcac caaacaccaa     360
caccgctccc accctccagg gagcttgacc cgaccatcct cagaagatgg acctccgag     420
cattcttacc accaaacacc cgtatcagtc tcggtcccga ctgagcagta catgctcgcc     480
cagcaacctt tttacccgca atcggcgaca ccaagtcatg agtttttactc gccccaaagt     540
gtgccgatgg gcaccgtgcc ggttcacgaa gctgcccctc cgatcgtggc ccagactgtc     600
```

```
cccggaacct cgccggtaaa catgccacac gctcaacagc cgcagccgca cccgcaacac    660
cacgcgcatc cacaacagca gcagcagcag cagcagcagc agcatcaaca atacttacaa    720
atgatgcaac agcgttacga cagtccacgg gcgaactacc tcccagaaca ataccaacat    780
ccatcttttc aaggccacca actgcctccc gaacagccaa tgatggtttc ataccaccca    840
aactatgcgt ataaaccccc cggctcccgt ctcttgaacc aagcggaggg gactgactgg    900
ggctttctgg gagtaggc                                                   918
```

<210> SEQ ID NO 60
<211> LENGTH: 306
<212> TYPE: PRT
<213> ORGANISM: Artificial Sequence
<220> FEATURE:
<223> OTHER INFORMATION: fungal gene

<400> SEQUENCE: 60

```
Met Ala Pro Gly Ser Gly Arg Asp Phe Asn Cys Ser Trp Glu His Cys
 1               5                  10                  15

Gly Lys Ser Phe Asn Arg Lys Ser Asp Leu Cys Arg His Tyr Arg Ile
            20                  25                  30

His Thr Asn Glu Arg Pro Tyr His Cys Thr Val Lys Asp Cys Asn Lys
        35                  40                  45

Ser Phe Ile Gln Arg Ser Ala Leu Thr Val His Ser Arg Thr His Thr
    50                  55                  60

Gly Glu Lys Pro His Val Cys Asp His Glu Gly Cys Gln Lys Ala Phe
65                  70                  75                  80

Ser Asp Ser Ser Ser Leu Ala Arg His Arg Arg Ile His Thr Gly Lys
                85                  90                  95

Arg Pro Tyr Ile Cys His Glu Pro Thr Cys Glu Arg Ser Phe Cys Arg
            100                 105                 110

Lys Thr Thr Leu Thr Lys His Gln His Arg Ser His Pro Pro Gly Ser
        115                 120                 125

Leu Thr Arg Pro Ser Ser Glu Asp Gly Thr Ser Glu His Ser Tyr His
    130                 135                 140

Gln Thr Pro Val Ser Val Ser Val Pro Thr Glu Gln Tyr Met Leu Ala
145                 150                 155                 160

Gln Gln Pro Phe Tyr Pro Gln Ser Ala Thr Pro Ser His Glu Phe Tyr
                165                 170                 175

Ser Pro Gln Ser Val Pro Met Gly Thr Val Pro Val His Glu Ala Ala
            180                 185                 190

Pro Pro Ile Val Ala Gln Thr Val Pro Gly Thr Ser Pro Val Asn Met
        195                 200                 205

Pro His Ala Gln Gln Pro Gln Pro His Pro Gln His His Ala His Pro
    210                 215                 220

Gln Gln Gln Gln Gln Gln Gln Gln Gln His Gln Gln Tyr Leu Gln
225                 230                 235                 240

Met Met Gln Gln Arg Tyr Asp Ser Pro Arg Ala Asn Tyr Leu Pro Glu
                245                 250                 255

Gln Tyr Gln His Pro Ser Phe Gln Gly His Gln Leu Pro Pro Glu Gln
            260                 265                 270

Pro Met Met Val Ser Tyr His Pro Asn Tyr Ala Tyr Lys Pro Pro Gly
        275                 280                 285

Ser Arg Leu Leu Asn Gln Ala Glu Gly Thr Asp Trp Gly Phe Leu Gly
    290                 295                 300
```

Val Gly
305

<210> SEQ ID NO 61
<211> LENGTH: 1095
<212> TYPE: DNA
<213> ORGANISM: Artificial Sequence
<220> FEATURE:
<223> OTHER INFORMATION: fungal gene

<400> SEQUENCE: 61

```
atggataccc attcggatac cgacttgagt catcctcgaa tgcgcggagc tattgaactg      60
ccccgctcc gcgatcattt caagcaggaa tctcttccgc cgtttacgcc tcgtcctcgc     120
gagcttcttc catccatcct caatcactcc ccgcccggtc gctcatccac attgccgcca    180
atccagcgga gagacaaatt ttcccgcccg cgcaaatctt ccatcactca atctgcgcgg    240
aaatccaggc aggatcgccc taaatcaaag gaattcgggc ggcgaccaag tctcggtgac    300
cgcaaagccc tttcggcaga ccgcaaacc gcggcctggg cgcaaggcaa cgctgggag     360
gatctgattg aagccgcgac atcagcaacc gaagtagacg atgagccgta ttcagaggct    420
ggtcggtctc caacgattgc cccactactt tccaacgtga cgtctgcccc ctctggggtg    480
aaaaatcggt cctcgctacc acccgctttc caatcctcgg gattgcctcc tatctcttca    540
catcggccat tcccacctca ttcatacgcc gcctcgcctt tgcacaagtc attgacccca    600
ccaccatacg agaaccaccg cagccgtgag agcgacttgg aaccattccc gtctattgaa    660
tcatcgctcg attccatgtc ttcggcatcc ggcagaaatt ttgcgtcatc ggtttcggga    720
gtcgcgccgt ccataaactc tgattccagc ccagttatga atcttatccc gcccatctcg    780
cagcgccagc accaccgatt ctccaatcct actccagcgt ctttccgcaa caaagaggtt    840
caggtgtttt gtgctcagtg caaacgacct tcggcactga atgagtgcta tgcctgtacg    900
gagtgcatct gtggagtctg ccgcgactgc gtgagcatgt tcatttcaag tccgcctact    960
tcattccgaa ccccagggaa cgggtcgtta ataccgtcc tgtcacaagg accaacaagt    1020
taccctggtc ctcaagggtg tccacgatgt cgaacagttg gaggcaaatg gaaggcattc    1080
caaatcgaca tcaag                                                    1095
```

<210> SEQ ID NO 62
<211> LENGTH: 365
<212> TYPE: PRT
<213> ORGANISM: Artificial Sequence
<220> FEATURE:
<223> OTHER INFORMATION: fungal gene

<400> SEQUENCE: 62

```
Met Asp Thr His Ser Asp Thr Asp Leu Ser His Pro Arg Met Arg Gly
  1               5                  10                  15

Ala Ile Glu Leu Pro Pro Leu Arg Asp His Phe Lys Gln Glu Ser Leu
             20                  25                  30

Pro Pro Phe Thr Pro Arg Pro Arg Glu Leu Leu Pro Ser Ile Leu Asn
         35                  40                  45

His Ser Pro Pro Gly Arg Ser Ser Thr Leu Pro Pro Ile Gln Arg Arg
     50                  55                  60

Asp Lys Phe Ser Arg Pro Arg Lys Ser Ser Ile Thr Gln Ser Ala Arg
 65                  70                  75                  80

Lys Ser Arg Gln Asp Arg Pro Lys Ser Lys Glu Phe Gly Arg Arg Pro
                 85                  90                  95
```

```
Ser Leu Gly Asp Arg Lys Ala Leu Ser Ala Glu Pro Gln Thr Ala Ala
            100                 105                 110
Trp Ala Gln Gly Lys Arg Trp Glu Asp Leu Ile Glu Ala Ala Thr Ser
        115                 120                 125
Ala Thr Glu Val Asp Asp Glu Pro Tyr Ser Glu Ala Gly Arg Ser Pro
    130                 135                 140
Thr Ile Ala Pro Leu Leu Ser Asn Val Thr Ser Ala Pro Ser Gly Val
145                 150                 155                 160
Lys Asn Arg Ser Ser Leu Pro Pro Ala Phe Gln Ser Ser Gly Leu Pro
                165                 170                 175
Pro Ile Ser Ser His Arg Pro Phe Pro Pro His Ser Tyr Ala Ala Ser
            180                 185                 190
Pro Leu His Lys Ser Leu Thr Pro Pro Tyr Glu Asn His Arg Ser
        195                 200                 205
Arg Glu Ser Asp Leu Glu Pro Phe Pro Ser Ile Glu Ser Ser Leu Asp
    210                 215                 220
Ser Met Ser Ser Ala Ser Gly Arg Asn Phe Ala Ser Val Ser Gly
225                 230                 235                 240
Val Ala Pro Ser Ile Asn Ser Asp Ser Ser Pro Val Met Asn Leu Ile
                245                 250                 255
Pro Pro Ile Ser Gln Arg Gln His His Arg Phe Ser Asn Pro Thr Pro
            260                 265                 270
Ala Ser Phe Arg Asn Lys Glu Val Gln Val Phe Cys Ala Gln Cys Lys
        275                 280                 285
Arg Pro Ser Ala Leu Asn Glu Cys Tyr Ala Cys Thr Glu Cys Ile Cys
    290                 295                 300
Gly Val Cys Arg Asp Cys Val Ser Met Phe Ile Ser Ser Pro Pro Thr
305                 310                 315                 320
Ser Phe Arg Thr Pro Gly Asn Gly Ser Leu Asn Thr Val Leu Ser Gln
                325                 330                 335
Gly Pro Thr Ser Tyr Pro Gly Pro Gln Gly Cys Pro Arg Cys Arg Thr
            340                 345                 350
Val Gly Gly Lys Trp Lys Ala Phe Gln Ile Asp Ile Lys
        355                 360                 365

<210> SEQ ID NO 63
<211> LENGTH: 1197
<212> TYPE: DNA
<213> ORGANISM: Artificial Sequence
<220> FEATURE:
<223> OTHER INFORMATION: fungal gene

<400> SEQUENCE: 63
atgaagagcg aatcaggtgg ctcggacaac cctgtcaatg catacccctcc tcatggtcct      60 ccgcccatgc agatggatgc tggacttgcg gattccttct attatgcaca gcccacgggt     120 tcaaccccctc gaaacatggc ctatgccccct gcgggatacg ctggcgatcc ccagatgcag    180
caggaacctg tcccgcaggg aagagcaggg gttgaaccac cgccaaagac tttccactgc     240
tcaacctgca caagggcttt cgcacggcgc agtgaccttg ctcgacatga gcgtattcac     300
accggagtta gacccccatgc atgcgagtgg ccggggtgtg gaaagcagtt cattcaacgc    360
tcggctttaa cagtgcactc ccgtgtacac actggagaga agcctcatat gtgtgagaga     420
tgtggcaagc cctttagcga ctcgtcctcg ctgccagac atcgtcgcat tcactccggc      480
aagcgaccct acaaatgccc gtacgccaac tgtcagaaga ccttcacgcg ccgtacgacg     540
```

-continued

```
ttgacacgcc accaaaacca ccacactggg accatcgaag aagccgctgc tgaaaccgag        600
gcccaattgc ggcaaaataa ggatcgtgga cgtcctggtg aaggaatgtt ctccgagcac        660
gcttccatcc actctacacc gtcacccgcg cagcatccat ccatgtcacc tggtggcgag        720
cttcccccgc tgaatatgca tcgctcagct ggcgactact acatgggcac cggtcctatc        780
ccgcctcatg tgcgtgggga tttcccccaa ggcagccctc gggcttcccc gactgcgacc        840
tctccttcgc tgtccagcta tggcagtgcg ccccacaccc ggccatccat gacctcgcat        900
ccctacgctc cgcctcagcc tcttgaaccc ccggccaaca gtgatcaccg tcccaatagt        960
gtgaacggca gtccacacat gactagtctc ggatgggcct cgccgtctca cggtagcatg       1020
ccgtcgcccg gatcggccaa cgacttcact taccccgagc ccactggccc tgcgtacccg       1080
acatcgatgc cgccacacat gtacttcccc aattctacta ttcgtcggcc taccagcacc       1140
gagccggaga actacgaaat gaagcctcga ggtgaccact catggtccac tgctgta          1197
```

<210> SEQ ID NO 64
<211> LENGTH: 399
<212> TYPE: PRT
<213> ORGANISM: Artificial Sequence
<220> FEATURE:
<223> OTHER INFORMATION: fungal gene

<400> SEQUENCE: 64

```
Met Lys Ser Glu Ser Gly Gly Ser Asp Asn Pro Val Asn Ala Tyr Pro
 1               5                  10                  15

Pro His Gly Pro Pro Pro Met Gln Met Asp Ala Gly Leu Ala Asp Ser
                20                  25                  30

Phe Tyr Tyr Ala Gln Pro Thr Gly Ser Thr Pro Arg Asn Met Ala Tyr
            35                  40                  45

Ala Pro Ala Gly Tyr Ala Gly Asp Pro Gln Met Gln Gln Glu Pro Val
        50                  55                  60

Pro Gln Gly Arg Ala Gly Val Glu Pro Pro Lys Thr Phe His Cys
 65                  70                  75                  80

Ser Thr Cys Asn Lys Gly Phe Ala Arg Arg Ser Asp Leu Ala Arg His
                85                  90                  95

Glu Arg Ile His Thr Gly Val Arg Pro His Ala Cys Glu Trp Pro Gly
            100                 105                 110

Cys Gly Lys Gln Phe Ile Gln Arg Ser Ala Leu Thr Val His Ser Arg
        115                 120                 125

Val His Thr Gly Glu Lys Pro His Met Cys Glu Arg Cys Gly Lys Pro
    130                 135                 140

Phe Ser Asp Ser Ser Leu Ala Arg His Arg Arg Ile His Ser Gly
145                 150                 155                 160

Lys Arg Pro Tyr Lys Cys Pro Tyr Ala Asn Cys Gln Lys Thr Phe Thr
                165                 170                 175

Arg Arg Thr Thr Leu Thr Arg His Gln Asn His Thr Gly Thr Ile
            180                 185                 190

Glu Glu Ala Ala Ala Glu Thr Glu Ala Gln Leu Arg Gln Asn Lys Asp
        195                 200                 205

Arg Gly Arg Pro Gly Glu Gly Met Phe Ser Glu His Ala Ser Ile His
    210                 215                 220

Ser Thr Pro Ser Pro Ala Gln His Pro Ser Met Ser Pro Gly Gly Glu
225                 230                 235                 240

Leu Pro Pro Leu Asn Met His Arg Ser Ala Gly Asp Tyr Tyr Met Gly
                245                 250                 255
```

-continued

```
Thr Gly Pro Ile Pro Pro His Val Arg Gly Asp Phe Pro Gln Gly Ser
            260                 265                 270
Pro Arg Ala Ser Pro Thr Ala Thr Ser Pro Ser Leu Ser Ser Tyr Gly
        275                 280                 285
Ser Ala Pro His Thr Arg Pro Ser Met Thr Ser His Pro Tyr Ala Pro
    290                 295                 300
Pro Gln Pro Leu Glu Pro Pro Ala Asn Ser Asp His Arg Pro Asn Ser
305                 310                 315                 320
Val Asn Gly Ser Pro His Met Thr Ser Leu Gly Trp Ala Ser Pro Ser
                325                 330                 335
His Gly Ser Met Pro Ser Pro Gly Ser Ala Asn Asp Phe Thr Tyr Pro
            340                 345                 350
Glu Pro Thr Gly Pro Ala Tyr Pro Thr Ser Met Pro Pro His Met Tyr
        355                 360                 365
Phe Pro Asn Ser Thr Ile Arg Arg Pro Thr Ser Thr Glu Pro Glu Asn
    370                 375                 380
Tyr Glu Met Lys Pro Arg Gly Asp His Ser Trp Ser Thr Ala Val
385                 390                 395
```

```
<210> SEQ ID NO 65
<211> LENGTH: 1098
<212> TYPE: DNA
<213> ORGANISM: Artificial Sequence
<220> FEATURE:
<223> OTHER INFORMATION: fungal gene

<400> SEQUENCE: 65
atgtctaacg caaggcattg ggaacaagat aaagaggcaa ccgtgtacat cggaaacctt      60
gatgaacggg tctcggacag cctggtatgg gaattgatgc tgcaggttgg gcgcatcgtt     120
aacgtccatc tgcccaaaga ccgggtcacg cagttacacc aggggtatgg atttgttgag     180
ttcatcagcg aggaagatgc cgaatatgca tcgaagatca tgaacggaat ccgtctccat     240
ggcaagccta tcgtgttaa caaggcatcg gctgataagc aaaaaactgt ggaaattggc      300
gctgagctgt ttgtgggtaa tcttgatcct atggttgccg agcaggttct ctttgatacg     360
ttcagccggt ttggcaatct tgtcaatccg cctaaaattg cccgtgatga acaatcctc      420
tctaagggat atggatttgt ttcttttgcc gatttcgaat cctcggacgc ggctatcgcc     480
aacatgaatg ccagtacct gatgaacaaa caggtttctg tacagtatgc atacaagaag     540
gatgggaaag gcgagagaca tggtgatgaa gcagaacgaa tgctggcagc ccaggctcgc     600
aagcataatg cacagccacc cactcagcaa gctccgcagt tccctggcac tggcccgggc     660
gtatcatcaa cgccggccat gtcgaatggc gacatctctc gacccttgag cacagccccg     720
tcacaaacac ccgatgtagg tatgaatcgg ggtgtgaccc cagccatggc tccagctatg     780
cctccagctt tgccctacca gagtgcgcct cctccaatgc ttaccagac cgttcccct      840
ccaaaccgac atgtcccacc tcccgtcct tcactcaata cgccacctcc ggggctccca      900
gctcggcctc cgccttccca agctggctac ggcggcccac agacctttt accacctgga     960
ttcaatggtg caggccaacc gcccttcatc ccacaggctg cacctcccc tgggttgggg    1020
ccgcccggat ttggacctcc atctggggcc ccttcattgc caccgggctt ccaacagccc    1080
ggatacggag gcagtcgg                                                   1098
```

```
<210> SEQ ID NO 66
<211> LENGTH: 366
```

<212> TYPE: PRT
<213> ORGANISM: Artificial Sequence
<220> FEATURE:
<223> OTHER INFORMATION: fungal gene

<400> SEQUENCE: 66

```
Met Ser Asn Ala Arg His Trp Glu Gln Asp Lys Glu Ala Thr Val Tyr
 1               5                  10                  15

Ile Gly Asn Leu Asp Glu Arg Val Ser Asp Ser Leu Val Trp Glu Leu
             20                  25                  30

Met Leu Gln Val Gly Arg Ile Val Asn Val His Leu Pro Lys Asp Arg
         35                  40                  45

Val Thr Gln Leu His Gln Gly Tyr Gly Phe Val Glu Phe Ile Ser Glu
     50                  55                  60

Glu Asp Ala Glu Tyr Ala Ser Lys Ile Met Asn Gly Ile Arg Leu His
 65                  70                  75                  80

Gly Lys Pro Ile Arg Val Asn Lys Ala Ser Ala Asp Lys Gln Lys Thr
                 85                  90                  95

Val Glu Ile Gly Ala Glu Leu Phe Val Gly Asn Leu Asp Pro Met Val
            100                 105                 110

Ala Glu Gln Val Leu Phe Asp Thr Phe Ser Arg Phe Gly Asn Leu Val
        115                 120                 125

Asn Pro Pro Lys Ile Ala Arg Asp Asp Asn Asn Leu Ser Lys Gly Tyr
    130                 135                 140

Gly Phe Val Ser Phe Ala Asp Phe Glu Ser Ser Asp Ala Ala Ile Ala
145                 150                 155                 160

Asn Met Asn Gly Gln Tyr Leu Met Asn Lys Gln Val Ser Val Gln Tyr
                165                 170                 175

Ala Tyr Lys Lys Asp Gly Lys Gly Glu Arg His Gly Asp Glu Ala Glu
            180                 185                 190

Arg Met Leu Ala Ala Gln Ala Arg Lys His Asn Ala Gln Pro Pro Thr
        195                 200                 205

Gln Gln Ala Pro Gln Phe Pro Gly Thr Gly Pro Gly Val Ser Ser Thr
    210                 215                 220

Pro Ala Met Ser Asn Gly Asp Ile Ser Arg Pro Leu Ser Thr Ala Pro
225                 230                 235                 240

Ser Gln Thr Pro Asp Val Gly Met Asn Arg Gly Val Thr Pro Ala Met
                245                 250                 255

Ala Pro Ala Met Pro Pro Ala Leu Pro Tyr Gln Ser Ala Pro Pro Pro
            260                 265                 270

Met Pro Tyr Gln Thr Val Pro Pro Asn Arg His Val Pro Pro Pro
        275                 280                 285

Val Pro Ser Leu Asn Thr Pro Pro Gly Leu Pro Ala Arg Pro Pro
    290                 295                 300

Pro Ser Gln Ala Gly Tyr Gly Pro Gln Thr Phe Leu Pro Pro Gly
305                 310                 315                 320

Phe Asn Gly Ala Gly Gln Pro Pro Phe Ile Pro Gln Ala Ala Pro Pro
                325                 330                 335

Pro Gly Phe Gly Pro Pro Gly Phe Gly Pro Ser Gly Ala Pro Ser
            340                 345                 350

Leu Pro Pro Gly Phe Gln Gln Pro Gly Tyr Gly Ser Arg
        355                 360                 365
```

<210> SEQ ID NO 67
<211> LENGTH: 1077

-continued

<212> TYPE: DNA
<213> ORGANISM: Artificial Sequence
<220> FEATURE:
<223> OTHER INFORMATION: fungal gene

<400> SEQUENCE: 67

```
atggttcttc tcaaaaagca tttgaaagat gtcaaccgtg aggatcagag gcaaatgccg      60
aggcaacggc tgccatctat tcaagaaata tttggggaga cttttctggc gattccttca    120
aatccatcat atgcactgcc ttctcacacc agacatgccg ctccaccggc tttgccggct    180
gtgtatgaaa ttgcccattc aatcgaaggg gctccgtcaa atgagcaagg tttattaccc    240
aaaatttcaa cagtggagag atctttgggc attatctctc ccgtcaatga gctccagcat    300
ccggaggtaa tacgcccgga aaatccatcc ttctctccga acggttgttc tcttaacgaa    360
agccgtcgct tttcaaagca cccggaccta tctatacctc aaccgggttt attgtcatgc    420
gatcccatgg atttagcaca gccgtccttt gtcgaacctc caaatgtgtt tcatggattt    480
cccatcagga aataccaaa ctcgataccg cctcagccaa agcagttatg tctgccggaa    540
aaacgaacac cgagttctct tgatttcagt ctgttttta aggtgatcga dacagtcagc    600
gcacagacct tggctttcgt gcggtatcac tccgcaatga gtcagtcaga caaccatcaa    660
agatccctcc ctggactatc tatcactgag ataaatggcc tcctcagtca ggagcagcaa    720
aagcaggatg tcttgattta tattagggat gaacttgtgc gcttcgacca ataccaagcc    780
ttagcgcagc agaatactcg ggcagccgca tgtatggcgg gtgggctga ccgaggtctt    840
tgttcatcag tcactaaaca gagcaagacc cataaagtct ctaaacaaaa aagagaatgg    900
cacgggata tgctcttcg ttgtcatagc tgcaaccgtt ctgaaacacc agaatggcgt    960
cgtggtccgg acgcccccg aactctttgt aacgcctgtg gtttacatta tgcaaaattg   1020
tctcgacgaa cgggcaaatt tgtggcgttg acgatattg gcatcagggg caaaaca       1077
```

<210> SEQ ID NO 68
<211> LENGTH: 359
<212> TYPE: PRT
<213> ORGANISM: Artificial Sequence
<220> FEATURE:
<223> OTHER INFORMATION: fungal gene

<400> SEQUENCE: 68

```
Met Val Leu Leu Lys Lys His Leu Lys Asp Val Asn Arg Glu Asp Gln
 1               5                  10                  15

Arg Gln Met Pro Arg Gln Arg Leu Pro Ser Ile Gln Glu Ile Phe Gly
             20                  25                  30

Glu Thr Phe Leu Ala Ile Pro Ser Asn Pro Ser Tyr Ala Leu Pro Ser
         35                  40                  45

His Thr Arg His Ala Ala Pro Ala Leu Pro Ala Val Tyr Glu Ile
     50                  55                  60

Ala His Ser Ile Glu Gly Ala Pro Ser Asn Glu Gln Gly Leu Leu Pro
 65                  70                  75                  80

Lys Ile Ser Thr Val Glu Arg Ser Leu Gly Ile Ile Ser Pro Val Asn
                 85                  90                  95

Glu Leu Gln His Pro Glu Val Ile Arg Pro Glu Asn Pro Ser Phe Ser
            100                 105                 110

Pro Asn Gly Cys Ser Leu Asn Glu Ser Arg Arg Phe Ser Lys His Pro
        115                 120                 125

Asp Leu Ser Ile Pro Gln Pro Gly Leu Leu Ser Cys Asp Pro Met Asp
    130                 135                 140
```

```
Leu Ala Gln Pro Ser Phe Val Glu Pro Pro Asn Val Phe His Gly Phe
145                 150                 155                 160

Pro Ile Arg Lys Ile Pro Asn Ser Ile Pro Pro Gln Pro Lys Gln Leu
                165                 170                 175

Cys Leu Pro Glu Lys Arg Thr Pro Ser Ser Leu Asp Phe Ser Leu Phe
            180                 185                 190

Phe Lys Val Ile Glu Thr Val Ser Ala Gln Thr Leu Ala Phe Val Arg
        195                 200                 205

Tyr His Ser Ala Met Ser Gln Ser Asp Asn His Gln Arg Ser Leu Pro
    210                 215                 220

Gly Leu Ser Ile Thr Glu Ile Asn Gly Leu Leu Ser Gln Glu Gln Gln
225                 230                 235                 240

Lys Gln Asp Val Leu Ile Tyr Ile Arg Asp Glu Leu Val Arg Phe Asp
                245                 250                 255

Gln Tyr Gln Ala Leu Ala Gln Gln Asn Thr Arg Ala Ala Ala Cys Met
            260                 265                 270

Ala Gly Gly Ala Asp Arg Gly Leu Cys Ser Ser Val Thr Lys Gln Ser
        275                 280                 285

Lys Thr His Lys Val Ser Lys Gln Lys Arg Glu Trp His Gly Asp Ser
    290                 295                 300

Ala Leu Arg Cys His Ser Cys Asn Arg Ser Glu Thr Pro Glu Trp Arg
305                 310                 315                 320

Arg Gly Pro Asp Gly Pro Arg Thr Leu Cys Asn Ala Cys Gly Leu His
                325                 330                 335

Tyr Ala Lys Leu Ser Arg Arg Thr Gly Lys Phe Val Ala Leu Asp Asp
            340                 345                 350

Ile Gly Ile Arg Gly Lys Thr
        355
```

<210> SEQ ID NO 69
<211> LENGTH: 621
<212> TYPE: DNA
<213> ORGANISM: Artificial Sequence
<220> FEATURE:
<223> OTHER INFORMATION: fungal gene

<400> SEQUENCE: 69

```
atgtccggct acgaccagta caaccagggt ggctacggcc agcaaggtta tggccagcaa      60
ggttacggcc agccaggtta cggccagcca ggttacggtg gtcaaccagg ttacggtggc     120
cagggtcacg accaacagca acagtacggt cagccccaac atggctacgg ccagcaaggc     180
tacggccagc agggtggttc ttccgactac tacgccggcc agcaacacca gcagcagggt     240
tacggccagc agcagggtgg ctcttccgac tactacgctg ccagcaaca ccagcagcat     300
ggctacggcc agcacgacca gaaccgtcag ggtggctacg agcagcagca gcatggtgcc     360
cccgatgagg cccaggatgg cgagcgtggt attgctggtg ccctcgcagg tggtgccgcc     420
ggtggcttcg ctggccacaa ggtcaaccac ggtttccttg aacaatcgg cggagccatc     480
atcggtagca tcgctgaaga cgccgtcaag aagcaccgca actccgacaa ccagtctcct     540
cctcagtacg gtggcccccc tccttccaac agcggcagcg gtggctccat gatggatcag     600
ctcggtggct tcttcaagaa g                                               621
```

<210> SEQ ID NO 70
<211> LENGTH: 207
<212> TYPE: PRT

<213> ORGANISM: Artificial Sequence
<220> FEATURE:
<223> OTHER INFORMATION: fungal gene

<400> SEQUENCE: 70

```
Met Ser Gly Tyr Asp Gln Tyr Asn Gln Gly Tyr Gly Gln Gln Gly
 1               5                  10                  15

Tyr Gly Gln Gln Gly Tyr Gly Gln Pro Gly Tyr Gly Gln Pro Gly Tyr
                20                  25                  30

Gly Gly Gln Pro Gly Tyr Gly Gln Gly His Asp Gln Gln Gln
            35                  40                  45

Tyr Gly Gln Pro Gln His Gly Tyr Gln Gln Gly Tyr Gly Gln Gln
        50                  55                  60

Gly Gly Ser Ser Asp Tyr Tyr Ala Gly Gln His Gln Gln Gly
 65                  70                  75                  80

Tyr Gly Gln Gln Gln Gly Gly Ser Ser Asp Tyr Tyr Ala Gly Gln Gln
                85                  90                  95

His Gln Gln His Gly Tyr Gly Gln His Asp Gln Asn Arg Gln Gly Gly
                100                 105                 110

Tyr Glu Gln Gln Gln His Gly Ala Pro Asp Glu Ala Gln Asp Gly Glu
            115                 120                 125

Arg Gly Ile Ala Gly Ala Leu Ala Gly Ala Ala Gly Gly Phe Ala
    130                 135                 140

Gly His Lys Val Asn His Gly Phe Leu Gly Thr Ile Gly Gly Ala Ile
145                 150                 155                 160

Ile Gly Ser Ile Ala Glu Asp Ala Val Lys Lys His Arg Asn Ser Asp
                165                 170                 175

Asn Gln Ser Pro Pro Gln Tyr Gly Gly Pro Pro Pro Ser Asn Ser Gly
                180                 185                 190

Ser Gly Gly Ser Met Met Asp Gln Leu Gly Gly Phe Phe Lys Lys
            195                 200                 205
```

<210> SEQ ID NO 71
<211> LENGTH: 789
<212> TYPE: DNA
<213> ORGANISM: Artificial Sequence
<220> FEATURE:
<223> OTHER INFORMATION: fungal gene

<400> SEQUENCE: 71

| | |
|---|---|
| atgctgcacc tggttgcaat tacctccccc gacccggagt tcaattcaga tgcccgagaa | 60 |
| ttcttcactc gtcatatgag aattctcgag acatgctccg ccgcctggcc catgccggag | 120 |
| attcaggctc agatcgattc attaagactg gctttctccg ccgatatgca gcgtcctttc | 180 |
| gagttgaagc ccagtttccc atacggcagt ccctcggaac cctaccatcc cagtccacct | 240 |
| atggatgcgc actaccatcc gcacttgaat caaatccaat ccagagtgcg ttacaacccg | 300 |
| ctcccggcaa cccctccgat ttcggctggt gctgaagatt cgaagtccga cacatcttcc | 360 |
| cagatacaat ccctcgggat ggttgcccat cagccttcaa caactcatcc tctagatgcc | 420 |
| ccttcggtcg atgaaaatca ctgggacccg acccgaatca tcactcaatg ggacatggcc | 480 |
| ttctccgtga acccttctac cgtcagcaca aactccccac caatgcctat aaacaattca | 540 |
| gtaccgagtg tacaaaacgt tatgaacccc caatacccta tccaatacga cacccaac | 600 |
| aaagtgccct ctgtcacatc tacccactct ctctcgcctt cgcagttcca gacacctcca | 660 |
| gttgtgtttt cagcacgaga ctggcagcaa agtgttgcca gtgtgtatga tccacaaggg | 720 |

```
ctgaaacggc gatggaatta tccagttgat gctagctccg acaataatat gtccaagcgc    780
caaagagga                                                              789
```

<210> SEQ ID NO 72
<211> LENGTH: 263
<212> TYPE: PRT
<213> ORGANISM: Artificial Sequence
<220> FEATURE:
<223> OTHER INFORMATION: fungal gene

<400> SEQUENCE: 72

```
Met Leu His Leu Val Ala Ile Thr Ser Pro Asp Pro Glu Phe Asn Ser
 1               5                  10                  15

Asp Ala Arg Glu Phe Phe Thr Arg His Met Arg Ile Leu Glu Thr Cys
            20                  25                  30

Ser Ala Ala Trp Pro Met Pro Glu Ile Gln Ala Gln Ile Asp Ser Leu
        35                  40                  45

Arg Leu Ala Phe Ser Ala Asp Met Gln Arg Pro Phe Glu Leu Lys Pro
    50                  55                  60

Ser Phe Pro Tyr Gly Ser Pro Ser Glu Pro Tyr His Pro Ser Pro Pro
65                  70                  75                  80

Met Asp Ala His Tyr His Pro His Leu Asn Gln Ile Gln Ser Arg Val
                85                  90                  95

Arg Tyr Asn Pro Leu Pro Ala Thr Pro Pro Ile Ser Ala Gly Ala Glu
            100                 105                 110

Asp Ser Lys Ser Asp Thr Ser Ser Gln Ile Gln Ser Leu Gly Met Val
        115                 120                 125

Ala His Gln Pro Ser Thr Thr His Pro Leu Asp Ala Pro Ser Val Asp
    130                 135                 140

Glu Asn His Trp Asp Pro Thr Arg Ile Ile Thr Gln Trp Asp Met Ala
145                 150                 155                 160

Phe Ser Val Asn Pro Ser Thr Val Ser Thr Asn Ser Pro Pro Met Pro
                165                 170                 175

Ile Asn Asn Ser Val Pro Ser Val Gln Asn Val Met Asn Pro Gln Tyr
            180                 185                 190

Pro Ile Gln Tyr Glu Thr Pro Asn Lys Val Pro Ser Val Thr Ser Thr
        195                 200                 205

His Ser Leu Ser Pro Ser Gln Phe Gln Thr Pro Val Val Phe Ser
    210                 215                 220

Ala Arg Asp Trp Gln Gln Ser Val Ala Ser Val Tyr Asp Pro Gln Gly
225                 230                 235                 240

Leu Lys Arg Arg Trp Asn Tyr Pro Val Asp Ala Ser Ser Asp Asn Asn
                245                 250                 255

Met Ser Lys Arg Gln Arg Gly
            260
```

<210> SEQ ID NO 73
<211> LENGTH: 2745
<212> TYPE: DNA
<213> ORGANISM: Artificial Sequence
<220> FEATURE:
<223> OTHER INFORMATION: fungal gene

<400> SEQUENCE: 73

```
atggagccca acgaactttc cttcctgctc aagatggtcc agcgaacctc acaagagggc    60
cagccccggg caaacggcat cagcgatgtc gcaaccccgt atataggctc cgcacccgag   120
```

```
cacatcatgt cgttcgatat caaggatgtc gtcgacattg ccgttccaaa cgttaccaca    180
gctgaagttt cagccaagga accaaacggt gcttcccagg gtttcaggac agacagtgat    240
atctccggaa acctagccat gcgagaacgc accttgcagc gctgggaacc ggctgagact    300
gacattgata tgtcactcga aacgagcaat acttctgcgg gatgggatca gtttgaggca    360
aacgagcgtc ttttcggcgc caagaccaac tacgatgaga acatctacac cactcgcctg    420
gaccgttcgg atcccaacta caaacagaag caggcggagg cagctcggat cgcccgtgag    480
attgagggac aagatgtgga caactcccac atgcgcgagg agcgtggcct tgtagcaccc    540
gataccggtg accaagacga agaagacaag tacagtggtg ttcgccgcga agacaaagcc    600
ttccctcccc tgcttttccgg ccagccaaac aagtacatgc ccccggacg ccgacaggca    660 gccccacagt ctactgcgac tcccagtgca tccaccaaac agcctgttgc tccggttccc    720
accgctccta tccccatccc ctctcaggcc gtggcgaagg aaactacacc agcagaccag    780
caaactgagc tggtcgcctc tctgcaaccc acaacagata ccgagcagaa gagtgcctta    840
ggcaagggtg tcacaccgcc agtatctact gcatcccccg caccagctgg aaagcggact    900
gcacctgaaa atgcgaccgc aaacgtggag gtggaggtgc ttgatcactt ccggcagttc    960
gcaaatagcg agaaaatcaa gatgcaggag cgccgtcgca accaggcctc gtatgaccgg   1020
accatgaaac tcaatgagct gatgaagttt ccaagagct tcaaactctc cactccggtg   1080
ccgaaagatc ttgttcctat cctagccaag gaccgactaa agcaagaagc aatcatgcaa   1140
cgagcgctgc aacaagggga cgacaaggct acgccgaagg tcactacgcc tcccacagag   1200
caacaaccgc ctactcgtgg tgccggacct agtggagctg tgcccccatc cgcacccgct   1260
gatcgtcaaa actacaaccg cactcgtcag ggttatcctc cagctggtcc gctcgctggt   1320
gctggtggca gattccctca gcaagttcca ccgggacgtc ctggtgttgg catgctcagt   1380
caccgactag cggacaatct gcagcaacga aagggcgcgg gtatgggacc tgttcccact   1440
cctcttccca ttcaagatgc ccgtggaccc ccgactggtc ctgccagcga tcagcagaga   1500
atcaccagcc ctgtcaagtc gcaggccggg tcttctgcgg caaccaagtt taatgttaaa   1560
gctatggagt tcaagccaaa ccccgcagcg agcactttca cccctggtac ctcgggaact   1620
gccgcaagcc cacggccttt ctctcgcaac cgctccgtgt cacgcgccac aaccccgact   1680
gcgttctttg gctcaaggaa gccactgcct gtctccgaac gaccctcgat cagtgaccaa   1740
ttcaatccca tcaagcgcat gaagaaggag cacgcagaga ccgctgagag gttgattatg   1800
ctgaatggag gtatccccc accctacaag actttgccaa cttgggacat cgcggacggc   1860
agcgaagaga agacgtacga tgagatgttc aaacagcccg tcgccgttcc cacagtacca   1920
ccccagggtc ggtccgtctc taacaacacc aatattcccc agcaacatca ggtgcccttc   1980
cacttccagc aaggtaaccc agccatgccg ccatcttctg gcccttcgaa tggacctcat   2040
ggccttcatt ctcagggtcc ccatggcccc tccatgtgg atgatcatca ccgcatgcag   2100
ttatccgcgt cgaactccca ggttttcccg tcccgcgga tgcaacatgg atacccatcc   2160
cctatggctc cccatgccca gctttccttc ccacaaccgg tcccgcagtt ttacggcggg   2220
ccccaacctg gccatatcag acctttccag ggtggtggtc ctcagtttgt gaatggcgct   2280
cctatgatgg tgcagcaggc ctcgaatgga ccctacatgg gagtcccgca aggcatgtct   2340
ccctataacg cacagatgcc aatgtactcc ccgaacccag ccacgcccta tccccaacat   2400
acaccccagc ctcatagtgg gtacccaagc ccgagccgtg gtgcgcccat gatgatgcac   2460
cagaactcgc aatctggaca gcctcctcaa tcaatgatgt ttatgcccgg ccaacccggt   2520
```

-continued

```
taccctcagc agtcgggaca catgcctccc aaccgtggca actacccaca gcagcctcac    2580
ttttcctcaa gtccccatca atcgcatcat ttcccaccta accagcatcg acacccagc    2640 aacggtttca accaaatgcc tcaaatgcca ccccagatgc ctgccgctac cccagcaaca    2700 accccctggag cttctcaccc ggccgaggca acggatgaag gaaaa                  2745
```

<210> SEQ ID NO 74
<211> LENGTH: 915
<212> TYPE: PRT
<213> ORGANISM: Artificial Sequence
<220> FEATURE:
<223> OTHER INFORMATION: fungal gene

<400> SEQUENCE: 74

```
Met Glu Pro Asn Glu Leu Ser Phe Leu Leu Lys Met Val Gln Arg Thr
  1               5                  10                  15

Ser Gln Glu Gly Gln Pro Arg Ala Asn Gly Ile Ser Asp Val Ala Thr
             20                  25                  30

Pro Tyr Ile Gly Ser Ala Pro Glu His Ile Met Ser Phe Asp Ile Lys
         35                  40                  45

Asp Val Val Asp Ile Ala Val Pro Asn Val Thr Thr Ala Glu Val Ser
     50                  55                  60

Ala Lys Glu Pro Asn Gly Ala Ser Gln Gly Phe Arg Thr Asp Ser Asp
 65                  70                  75                  80

Ile Ser Gly Asn Leu Ala Met Arg Glu Arg Thr Leu Gln Arg Trp Glu
                 85                  90                  95

Pro Ala Glu Thr Asp Ile Asp Met Ser Leu Glu Thr Ser Asn Thr Ser
            100                 105                 110

Ala Gly Trp Asp Gln Phe Glu Ala Asn Glu Arg Leu Phe Gly Ala Lys
        115                 120                 125

Thr Asn Tyr Asp Glu Asn Ile Tyr Thr Thr Arg Leu Asp Arg Ser Asp
    130                 135                 140

Pro Asn Tyr Lys Gln Lys Gln Ala Glu Ala Ala Arg Ile Ala Arg Glu
145                 150                 155                 160

Ile Glu Gly Gln Asp Val Asp Asn Ser His Met Arg Glu Glu Arg Gly
                165                 170                 175

Leu Val Ala Pro Asp Thr Gly Asp Gln Asp Glu Asp Lys Tyr Ser
            180                 185                 190

Gly Val Arg Arg Glu Asp Lys Ala Phe Pro Pro Leu Leu Ser Gly Gln
        195                 200                 205

Pro Asn Lys Tyr Met Pro Pro Gly Arg Arg Gln Ala Ala Pro Gln Ser
    210                 215                 220

Thr Ala Thr Pro Ser Ala Ser Thr Lys Gln Pro Val Ala Pro Val Pro
225                 230                 235                 240

Thr Ala Pro Ile Pro Ile Pro Ser Gln Ala Val Ala Lys Glu Thr Thr
                245                 250                 255

Pro Ala Asp Gln Gln Thr Glu Leu Val Ala Ser Leu Gln Pro Thr Thr
            260                 265                 270

Asp Thr Glu Gln Lys Ser Ala Leu Gly Lys Gly Val Thr Pro Pro Val
        275                 280                 285

Ser Thr Ala Ser Pro Ala Pro Ala Gly Lys Arg Thr Ala Pro Glu Asn
    290                 295                 300

Ala Thr Ala Asn Val Glu Val Glu Val Leu Asp His Phe Arg Gln Phe
305                 310                 315                 320
```

-continued

```
Ala Asn Ser Glu Lys Ile Lys Met Gln Glu Arg Arg Asn Gln Ala
            325                 330                 335

Ser Tyr Asp Arg Thr Met Lys Leu Asn Glu Leu Met Lys Phe Ser Lys
            340                 345                 350

Ser Phe Lys Leu Ser Thr Pro Val Pro Lys Asp Leu Val Pro Ile Leu
            355                 360                 365

Ala Lys Asp Arg Leu Lys Gln Glu Ala Ile Met Gln Arg Ala Leu Gln
        370                 375                 380

Gln Gly Asp Asp Lys Ala Thr Pro Lys Val Thr Thr Pro Pro Thr Glu
385                 390                 395                 400

Gln Gln Pro Pro Thr Arg Gly Ala Gly Pro Ser Gly Ala Val Pro Pro
                    405                 410                 415

Ser Ala Pro Ala Asp Arg Gln Asn Tyr Asn Arg Thr Arg Gln Gly Tyr
                420                 425                 430

Pro Pro Ala Gly Pro Leu Ala Gly Ala Gly Arg Phe Pro Gln Gln
            435                 440                 445

Val Pro Pro Gly Arg Pro Gly Val Gly Met Leu Ser His Arg Leu Ala
    450                 455                 460

Asp Asn Leu Gln Gln Arg Lys Gly Ala Gly Met Gly Pro Val Pro Thr
465                 470                 475                 480

Pro Leu Pro Ile Gln Asp Ala Arg Gly Pro Pro Thr Gly Pro Ala Ser
                485                 490                 495

Asp Gln Gln Arg Ile Thr Ser Pro Val Lys Ser Gln Ala Gly Ser Ser
                500                 505                 510

Ala Ala Thr Lys Phe Asn Val Lys Ala Met Glu Phe Lys Pro Asn Pro
        515                 520                 525

Ala Ala Ser Thr Phe Thr Pro Gly Thr Ser Gly Thr Ala Ala Ser Pro
    530                 535                 540

Arg Pro Phe Ser Arg Asn Arg Ser Val Ser Arg Ala Thr Thr Pro Thr
545                 550                 555                 560

Ala Phe Phe Gly Ser Arg Lys Pro Leu Pro Val Ser Glu Arg Pro Ser
                565                 570                 575

Ile Ser Asp Gln Phe Asn Pro Ile Lys Arg Met Lys Lys Glu His Ala
                580                 585                 590

Glu Thr Ala Glu Arg Leu Ile Met Leu Asn Gly Gly Ile Pro Pro Pro
        595                 600                 605

Tyr Lys Thr Leu Pro Thr Trp Asp Ile Ala Asp Gly Ser Glu Glu Lys
    610                 615                 620

Thr Tyr Asp Glu Met Phe Lys Gln Pro Val Ala Val Pro Thr Val Pro
625                 630                 635                 640

Pro Gln Gly Arg Ser Val Ser Asn Asn Thr Asn Ile Pro Gln Gln His
                645                 650                 655

Gln Val Pro Phe His Phe Gln Gln Gly Asn Pro Ala Met Pro Pro Ser
                660                 665                 670

Ser Gly Pro Ser Asn Gly Pro His Gly Leu His Ser Gln Gly Pro His
            675                 680                 685

Gly Pro Ser His Val Asp Asp His His Arg Met Gln Leu Ser Ala Ser
            690                 695                 700

Asn Ser Gln Val Phe Pro Ser Pro Arg Met Gln His Gly Tyr Pro Ser
705                 710                 715                 720

Pro Met Ala Pro His Ala Gln Leu Ser Phe Pro Gln Pro Val Pro Gln
                725                 730                 735

Phe Tyr Gly Gly Pro Gln Pro Gly His Ile Arg Pro Phe Gln Gly Gly
```

```
                740                 745                 750
    Gly Pro Gln Phe Val Asn Gly Ala Pro Met Met Val Gln Gln Ala Ser
            755                 760                 765

Asn Gly Pro Tyr Met Gly Val Pro Gln Gly Met Ser Pro Tyr Asn Ala
            770                 775                 780

Gln Met Pro Met Tyr Ser Pro Asn Pro Gly His Ala Tyr Pro Gln His
    785                 790                 795                 800

Thr Pro Gln Pro His Ser Gly Tyr Pro Ser Pro Ser Arg Gly Ala Pro
                    805                 810                 815

Met Met Met His Gln Asn Ser Gln Ser Gly Gln Pro Pro Gln Ser Met
                820                 825                 830

Met Phe Met Pro Gly Gln Pro Gly Tyr Pro Gln Gln Ser Gly His Met
            835                 840                 845

Pro Pro Asn Arg Gly Asn Tyr Pro Gln Gln Pro His Phe Ser Ser Ser
    850                 855                 860

Pro His Gln Ser His His Phe Pro Pro Asn Gln His Arg Thr Pro Ser
    865                 870                 875                 880

Asn Gly Phe Asn Gln Met Pro Gln Met Pro Gln Met Pro Ala Ala
                    885                 890                 895

Thr Pro Ala Thr Thr Pro Gly Ala Ser His Pro Ala Glu Ala Thr Asp
                900                 905                 910

Glu Gly Lys
            915

<210> SEQ ID NO 75
<211> LENGTH: 1470
<212> TYPE: DNA
<213> ORGANISM: Artificial Sequence
<220> FEATURE:
<223> OTHER INFORMATION: fungal gene

<400> SEQUENCE: 75
atgggttttg ctcagaaaat cgccgcagct cagaatagcc agaacatggc taacagtggt      60
tcatatggag gtgcacctcc gtcaggatac actgggggtc ctcctgccgc tctgcagcct     120
ggtggatcga gccaacagcc ccaataccag gcttattcag atccccagc cccccaggga     180 tcggcaccac cctaccctac ccagggttcc ccgtaccccg gtggccaggg ccgtcctggt     240
ccctcaccag gaccaccaag cggaccgccg ccaggccaat atgcgcacc cggtggcgcc     300 cctccctccg catctccccc ggccactcag caacaggtcg cagcctaccg atcgcttttg     360
atttccgcga ttcaggagaa gaacctccaa agcttctacc ctcccgagcg actggaccga     420
ctcgttcagt cgcttgccgc tgaagcacca ggcaagctca ataggctgat tcatgaatgg     480
gccgtgccta tggaggttgc gaccgatgtc atgaagcttt cgctgtttga cgtggttctc     540
tatgttgatg acagtggatc tatcgaattc gaagagaagg gactccgaaa ggaccagctc     600
aaacaaattc tcggcatcgt agctactgcc gcatctacct ttgaccagga tggtatttct     660
gtccgattca tgaactccag cgagaagggc gatggcatcc gcaatgcaga ggatgtcgag     720
cgcctagtgt cccgagtccg ttttttcagg ctgacccctc tgggcaccag tctgaggagc     780
aaagtcatcg accccatggt tgttcaaccc gcccaggcca accgtctcga caagcccgtt     840
ctggtgatca ccatcaccga cggacagcct gctggcgagc tcatggtac cgtgggtgat     900 gtcattcgct acgcagtgga ggagacgtca cggaccgtt atggcccgg caccgtagcc     960 ttccagttct cgcaggtggg aactgatcag cgggctcgcg acttcttggg ctctctggat    1020
```

-continued

```
gaggaccctc atatcggcca tctgatcgac tgtacttcca actttgaggt tgagcaggat    1080
gagatgtcgc gtgctaaccc acccgtgcat ctcactcgcg agctttggtg ccccaaactg    1140
atgctcggcg ctatcgattc ttcttacgac accaaggatg agcgagagaa tcaacgtcgt    1200
ggtgcacccc caccaacagg ccagtacgga ggagggtacg ccaacctcc gccaccccag     1260 ggccaagctc agcctccgta tggtccgccc cctggtgccc caccggcttc gtacggttct    1320
cagccaggct acccaccgca gggccaatac aacagcctc cccagcagcc tccctaccag     1380
ggatcgcggg gtgggtatgg ccaacagcag ccacatgggt atggatcccc tggacctggc    1440
taccagtatg gtggacagcc gccacgctat                                     1470
```

<210> SEQ ID NO 76
<211> LENGTH: 490
<212> TYPE: PRT
<213> ORGANISM: Artificial Sequence
<220> FEATURE:
<223> OTHER INFORMATION: fungal gene

<400> SEQUENCE: 76

```
Met Gly Phe Ala Gln Lys Ile Ala Ala Gln Asn Ser Gln Asn Met
 1               5                  10                  15

Ala Asn Ser Gly Ser Tyr Gly Gly Ala Pro Pro Ser Gly Tyr Thr Gly
                20                  25                  30

Gly Pro Pro Ala Ala Leu Gln Pro Gly Gly Ser Ser Gln Gln Pro Gln
                35                  40                  45

Tyr Gln Ala Tyr Ser Gly Ser Pro Ala Pro Gln Gly Ser Ala Pro Pro
 50                  55                  60

Tyr Pro Thr Gln Gly Ser Pro Tyr Pro Gly Gly Gln Gly Arg Pro Gly
65                  70                  75                  80

Pro Ser Pro Gly Pro Pro Ser Gly Pro Pro Pro Gly Gln Tyr Gly Ala
                85                  90                  95

Pro Gly Gly Ala Pro Pro Ser Ala Ser Pro Pro Ala Thr Gln Gln Gln
                100                 105                 110

Val Ala Ala Tyr Arg Ser Leu Leu Ile Ser Ala Ile Gln Glu Lys Asn
                115                 120                 125

Leu Gln Ser Phe Tyr Pro Pro Glu Arg Leu Asp Arg Leu Val Gln Ser
130                 135                 140

Leu Ala Ala Glu Ala Pro Gly Lys Leu Asn Arg Leu Ile His Glu Trp
145                 150                 155                 160

Ala Val Pro Met Glu Val Ala Thr Asp Val Met Lys Leu Ser Leu Phe
                165                 170                 175

Asp Val Val Leu Tyr Val Asp Asp Ser Gly Ser Ile Glu Phe Glu Glu
                180                 185                 190

Lys Gly Leu Arg Lys Asp Gln Leu Lys Gln Ile Leu Gly Ile Val Ala
                195                 200                 205

Thr Ala Ala Ser Thr Phe Asp Gln Asp Gly Ile Ser Val Arg Phe Met
        210                 215                 220

Asn Ser Ser Glu Lys Gly Asp Gly Ile Arg Asn Ala Glu Asp Val Glu
225                 230                 235                 240

Arg Leu Val Ser Arg Val Arg Phe Ser Gly Leu Thr Pro Leu Gly Thr
                245                 250                 255

Ser Leu Arg Ser Lys Val Ile Asp Pro Met Val Val Gln Pro Ala Gln
                260                 265                 270

Ala Asn Arg Leu Asp Lys Pro Val Leu Val Ile Thr Ile Thr Asp Gly
                275                 280                 285
```

```
Gln Pro Ala Gly Glu Pro His Gly Thr Val Gly Asp Val Ile Arg Tyr
        290                 295                 300
Ala Val Glu Glu Thr Ser Arg Thr Arg Tyr Gly Pro Gly Thr Val Ala
305                 310                 315                 320
Phe Gln Phe Ser Gln Val Gly Thr Asp Gln Arg Ala Arg Asp Phe Leu
                325                 330                 335
Gly Ser Leu Asp Glu Asp Pro His Ile Gly His Leu Ile Asp Cys Thr
            340                 345                 350
Ser Asn Phe Glu Val Glu Gln Asp Glu Met Ser Arg Ala Asn Pro Pro
        355                 360                 365
Val His Leu Thr Arg Glu Leu Trp Cys Pro Lys Leu Met Leu Gly Ala
    370                 375                 380
Ile Asp Ser Ser Tyr Asp Thr Lys Asp Glu Arg Glu Asn Gln Arg Arg
385                 390                 395                 400
Gly Ala Pro Pro Thr Gly Gln Tyr Gly Gly Tyr Gly Gln Pro
                405                 410                 415
Pro Pro Pro Gln Gly Gln Ala Gln Pro Pro Tyr Gly Pro Pro Pro Gly
                420                 425                 430
Ala Pro Pro Ala Ser Tyr Gly Ser Gln Pro Gly Tyr Pro Pro Gln Gly
            435                 440                 445
Gln Tyr Gln Gln Pro Pro Gln Gly Pro Pro Tyr Gln Gly Ser Arg Gly
        450                 455                 460
Gly Tyr Gly Gln Gln Pro His Gly Tyr Gly Ser Pro Gly Pro Gly
465                 470                 475                 480
Tyr Gln Tyr Gly Gly Gln Pro Pro Arg Tyr
                485                 490

<210> SEQ ID NO 77
<211> LENGTH: 1215
<212> TYPE: DNA
<213> ORGANISM: Artificial Sequence
<220> FEATURE:
<223> OTHER INFORMATION: fungal gene

<400> SEQUENCE: 77
atgcaaagcc cccagcagcc acccgacttt ctactgtacc cgactcagtc cacgcgtggg      60
agcaaaatga tcgccttgga ttcgtcccgc cagcagcaga ccccattctt ccagaatttc     120
accatggatc ctgcattcac ggacccttc gcattccagg tggacacctt cgctagcttc      180
ggacagcccg ccagttcctc tcgaggcccc cagacttcat attatgatac ccctccgctc     240
tacacggatt cttactccga ctccaataag accgcccctg ggtttccttc catgccgggt     300 acgccccga cgcttccctc cacccagccg ctggactccc acgttccggg cctgaccgcc      360
ccgtcgggtc cgtctgtcgc cagcgcctcc tcctcggcca ttgggtcgcc gtactccggc     420
acggcccatg ccaaccagga gaactgggtc gatacgaacc acggcctggg ccttcccgcc     480
gcggtgatgg gggatctgtt tccgaacgac tacacgggga cgaccctgga ccccgattac     540
tttgccaata aggcgcgga cagctttgtt gaccttctt tgatcccgct tcagcagcag      600
tcgaatctgt cgaccccggc catctcctac ccggaacaga ctgattatag cctggtcccc     660
ggcggattct tccctcagtc ccctgaccct tcccaattcc aatttgcgga ccccatggt      720 ccattcacac agcagccatg ccccatgccc gcctcatccc catctctgat gccctcccat     780
gtcccgcccc gtcgtctctc cctctacgac cgtcggtcct cggtctcttc cgtgcagtcc     840
cgtcgctcgc agctgagccc ggcggccagc aacgccgaga tcgaggagga cgccaaggaa     900
```

```
aagggccgat gccctcatcc ggattgcggt cgagtcttcc gggacctgaa agcgcacatg    960
ctgacgcatc agtcggagcg tccggagaaa tgccccattg tcacttgcga gtaccacacc   1020
aaggggtttg cccgcaagta cgacaagaac cgccacaccc tgacccacta caagggaacg   1080
atggtttgcg gcttctgccc gggatccggg tcgccggccg agaagagctt caaccgggcg   1140
gatgtgttca acgtcatct gacctctgtg cacggtgtgg aacagacccc tcccaactgc   1200
cggaagagaa gcccc                                                    1215
```

<210> SEQ ID NO 78
<211> LENGTH: 405
<212> TYPE: PRT
<213> ORGANISM: Artificial Sequence
<220> FEATURE:
<223> OTHER INFORMATION: fungal gene

<400> SEQUENCE: 78

```
Met Gln Ser Pro Gln Gln Pro Asp Phe Leu Leu Tyr Pro Thr Gln
 1               5                  10                  15

Ser Thr Arg Gly Ser Lys Met Ile Ala Leu Asp Ser Ser Arg Gln Gln
                20                  25                  30

Gln Thr Pro Phe Phe Gln Asn Phe Thr Met Asp Pro Ala Phe Thr Asp
            35                  40                  45

Pro Phe Ala Phe Gln Val Asp Thr Phe Ala Ser Phe Gly Gln Pro Ala
        50                  55                  60

Ser Ser Ser Arg Gly Pro Gln Thr Ser Tyr Tyr Asp Thr Pro Pro Leu
65                  70                  75                  80

Tyr Thr Asp Ser Tyr Ser Asp Ser Asn Lys Thr Ala Pro Gly Phe Pro
                85                  90                  95

Ser Met Pro Gly Thr Pro Pro Thr Leu Pro Ser Thr Gln Pro Leu Asp
            100                 105                 110

Ser His Val Pro Gly Leu Thr Ala Pro Ser Gly Pro Ser Val Ala Ser
        115                 120                 125

Ala Ser Ser Ala Ile Gly Ser Pro Tyr Ser Gly Thr Ala His Ala
    130                 135                 140

Asn Gln Glu Asn Trp Val Asp Thr Asn His Gly Leu Gly Leu Pro Ala
145                 150                 155                 160

Ala Val Met Gly Asp Leu Phe Pro Asn Asp Tyr Thr Gly Thr Thr Leu
                165                 170                 175

Asp Pro Asp Tyr Phe Ala Asn Lys Gly Ala Asp Ser Phe Val Asp Pro
            180                 185                 190

Ser Leu Ile Pro Leu Gln Gln Gln Ser Asn Leu Ser Thr Pro Ala Ile
        195                 200                 205

Ser Tyr Pro Glu Gln Thr Asp Tyr Ser Leu Val Pro Gly Gly Phe Phe
    210                 215                 220

Pro Gln Ser Pro Asp Pro Ser Gln Phe Gln Phe Ala Asp Pro Tyr Gly
225                 230                 235                 240

Pro Phe Thr Gln Gln Pro Cys Pro Met Pro Ala Ser Ser Pro Ser Leu
                245                 250                 255

Met Pro Ser His Val Pro Pro Arg Arg Leu Ser Leu Tyr Asp Arg Arg
            260                 265                 270

Ser Ser Val Ser Ser Val Gln Ser Arg Arg Ser Gln Leu Ser Pro Ala
        275                 280                 285

Ala Ser Asn Ala Glu Ile Glu Glu Asp Ala Lys Glu Lys Gly Arg Cys
    290                 295                 300
```

```
Pro His Pro Asp Cys Gly Arg Val Phe Arg Asp Leu Lys Ala His Met
305                 310                 315                 320

Leu Thr His Gln Ser Glu Arg Pro Glu Lys Cys Pro Ile Val Thr Cys
            325                 330                 335

Glu Tyr His Thr Lys Gly Phe Ala Arg Lys Tyr Asp Lys Asn Arg His
            340                 345                 350

Thr Leu Thr His Tyr Lys Gly Thr Met Val Cys Gly Phe Cys Pro Gly
        355                 360                 365

Ser Gly Ser Pro Ala Glu Lys Ser Phe Asn Arg Ala Asp Val Phe Lys
    370                 375                 380

Arg His Leu Thr Ser Val His Gly Val Glu Gln Thr Pro Pro Asn Cys
385                 390                 395                 400

Arg Lys Arg Ser Pro
            405

<210> SEQ ID NO 79
<211> LENGTH: 1389
<212> TYPE: DNA
<213> ORGANISM: Artificial Sequence
<220> FEATURE:
<223> OTHER INFORMATION: fungal gene

<400> SEQUENCE: 79
atggagacgt actacggcca tgtccgcact cctgcggacg ccatcatcct cttcgaggcc      60
tgtcgcattg gtcttctccc tcgcgtccag cgtcgactgt ccgagaaaga acggcagttg     120
atccgctctg ggtccgtctt tgtctgggat gagcgagaag ccggcatgcg ccgctggacg     180
gacggcaagt cctggagcgc cagtcgcgtg tctggcagct ttctcacgta tcgcgagatg     240
gaaggcaagc gaggaggcac cggagtatcg cagagcacca ttccgcgagc cgggaaaact     300
cccgagagca cccgcggcag tgacgacgac cgcggcgatg cgcagacga aggccccgat      360
ggctaccgat ataagcccga cggcttgatg aagcagtcct tcagtatcac cacctccgcc     420
ggccaacacc tccatctcat cagctactac tcgcgctccc atccgtccgc cgccaacctg     480
caacagccca ccaacgatcc caccctgcgc catgttcgac cccagaaagg cctctatccc     540
gaatccacgg tcaacgacca gcagaacctg ccgtcgtga ctcgcggccc catgggcggt      600
gcttactccg tccaccaccc catgcctccc tacgctcgct ccggcgccac gcatccgcaa     660
tcatacactc cgcccctatgc ctggcccccg acgccgctgg ccaccccgcc cgtcaccgtc    720
cattactcgc ataccctccc gccggtgtcg ggcgccaacg ccaactcta cgctcatcat     780
catcaacccc cgcacgccgg gctgccgccc cgcccccgc cgcagccagg cctgtccgcc     840
gcctacgaac gccccgtgca ccctatcgag agcgctatcg cgccgcccgc catccatgcc     900
tccggcgtcc accatcctgc gctccctgtg atccgcggcc gctccccgcg tctcgtcgcc     960
gacgcccacg acgtccacca gcgcagcccg ccgcctacg cggccaccga ccccgccgc      1020
gcctctccgc gcacccaacc gcccccatc ccgcaacaa acggctacgg cccggccgca     1080
cgcagcccag ccacgctgac ccagccgccg ccgccaccgc cgccgccgcc gcagcagcag     1140
cagcctccat cgacatcggc tcaaatcccg ccgcccaagc tcgccgaacc ctccaccacg     1200
gggaccacgt acccagcat cggggccctg atgaacggcg ccgcagccgg cggcggcctg      1260
ccctccatca cggccacggc agcgtcgacc ggccgcgccg acgggcccg cgatatcccc     1320
agcgagaaga tcgggttcgg cggcgaggat atgcgcgcgc tccgacaatt ggaccgcgtg     1380
ttcacggcg                                                           1389
```

<210> SEQ ID NO 80
<211> LENGTH: 463
<212> TYPE: PRT
<213> ORGANISM: Artificial Sequence
<220> FEATURE:
<223> OTHER INFORMATION: fungal gene

<400> SEQUENCE: 80

```
Met Glu Thr Tyr Tyr Gly His Val Arg Thr Pro Ala Asp Ala Ile Ile
1               5                   10                  15

Leu Phe Glu Ala Cys Arg Ile Gly Leu Leu Pro Arg Val Gln Arg Arg
                20                  25                  30

Leu Ser Glu Lys Glu Arg Gln Leu Ile Arg Ser Gly Ser Val Phe Val
            35                  40                  45

Trp Asp Glu Arg Glu Ala Gly Met Arg Arg Trp Thr Asp Gly Lys Ser
        50                  55                  60

Trp Ser Ala Ser Arg Val Ser Gly Ser Phe Leu Thr Tyr Arg Glu Met
65                  70                  75                  80

Glu Gly Lys Arg Gly Gly Thr Gly Val Ser Gln Ser Thr Ile Pro Arg
                85                  90                  95

Ala Gly Lys Thr Pro Glu Ser Thr Arg Gly Ser Asp Asp Arg Gly
                100                 105                 110

Asp Gly Ala Asp Glu Gly Pro Asp Gly Tyr Arg Tyr Lys Pro Asp Gly
            115                 120                 125

Leu Met Lys Gln Ser Phe Ser Ile Thr Thr Ser Ala Gly Gln His Leu
        130                 135                 140

His Leu Ile Ser Tyr Tyr Ser Arg Ser His Pro Ser Ala Ala Asn Leu
145                 150                 155                 160

Gln Gln Pro Thr Asn Asp Pro Thr Leu Arg His Val Arg Pro Gln Lys
                165                 170                 175

Gly Leu Tyr Pro Glu Ser Thr Val Asn Asp Gln Asn Leu Pro Val
            180                 185                 190

Val Thr Arg Gly Pro Met Gly Gly Ala Tyr Ser Val His His Pro Met
        195                 200                 205

Pro Pro Tyr Ala Arg Ser Gly Ala Thr His Pro Gln Ser Tyr Thr Pro
    210                 215                 220

Pro Tyr Ala Trp Pro Pro Thr Pro Leu Ala Thr Pro Pro Val Thr Val
225                 230                 235                 240

His Tyr Ser Pro Tyr Leu Pro Pro Val Ser Gly Ala Asn Gly Gln Leu
                245                 250                 255

Tyr Ala His His His Gln Pro Pro His Ala Gly Leu Pro Pro Pro
            260                 265                 270

Pro Pro Gln Pro Gly Leu Ser Ala Ala Tyr Glu Arg Pro Val His Pro
        275                 280                 285

Ile Glu Ser Ala Ile Ala Pro Pro Ala Ile His Ala Ser Gly Val His
    290                 295                 300

His Pro Ala Leu Pro Val Ile Ala Gly Arg Ser Pro Arg Leu Val Ala
305                 310                 315                 320

Asp Ala His Asp Val His Gln Arg Ser Pro Ala Tyr Ala Ala Thr
                325                 330                 335

Asp Pro Arg Arg Ala Ser Pro Arg Thr Gln Pro Pro Ile Pro Ala
            340                 345                 350

Thr Asn Gly Tyr Gly Pro Ala Ala Arg Ser Pro Ala Thr Leu Thr Gln
        355                 360                 365
```

```
Pro Pro Pro Pro Pro Pro Pro Gln Gln Gln Pro Pro Ser
    370             375             380
Thr Ser Ala Gln Ile Pro Pro Lys Leu Ala Glu Pro Ser Thr Thr
385             390             395                 400
Gly Thr Thr Val Pro Ser Ile Gly Ala Leu Met Asn Gly Ala Ala Ala
                405             410             415
Gly Gly Gly Leu Pro Ser Ile Thr Ala Thr Ala Ser Thr Gly Arg
            420             425             430
Ala Asp Gly Pro Arg Asp Ile Pro Ser Glu Lys Ile Gly Phe Gly Gly
            435             440             445
Glu Asp Met Arg Ala Leu Arg Gln Leu Asp Arg Val Phe Thr Ala
    450             455             460

<210> SEQ ID NO 81
<211> LENGTH: 2055
<212> TYPE: DNA
<213> ORGANISM: Artificial Sequence
<220> FEATURE:
<223> OTHER INFORMATION: fungal gene

<400> SEQUENCE: 81
atgtcgtcgc caaggattc ccagtacgac acaacccttc ggcgccatcc ccgccggagg      60
gctgctttgt ccacttctcc tccatcttta cttaattctt ccaactgtcg atctgtcgac    120
tcgaacccct caaacccgct gttcagaaag agcgaaacct ttcatgcagc gagaaaccgt    180
cccaccccac gcgatcctcg tctcagcttg cctcttgcac cccgccgctc tcctacatct    240
cccgctgccc tcgaagccat cgcggccggc agagagcgca tgagcaagat cctcgatacc    300
ctcgacctcg ataccttcac tccctcggaa tccgttgatg aggaactccc cgtgccccgc    360
agtgtcttgc aacttcattt cgactctttg catatctcgg accctcccca gagtccgtcc    420
gtccgttcag ctcccaagaa gccgctccaa agagtcaacc atcacacttc cgacagcggt    480
ctcgggacct ctgtttgtag cgaagaagcg ctgtcttgta ccgaatccgc cgatctggac    540
tcgaacgccc ccatgtccgc ctcacatctt cggaaattgt cgcctgacgg ggtcgacaag    600
atagagcacc gtgtcttcta ccctcttctt atgaacacgc agttcgataa gttccacagc    660
actgttcgat atgccgctca aggggtcaag gacaatcgat tccgctgtct ccgtgacgtg    720
gaaaatttat tccgcaatcc attccctatt gaccatgtta atgagaagga ggaattttct    780
cttttcctga atcaggtggt cctgtgcctc gacgacactt ggcaccgcct cgatgaatcg    840
gaccgcacta tgcctggtga tgtcccgtac tcgaatgagt acatcctcga cctttacgat    900
caaatcgtcc gcttcaaggc gctctgtgag cgagcgaaac agactctctc gcagacggat    960
agcaacagtg ccacccccaa gttgcccaag ctcgtgttca aggcggcttt ggccaaaaca   1020
ggacgccagg cggaactggt cgctcagtcc gatgaccaga tgatgtcgct ccgcacgggt   1080
aaaccctacc aggagagcca ggtgccgagc atgaagcgtg gcctcagcct atgctcgacg   1140
gatggagagg gcgcccaccg atgcatggcc cgccgccgga agaacgaggc tcccatgaac   1200
atcaacactc cgtgcgactt ttgcgggcaa attttcgcga gaccctgtga cctcactaaa   1260
cacatgaaga cccacacacg cccgttcaag tgttcggtgc ctgagtgcaa gtactacacc   1320
tatggattcc cgactgaaaa ggagaaagac cgtcatttca acgacaagca caaccccgac   1380
ccggaaccgt acgaatgcga tctgggagga tgcaattatc gctctaagcg gttgagtaat   1440
ttgaagcagc ataaggagaa gaagcacggc tggcaatacg tccggaccaa gagcaacggc   1500
```

-continued

```
aagcgcaagg agaagggcaa gggcaagaaa gccagtcctc agtctactcc ggatactccc    1560
ggccttacca ctcccggcac cagcaccgcg cagtccttct cgactccgaa cactggaccc    1620
agtccgtccc ccccgcaggc agtctcccga cctctgccga ctaccgactt caactttgct    1680
gatcctccgt tgcccacccc ggttgcggac ttccaactgt tcaacgcgaa cagccccatg    1740
ggagggaacg gaagcgtgaa catgggttat gcggatttgg gctttccgga aatgactcgg    1800
tcaatggacg gcgacgtggt tcatatgaac aactttgaag acatgttcgc caacgtcaac    1860
aacccttacc tggatggact cagcgggggt tatcaagtcc ccagcggcta tgaagccggc    1920
aacattgact ttccggatct gggttatggc acggccgtgc ctccgtctgc ggtcttccac    1980
gaagaccaat tcctgccgga cgatcaac tgggaagaat cgccatgct taacggaatg     2040 gatacgatgt ccaag                                                    2055
```

<210> SEQ ID NO 82
<211> LENGTH: 685
<212> TYPE: PRT
<213> ORGANISM: Artificial Sequence
<220> FEATURE:
<223> OTHER INFORMATION: fungal gene

<400> SEQUENCE: 82

```
Met Ser Ser Pro Lys Asp Ser Gln Tyr Asp Thr Thr Leu Arg Arg His
 1               5                  10                  15

Pro Arg Arg Arg Ala Ala Leu Ser Thr Ser Pro Pro Ser Leu Leu Asn
            20                  25                  30

Ser Ser Asn Cys Arg Ser Val Asp Ser Asn Pro Ser Asn Pro Leu Phe
        35                  40                  45

Arg Lys Ser Glu Thr Phe His Ala Ala Arg Asn Arg Pro Thr Pro Arg
    50                  55                  60

Asp Pro Arg Leu Ser Leu Pro Leu Ala Pro Arg Arg Ser Pro Thr Ser
65                  70                  75                  80

Pro Ala Ala Leu Glu Ala Ile Ala Ala Gly Arg Glu Arg Met Ser Lys
                85                  90                  95

Ile Leu Asp Thr Leu Asp Leu Asp Thr Phe Thr Pro Ser Glu Ser Val
            100                 105                 110

Asp Glu Glu Leu Pro Val Pro Arg Ser Val Leu Gln Leu His Phe Asp
        115                 120                 125

Ser Leu His Ile Ser Asp Pro Pro Gln Ser Pro Ser Val Arg Ser Ala
    130                 135                 140

Pro Lys Lys Pro Leu Gln Arg Val Asn His His Thr Ser Asp Ser Gly
145                 150                 155                 160

Leu Gly Thr Ser Val Cys Ser Glu Glu Ala Leu Ser Cys Thr Glu Ser
                165                 170                 175

Ala Asp Leu Asp Ser Asn Ala Pro Met Ser Ala Ser His Leu Arg Lys
            180                 185                 190

Leu Ser Pro Asp Gly Val Asp Lys Ile Glu His Arg Val Phe Tyr Pro
        195                 200                 205

Leu Leu Met Asn Thr Gln Phe Asp Lys Phe His Ser Thr Val Arg Tyr
    210                 215                 220

Ala Ala Gln Gly Val Lys Asp Asn Arg Phe Arg Cys Leu Arg Asp Val
225                 230                 235                 240

Glu Asn Leu Phe Arg Asn Pro Phe Pro Ile Asp His Val Asn Glu Lys
                245                 250                 255

Glu Glu Phe Ser Leu Phe Leu Asn Gln Val Val Leu Cys Leu Asp Asp
```

```
                    260                 265                 270
Thr Trp His Arg Leu Asp Glu Ser Asp Arg Thr Met Pro Gly Asp Val
        275                 280                 285
Pro Tyr Ser Asn Glu Tyr Ile Leu Asp Leu Tyr Asp Gln Ile Val Arg
    290                 295                 300
Phe Lys Ala Leu Cys Glu Arg Ala Lys Gln Thr Leu Ser Gln Thr Asp
305                 310                 315                 320
Ser Asn Ser Ala Thr Pro Lys Leu Pro Lys Leu Val Phe Lys Gly Gly
                325                 330                 335
Leu Ala Lys Thr Gly Arg Gln Ala Glu Leu Val Ala Gln Ser Asp Asp
            340                 345                 350
Gln Met Met Ser Leu Arg Thr Gly Lys Pro Tyr Gln Glu Ser Gln Val
                355                 360                 365
Pro Ser Met Lys Arg Gly Leu Ser Leu Cys Ser Thr Asp Gly Glu Gly
    370                 375                 380
Ala His Arg Cys Met Ala Arg Arg Lys Asn Glu Ala Pro Met Asn
385                 390                 395                 400
Ile Asn Thr Pro Cys Asp Phe Cys Gly Gln Ile Phe Ala Arg Pro Cys
                405                 410                 415
Asp Leu Thr Lys His Met Lys Thr His Thr Arg Pro Phe Lys Cys Ser
            420                 425                 430
Val Pro Glu Cys Lys Tyr Tyr Thr Tyr Gly Phe Pro Thr Glu Lys Glu
    435                 440                 445
Lys Asp Arg His Phe Asn Asp Lys His Asn Pro Asp Pro Glu Pro Tyr
    450                 455                 460
Glu Cys Asp Leu Gly Gly Cys Asn Tyr Arg Ser Lys Arg Leu Ser Asn
465                 470                 475                 480
Leu Lys Gln His Lys Glu Lys His Gly Trp Gln Tyr Val Arg Thr
            485                 490                 495
Lys Ser Asn Gly Lys Arg Lys Glu Lys Gly Lys Gly Lys Lys Ala Ser
                500                 505                 510
Pro Gln Ser Thr Pro Asp Thr Pro Gly Leu Thr Thr Pro Gly Thr Ser
            515                 520                 525
Thr Ala Gln Ser Phe Ser Thr Pro Asn Thr Gly Pro Ser Pro Ser Pro
    530                 535                 540
Pro Gln Ala Val Ser Arg Pro Leu Pro Thr Thr Asp Phe Asn Phe Ala
545                 550                 555                 560
Asp Pro Pro Leu Pro Thr Pro Val Ala Asp Phe Gln Leu Phe Asn Ala
                565                 570                 575
Asn Ser Pro Met Gly Gly Asn Gly Ser Val Asn Met Gly Tyr Ala Asp
            580                 585                 590
Leu Gly Phe Pro Glu Met Thr Arg Ser Met Asp Gly Asp Val Val His
                595                 600                 605
Met Asn Asn Phe Glu Asp Met Phe Ala Asn Val Asn Asn Pro Tyr Leu
            610                 615                 620
Asp Gly Leu Ser Gly Gly Tyr Gln Val Pro Ser Gly Tyr Glu Ala Gly
625                 630                 635                 640
Asn Ile Asp Phe Pro Asp Leu Gly Tyr Gly Thr Ala Val Pro Pro Ser
                645                 650                 655
Ala Val Phe His Glu Asp Gln Phe Leu Pro Glu Thr Ile Asn Trp Glu
            660                 665                 670
Glu Phe Ala Met Leu Asn Gly Met Asp Thr Met Ser Lys
    675                 680                 685
```

-continued

<210> SEQ ID NO 83
<211> LENGTH: 1239
<212> TYPE: DNA
<213> ORGANISM: Artificial Sequence
<220> FEATURE:
<223> OTHER INFORMATION: fungal gene

<400> SEQUENCE: 83

| | | | | | |
|---|---|---|---|---|---|
| atggtcaaca | ccccacccga | tcaacggccc | cagctctccc | cgtccaaccc | caatcccccg | 60 |
| tctcgacgac | gcaatgatcg | cgacatctac | gtcgccgatg | ccagtgagcc | cgccaccccg | 120 |
| cgccccatgg | acgatacccc | ccccgccgcc | gccaccgccg | ccgttgccct | ggcccaatta | 180 |
| caccacaatc | gcttggtctc | cgactgggag | acggacatgg | aatcccactc | cgacaatgac | 240 |
| atcagccgcg | accgcatgcg | atcctccatc | gagctcccct | ctctgcgcga | ccacttcaag | 300 |
| caggactccc | tcccaccctt | ctcccgcgca | ccgcgcgaac | tgctcccctc | catcctcaac | 360 |
| cactcgcccc | caggtcgctc | ctccactctt | cccccatcc | agcaaaagaa | gtggccgcgc | 420 |
| ccgcgcaaat | cctccatctc | cggcgctcgc | aagcccaaac | atgaacgctc | caagtccaag | 480 |
| gagtacggtc | gccgccccag | cttaggcgat | cgcaaagccc | tgtccgccga | acccagacc | 540 |
| gccgcctggg | ctcagggcaa | cgctgggag | gatctgatcg | aagccgcgac | ttcggcgacc | 600 |
| gaggccgacg | acgaacgcca | ttctgaggtc | ggtcggtcgc | ccaccatccc | tccggtgtcc | 660 |
| agcttcacct | ccgcccccat | ggggaagaat | cgctcgtcgc | ttccccgggg | attccaagga | 720 |
| ctaccacccc | ccacctcgca | tcgtccgttc | cgcctcatc | cctacgccgc | gtcgccgttg | 780 |
| aacaacgacc | tggagcccctt | cccctcgata | gagtcgtccc | tcgactccgc | ctcgaccgcg | 840 |
| tccggaaaga | ccctccacta | taatcacgtc | ggtccggcca | acgactccag | tccggtgctg | 900 |
| aacatgttcc | cgtcgtcggc | cgtgcagcgc | caacaccatc | gcttttccaa | ccccaccccc | 960 |
| gcctccatgc | ggagccgcga | gatccagatc | tattgcgccc | actgcaagcg | accgtgggcg | 1020 |
| ctcaacgaat | gctacgcctg | caccgagtgc | atctgcggcg | tctgtcgcga | atgtgtcgga | 1080 |
| atgttcatcg | gcagcccgcc | cacctccttc | cgcaacgtca | cctccagccc | gggcagtgcc | 1140 |
| ttgccccacg | gcccgaccag | ctatcctagc | gcccgaggtt | gtccccgctg | tcgcaccgtc | 1200 |
| ggcggcaagt | ggaaggcttt | tcagctggat | ttcaagtag | | | 1239 |

<210> SEQ ID NO 84
<211> LENGTH: 412
<212> TYPE: PRT
<213> ORGANISM: Artificial Sequence
<220> FEATURE:
<223> OTHER INFORMATION: fungal gene

<400> SEQUENCE: 84

Met Val Asn Thr Pro Pro Asp Gln Arg Pro Gln Leu Ser Pro Ser Asn
1               5                   10                  15

Pro Asn Pro Pro Ser Arg Arg Arg Asn Asp Arg Asp Ile Tyr Val Ala
            20                  25                  30

Asp Ala Ser Glu Pro Ala Thr Pro Arg Pro Met Asp Thr His Pro
        35                  40                  45

Ala Ala Ala Thr Ala Ala Val Ala Leu Ala Gln Leu His His Asn Arg
    50                  55                  60

Leu Val Ser Asp Trp Glu Thr Asp Met Glu Ser His Ser Asp Asn Asp
65                  70                  75                  80

Ile Ser Arg Asp Arg Met Arg Ser Ser Ile Glu Leu Pro Ser Leu Arg

```
                85                  90                  95
Asp His Phe Lys Gln Asp Ser Leu Pro Pro Phe Ser Pro Arg Pro Arg
            100                 105                 110

Glu Leu Leu Pro Ser Ile Leu Asn His Ser Pro Pro Gly Arg Ser Ser
            115                 120                 125

Thr Leu Pro Pro Ile Gln Gln Lys Lys Trp Pro Arg Pro Arg Lys Ser
            130                 135                 140

Ser Ile Ser Gly Ala Arg Lys Pro Lys His Glu Arg Ser Lys Ser Lys
145                 150                 155                 160

Glu Tyr Gly Arg Arg Pro Ser Leu Gly Asp Arg Lys Ala Leu Ser Ala
                165                 170                 175

Glu Pro Gln Thr Ala Ala Trp Ala Gln Gly Lys Arg Trp Glu Asp Leu
            180                 185                 190

Ile Glu Ala Ala Thr Ser Ala Thr Glu Ala Asp Asp Glu Arg His Ser
            195                 200                 205

Glu Val Gly Arg Ser Pro Thr Ile Pro Pro Val Ser Ser Phe Thr Ser
210                 215                 220

Ala Pro Met Gly Lys Asn Arg Ser Ser Leu Pro Pro Gly Phe Gln Gly
225                 230                 235                 240

Leu Pro Pro Pro Thr Ser His Arg Pro Phe Pro Pro His Pro Tyr Ala
                245                 250                 255

Ala Ser Pro Leu Asn Asn Asp Leu Glu Pro Phe Pro Ser Ile Glu Ser
            260                 265                 270

Ser Leu Asp Ser Ala Ser Thr Ala Ser Gly Lys Thr Leu His Tyr Asn
            275                 280                 285

His Val Gly Pro Ala Asn Asp Ser Ser Pro Val Leu Asn Met Phe Pro
290                 295                 300

Ser Ser Ala Val Gln Arg Gln His Arg Phe Ser Asn Pro Thr Pro
305                 310                 315                 320

Ala Ser Met Arg Ser Arg Glu Ile Gln Ile Tyr Cys Ala His Cys Lys
                325                 330                 335

Arg Pro Trp Ala Leu Asn Glu Cys Tyr Ala Cys Thr Glu Cys Ile Cys
            340                 345                 350

Gly Val Cys Arg Glu Cys Val Gly Met Phe Ile Gly Ser Pro Pro Thr
            355                 360                 365

Ser Phe Arg Asn Val Thr Ser Ser Pro Gly Ser Ala Leu Pro His Gly
            370                 375                 380

Pro Thr Ser Tyr Pro Ser Ala Arg Gly Cys Pro Arg Cys Arg Thr Val
385                 390                 395                 400

Gly Gly Lys Trp Lys Ala Phe Gln Leu Asp Phe Lys
                405                 410

<210> SEQ ID NO 85
<211> LENGTH: 282
<212> TYPE: DNA
<213> ORGANISM: Artificial Sequence
<220> FEATURE:
<223> OTHER INFORMATION: fungal gene

<400> SEQUENCE: 85
atgctggaca ttccgaagga catcgagaag atctcgatcc ctgtgagctt tgccttgggc      60
gagcatgaca gcgcaatcaa gccggctcag gtcactcaga tcaagcaaac tctgaatgca     120
aaggaagaga atgtggctag tgaagtgaag atgtattacg gtgttggtca cggcttctgc     180
gtgagagcgg ataccaaact ggtggacgca gacacacaag caactgaggc agagaatcag     240
```

```
gccctggctt ggttcaatcg tcatttcgcg gacttttcat cc                    282
```

<210> SEQ ID NO 86
<211> LENGTH: 94
<212> TYPE: PRT
<213> ORGANISM: Artificial Sequence
<220> FEATURE:
<223> OTHER INFORMATION: fungal gene

<400> SEQUENCE: 86

```
Met Leu Asp Ile Pro Lys Asp Ile Glu Lys Ile Ser Ile Pro Val Ser
 1               5                  10                  15

Phe Ala Leu Gly Glu His Asp Ser Ala Ile Lys Pro Ala Gln Val Thr
                20                  25                  30

Gln Ile Lys Gln Thr Leu Asn Ala Lys Glu Glu Asn Val Ala Ser Glu
            35                  40                  45

Val Lys Met Tyr Tyr Gly Val Gly His Gly Phe Cys Val Arg Ala Asp
        50                  55                  60

Thr Lys Leu Val Asp Ala Asp Thr Gln Ala Thr Glu Ala Glu Asn Gln
65                  70                  75                  80

Ala Leu Ala Trp Phe Asn Arg His Phe Ala Asp Phe Ser Ser
                85                  90
```

<210> SEQ ID NO 87
<211> LENGTH: 378
<212> TYPE: DNA
<213> ORGANISM: Artificial Sequence
<220> FEATURE:
<223> OTHER INFORMATION: fungal gene

<400> SEQUENCE: 87

```
atgtctagcc aacctctcct ccaaaccgct ccgggcaagc gaattgccct cccaacccga     60
gtcgaaccca aggtcttctt cgctaacgag cgcaccttcc tctcatggct taacttcacc    120
gtcatcctgg gcggcctagc ggtcggcctc ctcaatttcg gcgaccgcat cggtcgcatc    180
tccgcagctc tcttcaccat catcgcgatg ggcgcaatga tctacgcctt ggtgacattc    240
cactggcgcg cgcagagtat ccgtcggcgc ggacagagcg gtatcgatga ccgattcggt    300
cctaccatcc tggccattgc cctcctcgcc gccgtcgttg ttaacttcat cttgcggatt    360
aaggacgggc agatgaac                                                  378
```

<210> SEQ ID NO 88
<211> LENGTH: 126
<212> TYPE: PRT
<213> ORGANISM: Artificial Sequence
<220> FEATURE:
<223> OTHER INFORMATION: fungal gene

<400> SEQUENCE: 88

```
Met Ser Ser Gln Pro Leu Leu Gln Thr Ala Pro Gly Lys Arg Ile Ala
 1               5                  10                  15

Leu Pro Thr Arg Val Glu Pro Lys Val Phe Phe Ala Asn Glu Arg Thr
                20                  25                  30

Phe Leu Ser Trp Leu Asn Phe Thr Val Ile Leu Gly Gly Leu Ala Val
            35                  40                  45

Gly Leu Leu Asn Phe Gly Asp Arg Ile Gly Arg Ile Ser Ala Ala Leu
        50                  55                  60

Phe Thr Ile Ile Ala Met Gly Ala Met Ile Tyr Ala Leu Val Thr Phe
65                  70                  75                  80
```

His Trp Arg Ala Gln Ser Ile Arg Arg Gly Gln Ser Gly Ile Asp
            85                  90                  95

Asp Arg Phe Gly Pro Thr Ile Leu Ala Ile Ala Leu Leu Ala Ala Val
            100                 105                 110

Val Val Asn Phe Ile Leu Arg Ile Lys Asp Gly Gln Met Asn
            115                 120                 125

<210> SEQ ID NO 89
<211> LENGTH: 387
<212> TYPE: DNA
<213> ORGANISM: Artificial Sequence
<220> FEATURE:
<223> OTHER INFORMATION: fungal gene

<400> SEQUENCE: 89
atgcatgatg actctggaaa aagcggcctg caaatccaaa acgtcgagac ggggggttgg      60
ctagaggtca cgaactccgg gacgcgagtc cagtgtggga tgacggaagt cggtagcgag     120
acggtctggg atcttgtctt gcttcctacg ccatcgtccc tgcttcaagg gttggcgggc     180
acagggcgg cttctcgtgg tggctctagc cgctcgtcgc gccctcgtgg gcgacgggat      240
gacgatgagg atacgaggaa agactctgac tcctctgtat tggaatatag tgatgactct     300
tgtgacgatg gtggacgat tagggcagac cccgttgtga ggcatcgaga cggcctggcg      360
catcaggaca ttaccatgcg caaatgc                                          387

<210> SEQ ID NO 90
<211> LENGTH: 129
<212> TYPE: PRT
<213> ORGANISM: Artificial Sequence
<220> FEATURE:
<223> OTHER INFORMATION: fungal gene

<400> SEQUENCE: 90

Met His Asp Asp Ser Gly Lys Ser Gly Leu Gln Ile Gln Asn Val Glu
1               5                   10                  15

Thr Gly Gly Trp Leu Glu Val Thr Asn Ser Gly Thr Arg Val Gln Cys
            20                  25                  30

Gly Met Thr Glu Val Gly Ser Glu Thr Val Trp Asp Leu Val Leu Leu
            35                  40                  45

Pro Thr Pro Ser Ser Leu Leu Gln Gly Leu Ala Gly Thr Gly Ala Ala
        50                  55                  60

Ser Arg Gly Gly Ser Ser Arg Ser Arg Pro Arg Gly Arg Arg Asp
65                  70                  75                  80

Asp Asp Glu Asp Thr Arg Lys Asp Ser Asp Ser Ser Val Leu Glu Tyr
            85                  90                  95

Ser Asp Asp Ser Cys Asp Asp Gly Trp Thr Ile Arg Ala Asp Pro Val
            100                 105                 110

Val Arg His Arg Asp Gly Leu Ala His Gln Asp Ile Thr Met Arg Lys
            115                 120                 125

Cys

<210> SEQ ID NO 91
<211> LENGTH: 2274
<212> TYPE: DNA
<213> ORGANISM: Artificial Sequence
<220> FEATURE:
<223> OTHER INFORMATION: fungal gene

<400> SEQUENCE: 91

-continued

```
atgatctccg ctccgggtcc cgagcgacgg cgcagacggc cggcagtgtc atgttctctt      60
tgcagaaggc gtaagattaa atgcaaccgc gaaagcccct gtagcaactg catcaagtct     120
aaggcggaac catgcgtcta cgagagcgac tcctcgtccc ggccgcagca gcatcttggc     180
ttcaatcaga cactggagct agggctctgc aaggcgtctg aacgccagat gctccctcca     240
gatgcggtaa cttctcaagt tcctagctat gcgtccaggt cattactctc agcgcgaga      300
gactcgtcat cccggacgag tcaagcttct gcatcggagg ttgagtctct gaagaccaag     360
atcagacagc tggaggaaca gctgtccagt gcgacgcagc cggcggaatc acctccacgg     420
ccgtctccaa actccagaat cgagaccagc acgtctcaga tagcagggac gttccacata     480
aaccatgaaa ggcggcttct ccacgattcc cagttcgtca accgaaatct ggtcatacat     540
aaaagtcgcc tgtttggctc cagtcattgg gcacaggctg catcgatgtt tagagatgta     600
tttgaaatga tcgaaccgtt tatccgcggg agtggttcca agccagtgc cggcatcaga      660
aggtgcaaag agctggcaag gattatcaaa acccaacgga cgccgcaatg ccgacgccg      720
cccactcagg atctacctcc aaaaggcgtc gctgatgagt tggttgactg ctatctccgt     780
acaatcgaga ctacattccg ggtcctgcac gtacctacat tcaggtccga atatgacgct     840
ctatgggtat ctgaagcacg gcccagcatc gcgttcacag tccaacttaa gctggtgttg     900
gcactgggt ctgtcactta cgacgagcgg ttttcaatga acccagtgc ggttcgttgg       960
gtatttgagg cgcacacctg gctctctgat ccagacttca acctcaact taacatacag     1020
tgtttgcaaa gcaggattct actattacta gcccgcgaga taatcaatgt tggtggcgat    1080
tcgagttgga tatctgccgg cggactactc cgcactgctc tacatatggg attacatagg    1140
gatccgtctg tactgccgcc taggtcggcg ctcgctgttg aaatgcgacg ccgactgtgg    1200
aacactatcc tcgagctatc actgcagtca agcatttcct ccggtggacc tccactaatt    1260
tccctgggcg atttcgactg tgcgcctcca gggaatttcg acgacgaaca gctactggct    1320
gaggacccgg tgccgaagag tgatgatgag tacactcaaa cagcaatcgc cagggcattg    1380
aggggaacct acccacagcg ccttgcaatt gtgaaattcc tgaacgatct aagttcatat    1440
gggacttacg aggaaactct tcgacttgac gcagatttaa gggaatctta cagggctatt    1500
tgccgtatcc tccagggta tcccagcaac gggccttccc cgtcacagtt cgaaaaatgc     1560
atgctcgact tcatcatcca cttctatgtg tgctgcctcc atattccta catcgagaag     1620
tcactgcggg caccggcata tgcattctcc aggaaagtcg cgatcgagag cgccctcaag    1680
atgtggtgcg ccatttaccc atcttccaga ttcatgagca cacccgtcg cgagattagc     1740
ggatccgttg aaaataagct gactcggttc gtggaatgcg ggtttgggtt tttccgcact    1800
ggtgttataa tcgcggccat gttcgtgacc ttggagctta agctcagct cctggatgat    1860
gacagcctag gtcccagccc gtatcgggta gatctttct ctctgctctg tgaggcgaaa    1920
gaccgttgtt ggaatatgat tcaatgtggt gagactaatg tcaagggcta cctcctcatt    1980
tgtctggtaa ccgcccagat cgaggggctg atgcatggag ttgaaccgag caaactcccc    2040
gaactccttc tccgcgcagc agaagaggcg gaggaccggt gtcttgactt catggaggag    2100
aaagccgatc tgggacggag tggtggttcc gttgaggtga tggacgaatc tgcgaataca    2160
gcgcccttca tgggcgactg ggagtttatt atgacagatc ctttccttaa ttatcctggg    2220
actactgaac cactcagctg ggttatgaat gaagaaacga gaccattcat aatg          2274
```

<210> SEQ ID NO 92

```
<211> LENGTH: 758
<212> TYPE: PRT
<213> ORGANISM: Artificial Sequence
<220> FEATURE:
<223> OTHER INFORMATION: fungal gene

<400> SEQUENCE: 92
```

| Met | Ile | Ser | Ala | Pro | Gly | Pro | Glu | Arg | Arg | Arg | Arg | Pro | Ala | Val |
|---|---|---|---|---|---|---|---|---|---|---|---|---|---|---|
| 1 | | | | 5 | | | | | 10 | | | | | 15 |

| Ser | Cys | Ser | Leu | Cys | Arg | Arg | Lys | Ile | Lys | Cys | Asn | Arg | Glu | Ser |
|---|---|---|---|---|---|---|---|---|---|---|---|---|---|---|
| | | | | 20 | | | | | 25 | | | | | 30 |

| Pro | Cys | Ser | Asn | Cys | Ile | Lys | Ser | Lys | Ala | Glu | Pro | Cys | Val | Tyr | Glu |
|---|---|---|---|---|---|---|---|---|---|---|---|---|---|---|---|
| | | | 35 | | | | | 40 | | | | | 45 | | |

| Ser | Asp | Ser | Ser | Ser | Arg | Pro | Gln | Gln | His | Leu | Gly | Phe | Asn | Gln | Thr |
|---|---|---|---|---|---|---|---|---|---|---|---|---|---|---|---|
| | 50 | | | | | 55 | | | | | 60 | | | | |

| Leu | Glu | Leu | Gly | Leu | Cys | Lys | Ala | Ser | Glu | Arg | Gln | Met | Leu | Pro | Pro |
|---|---|---|---|---|---|---|---|---|---|---|---|---|---|---|---|
| 65 | | | | | 70 | | | | | 75 | | | | | 80 |

| Asp | Ala | Val | Thr | Ser | Gln | Val | Pro | Ser | Tyr | Ala | Ser | Arg | Ser | Leu | Leu |
|---|---|---|---|---|---|---|---|---|---|---|---|---|---|---|---|
| | | | | 85 | | | | | 90 | | | | | 95 | |

| Ser | Ser | Ala | Arg | Asp | Ser | Ser | Ser | Arg | Thr | Ser | Gln | Ala | Ser | Ala | Ser |
|---|---|---|---|---|---|---|---|---|---|---|---|---|---|---|---|
| | | | 100 | | | | | 105 | | | | | 110 | | |

| Glu | Val | Glu | Ser | Leu | Lys | Thr | Lys | Ile | Arg | Gln | Leu | Glu | Glu | Gln | Leu |
|---|---|---|---|---|---|---|---|---|---|---|---|---|---|---|---|
| | | | 115 | | | | | 120 | | | | | 125 | | |

| Ser | Ser | Ala | Thr | Gln | Pro | Ala | Glu | Ser | Pro | Pro | Arg | Pro | Ser | Pro | Asn |
|---|---|---|---|---|---|---|---|---|---|---|---|---|---|---|---|
| | 130 | | | | | 135 | | | | | 140 | | | | |

| Ser | Arg | Ile | Glu | Thr | Ser | Thr | Ser | Gln | Ile | Ala | Gly | Thr | Phe | His | Ile |
|---|---|---|---|---|---|---|---|---|---|---|---|---|---|---|---|
| 145 | | | | | 150 | | | | | 155 | | | | | 160 |

| Asn | His | Glu | Arg | Arg | Leu | Leu | His | Asp | Ser | Gln | Phe | Val | Asn | Arg | Asn |
|---|---|---|---|---|---|---|---|---|---|---|---|---|---|---|---|
| | | | | 165 | | | | | 170 | | | | | 175 | |

| Leu | Val | Ile | His | Lys | Ser | Arg | Leu | Phe | Gly | Ser | Ser | His | Trp | Ala | Gln |
|---|---|---|---|---|---|---|---|---|---|---|---|---|---|---|---|
| | | | 180 | | | | | 185 | | | | | 190 | | |

| Ala | Ala | Ser | Met | Phe | Arg | Asp | Val | Phe | Glu | Met | Ile | Glu | Pro | Phe | Ile |
|---|---|---|---|---|---|---|---|---|---|---|---|---|---|---|---|
| | | | 195 | | | | | 200 | | | | | 205 | | |

| Arg | Gly | Ser | Gly | Ser | Lys | Ala | Ser | Ala | Gly | Ile | Arg | Arg | Cys | Lys | Glu |
|---|---|---|---|---|---|---|---|---|---|---|---|---|---|---|---|
| | 210 | | | | | 215 | | | | | 220 | | | | |

| Leu | Ala | Arg | Ile | Ile | Lys | Thr | Gln | Arg | Thr | Pro | Gln | Trp | Pro | Thr | Pro |
|---|---|---|---|---|---|---|---|---|---|---|---|---|---|---|---|
| 225 | | | | | 230 | | | | | 235 | | | | | 240 |

| Pro | Thr | Gln | Asp | Leu | Pro | Pro | Lys | Gly | Val | Ala | Asp | Glu | Leu | Val | Asp |
|---|---|---|---|---|---|---|---|---|---|---|---|---|---|---|---|
| | | | | 245 | | | | | 250 | | | | | 255 | |

| Cys | Tyr | Leu | Arg | Thr | Ile | Glu | Thr | Thr | Phe | Arg | Val | Leu | His | Val | Pro |
|---|---|---|---|---|---|---|---|---|---|---|---|---|---|---|---|
| | | | 260 | | | | | 265 | | | | | 270 | | |

| Thr | Phe | Arg | Ser | Glu | Tyr | Asp | Ala | Leu | Trp | Val | Ser | Glu | Ala | Arg | Pro |
|---|---|---|---|---|---|---|---|---|---|---|---|---|---|---|---|
| | | 275 | | | | | 280 | | | | | 285 | | | |

| Ser | Ile | Ala | Phe | Thr | Val | Gln | Leu | Lys | Leu | Val | Leu | Ala | Leu | Gly | Ser |
|---|---|---|---|---|---|---|---|---|---|---|---|---|---|---|---|
| | 290 | | | | | 295 | | | | | 300 | | | | |

| Val | Thr | Tyr | Asp | Glu | Arg | Phe | Ser | Met | Arg | Pro | Ser | Ala | Val | Arg | Trp |
|---|---|---|---|---|---|---|---|---|---|---|---|---|---|---|---|
| 305 | | | | | 310 | | | | | 315 | | | | | 320 |

| Val | Phe | Glu | Ala | His | Thr | Trp | Leu | Ser | Asp | Pro | Asp | Phe | Lys | Pro | Gln |
|---|---|---|---|---|---|---|---|---|---|---|---|---|---|---|---|
| | | | | 325 | | | | | 330 | | | | | 335 | |

| Leu | Asn | Ile | Gln | Cys | Leu | Gln | Ser | Arg | Ile | Leu | Leu | Leu | Ala | Arg |
|---|---|---|---|---|---|---|---|---|---|---|---|---|---|---|
| | | | 340 | | | | | 345 | | | | | 350 | |

| Glu | Ile | Ile | Asn | Val | Gly | Gly | Asp | Ser | Ser | Trp | Ile | Ser | Ala | Gly | Gly |
|---|---|---|---|---|---|---|---|---|---|---|---|---|---|---|---|
| | | 355 | | | | | 360 | | | | | 365 | | | |

| Leu | Leu | Arg | Thr | Ala | Leu | His | Met | Gly | Leu | His | Arg | Asp | Pro | Ser | Val |
|---|---|---|---|---|---|---|---|---|---|---|---|---|---|---|---|
| | 370 | | | | | 375 | | | | | 380 | | | | |

```
Leu Pro Pro Arg Ser Ala Leu Ala Val Glu Met Arg Arg Leu Trp
385                 390                 395                 400

Asn Thr Ile Leu Glu Leu Ser Leu Gln Ser Ser Ile Ser Ser Gly Gly
            405                 410                 415

Pro Pro Leu Ile Ser Leu Gly Asp Phe Asp Cys Ala Pro Pro Gly Asn
            420                 425                 430

Phe Asp Asp Glu Gln Leu Leu Ala Glu Asp Pro Val Pro Lys Ser Asp
            435                 440                 445

Asp Glu Tyr Thr Gln Thr Ala Ile Ala Arg Ala Leu Arg Gly Thr Tyr
450                 455                 460

Pro Gln Arg Leu Ala Ile Val Lys Phe Leu Asn Asp Leu Ser Ser Tyr
465                 470                 475                 480

Gly Thr Tyr Glu Glu Thr Leu Arg Leu Asp Ala Asp Leu Arg Glu Ser
                485                 490                 495

Tyr Arg Ala Ile Cys Arg Ile Leu Arg Gly Tyr Pro Ser Asn Gly Pro
                500                 505                 510

Ser Pro Ser Gln Phe Glu Lys Cys Met Leu Asp Phe Ile Ile His Phe
            515                 520                 525

Tyr Val Cys Cys Leu His Ile Pro Tyr Ile Glu Lys Ser Leu Arg Ala
            530                 535                 540

Pro Ala Tyr Ala Phe Ser Arg Lys Val Ala Ile Glu Ser Ala Leu Lys
545                 550                 555                 560

Met Trp Cys Ala Ile Tyr Pro Ser Ser Arg Phe Met Ser Asn Thr Arg
                565                 570                 575

Arg Glu Ile Ser Gly Ser Val Glu Asn Lys Leu Thr Arg Phe Val Glu
                580                 585                 590

Cys Gly Phe Gly Phe Arg Thr Gly Val Ile Ile Ala Ala Met Phe
                595                 600                 605

Val Thr Leu Glu Leu Lys Ala Gln Leu Leu Asp Asp Ser Leu Gly
            610                 615                 620

Pro Ser Pro Tyr Arg Val Asp Leu Phe Ser Leu Leu Cys Glu Ala Lys
625                 630                 635                 640

Asp Arg Cys Trp Asn Met Ile Gln Cys Gly Glu Thr Asn Val Lys Gly
                645                 650                 655

Tyr Leu Leu Ile Cys Leu Val Thr Ala Gln Ile Glu Gly Leu Met His
                660                 665                 670

Gly Val Glu Pro Ser Lys Leu Pro Glu Leu Leu Leu Arg Ala Ala Glu
            675                 680                 685

Glu Ala Glu Asp Arg Cys Leu Asp Phe Met Glu Glu Lys Ala Asp Leu
690                 695                 700

Gly Arg Ser Gly Gly Ser Val Glu Val Met Asp Glu Ser Ala Asn Thr
705                 710                 715                 720

Ala Pro Phe Met Gly Asp Trp Glu Phe Ile Met Thr Asp Pro Phe Leu
                725                 730                 735

Asn Tyr Pro Gly Thr Thr Glu Pro Leu Ser Trp Val Met Asn Glu Glu
                740                 745                 750

Thr Arg Pro Phe Ile Met
        755
```

<210> SEQ ID NO 93
<211> LENGTH: 1530
<212> TYPE: DNA
<213> ORGANISM: Artificial Sequence
<220> FEATURE:

<223> OTHER INFORMATION: fungal gene

<400> SEQUENCE: 93

| | | | | | |
|---|---|---|---|---|---|
| atgaccagca | caatagcccg | cactgaggaa | cgccagaacg | ctggcaccat | tgaactgaaa | 60 |
| gatgacacgg | tcatcgtggt | cctcggtgcc | tccggagatc | tcgcaaagaa | gaagacgttc | 120 |
| cctgcactgt | tcggtcttta | ccgtaacaaa | ttcctcccca | aggggatcaa | gatcgtcgga | 180 |
| tatgctcgga | cgaacatgga | ccacgaagaa | tatctgagac | gggtgcgctc | gtacatcaag | 240 |
| acccccacca | aggaaatcga | gaacagctg | gatggcttct | gccagctgtg | cacctacatc | 300 |
| agcggccaat | atgacaagga | tgactcgttc | attaaccctca | ctaagcacct | cgaggacgtc | 360 |
| gagaagggcc | ataaggaaca | gaacagagtc | ttctacatgg | cgctgcctcc | tagcgtcttc | 420 |
| attaccgtgt | cggatcaatt | gaagagaaac | tgctacccca | gaacggcat | gcccgtatt | 480 |
| attgtcgaga | gcccttcgg | caaggatctc | cagagttctc | gtgacctcca | gaaggcccttt | 540 |
| gagcccaact | ggaagagga | ggagatcttc | cgtattgacc | actacctggg | taaggagatg | 600 |
| gtcaagaaca | tcctcatcat | gcgcttcgga | aacgagttct | tcaacgctac | ctggaaccgt | 660 |
| caccacattg | ataacgtgca | gatcacattc | aaggagccgt | tcggcacgga | gggccgtgga | 720 |
| ggctactttg | atgagttcgg | catcattcgt | gatgtcatgc | agaaccacct | tctgcaggtg | 780 |
| ttgacgcttc | ttgccatgga | gcgtcccatc | tctttctctg | ctgaagacat | tcgtgacgag | 840 |
| aaggtgcgtg | ttctgcgcgc | gatggacccc | attgagccca | gaacgtcat | catcggccag | 900 |
| tacggaaagt | cgctcgacgg | tagcaagccc | gcctacaagg | aggatgatac | tgtgcctcaa | 960 |
| gactcgcgct | gcccgacttt | ctgcgccatg | gttgcgtaca | tcaagaacga | gagatgggat | 1020 |
| ggcgttccct | tcatcatgaa | ggccggtaaa | gccctgaacg | agcagaagac | cgagatccgt | 1080 |
| atccagttcc | gtgacgtcac | ttccggcatc | ttcaaggaca | tccccgcaa | cgaacttgtc | 1140 |
| attcgtgtcc | agcccaacga | gtcggtgtac | attaagatga | actcgaagct | accgggtctc | 1200 |
| tccatgcaga | cggtcgttac | cgagcttgac | cttacctacc | gccgccgttt | ctccgacctc | 1260 |
| aagatcccgg | aggcctacga | gtctctgatt | ctggatgctc | tgaagggtga | ccactcgaac | 1320 |
| tttgtccgtg | acgatgaact | tgactcgagc | tggaagatct | tcaccctct | gctgcactac | 1380 |
| ctggacgaca | caaggagat | tatccccatg | gaatacccct | acggctctcg | cggacctgct | 1440 |
| gtgctcgacg | acttcaccgc | gtcgttcggg | tacaagttca | gtgatgctgc | tggctaccag | 1500 |
| tggccccctga | cttcggctcc | caacagactg | | | | 1530 |

<210> SEQ ID NO 94
<211> LENGTH: 510
<212> TYPE: PRT
<213> ORGANISM: Artificial Sequence
<220> FEATURE:
<223> OTHER INFORMATION: fungal gene

<400> SEQUENCE: 94

```
Met Thr Ser Thr Ile Ala Arg Thr Glu Glu Arg Gln Asn Ala Gly Thr
  1               5                  10                  15

Ile Glu Leu Lys Asp Asp Thr Val Ile Val Leu Gly Ala Ser Gly
             20                  25                  30

Asp Leu Ala Lys Lys Lys Thr Phe Pro Ala Leu Phe Gly Leu Tyr Arg
         35                  40                  45

Asn Lys Phe Leu Pro Lys Gly Ile Lys Ile Val Gly Tyr Ala Arg Thr
     50                  55                  60

Asn Met Asp His Glu Glu Tyr Leu Arg Arg Val Arg Ser Tyr Ile Lys
```

-continued

```
             65                  70                  75                  80
Thr Pro Thr Lys Glu Ile Glu Glu Gln Leu Asp Gly Phe Cys Gln Leu
                    85                  90                  95
Cys Thr Tyr Ile Ser Gly Gln Tyr Asp Lys Asp Ser Phe Ile Asn
                100                 105                 110
Leu Thr Lys His Leu Glu Asp Val Glu Lys Gly His Lys Glu Gln Asn
                115                 120                 125
Arg Val Phe Tyr Met Ala Leu Pro Pro Ser Val Phe Ile Thr Val Ser
            130                 135                 140
Asp Gln Leu Lys Arg Asn Cys Tyr Pro Lys Asn Gly Ile Ala Arg Ile
145                 150                 155                 160
Ile Val Glu Lys Pro Phe Gly Lys Asp Leu Gln Ser Ser Arg Asp Leu
                165                 170                 175
Gln Lys Ala Leu Glu Pro Asn Trp Lys Glu Glu Ile Phe Arg Ile
                180                 185                 190
Asp His Tyr Leu Gly Lys Glu Met Val Lys Asn Ile Leu Ile Met Arg
                195                 200                 205
Phe Gly Asn Glu Phe Phe Asn Ala Thr Trp Asn Arg His His Ile Asp
210                 215                 220
Asn Val Gln Ile Thr Phe Lys Glu Pro Phe Gly Thr Glu Gly Arg Gly
225                 230                 235                 240
Gly Tyr Phe Asp Glu Phe Gly Ile Ile Arg Asp Val Met Gln Asn His
                245                 250                 255
Leu Leu Gln Val Leu Thr Leu Leu Ala Met Glu Arg Pro Ile Ser Phe
                260                 265                 270
Ser Ala Glu Asp Ile Arg Asp Glu Lys Val Arg Val Leu Arg Ala Met
                275                 280                 285
Asp Pro Ile Glu Pro Lys Asn Val Ile Ile Gly Gln Tyr Gly Lys Ser
290                 295                 300
Leu Asp Gly Ser Lys Pro Ala Tyr Lys Glu Asp Thr Val Pro Gln
305                 310                 315                 320
Asp Ser Arg Cys Pro Thr Phe Cys Ala Met Val Ala Tyr Ile Lys Asn
                325                 330                 335
Glu Arg Trp Asp Gly Val Pro Phe Ile Met Lys Ala Gly Lys Ala Leu
                340                 345                 350
Asn Glu Gln Lys Thr Glu Ile Arg Ile Gln Phe Arg Asp Val Thr Ser
                355                 360                 365
Gly Ile Phe Lys Asp Ile Pro Arg Asn Glu Leu Val Ile Arg Val Gln
                370                 375                 380
Pro Asn Glu Ser Val Tyr Ile Lys Met Asn Ser Lys Leu Pro Gly Leu
385                 390                 395                 400
Ser Met Gln Thr Val Val Thr Glu Leu Asp Leu Thr Tyr Arg Arg
                405                 410                 415
Phe Ser Asp Leu Lys Ile Pro Glu Ala Tyr Glu Ser Leu Ile Leu Asp
                420                 425                 430
Ala Leu Lys Gly Asp His Ser Asn Phe Val Arg Asp Glu Leu Asp
                435                 440                 445
Ser Ser Trp Lys Ile Phe Thr Pro Leu Leu His Tyr Leu Asp Asp Asn
                450                 455                 460
Lys Glu Ile Ile Pro Met Glu Tyr Pro Tyr Gly Ser Arg Gly Pro Ala
465                 470                 475                 480
Val Leu Asp Asp Phe Thr Ala Ser Phe Gly Tyr Lys Phe Ser Asp Ala
                485                 490                 495
```

Ala Gly Tyr Gln Trp Pro Leu Thr Ser Ala Pro Asn Arg Leu
            500                 505                 510

<210> SEQ ID NO 95
<211> LENGTH: 2550
<212> TYPE: DNA
<213> ORGANISM: Artificial Sequence
<220> FEATURE:
<223> OTHER INFORMATION: fungal gene

<400> SEQUENCE: 95

| | | | | | |
|---|---|---|---|---|---|
| atgacaccga | ctcccccgtc | aaccacctcg | tccagcgccg | gtggaatctc | accggagggc | 60 |
| cattatcgag | tcatccgaaa | gcgaaaccgg | gtgcctctat | cctgcggccc | ctgccgacat | 120 |
| agaaaactca | aatgcaaccg | tgctcatcca | tgtgaaaact | gcgtcaaacg | gggcgatgcc | 180 |
| tcgtcctgta | cctatgcaca | agccaacgcg | cggaaaaaga | actcaccgct | tcagaccgct | 240 |
| tcgagctcac | ccgacgacat | gcaaaaccgg | atagatcgtc | ttgagagctt | ggtgctctct | 300 |
| ttgatgacca | atggatctca | gtccgcaggc | cccacggcag | ctatggcggt | catttccggc | 360 |
| aactccagca | gcatcggctc | cgctcaacat | acgtcggaag | atgtagagct | ggacgatgat | 420 |
| gatgggcaag | gtcccgagga | gagtgatacg | gagcaattga | ccaagtcgat | cggtatcatg | 480 |
| aaggtcgaca | caacaaatc | gtggtatatc | agtgatgcac | attgggcatc | ggtcctgagc | 540 |
| gatatagcgg | aagtcaaaaa | ttacttcaac | acgcacaaga | agcaatatga | agaacacgca | 600 |
| gagaaaatta | aagcgacgcg | actcccaaca | gatgttcccg | gctcgacctt | gctcttcggt | 660 |
| gggacgaaaa | cgataagtcg | cgaggaaatc | atggcctctt | tcccatccag | gtatactgcg | 720 |
| gatatcctcg | ttgcgcgcta | tttcaaccac | tatgacccct | tccacgcacat | tcttcatggc | 780 |
| cctacctttc | aggcgcagta | caataaacac | tgggaggacc | cctccaaaac | ctgtattgtt | 840 |
| tggatcggta | tgcttttgc | tatgatgcga | ctcgccatgc | tctcatatca | tcgcgagggc | 900 |
| gacgaacctc | cggagtttcg | cgggaaggcg | ctggacatgg | cgggcacata | ccggaatctc | 960 |
| atggcccagt | gtttgacgtt | ggccgactac | accaaaccgt | accccttgttt | gatcgaatct | 1020 |
| ttagtcttcc | atctttacgg | cgacttctgt | cagtcaaagg | atgccgacgt | gtctggatgg | 1080 |
| gtgctggtgg | gcgtgattgc | gagactggcc | atgaggatgg | gttaccaccg | ggattcgaag | 1140 |
| atgttcccta | atatcacccc | gttccaaggt | gagatgcgac | ggcgggtgtg | ggcttttgtc | 1200 |
| cggcaagcag | acttgctctt | ttctgcccaa | gtcggcctgc | ccagcatgat | tcgcacttcg | 1260 |
| gatagtgata | cggagctacc | acgcaatctc | tatgacgacg | attttgacga | aattgcacg | 1320 |
| gaactcccac | cgtctcgacc | atctaccgaa | accacgccca | tctctttctt | gatcgcgaag | 1380 |
| gcccgtatca | catatgcttt | cggccgcgtt | atagaagaca | catcttctct | ccgaagcgct | 1440 |
| ccatacgaca | aggtcatgga | aattgacgag | gagcttcgtc | gggcaaggga | tttggtacca | 1500 |
| gagcacttga | gagttcgctc | tgtcgaagag | acacaactgg | atcccgcgaa | ccttatcatg | 1560 |
| tctcggtttg | agatcatgag | tgtgtaccac | aaagctcaat | gcgttctcca | tcggcgattc | 1620 |
| ctcgcccggg | cgcgcgaaaa | ccctcgattt | acctattctc | gaagaacctg | cattgattcg | 1680 |
| gctctggagc | tactgcgata | tcagtccatg | attcataccg | acacccgtcc | caacggtcgt | 1740 |
| ctgcgaggga | agctcaaccg | gaccacgtcc | ctctgttcga | gcgactttct | gcttgccgct | 1800 |
| accattgtgt | gcctagatct | ctatcatgga | cttcagctac | aagctggagg | tcgcgcttca | 1860 |
| gatgacacct | acacctgggg | acgggagcgt | cgcgacgaaa | tggttgcggc | tctacagcgc | 1920 |
| tcgaaggaga | tctgggacga | gcttcaagac | gagaccatag | acgcgtggaa | ggcttcagga | 1980 |

-continued

```
gtcctcggcg tgatgcttgc ccggctgaac ctagacggca acaccgcttc gaccacgttc    2040
gaaccgcaag acgagaagca gagtgccgcg atgacgttag gcctgcttag cagtggcatg    2100
aactatatga atccaggaac acctggcttt ggagaagcca caaccaagat ggcagataca    2160
ccagtgccgc ccccgggcgg ctttggtgcc gctgatatgc ctggtgcccc atcacccttc    2220
agcgccatgt tcggacagat gccagatatg caggtcaatt tggattggga cgcttgggac    2280
aactacattc aaaactcctc gattgacttt tccaatcagt ggtggccggc tatggacgca    2340
cagcaagcgc cacagcctcc gcaaccaggg aacccgcttt cgccatctca gttggctgca    2400
acacagggcg gaattgcagg aaggatgcgt acgatgccgt cgctttctag cgcattccca    2460
gaacccaatg ggtacgatgc ggctttccct acatccttca gcgtgaatgc gccgaaaaac    2520
ccacacaatc ctgcttcagg cccaggaaca                                     2550
```

<210> SEQ ID NO 96
<211> LENGTH: 850
<212> TYPE: PRT
<213> ORGANISM: Artificial Sequence
<220> FEATURE:
<223> OTHER INFORMATION: fungal gene

<400> SEQUENCE: 96

```
Met Thr Pro Thr Pro Pro Ser Thr Thr Ser Ser Ala Gly Gly Ile
 1               5                  10                  15

Ser Pro Glu Gly His Tyr Arg Val Ile Arg Lys Arg Asn Arg Val Pro
                20                  25                  30

Leu Ser Cys Gly Pro Cys Arg His Arg Lys Leu Lys Cys Asn Arg Ala
             35                  40                  45

His Pro Cys Glu Asn Cys Val Lys Arg Gly Asp Ala Ser Ser Cys Thr
         50                  55                  60

Tyr Ala Gln Ala Asn Ala Arg Lys Lys Asn Ser Pro Leu Gln Thr Ala
 65                  70                  75                  80

Ser Ser Ser Pro Asp Asp Met Gln Asn Arg Ile Asp Arg Leu Glu Ser
                 85                  90                  95

Leu Val Leu Ser Leu Met Thr Asn Gly Ser Gln Ser Ala Gly Pro Thr
            100                 105                 110

Ala Ala Met Ala Val Ile Ser Gly Asn Ser Ser Ile Gly Ser Ala
        115                 120                 125

Gln His Thr Ser Glu Asp Val Glu Leu Asp Asp Asp Gly Gln Gly
    130                 135                 140

Pro Glu Glu Ser Asp Thr Glu Gln Leu Thr Lys Ser Ile Gly Ile Met
145                 150                 155                 160

Lys Val Asp Asn Asn Lys Ser Trp Tyr Ile Ser Asp Ala His Trp Ala
                165                 170                 175

Ser Val Leu Ser Asp Ile Ala Glu Val Lys Asn Tyr Phe Asn Thr His
            180                 185                 190

Lys Lys Gln Tyr Glu Glu His Ala Glu Lys Ile Lys Ala Thr Arg Leu
        195                 200                 205

Pro Thr Asp Val Pro Gly Ser Thr Leu Leu Phe Gly Gly Thr Lys Thr
    210                 215                 220

Ile Ser Arg Glu Glu Ile Met Ala Ser Phe Pro Ser Arg Tyr Thr Ala
225                 230                 235                 240

Asp Ile Leu Val Ala Arg Tyr Phe Asn His Tyr Asp Pro Ser Thr His
                245                 250                 255
```

-continued

```
Ile Leu His Gly Pro Thr Phe Gln Ala Gln Tyr Asn Lys His Trp Glu
            260                 265                 270

Asp Pro Ser Lys Thr Cys Ile Val Trp Ile Gly Met Leu Phe Ala Met
            275                 280                 285

Met Arg Leu Ala Met Leu Ser Tyr His Arg Glu Gly Asp Glu Pro Pro
            290                 295                 300

Glu Phe Arg Gly Lys Ala Leu Asp Met Ala Gly Thr Tyr Arg Asn Leu
305                 310                 315                 320

Met Ala Gln Cys Leu Thr Leu Ala Asp Tyr Thr Lys Pro Tyr Pro Cys
                325                 330                 335

Leu Ile Glu Ser Leu Val Phe His Leu Tyr Gly Asp Phe Cys Gln Ser
            340                 345                 350

Lys Asp Ala Asp Val Ser Gly Trp Val Leu Val Gly Val Ile Ala Arg
            355                 360                 365

Leu Ala Met Arg Met Gly Tyr His Arg Asp Ser Lys Met Phe Pro Asn
370                 375                 380

Ile Thr Pro Phe Gln Gly Glu Met Arg Arg Val Trp Ala Phe Val
385                 390                 395                 400

Arg Gln Ala Asp Leu Leu Phe Ser Ala Gln Val Gly Leu Pro Ser Met
                405                 410                 415

Ile Arg Thr Ser Asp Ser Asp Thr Glu Leu Pro Arg Asn Leu Tyr Asp
            420                 425                 430

Asp Asp Phe Asp Glu Asn Cys Thr Glu Leu Pro Pro Ser Arg Pro Ser
            435                 440                 445

Thr Glu Thr Thr Pro Ile Ser Phe Leu Ile Ala Lys Ala Arg Ile Thr
            450                 455                 460

Tyr Ala Phe Gly Arg Val Ile Glu Asp Thr Ser Ser Leu Arg Ser Ala
465                 470                 475                 480

Pro Tyr Asp Lys Val Met Glu Ile Asp Glu Glu Leu Arg Arg Ala Arg
                485                 490                 495

Asp Leu Val Pro Glu His Leu Arg Val Arg Ser Val Glu Glu Thr Gln
            500                 505                 510

Leu Asp Pro Ala Asn Leu Ile Met Ser Arg Phe Glu Ile Met Ser Val
            515                 520                 525

Tyr His Lys Ala Gln Cys Val Leu His Arg Arg Phe Leu Ala Arg Ala
            530                 535                 540

Arg Glu Asn Pro Arg Phe Thr Tyr Ser Arg Arg Thr Cys Ile Asp Ser
545                 550                 555                 560

Ala Leu Glu Leu Leu Arg Tyr Gln Ser Met Ile His Thr Asp Thr Arg
                565                 570                 575

Pro Asn Gly Arg Leu Arg Gly Lys Leu Asn Arg Thr Thr Ser Leu Cys
            580                 585                 590

Ser Ser Asp Phe Leu Leu Ala Ala Thr Ile Val Cys Leu Asp Leu Tyr
            595                 600                 605

His Gly Leu Gln Leu Gln Ala Gly Arg Ala Ser Asp Asp Thr Tyr
            610                 615                 620

Thr Trp Gly Arg Glu Arg Asp Glu Met Val Ala Ala Leu Gln Arg
625                 630                 635                 640

Ser Lys Glu Ile Trp Asp Glu Leu Gln Asp Glu Thr Ile Asp Ala Trp
                645                 650                 655

Lys Ala Ser Gly Val Leu Gly Val Met Leu Ala Arg Leu Asn Leu Asp
            660                 665                 670

Gly Asn Thr Ala Ser Thr Thr Phe Glu Pro Gln Asp Glu Lys Gln Ser
```

```
                675             680             685
Ala Ala Met Thr Leu Gly Leu Leu Ser Ser Gly Met Asn Tyr Met Asn
        690             695             700
Pro Gly Thr Pro Gly Phe Gly Glu Ala Thr Thr Lys Met Ala Asp Thr
705             710             715             720
Pro Val Pro Pro Gly Gly Phe Gly Ala Ala Asp Met Pro Gly Ala
            725             730             735
Pro Ser Pro Phe Ser Ala Met Phe Gly Gln Met Pro Asp Met Gln Val
            740             745             750
Asn Leu Asp Trp Asp Ala Trp Asp Asn Tyr Ile Gln Asn Ser Ser Ile
            755             760             765
Asp Phe Ser Asn Gln Trp Trp Pro Ala Met Asp Ala Gln Gln Ala Pro
770             775             780
Gln Pro Pro Gln Pro Gly Asn Pro Leu Ser Pro Ser Gln Leu Ala Ala
785             790             795             800
Thr Gln Gly Gly Ile Ala Gly Arg Met Arg Thr Met Pro Ser Leu Ser
            805             810             815
Ser Ala Phe Pro Glu Pro Asn Gly Tyr Asp Ala Ala Phe Pro Thr Ser
            820             825             830
Phe Ser Val Asn Ala Pro Lys Asn Pro His Asn Pro Ala Ser Gly Pro
            835             840             845
Gly Thr
    850

<210> SEQ ID NO 97
<211> LENGTH: 927
<212> TYPE: DNA
<213> ORGANISM: Artificial Sequence
<220> FEATURE:
<223> OTHER INFORMATION: fungal gene

<400> SEQUENCE: 97
atgacaccgc gacaatcctc cccatccgaa cactcgcact ccgacaacaa tgtgcgcaag     60
cgcgtatgta aagcctgcga tcgctgtcgc ctgaaaaagt ccaagtgtga cggaggcaac    120
ccgtgcggcc ggtgtcgcgc agacaatgcc atctgcgtct ttggcgagcg caaaaaggcg    180
catgacaaag tgtaccccaa gggatacgtt gagatgcttg aacagcagca ggcctggctc    240
gtctacggcc tgcaggaact gtaccgccgc accagcgacg gcgaaggctg gcccggcgag    300
ccgctcaagt gcgaggccaa cggccacccg ctcacgcacg acctgctcac ccgcctcggc    360
gccctcgacc aggccaaggg cgagcgcttc gaggaaaacc ccgacgccat gcagcaggag    420
ctctggcgcc agaacgccgg ccacatgcag cgccaggact cgtccgacgc cagctccgac    480
agcgcccact cgcccgtcgt ccctccgtc gccgccgccg ccgccgctcg cttcgccgac    540
cccttcgccc agccccagct gccccccacc ccgccaaata tcagccccag cgcccgcccc    600
gtcaagtccg agtcgtcgca gatgccgccg gcctttgcgt ccgcgccgct gggcatgcag    660
ggcgtcgtca accccatggt gctgcaggcg ccgcagcagc aacagcagca gcagcagtcg    720
tggggaggga atgggttcgg cgggttcgat gatatcgaca tgatgggcac gacggatttt    780
accaacctgt cgtttgacga tccgctgtcg tcgccgatgt tcaatcgacc cgtgccgatc    840
aactgcatgt cgtatatgga cttgaagggc gactacgacg atctgaacca gtttgtcaat    900
gcgaatgcgc cggagatcgc gtcgacg                                       927

<210> SEQ ID NO 98
```

<211> LENGTH: 309
<212> TYPE: PRT
<213> ORGANISM: Artificial Sequence
<220> FEATURE:
<223> OTHER INFORMATION: fungal gene

<400> SEQUENCE: 98

```
Met Thr Pro Arg Gln Ser Ser Pro Ser Glu His Ser His Ser Asp Asn
 1               5                  10                  15

Asn Val Arg Lys Arg Val Cys Lys Ala Cys Asp Arg Cys Arg Leu Lys
                20                  25                  30

Lys Ser Lys Cys Asp Gly Gly Asn Pro Cys Gly Arg Cys Arg Ala Asp
            35                  40                  45

Asn Ala Ile Cys Val Phe Gly Glu Arg Lys Lys Ala His Asp Lys Val
        50                  55                  60

Tyr Pro Lys Gly Tyr Val Glu Met Leu Glu Gln Gln Ala Trp Leu
 65                  70                  75                  80

Val Tyr Gly Leu Gln Glu Leu Tyr Arg Arg Thr Ser Asp Gly Glu Gly
                85                  90                  95

Trp Pro Gly Glu Pro Leu Lys Cys Glu Ala Asn Gly His Pro Leu Thr
            100                 105                 110

His Asp Leu Leu Thr Arg Leu Gly Ala Leu Asp Gln Ala Lys Gly Glu
        115                 120                 125

Arg Phe Glu Glu Asn Pro Asp Ala Met Gln Gln Glu Leu Trp Arg Gln
130                 135                 140

Asn Ala Gly His Met Gln Arg Gln Asp Ser Ser Asp Ala Ser Ser Asp
145                 150                 155                 160

Ser Ala His Ser Pro Val Val Pro Ser Val Ala Ala Ala Ala Ala
                165                 170                 175

Arg Phe Ala Asp Pro Phe Ala Gln Pro Gln Leu Pro Thr Pro Pro
            180                 185                 190

Asn Ile Ser Pro Ser Ala Arg Pro Val Lys Ser Glu Ser Ser Gln Met
        195                 200                 205

Pro Pro Ala Phe Ala Ser Ala Pro Leu Gly Met Gln Gly Val Val Asn
    210                 215                 220

Pro Met Val Leu Gln Ala Pro Gln Gln Gln Gln Gln Gln Gln Gln Ser
225                 230                 235                 240

Trp Gly Gly Asn Gly Phe Gly Phe Asp Asp Ile Asp Met Met Gly
                245                 250                 255

Thr Thr Asp Phe Thr Asn Leu Ser Phe Asp Pro Leu Ser Ser Pro
            260                 265                 270

Met Phe Asn Arg Pro Val Pro Ile Asn Cys Met Ser Tyr Met Asp Leu
        275                 280                 285

Lys Gly Asp Tyr Asp Asp Leu Asn Gln Phe Val Asn Ala Asn Ala Pro
    290                 295                 300

Glu Ile Ala Ser Thr
305
```

<210> SEQ ID NO 99
<211> LENGTH: 1374
<212> TYPE: DNA
<213> ORGANISM: Artificial Sequence
<220> FEATURE:
<223> OTHER INFORMATION: fungal gene

<400> SEQUENCE: 99
atgctctgtc acatcatgac agtggctaca cccgctgtga cgcaagtcca tgaaaatggc    60

-continued

```
ctgaacggac atgtcccaca tcaacatcac caccaccacc atcatccgca ccaaaccaat    120
gtgaacctgc ctcggtttca cccaatcgcc atgaacccga gccagccagt ccatccagag    180
cacatggccg tgccaaatca tcctcacttt cgcccatttc cgccgccgcc gccaatgcat    240
gaacccgggc cgcctccccc gggggctcat cccgcccata tagatcatat cgaagctcga    300
ctgaggcagt ggagcatga ggaagccgct cgcatggcgg ctcgtagtca actactcgca    360
atccgcaagc gggaagacga agaattccgt aggatgaccg agaacgctga agcggaagaa    420
gaggaactac gtagacagcg gaaacgcctg aagcgcgagt ccatgggtct ggggttcaat    480
gccaccgttg actcgcctcc cctacgtccc acgccgcctc gccggctatc agaaacaaac    540
gcagccacca ctctggcctt cttcaagcaa caaagcccgc cagagccacg accgattccc    600
gtgcaggcgc cgccgcacca cccgccaccg cctccgcagc atctgcacga ctcgacgggg    660
gccaccatcc gccgcaagca gaaatacacg atcaaaaacg tcgaagcatg gggcgagcgc    720
cacggccgtc ccgcggcgca cgacccgtcc ggccgcgcgc tgtggaagcg gccctccgac    780
ggcagcctgg tgtacctcac ctgcccggtg tcgggctgcg gcaaggccga ctttgtcacg    840
ctgcacgggt tcatgtgcca tctgaccaag aagcacaagg accgcagcct gggcagccag    900
tcgcgcgcgc tggaagtctg cggcatcgtc tacgacccca cgcgccgct gccgcccgtg    960 gccgccgtgc ccgcgcctc caccgaggag agccgcctcg agtcgccgca cccggacggc    1020
tatccgcagg agatggacac gtcttcggta tcggacgagg agcagcgcga gcacaccgtc    1080
aagaccgagt ccaccgagag atcgttgccg gcgcacgcgg cgcccttccc gcccccccgac    1140 gagcccgtca agcatcccg tctcaacggc tccacgaaac agaccatctc gtccatcatc    1200
gaccgcgagc cggacgatga gccgcgcgag cggcccgcct ccatccccccc cgtccagccc    1260 gagtcggccg tcctgccttc cccggagcag aagtcggtcg ttcgggagga ggagcccaag    1320
tcggcggata gcgaaaagga aaatacggag ccgaaagacg tgtcggaaac aaag    1374
```

<210> SEQ ID NO 100
<211> LENGTH: 458
<212> TYPE: PRT
<213> ORGANISM: Artificial Sequence
<220> FEATURE:
<223> OTHER INFORMATION: fungal gene

<400> SEQUENCE: 100

```
Met Leu Cys His Ile Met Thr Val Ala Thr Pro Ala Val Thr Gln Val
 1               5                  10                  15

His Glu Asn Gly Leu Asn Gly His Val Pro His Gln His His His
                20                  25                  30

His His His Pro His Gln Thr Asn Val Asn Leu Pro Arg Phe His Pro
            35                  40                  45

Ile Ala Met Asn Pro Ser Gln Pro Val His Pro Glu His Met Ala Val
        50                  55                  60

Pro Asn His Pro His Phe Arg Pro Phe Pro Pro Pro Met His
65                  70                  75                  80

Glu Pro Gly Pro Pro Pro Gly Ala His Pro Ala His Ile Asp His
                85                  90                  95

Ile Glu Ala Arg Leu Arg Gln Leu Glu His Glu Ala Ala Arg Met
            100                 105                 110

Ala Ala Arg Ser Gln Leu Leu Ala Ile Arg Lys Arg Glu Asp Glu Glu
        115                 120                 125
```

```
Phe Arg Arg Met Thr Glu Asn Ala Glu Ala Glu Glu Glu Leu Arg
    130                 135                 140

Arg Gln Arg Lys Arg Leu Lys Arg Glu Ser Met Gly Leu Gly Phe Asn
145                 150                 155                 160

Ala Thr Val Asp Ser Pro Pro Leu Arg Pro Thr Pro Pro Arg Arg Leu
                165                 170                 175

Ser Glu Thr Asn Ala Ala Thr Thr Leu Ala Phe Phe Lys Gln Gln Ser
            180                 185                 190

Pro Pro Glu Pro Arg Pro Ile Pro Val Gln Ala Pro Pro His His Pro
            195                 200                 205

Pro Pro Pro Gln His Leu His Asp Ser Thr Gly Ala Thr Ile Arg
    210                 215                 220

Arg Lys Gln Lys Tyr Thr Ile Lys Asn Val Glu Ala Trp Gly Glu Arg
225                 230                 235                 240

His Gly Arg Pro Ala Ala His Asp Pro Ser Gly Arg Ala Leu Trp Lys
                245                 250                 255

Arg Pro Ser Asp Gly Ser Leu Val Tyr Leu Thr Cys Pro Val Ser Gly
            260                 265                 270

Cys Gly Lys Ala Asp Phe Val Thr Leu His Gly Phe Met Cys His Leu
            275                 280                 285

Thr Lys Lys His Lys Asp Arg Ser Leu Gly Ser Gln Ser Arg Ala Leu
    290                 295                 300

Glu Val Cys Gly Ile Val Tyr Asp Pro Asn Ala Pro Leu Pro Pro Val
305                 310                 315                 320

Ala Ala Val Pro Arg Ala Ser Thr Glu Glu Ser Arg Leu Glu Ser Pro
                325                 330                 335

His Pro Asp Gly Tyr Pro Gln Glu Met Asp Thr Ser Ser Val Ser Asp
            340                 345                 350

Glu Glu Gln Arg Glu His Thr Val Lys Thr Glu Ser Thr Glu Arg Ser
            355                 360                 365

Leu Pro Ala His Ala Ala Pro Phe Pro Pro Pro Asp Glu Pro Val Lys
    370                 375                 380

Ala Ser Arg Leu Asn Gly Ser Thr Lys Gln Thr Ile Ser Ser Ile Ile
385                 390                 395                 400

Asp Arg Glu Pro Asp Asp Glu Pro Arg Glu Arg Pro Ala Ser Ile Pro
                405                 410                 415

Pro Val Gln Pro Glu Ser Ala Val Leu Pro Ser Pro Glu Gln Lys Ser
            420                 425                 430

Val Val Arg Glu Glu Pro Lys Ser Ala Asp Ser Glu Lys Glu Asn
            435                 440                 445

Thr Glu Pro Lys Asp Val Ser Glu Thr Lys
    450                 455

<210> SEQ ID NO 101
<211> LENGTH: 1728
<212> TYPE: DNA
<213> ORGANISM: Artificial Sequence
<220> FEATURE:
<223> OTHER INFORMATION: fungal gene

<400> SEQUENCE: 101
atgaacgatc ctttcgtccc cgccaaaaat cccggcccga cgaaagccgc gggtccctcg      60
ctgttggcct gtcttctgtg ccgtcacaaa cacctcaaat gtgatgggaa aactccagtg     120
tgcggacgct gtgccgctac tggatcggaa tgccaatata ccccgtcgcg tcgtgggtac     180
```

-continued

```
aagggcccgt cgaagaagcg acgcgcaaac ccgtcgtctc cagagcaaac gcccgccgat      240
ctggccgcct cgttcgatcc gcagtccatc ggtttggtca atgtcacccc tgactggagc      300
ctgcaaaaca cggtcccttt catgcccgtc gctaccttcc cgtcctcctc gtcgaccagc      360
ccgggcttga ccgactacac caattcttcg caacccatcc ggttcacgaa tgaccccta       420 actcccgact cttccgcctc ggtccccggt gatgggtatt tgatcgatat ctactatacc      480
tatttccatc cctcgcaccc aattctccct ccgctccgct ttctctaccg ctcctatctc      540
ccgaccttcc tggagcaggt catcaagttc atcggtgctc atttcactcc ggccgcttcg      600
agcgagacgt atcgacccac cgttgtgtca aatgtgaagg agcaagaggg ctctatagag      660
aagctgcagg ctctcttgtt gctcgcggtg gtcctccact ctcgcaatga acgtcccgaa      720
gctggcgagt gtctcgccgg agctgttgac ctagcgtttg agctgggact ccagacgcag      780
agtttcgcca ccgcgatgag cgacggtgac cccatccgcg cggaatgcct gcggcgcaca      840
tggtgggagc tgttcattat cgaggggatg ctgactgcac ttggggttca gagcacttac      900
cgtaccaaca tggtgccgcc ggaggtggga ctaccatgtg aggaacggat ctaccaggat      960
ggcctggcgc cgcccccgcc tccaacgatc gctcaattcg acaatcgcgt cttcgccgac     1020
gaggagcgcg acttctcttc cttcacctac cgtatcgagg cggtccgcat tctcgggcgc     1080
gtggtcggca tccaggacat ggtcgagggc aacaggacc atgtggaggc cattgacgcc      1140
cgaatcacga gttggttcca ccacctcccc gagtccaagg cggagctgct gcgtcccgat     1200
ggttccgtgg atgagatgat gttccaagcc accatgatcg tgaacggcgc gtcgatatac     1260
ctccacttcc cccgttctga tttgctgtca tcgcccgcca tggccgcgga agtgatctgc     1320
ggtcaccacg accctgcag cattcccgca ttttcacacc acgccatgc aatgaaggcc      1380 ctcaaagccg ccagcgagat ctcctcgctg gcttccatcc gcatgccggt ggtcaaacac     1440
acgcccttct tcatctgcgc cctggttatg agctcgatcg tgcagctggc tgcatgctcc     1500
gtcaaggccg ggcagatgcc cgatcccagc cgggatcgcc tcaccctgac cattggcgtc     1560
ttcaaatccc tggcccgcac gtgggccatc tcccagacaa tcatgaggca gatcaaagcc     1620
gtgtcgcgcg atgttatgga catgggactg cggccggcca tggaccagat tgatctgacg     1680
accctcctcg atagcggtcg gttcttgatg cccgatggac tgatgcga                  1728
```

<210> SEQ ID NO 102
<211> LENGTH: 576
<212> TYPE: PRT
<213> ORGANISM: Artificial Sequence
<220> FEATURE:
<223> OTHER INFORMATION: fungal gene

<400> SEQUENCE: 102

```
Met Asn Asp Pro Phe Val Pro Ala Lys Asn Pro Gly Pro Thr Lys Ala
 1               5                  10                  15

Ala Gly Pro Ser Leu Leu Ala Cys Leu Cys Arg His Lys His Leu
                20                  25                  30

Lys Cys Asp Gly Lys Thr Pro Val Cys Gly Arg Cys Ala Ala Thr Gly
            35                  40                  45

Ser Glu Cys Gln Tyr Thr Pro Ser Arg Arg Gly Tyr Lys Gly Pro Ser
        50                  55                  60

Lys Lys Arg Arg Ala Asn Pro Ser Ser Pro Glu Gln Thr Pro Ala Asp
65                  70                  75                  80

Leu Ala Ala Ser Phe Asp Pro Gln Ser Ile Gly Leu Val Asn Val Thr
                85                  90                  95
```

-continued

```
Pro Asp Trp Ser Leu Gln Asn Thr Val Pro Phe Met Pro Val Ala Thr
            100                 105                 110
Phe Pro Ser Ser Ser Thr Ser Pro Gly Leu Thr Asp Tyr Thr Asn
        115                 120                 125
Ser Ser Gln Pro Ile Arg Phe Thr Asn Asp Pro Leu Thr Pro Asp Ser
    130                 135                 140
Ser Ala Ser Val Pro Gly Asp Gly Tyr Leu Ile Asp Ile Tyr Tyr Thr
145                 150                 155                 160
Tyr Phe His Pro Ser His Pro Ile Leu Pro Pro Leu Arg Phe Leu Tyr
                165                 170                 175
Arg Ser Tyr Leu Pro Thr Phe Leu Glu Gln Val Ile Lys Phe Ile Gly
            180                 185                 190
Ala His Phe Thr Pro Ala Ala Ser Glu Thr Tyr Arg Pro Thr Val
        195                 200                 205
Val Ser Asn Val Lys Glu Gln Glu Gly Ser Ile Glu Lys Leu Gln Ala
    210                 215                 220
Leu Leu Leu Leu Ala Val Val Leu His Ser Arg Asn Glu Arg Pro Glu
225                 230                 235                 240
Ala Gly Glu Cys Leu Ala Gly Ala Val Asp Leu Ala Phe Glu Leu Gly
                245                 250                 255
Leu Gln Thr Gln Ser Phe Ala Thr Ala Met Ser Asp Gly Asp Pro Ile
            260                 265                 270
Arg Ala Glu Cys Leu Arg Arg Thr Trp Trp Glu Leu Phe Ile Ile Glu
        275                 280                 285
Gly Met Leu Thr Ala Leu Gly Val Gln Ser Thr Tyr Arg Thr Asn Met
    290                 295                 300
Val Pro Pro Glu Val Gly Leu Pro Cys Glu Glu Arg Ile Tyr Gln Asp
305                 310                 315                 320
Gly Leu Ala Pro Pro Pro Pro Thr Ile Ala Gln Phe Asp Asn Arg
                325                 330                 335
Val Phe Ala Asp Glu Glu Arg Asp Phe Ser Ser Phe Thr Tyr Arg Ile
            340                 345                 350
Glu Ala Val Arg Ile Leu Gly Arg Val Val Gly Ile Gln Asp Met Val
        355                 360                 365
Glu Gly Gln Gln Asp His Val Glu Ala Ile Asp Ala Arg Ile Thr Ser
    370                 375                 380
Trp Phe His His Leu Pro Glu Ser Lys Ala Glu Leu Leu Arg Pro Asp
385                 390                 395                 400
Gly Ser Val Asp Glu Met Met Phe Gln Ala Thr Met Ile Val Asn Gly
                405                 410                 415
Ala Ser Ile Tyr Leu His Phe Pro Arg Ser Asp Leu Leu Ser Ser Pro
            420                 425                 430
Ala Met Ala Ala Glu Val Ile Cys Gly His His Gly Pro Cys Ser Ile
        435                 440                 445
Pro Ala Phe Ser His His Ala His Ala Met Lys Ala Leu Lys Ala Ala
    450                 455                 460
Ser Glu Ile Ser Ser Leu Ala Ser Ile Arg Met Pro Val Val Lys His
465                 470                 475                 480
Thr Pro Phe Phe Ile Cys Ala Leu Val Met Ser Ser Ile Val Gln Leu
                485                 490                 495
Ala Ala Cys Ser Val Lys Ala Gly Gln Met Pro Asp Pro Ser Arg Asp
            500                 505                 510
```

```
Arg Leu Thr Leu Thr Ile Gly Val Phe Lys Ser Leu Ala Arg Thr Trp
        515                 520                 525

Ala Ile Ser Gln Thr Ile Met Arg Gln Ile Lys Ala Val Ser Arg Asp
    530                 535                 540

Val Met Asp Met Gly Leu Arg Pro Ala Met Asp Gln Ile Asp Leu Thr
545                 550                 555                 560

Thr Leu Leu Asp Ser Gly Arg Phe Leu Met Pro Asp Gly Leu Met Arg
                565                 570                 575
```

<210> SEQ ID NO 103
<211> LENGTH: 1272
<212> TYPE: DNA
<213> ORGANISM: Artificial Sequence
<220> FEATURE:
<223> OTHER INFORMATION: fungal gene

<400> SEQUENCE: 103

```
atggccaaac ccaaccagcg ccatgcctgt gaccgctgtc acggtcaaaa actgcgatgc     60
atccactccg ggggtgggcc gtgtgtacgc tgcgccaaag ccaaagccac ctgcagctgg    120
agccagtcct tacgttccaa ccgactcaag agacataacg cgccgatatc tgatgttcct    180
ttggcgtgtg cgcaactagc aacccagtcg accgacccaa acacacctca atttggtgca    240
tacatgagcc aaccctcctc cgccggcgtt gacattgaca tcaacttgct gcagactcaa    300
ttcaccgaca gtactccctg ggctctgccg gccggccgct atccctctcc agcatcacag    360
gaaatggaga cttacaatgt gggtcacact gaggcggacc ttccggccac cgcggactgg    420
atgtggcccg ccgtcgccaa tggtcccgtt caaacgactc ccccggcaaa ttggcagcaa    480
gcattcaatc aggaatgggc tatgattggcg tcgcagcacc ctgtcgcaac gatggacacg    540
ccgtctcgga catcgccagt aagcgacgcc gtggacccgc cgaagacggt gtgccttctt    600
gcgaccatcc gcgagttgtc agagcttaac gtcgacctgt acgcacacga agcgacggtc    660
cccagaccctc ctgcatctct ggaggaaccg atcagctgga agaacaagga tttcgccatc    720
gatcggactt ccacctgtc ccagcggctc attgagatcg tcaacaaacg atatccgcgc    780
tacctcgaga cggcccgcat gcagacccg gaggggactc ccgaacggac ctccgaaagc    840
agtctgtctg gcccgccact tgaccaaggc tcatgtctcc tcgttctctc atgttacact    900
cgactcatcg agacctacga tcgaatcttt gccaatatgc agggatgtct ggatcgttcc    960
tcggtcacgg cccgagaaga ctacgtcaat atgccgtcgg tccaagtcgg ctccttctcc   1020
ttgccacact cgtcctcgtt gcaaatcgtc ctcatcctgc agttggcgcg tcaactccta   1080
actcgaatgg gcgagatcat caaagccgtt cagccggaga aagaactaa ccccgctgat   1140
gtcaccttgt ccgaatccgc aaccgggggt ctcctactgt ctagcgcttt ggagaccgtc   1200
tccgccgaag aagaccgtct gatgaaaaga atcacgaaac tacgaagcac cttgattgag   1260
ctaaacattc tg                                                      1272
```

<210> SEQ ID NO 104
<211> LENGTH: 424
<212> TYPE: PRT
<213> ORGANISM: Artificial Sequence
<220> FEATURE:
<223> OTHER INFORMATION: fungal gene

<400> SEQUENCE: 104

```
Met Ala Lys Pro Asn Gln Arg His Ala Cys Asp Arg Cys His Gly Gln
1               5                   10                  15
```

```
-continued

Lys Leu Arg Cys Ile His Ser Gly Gly Pro Cys Val Arg Cys Ala
         20                  25                  30
Lys Ala Lys Ala Thr Cys Ser Trp Ser Gln Ser Leu Arg Ser Asn Arg
         35                  40                  45
Leu Lys Arg His Asn Ala Pro Ile Ser Asp Val Pro Leu Ala Cys Ala
     50                  55                  60
Gln Leu Ala Thr Gln Ser Thr Asp Pro Asn Thr Pro Gln Phe Gly Ala
65                  70                  75                  80
Tyr Met Ser Gln Pro Ser Ser Ala Gly Val Asp Ile Asp Ile Asn Leu
                 85                  90                  95
Leu Gln Thr Gln Phe Thr Asp Ser Thr Pro Trp Ala Leu Pro Ala Gly
             100                 105                 110
Arg Tyr Pro Ser Pro Ala Ser Gln Glu Met Glu Thr Tyr Asn Val Gly
             115                 120                 125
His Thr Glu Ala Asp Leu Pro Ala Thr Ala Asp Trp Met Trp Pro Ala
    130                 135                 140
Val Ala Asn Gly Pro Val Gln Thr Thr Pro Ala Asn Trp Gln Gln
145                 150                 155                 160
Ala Phe Asn Gln Glu Trp Ala Met Met Ala Ser Gln His Pro Val Ala
             165                 170                 175
Thr Met Asp Thr Pro Ser Arg Thr Ser Pro Val Ser Asp Ala Val Asp
             180                 185                 190
Pro Pro Lys Thr Val Cys Leu Leu Ala Thr Ile Arg Glu Leu Ser Glu
         195                 200                 205
Leu Asn Val Asp Leu Tyr Ala His Glu Ala Thr Val Pro Arg Pro Pro
     210                 215                 220
Ala Ser Leu Glu Glu Pro Ile Ser Trp Lys Asn Lys Asp Phe Ala Ile
225                 230                 235                 240
Asp Arg Thr Phe His Leu Ser Gln Arg Leu Ile Glu Ile Val Asn Lys
             245                 250                 255
Arg Tyr Pro Arg Tyr Leu Glu Thr Ala Arg Met Gln Thr Pro Glu Gly
             260                 265                 270
Thr Pro Glu Arg Thr Ser Glu Ser Ser Leu Ser Gly Pro Pro Leu Asp
         275                 280                 285
Gln Gly Ser Cys Leu Leu Val Leu Ser Cys Tyr Thr Arg Leu Ile Glu
     290                 295                 300
Thr Tyr Asp Arg Ile Phe Ala Asn Met Gln Gly Cys Leu Asp Arg Ser
305                 310                 315                 320
Ser Val Thr Ala Arg Glu Asp Tyr Val Asn Met Pro Ser Val Gln Val
             325                 330                 335
Gly Ser Phe Ser Leu Pro His Ser Ser Leu Gln Ile Val Leu Ile
             340                 345                 350
Leu Gln Leu Ala Arg Gln Leu Leu Thr Arg Met Gly Glu Ile Ile Lys
     355                 360                 365
Ala Val Gln Pro Glu Lys Arg Thr Asn Pro Ala Asp Val Thr Leu Ser
     370                 375                 380
Glu Ser Ala Thr Gly Gly Leu Leu Leu Ser Ser Ala Leu Glu Thr Val
385                 390                 395                 400
Ser Ala Glu Glu Asp Arg Leu Met Lys Arg Ile Thr Lys Leu Arg Ser
             405                 410                 415
Thr Leu Ile Glu Leu Asn Ile Leu
             420
```

<210> SEQ ID NO 105
<211> LENGTH: 1473
<212> TYPE: DNA
<213> ORGANISM: Artificial Sequence
<220> FEATURE:
<223> OTHER INFORMATION: fungal gene

<400> SEQUENCE: 105

| | | | | | |
|---|---|---|---|---|---|
| atggagacgt | attacgggca | cgttcgcaca | cctgcggacg | ctattattct | ttttgaggct | 60 |
| tgccgtatcg | gccttttacc | tcgcgtgcaa | agacgattat | cagagaaaga | gagacaatca | 120 |
| atccgttccg | gttcggtctt | tgtatgggat | gagcgagaag | cgggtatgcg | gcgatggacc | 180 |
| gatgggaagt | catggagcgc | cagccgtgtg | tctggtagct | ttttgacgta | tcgtgaaatg | 240 |
| gaaggcaagc | gtggaggtgg | tagcgtctct | cagggttctg | cgtcccgagg | aggtaaaacg | 300 |
| cctgagagtc | ggggcagtga | cgatgatcgt | gcggatggaa | cagatgaggg | accagatggg | 360 |
| taccgttaca | aaccagatgg | cttgatgaag | cagtctttca | gtatcacaac | ctccaacggt | 420 |
| caacatctgc | atctcattag | ctactattca | cgatctcacc | cttcggccgc | caacttacaa | 480 |
| caaccaacta | cggatcctgc | gctacgccat | gttcgccccc | agaaaggcct | ctatcccgag | 540 |
| tcaacagtca | acgatcagca | aaacctccct | gtcgttaccc | gtggacctat | gcaaggcgct | 600 |
| gcgtaccccca | taactcccca | tcctctcggc | gcatacccgc | gcgtcactca | tacacagcca | 660 |
| tatccacctg | cctatgcttg | gccgcccacc | cctctagcca | caccaccgac | tgtctcggtt | 720 |
| caatacggcc | ctggtccttc | ttatctgccc | ccggtaggtg | ccaatggaca | tcctcattat | 780 |
| ggcccgccac | atcatcagcc | tccacctcat | caacatggcg | gtggactacc | accccctcca | 840 |
| cacgggatga | caagcccgta | tgatcgacca | cctcacaatg | aatcaacatt | gcctccagct | 900 |
| ggaccaccgt | cacaacagcc | aagctacatg | aaccggtcac | cgcgctcaat | acacgaccat | 960 |
| gctcaagccc | acgccatgc | tcacgctcac | gctcaagctc | aggctcaagc | tcaagctcag | 1020 |
| gctcaagctc | aagctcaggc | acaggcccat | gcccacgagc | aacgcacccc | gcctgtctac | 1080 |
| gggcatcctt | tagttgaccc | tcgcatggca | tcaccgcgcg | tgccagtcca | gtccctggcg | 1140 |
| cagccaaatg | ccacgcgca | cagccctcat | ctggcgaagc | aggagcatcc | cgccgcgctg | 1200 |
| ccctctctta | accccatcgc | cgcatcacca | aagtcttccg | atcccgcgag | cgctggaaat | 1260 |
| gcagttcctg | gaattggctc | attaatgaac | ggtgcaggcc | tggcccctct | ttcctcatcg | 1320 |
| actgcctctc | ccggtggccc | cgccgcgagc | tcgaacgaa | ccccgccgc | gtcctctttc | 1380 |
| gctgagggtc | cacgggatat | ccctaacgag | aagatcagat | tcggaggcga | ggacacgagg | 1440 |
| gcactgcgcc | agctggatcg | cgccttcatt | gca | | | 1473 |

<210> SEQ ID NO 106
<211> LENGTH: 491
<212> TYPE: PRT
<213> ORGANISM: Artificial Sequence
<220> FEATURE:
<223> OTHER INFORMATION: fungal gene

<400> SEQUENCE: 106

Met Glu Thr Tyr Tyr Gly His Val Arg Thr Pro Ala Asp Ala Ile Ile
 1               5                  10                  15

Leu Phe Glu Ala Cys Arg Ile Gly Leu Leu Pro Arg Val Gln Arg Arg
            20                  25                  30

Leu Ser Glu Lys Glu Arg Gln Ser Ile Arg Ser Gly Ser Val Phe Val
        35                  40                  45

Trp Asp Glu Arg Glu Ala Gly Met Arg Arg Trp Thr Asp Gly Lys Ser

-continued

```
            50                  55                  60
Trp Ser Ala Ser Arg Val Ser Gly Ser Phe Leu Thr Tyr Arg Glu Met
 65                  70                  75                  80

Glu Gly Lys Arg Gly Gly Gly Ser Val Ser Gln Gly Ser Ala Ser Arg
                 85                  90                  95

Gly Gly Lys Thr Pro Glu Ser Arg Gly Ser Asp Asp Arg Ala Asp
                100                 105                 110

Gly Thr Asp Glu Gly Pro Asp Gly Tyr Arg Tyr Lys Pro Asp Gly Leu
                115                 120                 125

Met Lys Gln Ser Phe Ser Ile Thr Thr Ser Asn Gly Gln His Leu His
    130                 135                 140

Leu Ile Ser Tyr Tyr Ser Arg Ser His Pro Ser Ala Ala Asn Leu Gln
145                 150                 155                 160

Gln Pro Thr Thr Asp Pro Ala Leu Arg His Val Arg Pro Gln Lys Gly
                    165                 170                 175

Leu Tyr Pro Glu Ser Thr Val Asn Asp Gln Gln Asn Leu Pro Val Val
                180                 185                 190

Thr Arg Gly Pro Met Gln Gly Ala Ala Tyr Pro Ile Thr Pro His Pro
                195                 200                 205

Leu Gly Ala Tyr Pro Arg Val Thr His Thr Gln Pro Tyr Pro Pro Ala
210                 215                 220

Tyr Ala Trp Pro Pro Thr Pro Leu Ala Thr Pro Pro Thr Val Ser Val
225                 230                 235                 240

Gln Tyr Gly Pro Gly Pro Ser Tyr Leu Pro Pro Val Gly Ala Asn Gly
                    245                 250                 255

His Pro His Tyr Gly Pro Pro His His Gln Pro Pro His Gln His
                260                 265                 270

Gly Gly Gly Leu Pro Pro Pro His Gly Met Thr Ser Pro Tyr Asp
                275                 280                 285

Arg Pro Pro His Asn Glu Ser Thr Leu Pro Pro Ala Gly Pro Pro Ser
    290                 295                 300

Gln Gln Pro Ser Tyr Met Asn Arg Ser Pro Arg Ser Ile His Asp His
305                 310                 315                 320

Ala Gln Ala His Ala His Ala His Ala Gln Ala Gln Ala Gln
                325                 330                 335

Ala Gln Ala Gln Ala Gln Ala Gln Ala Gln Ala His Ala His
                340                 345                 350

Glu Gln Arg Thr Pro Pro Val Tyr Gly His Pro Leu Val Asp Pro Arg
                355                 360                 365

Met Ala Ser Pro Arg Val Pro Val Gln Ser Leu Ala Gln Pro Asn Gly
    370                 375                 380

His Ala His Ser Pro His Leu Ala Lys Gln Glu His Pro Ala Ala Leu
385                 390                 395                 400

Pro Ser Leu Asn Pro Ile Ala Ala Ser Pro Lys Ser Ser Asp Pro Ala
                405                 410                 415

Ser Ala Gly Asn Ala Val Pro Gly Ile Gly Ser Leu Met Asn Gly Ala
                420                 425                 430

Gly Leu Ala Pro Leu Ser Ser Thr Ala Ser Pro Gly Gly Pro Ala
                435                 440                 445

Ala Ser Ser Asn Gly Thr Pro Ala Ala Ser Ser Phe Ala Glu Gly Pro
    450                 455                 460

Arg Asp Ile Pro Asn Glu Lys Ile Arg Phe Gly Gly Glu Asp Thr Arg
465                 470                 475                 480
```

Ala Leu Arg Gln Leu Asp Arg Ala Phe Ile Ala
              485                 490

<210> SEQ ID NO 107
<211> LENGTH: 2577
<212> TYPE: DNA
<213> ORGANISM: Artificial Sequence
<220> FEATURE:
<223> OTHER INFORMATION: fungal gene

<400> SEQUENCE: 107

| | | | | | |
|---|---|---|---|---|---|
| atgatcatgc | cataccccac | caaaatgacc | ccgacacctc | cttctacaaa | ttcctcgagt | 60 |
| gctggccact | ctccagatta | cagagtcgtc | cggaaacgaa | accgggtacc | tttgtcatgt | 120 |
| gggccttgtc | ggcacagaaa | gctgaaatgc | aatcgtacac | atccttgcga | aaattgtgtc | 180 |
| aaacgagggg | atgctgcttc | atgtaactat | gcgcaaccca | actcgcgcaa | gaagaacccc | 240 |
| cagcaatcat | ctactacacc | ggatgatatg | caaaaccgca | tcgatcggtt | agaaggcttg | 300 |
| gtcctttcat | tgatgacaaa | cggctcacag | tctgcgggcc | cgaatgctgc | catggccgcg | 360 |
| atttcaggtg | aaagtagtgc | gggctccacc | cggttctccc | atgacctcga | cgccgaagag | 420 |
| gagggtatgg | agggcgccga | agagagtgac | acggaccagg | tgacgaagtc | atttggcatc | 480 |
| atgaagatgg | acaataacaa | gtcctattac | atcagtgacg | ctcattgggc | gtctgtattg | 540 |
| agtgatatcg | ccgaggtgaa | aagttttttc | tcaacgcaca | agaagcaaat | ggatgcgcaa | 600 |
| attgagaaag | tcaaagcgtc | ccaaccacct | agtgaggcat | caggctcgac | tttgttgttt | 660 |
| ggtatcaata | aaccaatgag | ccgtggggag | atcatgtccg | gtttgccttc | gaagtataca | 720 |
| actgacattc | ttattgctcg | ctatttcaac | tgctacgacc | ctgcaactca | tgttcttcat | 780 |
| gggccgacat | tccaagctca | gtataataaa | cattgggatg | atcctagcgc | gaccgaactc | 840 |
| gtctggatcg | ccatgctctt | tggaatgatg | agattagcga | tgctgtctta | ccaccgcgaa | 900 |
| ggcgacgagc | cacccgaatt | ccggggcaag | tccttggaca | tggccggcgg | attccgaaat | 960 |
| tctgtagcac | agtgcctgac | attggctgac | tacacgaaac | cccacccctt | cttgattgag | 1020 |
| gcgcttgtat | ttcacttgca | tggcgatttc | tctctgaccc | gagaggcgga | catctccatc | 1080 |
| tgggtcatga | ctggcgttgt | tactcgccta | gcaatgcgat | cagggtatca | ccgtgactcc | 1140 |
| aaaatgtacc | caaacatcac | acctttccag | ggtgagatgc | gacgtcgggt | gtggactttt | 1200 |
| gtgcgccaag | ccgacattct | attctcatac | caggtcggct | tgccgggcat | gatccgaggt | 1260 |
| gcagatagcg | atactgaact | gccacggaat | tgtacgatg | atgattttga | tgaagattgc | 1320 |
| aaggagctcc | cgccgccacg | tcaactgaac | gagcccacac | ccatctcgta | tttgattgcc | 1380 |
| aaggcgcgct | tgtcgtatgt | attcggtcgc | gtggttgaac | aaagctcttc | tgtgtcgtcc | 1440 |
| gtcccatacg | aaaaagtaat | ggaactggac | gcagaactcc | gacaggcaag | ggacttgatc | 1500 |
| ccagagcact | acatattcg | gcctatggag | gagtgccagt | tggatcctat | caatattatc | 1560 |
| atgtcgcggt | tttccgtaat | ggctgtatac | gacaaagctc | agtgtgtgct | tcatcgcccg | 1620 |
| tatctggttc | gcgcccgaga | aaatcctcgt | ttcacctatt | ctcggaggac | atgtatcgac | 1680 |
| tcagcaatgg | agttattgcg | ggtccaggcg | cttctgcacg | cggagacgcg | caacggacgc | 1740 |
| ctccgcagtc | gccagagccg | agtaacttcc | ctcacttcag | cggactttttt | actagcaggc | 1800 |
| accattgtta | ctctcgacct | ataccacggc | ctgtcattgc | aggtcagcgg | ccggccatca | 1860 |
| ggagacacgt | atacatgggg | ccgagagcgg | cgcgatgaaa | tgaccgccgc | gatccaacac | 1920 |
| tcgaaagaaa | tttgggacga | gtcgcgtgat | gagagcatgg | aagcatggaa | agcatccact | 1980 |

-continued

```
gttctcggtg tgatgctcag caagctacac atgacggtcc caggccttga gaatagcgcc    2040
ggagctgctt catttgagcc acaagacgag aagcagaacg cggccatgac cctcggccta    2100
ctgagcagcg gaatgagccc gatgaacccg ggccagccgc cgtttgctga tcccatgttc    2160
aagatgggag attcgccgat gggaactgga acaggtgctg tgggcgcctc ggccgaaatg    2220
ccgggtgctc tttcgccctt tagcagcatg ttcgggcaga tgccggacat gcaggttaac    2280
cttgattggg atgcctggga cacatacatc cagaacccaa ccctcgacac aacaaatcag    2340
ttctggccta tgatggatgc acagcgccag gcaaccccac agtctggagg catgtcacag    2400
ccttcagtgt ctagtcctct ggcctcaggg cgggtgccat caattagtgg tgttccacgg    2460
ataccgacaa tgtactcagc atcctccaac agtcccgata gtgcaggtgt gccagtgaca    2520
ggatacggca tgacgccaat gcctcaacaa aacgatggtc ggggccaagg ctcccaa       2577
```

<210> SEQ ID NO 108
<211> LENGTH: 859
<212> TYPE: PRT
<213> ORGANISM: Artificial Sequence
<220> FEATURE:
<223> OTHER INFORMATION: fungal gene

<400> SEQUENCE: 108

```
Met Ile Met Pro Tyr Pro Thr Lys Met Thr Pro Thr Pro Pro Ser Thr
 1               5                  10                  15

Asn Ser Ser Ser Ala Gly His Ser Pro Asp Tyr Arg Val Val Arg Lys
             20                  25                  30

Arg Asn Arg Val Pro Leu Ser Cys Gly Pro Cys Arg His Arg Lys Leu
         35                  40                  45

Lys Cys Asn Arg Thr His Pro Cys Glu Asn Cys Val Lys Arg Gly Asp
     50                  55                  60

Ala Ala Ser Cys Asn Tyr Ala Gln Pro Asn Ser Arg Lys Lys Asn Pro
 65                  70                  75                  80

Gln Gln Ser Ser Thr Thr Pro Asp Asp Met Gln Asn Arg Ile Asp Arg
                 85                  90                  95

Leu Glu Gly Leu Val Leu Ser Leu Met Thr Asn Gly Ser Gln Ser Ala
            100                 105                 110

Gly Pro Asn Ala Ala Met Ala Ala Ile Ser Gly Glu Ser Ser Ala Gly
        115                 120                 125

Ser Thr Arg Phe Ser His Asp Leu Asp Ala Glu Glu Gly Met Glu
    130                 135                 140

Gly Ala Glu Glu Ser Asp Thr Asp Gln Val Thr Lys Ser Phe Gly Ile
145                 150                 155                 160

Met Lys Met Asp Asn Asn Lys Ser Tyr Tyr Ile Ser Asp Ala His Trp
                165                 170                 175

Ala Ser Val Leu Ser Asp Ile Ala Glu Val Lys Ser Phe Phe Ser Thr
            180                 185                 190

His Lys Lys Gln Met Asp Ala Gln Ile Glu Lys Val Lys Ala Ser Gln
        195                 200                 205

Pro Pro Ser Glu Ala Ser Gly Ser Thr Leu Leu Phe Gly Ile Asn Lys
    210                 215                 220

Pro Met Ser Arg Gly Glu Ile Met Ser Gly Leu Pro Ser Lys Tyr Thr
225                 230                 235                 240

Thr Asp Ile Leu Ile Ala Arg Tyr Phe Asn Cys Tyr Asp Pro Ala Thr
                245                 250                 255
```

-continued

```
His Val Leu His Gly Pro Thr Phe Gln Ala Gln Tyr Asn Lys His Trp
            260                 265                 270
Asp Asp Pro Ser Ala Thr Glu Leu Val Trp Ile Ala Met Leu Phe Gly
            275                 280                 285
Met Met Arg Leu Ala Met Leu Ser Tyr His Arg Glu Gly Asp Glu Pro
            290                 295                 300
Pro Glu Phe Arg Gly Lys Ser Leu Asp Met Ala Gly Gly Phe Arg Asn
305                 310                 315                 320
Ser Val Ala Gln Cys Leu Thr Leu Ala Asp Tyr Thr Lys Pro His Pro
                    325                 330                 335
Phe Leu Ile Glu Ala Leu Val Phe His Leu His Gly Asp Phe Ser Leu
                340                 345                 350
Thr Arg Glu Ala Asp Ile Ser Ile Trp Val Met Thr Gly Val Val Thr
            355                 360                 365
Arg Leu Ala Met Arg Ser Gly Tyr His Arg Asp Ser Lys Met Tyr Pro
            370                 375                 380
Asn Ile Thr Pro Phe Gln Gly Glu Met Arg Arg Arg Val Trp Thr Phe
385                 390                 395                 400
Val Arg Gln Ala Asp Ile Leu Phe Ser Tyr Gln Val Gly Leu Pro Gly
                    405                 410                 415
Met Ile Arg Gly Ala Asp Ser Asp Thr Glu Leu Pro Arg Asn Leu Tyr
                420                 425                 430
Asp Asp Asp Phe Asp Glu Asp Cys Lys Glu Leu Pro Pro Pro Arg Gln
            435                 440                 445
Leu Asn Glu Pro Thr Pro Ile Ser Tyr Leu Ile Ala Lys Ala Arg Leu
450                 455                 460
Ser Tyr Val Phe Gly Arg Val Val Glu Gln Ser Ser Val Ser Ser
465                 470                 475                 480
Val Pro Tyr Glu Lys Val Met Glu Leu Asp Ala Glu Leu Arg Gln Ala
                    485                 490                 495
Arg Asp Leu Ile Pro Glu His Leu His Ile Arg Pro Met Glu Glu Cys
            500                 505                 510
Gln Leu Asp Pro Ile Asn Ile Ile Met Ser Arg Phe Ser Val Met Ala
            515                 520                 525
Val Tyr Asp Lys Ala Gln Cys Val Leu His Arg Pro Tyr Leu Val Arg
            530                 535                 540
Ala Arg Glu Asn Pro Arg Phe Thr Tyr Ser Arg Arg Thr Cys Ile Asp
545                 550                 555                 560
Ser Ala Met Glu Leu Leu Arg Val Gln Ala Leu Leu His Ala Glu Thr
                    565                 570                 575
Arg Asn Gly Arg Leu Arg Ser Arg Gln Ser Arg Val Thr Ser Leu Thr
            580                 585                 590
Ser Ala Asp Phe Leu Leu Ala Gly Thr Ile Val Thr Leu Asp Leu Tyr
            595                 600                 605
His Gly Leu Ser Leu Gln Val Ser Gly Arg Pro Ser Gly Asp Thr Tyr
            610                 615                 620
Thr Trp Gly Arg Glu Arg Asp Glu Met Thr Ala Ala Ile Gln His
625                 630                 635                 640
Ser Lys Glu Ile Trp Asp Glu Ser Arg Asp Glu Ser Met Glu Ala Trp
                    645                 650                 655
Lys Ala Ser Thr Val Leu Gly Val Met Leu Ser Lys Leu His Met Thr
            660                 665                 670
Val Pro Gly Leu Glu Asn Ser Ala Gly Ala Ala Ser Phe Glu Pro Gln
```

```
                 675              680              685
Asp Glu Lys Gln Asn Ala Ala Met Thr Leu Gly Leu Leu Ser Ser Gly
        690              695              700

Met Ser Pro Met Asn Pro Gly Gln Pro Pro Phe Ala Asp Pro Met Phe
705              710              715              720

Lys Met Gly Asp Ser Pro Met Gly Thr Gly Thr Gly Ala Val Gly Ala
            725              730              735

Ser Ala Glu Met Pro Gly Ala Leu Ser Pro Phe Ser Ser Met Phe Gly
            740              745              750

Gln Met Pro Asp Met Gln Val Asn Leu Asp Trp Asp Ala Trp Asp Thr
            755              760              765

Tyr Ile Gln Asn Pro Thr Leu Asp Thr Thr Asn Gln Phe Trp Pro Met
    770              775              780

Met Asp Ala Gln Arg Gln Ala Thr Pro Gln Ser Gly Gly Met Ser Gln
785              790              795              800

Pro Ser Val Ser Ser Pro Leu Ala Ser Gly Arg Val Pro Ser Ile Ser
                805              810              815

Gly Val Pro Arg Ile Pro Thr Met Tyr Ser Ala Ser Ser Asn Ser Pro
            820              825              830

Asp Ser Ala Gly Val Pro Val Thr Gly Tyr Gly Met Thr Pro Met Pro
            835              840              845

Gln Gln Asn Asp Gly Arg Gly Gln Gly Ser Gln
    850              855

<210> SEQ ID NO 109
<211> LENGTH: 3732
<212> TYPE: DNA
<213> ORGANISM: Artificial Sequence
<220> FEATURE:
<223> OTHER INFORMATION: fungal gene

<400> SEQUENCE: 109
atgaatcccg caaacttcaa cgtgggcggc tccatgcccg ccgcgcccac cccccagatg      60
ccgagactcg acaataacca ggtcatgatg aactatgtcg cccaggcttt acatgcacaa     120 ggcaccctata ccggttggcg cgccgaagtg cccatgaaag agcgcgtggt tcgagtgtat    180
caaatgttca cctcccttcg ccttatccaa ccccaagcag atctgcaaca cctgccccaa     240
gctgccctca gctttgagca gaaggccttc aaagacgctc agcagaaagt cgattacgac     300
aaagaatgta cgacaaaatt attgcatatt cgagatactc gagcgagaca ggccgccgtc     360
atgcagaatg gcatgattcc cccgggcgct cccaaagccg gcggcatgcg tggcgtcgga     420
caaccctcct tcccgcaaca gatgaatcga gccatgcaat ccatcccat ggccggtcaa      480 caagccatgg ccatggggat gaccgatccg aatcaacagg ccgccatgcc gcagcgatcg    540
caacagcagc aagccatgat gcagcagcag cagcaacaac agcaacaaca gcaacagcag    600
cagcagcagc agcagccacg cgctcaacaa cgctccgcca ataccctcgc cctggtcgac    660
gagctgaata acctgactcc gcaagagtac gagaacgtca atcgcgtcgc tcaccagatc    720
atgaccaaga cctcgccggt ggatgcggag aaaatcaaac gcaacctgca gaacatgaat    780
cctgtacaac gccggtacct gactgaaaga aacatcgacc cggtcgcgta tttctttcgc    840
tcgcaggccc tcgcccacct caagcggcag atgaaggccc gtgtggacat gtctcacccc    900
cagaataccg cgtcgaccc gaacaatgtg atgatgggcg ccgatccgac gatgaacccc    960
cagatgttcc cgaacatgat gaacctacag cgcaattcgg ccttcgccat gggcaaccag    1020
```

-continued

```
ccaaacatgg accctcttc cttcattggc aacgtggaga acatccaagg acagcaggcg    1080
gatggcctcc gttcgcagga agctggtcag ctggtcgtcc ccgcgagctc ctcccagatg    1140
aaccaacaac cgttcaacaa cgcccagaac accttcccga tgggccaaca gctcgcgcag    1200
ggaggacagg ctaatctggg cgctgccggc atcaaccccc agatgttcgc ccaacaacac    1260
atgcaaaaca ccccgaatat gccgccggat cggccccagc cggccgcccc tttccagccc    1320
cagactcaag cacagaacca ggctcaggcc caggcccgcg cccaggcagc tcaaaaagcc    1380
cagatggcga tttcccaggc cggccaagct aattcgcacc tgcaacagcc catgccgcag    1440
caaagccctg ccatgcccat gttgaaccga cccatgcctc cgggccagat gtctcccgcg    1500
cagatggcag cgcaagtccg tcctccgtcg cgggcacccg ccatgggcca gcagccttcc    1560
atgggaggcc agcagcctat gcagggtcga ccgcaaatcc ccccgggtct ccccccggcc    1620
attcaagaac aactggcgca aatgtctcca gagcagctga accgggtctt ggcccagcgg    1680
cgcgccatgg cgaataatcc ggccctggcg agagccaacg cggcccggca tccgtgccc     1740 atgcagcaga gcgtgtccca gtccgcgcag gcccagtcga tggcgaacaa ccagaacatg    1800
cgagcgatga atgtacaagc gcagctagct gggatgggcg gggcgcaaca aatgatgcct    1860
ggtcaacaaa tgtccctcca acagcagcag cagcaacagc agcagcagca gcgtcaagag    1920
ctatataaga tgcagctact ccaacagtca ggcggtaatc tagagctctc gaatgagcaa    1980
agcaaggaga tggaccggtt acacttccca ccctcactcc tgggaaataa cccgaacata    2040
gtttcgctgg tgcccaagaa tatcaagacg tggggtcagc tcaaacagtg ggccgcgaca    2100
aatccacaac tcccaggagg gctgaatctg cagaagttga tggccctcca gaaattccac    2160
tttacgcaaa tactcaacca gagcaaagaa cgcagtcgca acccagacca ggcggggcag    2220
ggtccctgga tgtcgggccc gacacaagcc ccccagcaac cgccgatgat gaaccctcag    2280
cagtttccgc cggggcaaca gcaagctgcg atcaacatgg ctgcgatccg tcccgtcacc    2340
gcacaagaca tccaagcggc tcgtcagcgg cacccggcca tggcacaaaa cttcacggat    2400
gaccaaattc gggaaagcct caacaaagcc cgacaacggc agttgatgct cttggctcag    2460
caacgcgcgg ctcaagcgca ggagttggcc gcccaacaac agcaaaccca ggcacttcag    2520
cagacccccg tgggcggacc agctcctggc ccccatctcc gcccagaggg ccctgggcag    2580
cccgcaacgc aaccgcagca acaaagcccg gcgacaaagg ccccctcgac cgtaccagga    2640
aagaaggccc ctccggcgaa gcaacaaccc gcgaagagga agttgccgag cgacgagacc    2700
gcagacgcgc aaaatcccga caatcaagtg gcgcagaagc ccactcaagc tggtgcccg     2760 caagggggtgg cggctcctgc accctccaag cccaatatgc cattcaccag agagcagttg    2820
gccgccatga cgccgcagca acgtgctcag attgaagcac atatgcgacg ccagcaaggc    2880
cagactcgta ccaaggctgc agccgaagag gcttggaaca atctgccgga aagatccgt     2940 caagcttatc atgataccti gaaacaagcg ccccgatga aattcgcagc catcacgccc     3000
gagcagcatg cggccatgaa ccagcaactt cgggactgta ctgatatgct gggccggatg    3060
gataccctgt ccagtggtt tgcaaaaatc cccggccaag agaagaatgt gcgcagtttg     3120
ctggcaatgc gaatccaatt gatgaggcag ttcaagaata gtccggactg ggttcttaac    3180
gacagcctga ccatctctcc cgaaaattta accgccacca taaattatat taagaagctc    3240
ttccatgcga tgatcacccg cgtcagtcag catcaaaatc aagctcctgg acaacgaccc    3300
ggcggtcccc agccaccctt gacacaagca agccaaaacg ccatgccagc cctgaatgcc    3360
acgaacctgc aacagctcca gcaacaagag gaagctctcc aacgggcgcg gcgagcgtcg    3420
```

-continued

```
agccagaccg ccgtgtctgc aacatcggct gtcccacccg ccccatttgg cgcgccgtcc    3480
cctcagggcg ttcctcatgc gtacgggccg ggaagcatgc cgccggagca gttgaagttg    3540
cctccgccga agaagagaaa gcagtcccat ccagggcta ccccaccgt cggcacgcct      3600 gctaccaagc cgccaaccac ccggcccgcc gacgtcaaaa tgcccgcggc cgcctcgagt    3660
catgtaatta gttatgtcac gcttacattc acgccctcct cccacatccg ctctaaccga   3720
aaaggaagga gt                                                        3732
```

<210> SEQ ID NO 110
<211> LENGTH: 1244
<212> TYPE: PRT
<213> ORGANISM: Artificial Sequence
<220> FEATURE:
<223> OTHER INFORMATION: fungal gene

<400> SEQUENCE: 110

```
Met Asn Pro Ala Asn Phe Asn Val Gly Gly Ser Met Pro Ala Ala Pro
 1               5                  10                  15

Thr Pro Gln Met Pro Arg Leu Asp Asn Asn Gln Val Met Met Asn Tyr
            20                  25                  30

Val Ala Gln Ala Leu His Ala Gln Gly Thr Tyr Thr Gly Trp Arg Ala
        35                  40                  45

Glu Val Pro Met Lys Glu Arg Val Arg Val Tyr Gln Met Phe Thr
    50                  55                  60

Ser Leu Arg Leu Ile Gln Pro Gln Ala Asp Leu Gln His Leu Ala Gln
65                  70                  75                  80

Ala Ala Leu Ser Phe Glu Gln Lys Ala Phe Lys Asp Ala Gln Gln Lys
                85                  90                  95

Val Asp Tyr Asp Lys Glu Cys Asn Asp Lys Leu Leu His Ile Arg Asp
            100                 105                 110

Thr Arg Ala Arg Gln Ala Ala Val Met Gln Asn Gly Met Ile Pro Pro
        115                 120                 125

Gly Ala Pro Lys Ala Gly Gly Met Arg Gly Val Gly Gln Pro Ser Phe
    130                 135                 140

Pro Gln Gln Met Asn Arg Ala Met Gln Ser Asn Pro Met Ala Gly Gln
145                 150                 155                 160

Gln Ala Met Ala Met Gly Met Thr Asp Pro Asn Gln Ala Ala Met
                165                 170                 175

Pro Gln Arg Ser Gln Gln Gln Ala Met Met Gln Gln Gln Gln
            180                 185                 190

Gln Gln Gln Gln Gln Gln Gln Gln Gln Gln Gln Pro Arg Ala
        195                 200                 205

Gln Gln Arg Ser Ala Asn Thr Leu Ala Leu Val Asp Glu Leu Asn Asn
    210                 215                 220

Leu Thr Pro Gln Glu Tyr Glu Asn Val Asn Arg Val Ala His Gln Ile
225                 230                 235                 240

Met Thr Lys Thr Ser Pro Val Asp Ala Glu Lys Ile Lys Arg Asn Leu
                245                 250                 255

Gln Asn Met Asn Pro Val Gln Arg Arg Tyr Leu Thr Glu Arg Asn Ile
            260                 265                 270

Asp Pro Val Ala Tyr Phe Phe Arg Ser Gln Ala Leu Ala His Leu Lys
        275                 280                 285

Arg Gln Met Lys Ala Arg Val Asp Met Ser His Pro Gln Asn Thr Gly
    290                 295                 300
```

```
Val Asp Pro Asn Asn Val Met Met Gly Ala Asp Pro Thr Met Asn Pro
305                 310                 315                 320

Gln Met Phe Pro Asn Met Met Asn Leu Gln Arg Asn Ser Ala Phe Ala
            325                 330                 335

Met Gly Asn Gln Pro Asn Met Asp Pro Ser Ser Phe Ile Gly Asn Val
            340                 345                 350

Glu Asn Ile Gln Gly Gln Ala Asp Gly Leu Arg Ser Gln Glu Ala
    355                 360                 365

Gly Gln Leu Val Val Pro Ala Ser Ser Gln Met Asn Gln Gln Pro
    370                 375                 380

Phe Asn Asn Ala Gln Asn Thr Phe Pro Met Gly Gln Gln Leu Ala Gln
385                 390                 395                 400

Gly Gly Gln Ala Asn Leu Gly Ala Ala Gly Ile Asn Pro Gln Met Phe
            405                 410                 415

Ala Gln Gln His Met Gln Asn Thr Pro Asn Met Pro Pro Asp Arg Pro
            420                 425                 430

Gln Pro Ala Ala Pro Phe Gln Pro Gln Thr Gln Ala Gln Asn Gln Ala
            435                 440                 445

Gln Ala Gln Ala Arg Ala Gln Ala Ala Gln Lys Ala Gln Met Ala Ile
    450                 455                 460

Ser Gln Ala Gly Gln Ala Asn Ser His Leu Gln Gln Pro Met Pro Gln
465                 470                 475                 480

Gln Ser Pro Ala Met Pro Met Leu Asn Arg Pro Met Pro Pro Gly Gln
            485                 490                 495

Met Ser Pro Ala Gln Met Ala Ala Gln Val Arg Pro Pro Ser Arg Ala
            500                 505                 510

Pro Ala Met Gly Gln Gln Pro Ser Met Gly Gln Gln Pro Met Gln
            515                 520                 525

Gly Arg Pro Gln Ile Pro Pro Gly Leu Pro Pro Ala Ile Gln Glu Gln
    530                 535                 540

Leu Ala Gln Met Ser Pro Glu Gln Leu Asn Arg Val Leu Ala Gln Arg
545                 550                 555                 560

Arg Ala Met Ala Asn Asn Pro Ala Leu Ala Arg Ala Asn Ala Ala Arg
            565                 570                 575

Gln Ser Val Pro Met Gln Gln Ser Val Ser Gln Ser Ala Gln Ala Gln
            580                 585                 590

Ser Met Ala Asn Asn Gln Asn Met Arg Ala Met Asn Val Gln Ala Gln
    595                 600                 605

Leu Ala Gly Met Gly Gly Ala Gln Gln Met Met Pro Gly Gln Gln Met
    610                 615                 620

Ser Leu Gln Gln Gln Gln Gln Gln Gln Gln Gln Gln Arg Gln Glu
625                 630                 635                 640

Leu Tyr Lys Met Gln Leu Leu Gln Gln Ser Gly Gly Asn Leu Glu Leu
            645                 650                 655

Ser Asn Glu Gln Ser Lys Glu Met Asp Arg Leu His Phe Pro Pro Ser
            660                 665                 670

Leu Leu Gly Asn Asn Pro Asn Ile Val Ser Leu Val Pro Lys Asn Ile
            675                 680                 685

Lys Thr Trp Gly Gln Leu Lys Gln Trp Ala Ala Thr Asn Pro Gln Leu
    690                 695                 700

Pro Gly Gly Leu Asn Leu Gln Lys Leu Met Ala Leu Gln Lys Phe His
705                 710                 715                 720
```

-continued

```
Phe Thr Gln Ile Leu Asn Gln Ser Lys Glu Arg Ser Arg Asn Pro Asp
            725                 730                 735

Gln Ala Gly Gln Gly Pro Trp Met Ser Gly Pro Thr Gln Ala Pro Gln
            740                 745                 750

Gln Pro Pro Met Met Asn Pro Gln Gln Phe Pro Pro Gly Gln Gln Gln
            755                 760                 765

Ala Ala Ile Asn Met Ala Ala Ile Arg Pro Val Thr Ala Gln Asp Ile
    770                 775                 780

Gln Ala Ala Arg Gln Arg His Pro Ala Met Ala Gln Asn Phe Thr Asp
785                 790                 795                 800

Asp Gln Ile Arg Glu Ser Leu Asn Lys Ala Arg Gln Arg Gln Leu Met
                805                 810                 815

Leu Leu Ala Gln Gln Arg Ala Ala Gln Ala Gln Glu Leu Ala Ala Gln
            820                 825                 830

Gln Gln Gln Thr Gln Ala Leu Gln Gln Thr Pro Val Gly Gly Pro Ala
            835                 840                 845

Pro Gly Pro His Leu Arg Pro Glu Gly Pro Gly Gln Pro Ala Thr Gln
    850                 855                 860

Pro Gln Gln Gln Ser Pro Ala Thr Lys Ala Pro Ser Thr Val Pro Gly
865                 870                 875                 880

Lys Lys Ala Pro Pro Ala Lys Gln Gln Pro Ala Lys Arg Lys Leu Pro
                885                 890                 895

Ser Asp Glu Thr Ala Asp Ala Gln Asn Pro Asp Asn Gln Val Ala Gln
            900                 905                 910

Lys Pro Thr Gln Ala Gly Ala Pro Gln Gly Val Ala Ala Pro Ala Pro
            915                 920                 925

Ser Lys Pro Asn Met Pro Phe Thr Arg Glu Gln Leu Ala Ala Met Thr
    930                 935                 940

Pro Gln Gln Arg Ala Gln Ile Glu Ala His Met Arg Arg Gln Gln Gly
945                 950                 955                 960

Gln Thr Arg Thr Lys Ala Ala Ala Glu Glu Ala Trp Asn Asn Leu Pro
                965                 970                 975

Glu Lys Ile Arg Gln Ala Tyr His Asp Thr Leu Lys Gln Ala Pro Pro
            980                 985                 990

Met Lys Phe Ala Ala Ile Thr Pro Glu Gln His Ala Ala Met Asn Gln
    995                 1000                1005

Gln Leu Arg Asp Cys Thr Asp Met Leu Gly Arg Met Asp Thr Leu Val
    1010                1015                1020

Gln Trp Phe Ala Lys Ile Pro Gly Gln Glu Lys Asn Val Arg Ser Leu
1025                1030                1035                1040

Leu Ala Met Arg Ile Gln Leu Met Arg Gln Phe Lys Asn Ser Pro Asp
                1045                1050                1055

Trp Val Leu Asn Asp Ser Leu Thr Ile Ser Pro Glu Asn Leu Thr Ala
            1060                1065                1070

Thr Ile Asn Tyr Ile Lys Lys Leu Phe His Ala Met Ile Thr Arg Val
    1075                1080                1085

Ser Gln His Gln Asn Gln Ala Pro Gly Gln Arg Pro Gly Gly Pro Gln
    1090                1095                1100

Pro Pro Leu Thr Gln Ala Ser Gln Asn Ala Met Pro Ala Leu Asn Ala
1105                1110                1115                1120

Thr Asn Leu Gln Gln Leu Gln Gln Gln Glu Glu Ala Leu Gln Arg Ala
                1125                1130                1135

Arg Arg Ala Ser Ser Gln Thr Ala Val Ser Ala Thr Ser Ala Val Pro
```

```
                    1140              1145              1150
        Pro Ala Pro Phe Gly Ala Pro Ser Pro Gln Val Pro His Ala Tyr
                1155              1160              1165

Gly Pro Gly Ser Met Pro Pro Glu Gln Leu Lys Leu Pro Pro Lys
                1170              1175              1180

Lys Arg Lys Gln Ser His Pro Gly Ala Thr Pro Thr Val Gly Thr Pro
        1185              1190              1195              1200

Ala Thr Lys Pro Pro Thr Thr Arg Pro Ala Asp Val Lys Met Pro Ala
                      1205              1210              1215

Ala Ala Ser Ser His Val Ile Ser Tyr Val Thr Leu Thr Phe Thr Pro
                  1220              1225              1230

Ser Ser His Ile Arg Ser Asn Arg Lys Gly Arg Ser
                1235              1240

<210> SEQ ID NO 111
<211> LENGTH: 1302
<212> TYPE: DNA
<213> ORGANISM: Artificial Sequence
<220> FEATURE:
<223> OTHER INFORMATION: fungal gene

<400> SEQUENCE: 111
atgcaaagcc cccagcagcc acccgacttt ctactgtacc cgactcagtc cacgcgtggg      60
agcaaaatga tcgccttgga ttcgtcccgc cagcagcaga ccccattctt ccagaatttc     120
accatggatc ctgcattcac ggaccctttc gcattccagg tggacacctt cgctagcttc     180
ggacagcccg ccagttcctc tcgaggcccc cagacttcat attatgatac ccctccgctc     240
tacacggatt cttactccga ctccaataag accgcccctg ggtttccttc catgccgggt     300
acgcccccga cgcttccctc cacccagccg ctggactccc acgttccggg cctgaccgcc     360
ccgtcgggtc cgtctgtcgc cagcgcctcc tcctcgggca ttgggtcgcc gtactccggc     420
acggcccatg ccaaccagga gaactgggtc gatacgaacc acggcctggg ccttcccgcc     480
gcggtgatgg gggatctgtt tccgaacgac tacacgggga cgaccctgga ccccgattac     540
tttgccaata aggcgcggac agctttgtt gaccttcctt tgatcccgct tcagcagcag     600
tcgaatctgt cgaccccggc catctcctac ccggaacaga ctgattatag cctggtcccc     660
ggcggattct tccctcagtc ccctgaccct tcccaattcc aatttgcgga ccctatggt     720 ccattcacac agcagccatg ccccatgccc gcctcatccc catctctgat gcctccccat     780
gtcccgcccc gtcgtctctc cctctacgac cgtcggtcct cggtctcttc cgtgcagtcc     840
cgtcgctcgc agctgagccc ggcggccagc aacgccgaga tcgaggagga cgccaaggaa     900
aagggccgat gccctcatcc ggattgcggt cgagtcttcc gggacctgaa agcgcacatg     960
ctgacgcatc agtcggagcg tccggagaaa tgccccattg tcacttgcga gtaccacacc    1020
aaggggtttg cccgcaagta cgacaagaac cgccacaccc tgacccacta caagggaacg    1080
atggtttgcg gcttctgccc gggatccggg tcgccggccg agaagagctt caaccgggcg    1140
gatgtgttca acgtcatctg acctctgtg cacggtgtgg aacagacccc tcccaactgc    1200
cggaagagaa gccccgcggc cgcctcgagt catgtaatta gttatgtcac gcttacattc    1260
acgccctcct cccacatccg ctctaaccga aaaggaagga gt                       1302

<210> SEQ ID NO 112
<211> LENGTH: 434
<212> TYPE: PRT
<213> ORGANISM: Artificial Sequence
```

```
<220> FEATURE:
<223> OTHER INFORMATION: fungal gene

<400> SEQUENCE: 112

Met Gln Ser Pro Gln Pro Pro Asp Phe Leu Leu Tyr Pro Thr Gln
 1               5                  10                  15

Ser Thr Arg Gly Ser Lys Met Ile Ala Leu Asp Ser Ser Arg Gln Gln
            20                  25                  30

Gln Thr Pro Phe Phe Gln Asn Phe Thr Met Asp Pro Ala Phe Thr Asp
        35                  40                  45

Pro Phe Ala Phe Gln Val Asp Thr Phe Ala Ser Phe Gly Gln Pro Ala
    50                  55                  60

Ser Ser Ser Arg Gly Pro Gln Thr Ser Tyr Tyr Asp Thr Pro Pro Leu
65                  70                  75                  80

Tyr Thr Asp Ser Tyr Ser Asp Ser Asn Lys Thr Ala Pro Gly Phe Pro
                85                  90                  95

Ser Met Pro Gly Thr Pro Pro Thr Leu Pro Ser Thr Gln Pro Leu Asp
            100                 105                 110

Ser His Val Pro Gly Leu Thr Ala Pro Ser Gly Pro Ser Val Ala Ser
        115                 120                 125

Ala Ser Ser Ser Ala Ile Gly Ser Pro Tyr Ser Gly Thr Ala His Ala
    130                 135                 140

Asn Gln Glu Asn Trp Val Asp Thr Asn His Gly Leu Gly Leu Pro Ala
145                 150                 155                 160

Ala Val Met Gly Asp Leu Phe Pro Asn Asp Tyr Thr Gly Thr Thr Leu
                165                 170                 175

Asp Pro Asp Tyr Phe Ala Asn Lys Gly Ala Asp Ser Phe Val Asp Pro
            180                 185                 190

Ser Leu Ile Pro Leu Gln Gln Gln Ser Asn Leu Ser Thr Pro Ala Ile
        195                 200                 205

Ser Tyr Pro Glu Gln Thr Asp Tyr Ser Leu Val Pro Gly Gly Phe Phe
    210                 215                 220

Pro Gln Ser Pro Asp Pro Ser Gln Phe Gln Phe Ala Asp Pro Tyr Gly
225                 230                 235                 240

Pro Phe Thr Gln Gln Pro Cys Pro Met Pro Ala Ser Ser Pro Ser Leu
                245                 250                 255

Met Pro Ser His Val Pro Pro Arg Arg Leu Ser Leu Tyr Asp Arg Arg
            260                 265                 270

Ser Ser Val Ser Ser Val Gln Ser Arg Arg Ser Gln Leu Ser Pro Ala
        275                 280                 285

Ala Ser Asn Ala Glu Ile Glu Glu Asp Ala Lys Glu Lys Gly Arg Cys
    290                 295                 300

Pro His Pro Asp Cys Gly Arg Val Phe Arg Asp Leu Lys Ala His Met
305                 310                 315                 320

Leu Thr His Gln Ser Glu Arg Pro Glu Lys Cys Pro Ile Val Thr Cys
                325                 330                 335

Glu Tyr His Thr Lys Gly Phe Ala Arg Lys Tyr Asp Lys Asn Arg His
            340                 345                 350

Thr Leu Thr His Tyr Lys Gly Thr Met Val Cys Gly Phe Cys Pro Gly
        355                 360                 365

Ser Gly Ser Pro Ala Glu Lys Ser Phe Asn Arg Ala Asp Val Phe Lys
    370                 375                 380

Arg His Leu Thr Ser Val His Gly Val Glu Gln Thr Pro Pro Asn Cys
385                 390                 395                 400
```

Arg Lys Arg Ser Pro Ala Ala Ala Ser Ser His Val Ile Ser Tyr Val
                405                 410                 415

Thr Leu Thr Phe Thr Pro Ser Ser His Ile Arg Ser Asn Arg Lys Gly
            420                 425                 430

Arg Ser

<210> SEQ ID NO 113
<211> LENGTH: 1071
<212> TYPE: DNA
<213> ORGANISM: Artificial Sequence
<220> FEATURE:
<223> OTHER INFORMATION: fungal gene

<400> SEQUENCE: 113

| | | | | | |
|---|---|---|---|---|---|
| atgctcgagt | tagtcgatgc | tattccgctt | cagacccagc | cagttcctcc | tgctcctgaa | 60 |
| gttcaggttc | agcccctcc | aatcgtggag | acggcccatt | tcaacccttc | atggggatat | 120 |
| gatttgaacc | ttctttctca | tgccgcgagt | catgtcgctc | ttgagggaca | caagaaagt | 180 |
| ctagagactc | ttcggaagcc | ttcgcaaaac | attcaagcgc | cgccgccgcc | gccgccgctt | 240 |
| tctcatatac | cagaaagagg | gatcactgat | aactatggtg | ttgagccttc | gattctagac | 300 |
| cttacagatt | taggtgatcc | ggttcaggac | tttaccgtct | tcctagaaag | cgtcggtctc | 360 |
| tcttcggact | gggactccgg | catcttctct | agtgtagaag | agcccttatt | gccaactagc | 420 |
| ctacccatgg | actcgaaacc | cccagcccgt | gagagttcca | ggctgggcat | cgatacaagt | 480 |
| ttgtacaaaa | aagcaggctc | cacaatgacg | gagaaccaca | ccccttctac | tacgcagccg | 540 |
| acgttgcctg | cgcctgttgc | tgaagccgcg | ccgatccaag | caaacccggc | tccttctgcc | 600 |
| tcagtcacgg | cgactgctgc | cgccgctact | gcggcggtga | caacgcccc | ctctatgaac | 660 |
| ggcgccggtg | agcagttgcc | ttgccagtgg | gttggttgca | cggagaagtc | ccccactgcc | 720 |
| gagtctctat | atgagcatgt | tgcgagcgt | catgttggac | gtaaaagcac | caacaacctc | 780 |
| aacctgacct | gccagtgggg | cacttgcaac | accacaacag | tcaagcgtga | tcatatcacc | 840 |
| tcccacatcc | gcgttcatgt | gccacttaag | ccgcacaaat | gcgactttg | tggtaaggct | 900 |
| ttcaagcgcc | cccaggattt | gaagaagcat | gtcaagactc | atgcggacga | ctccgagatc | 960 |
| cgctccccg | aaccgggcat | gaagcaccct | gatatgatgt | tcccccaaaa | ccctaagggt | 1020 |
| tacgctgctg | ccacacatta | cttcgaaagc | cctatcaacg | gcatcaatgg | g | 1071 |

<210> SEQ ID NO 114
<211> LENGTH: 1035
<212> TYPE: DNA
<213> ORGANISM: Artificial Sequence
<220> FEATURE:
<223> OTHER INFORMATION: fungal gene

<400> SEQUENCE: 114

| | | | | | |
|---|---|---|---|---|---|
| atgctcgagt | tagtcgatgc | tattccgctt | cagacccagc | cagttcctcc | tgctcctgaa | 60 |
| gttcaggttc | agcccctcc | aatcgtggag | acggcccatt | tcaacccttc | atggggatat | 120 |
| gatttgaacc | ttctttctca | tgccgcgagt | catgtcgctc | ttgagggaca | caagaaagt | 180 |
| ctagagactc | ttcggaagcc | ttcgcaaaac | attcaagcgc | cgccgccgcc | gccgccgctt | 240 |
| tctcatatac | cagaaagagg | gatcactgat | aactatggtg | ttgagccttc | gattctagac | 300 |
| cttacagatt | taggtgatcc | ggttcaggac | tttaccgtct | tcctagaaag | cgtcggtctc | 360 |
| tcttcggact | gggactccgg | catcttctct | agtgtagaag | agcccttatt | gccaactagc | 420 |

-continued

```
ctacccatgg actcgaaacc cccagcccgt gagagttcca ggctgggcat gacggagaac    480
cacacccctt ctactacgca gccgacgttg cctgcgcctg ttgctgaagc cgcgccgatc    540
caagcaaacc cggctccttc tgcctcagtc acggcgactg ctgccgccgc tactgcggcg    600
gtgaacaacg cccctctat gaacggcgcc ggtgagcagt tgccttgcca gtgggttggt     660
tgcacggaga gtcccccac tgccgagtct ctatatgagc atgtttgcga gcgtcatgtt     720
ggacgtaaaa gcaccaacaa cctcaacctg acctgccagt ggggcacttg caacaccaca    780
acagtcaagc gtgatcatat cacctcccac atccgcgttc atgtgccact taagccgcac    840
aaatgcgact tttgtggtaa ggctttcaag cgccccagg atttgaagaa gcatgtcaag     900
actcatgcgg acgactccga gatccgctcc cccgaaccgg gcatgaagca ccctgatatg    960
atgttccccc aaaaccctaa gggttacgct gctgccacac attacttcga aagccctatc   1020
aacggcatca atggg                                                    1035
```

<210> SEQ ID NO 115
<211> LENGTH: 357
<212> TYPE: PRT
<213> ORGANISM: Artificial Sequence
<220> FEATURE:
<223> OTHER INFORMATION: fungal gene

<400> SEQUENCE: 115

```
Met Leu Glu Leu Val Asp Ala Ile Pro Leu Gln Thr Gln Pro Val Pro
 1               5                  10                  15

Pro Ala Pro Glu Val Gln Val Gln Pro Pro Ile Val Glu Thr Ala
             20                  25                  30

His Phe Asn Pro Ser Trp Gly Tyr Asp Leu Asn Leu Leu Ser His Ala
         35                  40                  45

Ala Ser His Val Ala Leu Glu Gly Gln Gln Glu Ser Leu Glu Thr Leu
     50                  55                  60

Arg Lys Pro Ser Gln Asn Ile Gln Ala Pro Pro Pro Pro Pro Pro Leu
 65                  70                  75                  80

Ser His Ile Pro Glu Arg Gly Ile Thr Asp Asn Tyr Gly Val Glu Pro
                 85                  90                  95

Ser Ile Leu Asp Leu Thr Asp Leu Gly Asp Pro Val Gln Asp Phe Thr
            100                 105                 110

Val Phe Leu Glu Ser Val Gly Leu Ser Ser Asp Trp Asp Ser Gly Ile
        115                 120                 125

Phe Ser Ser Val Glu Glu Pro Leu Leu Pro Thr Ser Leu Pro Met Asp
    130                 135                 140

Ser Lys Pro Pro Ala Arg Glu Ser Ser Arg Leu Gly Ile Asp Thr Ser
145                 150                 155                 160

Leu Tyr Lys Lys Ala Gly Ser Thr Met Thr Glu Asn His Thr Pro Ser
                165                 170                 175

Thr Thr Gln Pro Thr Leu Pro Ala Pro Val Ala Glu Ala Ala Pro Ile
            180                 185                 190

Gln Ala Asn Pro Ala Pro Ser Ala Ser Val Thr Ala Thr Ala Ala Ala
        195                 200                 205

Ala Thr Ala Ala Val Asn Asn Ala Pro Ser Met Asn Gly Ala Gly Glu
    210                 215                 220

Gln Leu Pro Cys Gln Trp Val Gly Cys Thr Glu Lys Ser Pro Thr Ala
225                 230                 235                 240

Glu Ser Leu Tyr Glu His Val Cys Glu Arg His Val Gly Arg Lys Ser
                245                 250                 255
```

```
Thr Asn Asn Leu Asn Leu Thr Cys Gln Trp Gly Thr Cys Asn Thr Thr
            260                 265                 270
Thr Val Lys Arg Asp His Ile Thr Ser His Ile Arg Val His Val Pro
            275                 280                 285
Leu Lys Pro His Lys Cys Asp Phe Cys Gly Lys Ala Phe Lys Arg Pro
            290                 295                 300
Gln Asp Leu Lys Lys His Val Lys Thr His Ala Asp Asp Ser Glu Ile
305                 310                 315                 320
Arg Ser Pro Glu Pro Gly Met Lys His Pro Asp Met Met Phe Pro Gln
                325                 330                 335
Asn Pro Lys Gly Tyr Ala Ala Thr His Tyr Phe Glu Ser Pro Ile
            340                 345                 350
Asn Gly Ile Asn Gly
            355

<210> SEQ ID NO 116
<211> LENGTH: 345
<212> TYPE: PRT
<213> ORGANISM: Artificial Sequence
<220> FEATURE:
<223> OTHER INFORMATION: fungal gene

<400> SEQUENCE: 116

Met Leu Glu Leu Val Asp Ala Ile Pro Leu Gln Thr Gln Pro Val Pro
1               5                   10                  15
Pro Ala Pro Glu Val Gln Val Gln Pro Pro Ile Val Glu Thr Ala
            20                  25                  30
His Phe Asn Pro Ser Trp Gly Tyr Asp Leu Asn Leu Leu Ser His Ala
            35                  40                  45
Ala Ser His Val Ala Leu Glu Gly Gln Gln Glu Ser Leu Glu Thr Leu
            50                  55                  60
Arg Lys Pro Ser Gln Asn Ile Gln Ala Pro Pro Pro Pro Pro Pro Leu
65                  70                  75                  80
Ser His Ile Pro Glu Arg Gly Ile Thr Asp Asn Tyr Gly Val Glu Pro
                85                  90                  95
Ser Ile Leu Asp Leu Thr Asp Leu Gly Asp Pro Val Gln Asp Phe Thr
            100                 105                 110
Val Phe Leu Glu Ser Val Gly Leu Ser Ser Asp Trp Asp Ser Gly Ile
            115                 120                 125
Phe Ser Ser Val Glu Glu Pro Leu Leu Pro Thr Ser Leu Pro Met Asp
            130                 135                 140
Ser Lys Pro Pro Ala Arg Glu Ser Ser Arg Leu Gly Met Thr Glu Asn
145                 150                 155                 160
His Thr Pro Ser Thr Thr Gln Pro Thr Leu Pro Ala Pro Val Ala Glu
                165                 170                 175
Ala Ala Pro Ile Gln Ala Asn Pro Ala Pro Ser Ala Ser Val Thr Ala
            180                 185                 190
Thr Ala Ala Ala Thr Ala Ala Val Asn Asn Ala Pro Ser Met Asn
            195                 200                 205
Gly Ala Gly Glu Gln Leu Pro Cys Gln Trp Val Gly Cys Thr Glu Lys
            210                 215                 220
Ser Pro Thr Ala Glu Ser Leu Tyr Glu His Val Cys Glu Arg His Val
225                 230                 235                 240
Gly Arg Lys Ser Thr Asn Asn Leu Asn Leu Thr Cys Gln Trp Gly Thr
                245                 250                 255
```

```
Cys Asn Thr Thr Thr Val Lys Arg Asp His Ile Thr Ser His Ile Arg
            260                 265                 270

Val His Val Pro Leu Lys Pro His Lys Cys Asp Phe Cys Gly Lys Ala
            275                 280                 285

Phe Lys Arg Pro Gln Asp Leu Lys Lys His Val Lys Thr His Ala Asp
            290                 295                 300

Asp Ser Glu Ile Arg Ser Pro Glu Pro Gly Met Lys His Pro Asp Met
305                 310                 315                 320

Met Phe Pro Gln Asn Pro Lys Gly Tyr Ala Ala Ala Thr His Tyr Phe
                325                 330                 335

Glu Ser Pro Ile Asn Gly Ile Asn Gly
            340                 345

<210> SEQ ID NO 117
<211> LENGTH: 1833
<212> TYPE: DNA
<213> ORGANISM: Artificial Sequence
<220> FEATURE:
<223> OTHER INFORMATION: fungal gene

<400> SEQUENCE: 117
atgaccgccc ccattaccga cgtcagcctg ggggacgagc tccacttaga cggcgaggac      60
gtggcgatgg cgcatgccga cgcgctagac gatttcgatc tggacatgtt ggggacggg     120 gattccccgg gtccgggatt taccccccac gactccgccc cctacggcgc tctggatatg    180
gccgacttcg agtttgagca gatgtttacc gatgccctgg gcattgacga ctttggggga    240
atcgatacaa gtttgtacaa aaaagcaggc tccacaatgg atcctagaaa ccatccctct    300
cggcctccgt ctaccagtct gcctcaagga tcggcgcctc ttccttctgc tcccatctcg    360
agcatgccaa tgcctcagta cacgatgcag cctcagtacc agtctctca gccgcacacc     420 ctgcctcctc tgcaaccca tcatagccag tcgcccgctc ctcactcgta catggggcag     480
ccgccgtacc ggcctgatct gaacaggtac cccgcatcaa gtcacgatgt ttacgcgtct    540
tctgctgcgc cgataatgcc ccacactacc gtgggcagct tgcctccgac atctttcctt    600
tctcatccca atccgcaggc gcaggcacag gcgcagcaat cgccgcacta tcctcctcct    660
catagcgtgc tcccgcccgc ttccagcgct cagtcgtacc cgcagccaat tgcgccggcg    720
cctccccggg accgtcgtgc tgacttcaac aatggacttc cttcaggagc attcagttat    780
tcggacggaa agcctcaagg ttgggacccc gttgctgcga atggtgctgc gccgtatccc    840
gggaaggact ccccccgaac ccaggttgtt ggttctcagg ggcgacgcgg tatccttccg    900
agtgttccgg gacgcgcaac tccggtcaca aatggtgtta acggcaccgg caagaacact    960
actatcccgg ccaaggatgc cgatggaaag ttcccttgcc cgaactgtaa caagactat   1020 cttcatgcca agcatctcaa cgccatctg ctacgccaca ctggtgaccg cccgtacatg    1080
tgtgttcttt gcaaagacac cttctctcgc agtgatatcc tgaaacgtca tttccaaaaa    1140
tgctcaatca ggcgtggtaa cccccaccgga gcaacgcact tgtcgcaccc caatgcgcat    1200
gtgaagaggt cccaacagca ggctgcggcg aatcctgtaa aacctgtcca ggatgaagtc    1260
agtagtaccg tcccgcctcc caatggcatc ccgggcacga cttacggcga gggagccgtc    1320
aacggcaatg gactagctcc ggcccggcca gggtacgcgg atcaccagac tatgggcttc    1380
ccaatgtcat ccgtcaacgg gatgggccgt ggtcagcctg aagacgcgtt cccggcggc    1440 cggccgcatc aaggagcccc ttggccacaa gctcccaagc agagcccgta tctcgtgcag    1500
```

| | |
|---|---:|
| ccgggtgctg acccttctgg ccaccagttg aatattgacc gaaacatcga gcaggtaaaa | 1560 |
| caaccggttg ttcaagaccc caagcgccct gtgatgccag acatcccgg ccaccccgt | 1620 |
| gagcttgact ggacgtctat gttccaacct caagctcccg agggctacat gttctcccag | 1680 |
| tctatgcctg gtggtcaaga gcccatccac gctcatgtcg agaccgagcg aaagtattac | 1740 |
| cccaccacta ccgctggtca agagagtgga atgaacggtc tctatctggc ttcgactatg | 1800 |
| agtggcgacg gcaccgttca gcccgccaga caa | 1833 |

<210> SEQ ID NO 118
<211> LENGTH: 1800
<212> TYPE: DNA
<213> ORGANISM: Artificial Sequence
<220> FEATURE:
<223> OTHER INFORMATION: fungal gene

<400> SEQUENCE: 118

| | |
|---|---:|
| atgaccgccc ccattaccga cgtcagcctg ggggacgagc tccacttaga cggcgaggac | 60 |
| gtggcgatgg cgcatgccga cgcgctagac gatttcgatc tggacatgtt ggggggacggg | 120 |
| gattccccgg gtccgggatt tacccccac gactccgccc cctacggcgc tctggatatg | 180 |
| gccgacttcg agtttgagca gatgtttacc gatgccctgg gcattgacga ctttggggga | 240 |
| atcatggatc ctagaaacca tccctctcgg cctccgtcta ccagtctgcc tcaaggatcg | 300 |
| gcgcctcttc cttctgctcc catctcgagc atgccaatgc tcagtacac gatgcagcct | 360 |
| cagtacccag tctctcagcc gcacaccctg cctcctctgc aaccccatca tagccagtcg | 420 |
| cccgctcctc actcgtacat ggggcagccg ccgtaccggc ctgatctgaa caggtacccc | 480 |
| gcatcaagtc acgatgttta cgcgtcttct gctgcgccga taatgcccca cactaccgtg | 540 |
| ggcagcttgc ctccgacatc tttcctttct catcccaatc cgcaggcgca ggcacaggcg | 600 |
| cagcaatcgc cgcactatcc tcctcctcat agcgtgctcc cgcccgcttc cagcgctcag | 660 |
| tcgtacccgc agccaattgc gccggcgcct ccccgggacc gtcgtgctga cttcaacaat | 720 |
| ggacttcctt caggagcatt cagttattcg gacggaaagc tcaaggttg ggaccccgtt | 780 |
| gctgcgaatg gtgctgcgcc gtatcccggg aaggactccc ccgaaccca ggttgttggt | 840 |
| tctcaggggc gacgcggtat ccttccgagt gttccgggac gcgcaactcc ggtcacaaat | 900 |
| ggtgttaacg gcaccggcaa gaacactact atcccggcca aggatgccga tggaaagttc | 960 |
| ccttgcccga actgtaacaa gacttatctt catgccaagc atctcaagcg ccatctgcta | 1020 |
| cgccacactg gtgaccgccc gtacatgtgt gttctttgca aagacacctt ctctcgcagt | 1080 |
| gatatcctga acgtcatttt ccaaaaatgc tcaatcaggc gtggtaaccc caccggagca | 1140 |
| acgcacttgt cgcaccccaa tgcgcatgtg aagaggtccc aacagcaggc tgcggcgaat | 1200 |
| cctgtaaaac ctgtccagga tgaagtcagt agtaccgtcc cgcctcccaa tggcatcccg | 1260 |
| ggcacgactt acgcgagggg agccgtcaac ggcaatggac tagctccggc ccggccaggg | 1320 |
| tacgcggatc accagactat gggcttccca atgtcatccg tcaacgggat gggccgtggt | 1380 |
| cagcctgaag acgcgtttcc cggcggccgg ccgcatcaag gagcccttg ccacaagct | 1440 |
| cccaagcaga gccgtatct cgtgcagccg ggtgctgacc cttctggcca ccagttgaat | 1500 |
| attgaccgaa acatcgagca ggtaaaacaa ccggttgttc aagaccccaa gcgcctgtg | 1560 |
| atgccaggac atcccggcca ccccggtgag cttgactgga cgtctatgtt ccaacctcaa | 1620 |
| gctcccgagg gctacatgtt ctcccagtct atgcctggtg gtcaagagcc catccacgct | 1680 |
| catgtcgaga ccgagcgaaa gtattacccc accactaccg ctggtcaaga gagtggaatg | 1740 |

-continued

```
aacggtctct atctggcttc gactatgagt ggcgacggca ccgttcagcc cgccagacaa    1800
```

<210> SEQ ID NO 119
<211> LENGTH: 611
<212> TYPE: PRT
<213> ORGANISM: Artificial Sequence
<220> FEATURE:
<223> OTHER INFORMATION: fungal gene

<400> SEQUENCE: 119

```
Met Thr Ala Pro Ile Thr Asp Val Ser Leu Gly Asp Glu Leu His Leu
 1               5                  10                  15

Asp Gly Glu Asp Val Ala Met Ala His Ala Asp Ala Leu Asp Asp Phe
            20                  25                  30

Asp Leu Asp Met Leu Gly Asp Gly Asp Ser Pro Gly Pro Gly Phe Thr
        35                  40                  45

Pro His Asp Ser Ala Pro Tyr Gly Ala Leu Asp Met Ala Asp Phe Glu
    50                  55                  60

Phe Glu Gln Met Phe Thr Asp Ala Leu Gly Ile Asp Asp Phe Gly Gly
65                  70                  75                  80

Ile Asp Thr Ser Leu Tyr Lys Lys Ala Gly Ser Thr Met Asp Pro Arg
                85                  90                  95

Asn His Pro Ser Arg Pro Ser Thr Ser Leu Pro Gln Gly Ser Ala
            100                 105                 110

Pro Leu Pro Ser Ala Pro Ile Ser Ser Met Pro Met Pro Gln Tyr Thr
        115                 120                 125

Met Gln Pro Gln Tyr Pro Val Ser Gln Pro His Thr Leu Pro Pro Leu
    130                 135                 140

Gln Pro His His Ser Gln Ser Pro Ala Pro His Ser Tyr Met Gly Gln
145                 150                 155                 160

Pro Pro Tyr Arg Pro Asp Leu Asn Arg Tyr Pro Ala Ser Ser His Asp
                165                 170                 175

Val Tyr Ala Ser Ser Ala Ala Pro Ile Met Pro His Thr Thr Val Gly
            180                 185                 190

Ser Leu Pro Pro Thr Ser Phe Leu Ser His Pro Asn Pro Gln Ala Gln
        195                 200                 205

Ala Gln Ala Gln Gln Ser Pro His Tyr Pro Pro His Ser Val Leu
    210                 215                 220

Pro Pro Ala Ser Ser Ala Gln Ser Tyr Pro Gln Pro Ile Ala Pro Ala
225                 230                 235                 240

Pro Pro Arg Asp Arg Arg Ala Asp Phe Asn Asn Gly Leu Pro Ser Gly
                245                 250                 255

Ala Phe Ser Tyr Ser Asp Gly Lys Pro Gln Gly Trp Asp Pro Val Ala
            260                 265                 270

Ala Asn Gly Ala Ala Pro Tyr Pro Gly Lys Asp Ser Pro Arg Thr Gln
        275                 280                 285

Val Val Gly Ser Gln Gly Arg Arg Gly Ile Leu Pro Ser Val Pro Gly
    290                 295                 300

Arg Ala Thr Pro Val Thr Asn Gly Val Asn Gly Thr Gly Lys Asn Thr
305                 310                 315                 320

Thr Ile Pro Ala Lys Asp Ala Asp Gly Lys Phe Pro Cys Pro Asn Cys
                325                 330                 335

Asn Lys Thr Tyr Leu His Ala Lys His Leu Lys Arg His Leu Leu Arg
            340                 345                 350
```

```
His Thr Gly Asp Arg Pro Tyr Met Cys Val Leu Cys Lys Asp Thr Phe
            355                 360                 365

Ser Arg Ser Asp Ile Leu Lys Arg His Phe Gln Lys Cys Ser Ile Arg
        370                 375                 380

Arg Gly Asn Pro Thr Gly Ala Thr His Leu Ser His Pro Asn Ala His
385                 390                 395                 400

Val Lys Arg Ser Gln Gln Ala Ala Ala Asn Pro Val Lys Pro Val
            405                 410                 415

Gln Asp Glu Val Ser Ser Thr Val Pro Pro Asn Gly Ile Pro Gly
            420                 425                 430

Thr Thr Tyr Gly Glu Gly Ala Val Asn Gly Asn Gly Leu Ala Pro Ala
            435                 440                 445

Arg Pro Gly Tyr Ala Asp His Gln Thr Met Gly Phe Pro Met Ser Ser
        450                 455                 460

Val Asn Gly Met Gly Arg Gly Gln Pro Glu Asp Ala Phe Pro Gly Gly
465                 470                 475                 480

Arg Pro His Gln Gly Ala Pro Trp Pro Gln Ala Pro Lys Gln Ser Pro
                485                 490                 495

Tyr Leu Val Gln Pro Gly Ala Asp Pro Ser Gly His Gln Leu Asn Ile
            500                 505                 510

Asp Arg Asn Ile Glu Gln Val Lys Gln Pro Val Val Gln Asp Pro Lys
        515                 520                 525

Arg Pro Val Met Pro Gly His Pro Gly His Pro Gly Glu Leu Asp Trp
        530                 535                 540

Thr Ser Met Phe Gln Pro Gln Ala Pro Glu Gly Tyr Met Phe Ser Gln
545                 550                 555                 560

Ser Met Pro Gly Gly Gln Glu Pro Ile His Ala His Val Glu Thr Glu
                565                 570                 575

Arg Lys Tyr Tyr Pro Thr Thr Thr Ala Gly Gln Glu Ser Gly Met Asn
            580                 585                 590

Gly Leu Tyr Leu Ala Ser Thr Met Ser Gly Asp Gly Thr Val Gln Pro
            595                 600                 605

Ala Arg Gln
        610

<210> SEQ ID NO 120
<211> LENGTH: 600
<212> TYPE: PRT
<213> ORGANISM: Artificial Sequence
<220> FEATURE:
<223> OTHER INFORMATION: fungal gene

<400> SEQUENCE: 120

Met Thr Ala Pro Ile Thr Asp Val Ser Leu Gly Asp Glu Leu His Leu
1               5                   10                  15

Asp Gly Glu Asp Val Ala Met Ala His Ala Asp Ala Leu Asp Asp Phe
            20                  25                  30

Asp Leu Asp Met Leu Gly Asp Gly Asp Ser Pro Gly Pro Gly Phe Thr
        35                  40                  45

Pro His Asp Ser Ala Pro Tyr Gly Ala Leu Asp Met Ala Asp Phe Glu
    50                  55                  60

Phe Glu Gln Met Phe Thr Asp Ala Leu Gly Ile Asp Asp Phe Gly Gly
65                  70                  75                  80

Ile Met Asp Pro Arg Asn His Pro Ser Arg Pro Pro Ser Thr Ser Leu
                85                  90                  95
```

-continued

```
Pro Gln Gly Ser Ala Pro Leu Pro Ser Ala Pro Ile Ser Ser Met Pro
            100                 105                 110

Met Pro Gln Tyr Thr Met Gln Pro Gln Tyr Pro Val Ser Gln Pro His
        115                 120                 125

Thr Leu Pro Pro Leu Gln Pro His His Ser Gln Ser Pro Ala Pro His
    130                 135                 140

Ser Tyr Met Gly Gln Pro Pro Tyr Arg Pro Asp Leu Asn Arg Tyr Pro
145                 150                 155                 160

Ala Ser Ser His Asp Val Tyr Ala Ser Ser Ala Pro Ile Met Pro
                165                 170                 175

His Thr Thr Val Gly Ser Leu Pro Pro Thr Ser Phe Leu Ser His Pro
            180                 185                 190

Asn Pro Gln Ala Gln Ala Gln Ala Gln Ser Pro His Tyr Pro Pro
        195                 200                 205

Pro His Ser Val Leu Pro Pro Ala Ser Ser Ala Gln Ser Tyr Pro Gln
    210                 215                 220

Pro Ile Ala Pro Ala Pro Pro Arg Asp Arg Arg Ala Asp Phe Asn Asn
225                 230                 235                 240

Gly Leu Pro Ser Gly Ala Phe Ser Tyr Ser Asp Gly Lys Pro Gln Gly
                245                 250                 255

Trp Asp Pro Val Ala Ala Asn Gly Ala Ala Pro Tyr Pro Gly Lys Asp
            260                 265                 270

Ser Pro Arg Thr Gln Val Val Gly Ser Gln Gly Arg Arg Gly Ile Leu
        275                 280                 285

Pro Ser Val Pro Gly Arg Ala Thr Pro Val Thr Asn Gly Val Asn Gly
    290                 295                 300

Thr Gly Lys Asn Thr Thr Ile Pro Ala Lys Asp Ala Asp Gly Lys Phe
305                 310                 315                 320

Pro Cys Pro Asn Cys Asn Lys Thr Tyr Leu His Ala Lys His Leu Lys
                325                 330                 335

Arg His Leu Leu Arg His Thr Gly Asp Arg Pro Tyr Met Cys Val Leu
            340                 345                 350

Cys Lys Asp Thr Phe Ser Arg Ser Asp Ile Leu Lys Arg His Phe Gln
        355                 360                 365

Lys Cys Ser Ile Arg Arg Gly Asn Pro Thr Gly Ala Thr His Leu Ser
    370                 375                 380

His Pro Asn Ala His Val Lys Arg Ser Gln Gln Gln Ala Ala Asn
385                 390                 395                 400

Pro Val Lys Pro Val Gln Asp Glu Val Ser Ser Thr Val Pro Pro Pro
                405                 410                 415

Asn Gly Ile Pro Gly Thr Thr Tyr Gly Glu Gly Ala Val Asn Gly Asn
            420                 425                 430

Gly Leu Ala Pro Ala Arg Pro Gly Tyr Ala Asp His Gln Thr Met Gly
        435                 440                 445

Phe Pro Met Ser Ser Val Asn Gly Met Gly Arg Gly Gln Pro Glu Asp
    450                 455                 460

Ala Phe Pro Gly Gly Arg Pro His Gln Gly Ala Pro Trp Pro Gln Ala
465                 470                 475                 480

Pro Lys Gln Ser Pro Tyr Leu Val Gln Pro Gly Ala Asp Pro Ser Gly
                485                 490                 495

His Gln Leu Asn Ile Asp Arg Asn Ile Glu Gln Val Lys Gln Pro Val
            500                 505                 510

Val Gln Asp Pro Lys Arg Pro Val Met Pro Gly His Pro Gly His Pro
```

```
            515                 520                 525
Gly Glu Leu Asp Trp Thr Ser Met Phe Gln Pro Gln Ala Pro Glu Gly
        530                 535                 540

Tyr Met Phe Ser Gln Ser Met Pro Gly Gly Gln Glu Pro Ile His Ala
545                 550                 555                 560

His Val Glu Thr Glu Arg Lys Tyr Tyr Pro Thr Thr Ala Gly Gln
                565                 570                 575

Glu Ser Gly Met Asn Gly Leu Tyr Leu Ala Ser Thr Met Ser Gly Asp
        580                 585                 590

Gly Thr Val Gln Pro Ala Arg Gln
        595                 600

<210> SEQ ID NO 121
<211> LENGTH: 1353
<212> TYPE: DNA
<213> ORGANISM: Artificial Sequence
<220> FEATURE:
<223> OTHER INFORMATION: fungal gene

<400> SEQUENCE: 121
atgaccgccc ccattaccga cgtcagcctg ggggacgagc tccacttaga cggcgaggac      60
gtggcgatgg cgcatgccga cgcgctagac gatttcgatc tggacatgtt ggggacgggg    120
gattccccgg gtccgggatt tacccccac gactccgccc cctacggcgc tctggatatg     180
gccgacttcg agtttgagca gatgtttacc gatgccctgg gcattgacga ctttggggga    240
atcgatacaa gtttgtacaa aaaagcaggc tccacaatgt tcttctcaa aaagcatttg     300 aaagatgtca accgtgagga tcagaggcaa atgccgaggc aacggctgcc atctattcaa    360
gaaatatttg gggagacttt tctggcgatt ccttcaaatc catcatatgc actgccttct    420
cacaccagac atgccgctcc accggctttg ccggctgtgt atgaaattgc ccattcaatc    480
gaaggggctc cgtcaaatga gcaaggttta ttacccaaaa tttcaacagt ggagagatct    540
ttgggcatta tctctcccgt caatgagctc cagcatccgg aggtaatacg cccggaaaat    600
ccatccttct ctccgaacgg ttgttctctt aacgaaagcc gtcgcttttc aaagcacccg    660
gacctatcta tacctcaacc gggtttattg tcatgcgatc ccatggattt agcacagccg    720
tcctttgtcg aacctccaaa tgtgtttcat ggatttccca tcaggaaaat accaaactcg    780
ataccgcctc agccaaagca gttatgtctg ccggaaaaac gaacaccgag ttctcttgat    840
ttcagtctgt ttttttaaggt gatcgagaca gtcagcgcac agaccttggc tttcgtgcgg    900
tatcactccg caatgagtca gtcagacaac catcaaagat ccctccctgg actatctatc    960
actgagataa atggcctcct cagtcaggag cagcaaaagc aggatgtctt gatttatatt   1020
agggatgaac ttgtgcgctt cgaccaatac caagccttag cgcagcagaa tactcgggca   1080
gccgcatgta tggcgggtgg ggctgaccga ggtctttgtt catcagtcac taaacagagc   1140
aagacccata agtctctaa acaaaaaaga gaatggcacg gggatagtgc tcttcgttgt    1200
catagctgca accgttctga aacaccagaa tggcgtcgtg gtccggacgg cccccgaact   1260
ctttgtaacg cctgtggttt acattatgca aaattgtctc gacgaacggg caaatttgtg   1320
gcgttggacg atattggcat caggggcaaa aca                                1353

<210> SEQ ID NO 122
<211> LENGTH: 1320
<212> TYPE: DNA
<213> ORGANISM: Artificial Sequence
<220> FEATURE:
```

<223> OTHER INFORMATION: fungal gene

<400> SEQUENCE: 122

```
atgaccgccc ccattaccga cgtcagcctg ggggacgagc tccacttaga cggcgaggac    60
gtggcgatgg cgcatgccga cgcgctagac gatttcgatc tggacatgtt ggggacggg    120
gattccccgg gtccgggatt tacccccac gactccgccc cctacggcgc tctggatatg    180
gccgacttcg agtttgagca gatgtttacc gatgccctgg gcattgacga ctttggggga    240
atcatggttc ttctcaaaaa gcatttgaaa gatgtcaacc gtgaggatca gaggcaaatg    300
ccgaggcaac ggctgccatc tattcaagaa atatttgggg agactttct ggcgattcct    360
tcaaatccat catatgcact gccttctcac accagacatg ccgctccacc ggctttgccg    420
gctgtgtatg aaattgccca ttcaatcgaa ggggctccgt caaatgagca aggtttatta    480
cccaaaattt caacagtgga gagatctttg gcattatct ctcccgtcaa tgagctccag    540
catccggagg taatacgccc ggaaaatcca tccttctctc cgaacggttg ttctcttaac    600
gaaagccgtc gcttttcaaa gcacccggac ctatctatac ctcaaccggg tttattgtca    660
tgcgatccca tggatttagc acagccgtcc tttgtcgaac ctccaaatgt gtttcatgga    720
tttcccatca ggaaaatacc aaactcgata ccgcctcagc caaagcagtt atgtctgccg    780
gaaaaacgaa caccgagttc tcttgatttc agtctgtttt taaggtgat cgagacagtc    840
agcgcacaga ccttggcttt cgtgcggtat cactccgcaa tgagtcagtc agacaaccat    900
caaagatccc tccctggact atctatcact gagataaatg gcctcctcag tcaggagcag    960
caaaagcagg atgtcttgat ttatattagg gatgaacttg tgcgcttcga ccaataccaa    1020
gccttagcgc agcagaatac tcgggcagcc gcatgtatgg cgggtggggc tgaccgaggt    1080
ctttgttcat cagtcactaa acagagcaag acccataaag tctctaaaca aaaaagagaa    1140
tggcacgggg atagtgctct tcgttgtcat agctgcaacc gttctgaaac accagaatgg    1200
cgtcgtggtc cggacggccc ccgaactctt tgtaacgcct gtggtttaca ttatgcaaaa    1260
ttgtctcgac gaacgggcaa atttgtggcg ttggacgata ttggcatcag gggcaaaaca    1320
```

<210> SEQ ID NO 123
<211> LENGTH: 451
<212> TYPE: PRT
<213> ORGANISM: Artificial Sequence
<220> FEATURE:
<223> OTHER INFORMATION: fungal gene

<400> SEQUENCE: 123

```
Met Thr Ala Pro Ile Thr Asp Val Ser Leu Gly Asp Glu Leu His Leu
  1               5                  10                  15

Asp Gly Glu Asp Val Ala Met Ala His Ala Asp Ala Leu Asp Asp Phe
             20                  25                  30

Asp Leu Asp Met Leu Gly Asp Gly Asp Ser Pro Gly Pro Gly Phe Thr
         35                  40                  45

Pro His Asp Ser Ala Pro Tyr Gly Ala Leu Asp Met Ala Asp Phe Glu
     50                  55                  60

Phe Glu Gln Met Phe Thr Asp Ala Leu Gly Ile Asp Asp Phe Gly Gly
 65                  70                  75                  80

Ile Asp Thr Ser Leu Tyr Lys Lys Ala Gly Ser Thr Met Val Leu Leu
                 85                  90                  95

Lys Lys His Leu Lys Asp Val Asn Arg Glu Asp Gln Arg Gln Met Pro
            100                 105                 110
```

```
Arg Gln Arg Leu Pro Ser Ile Gln Glu Ile Phe Gly Glu Thr Phe Leu
        115                 120                 125

Ala Ile Pro Ser Asn Pro Ser Tyr Ala Leu Pro Ser His Thr Arg His
130                 135                 140

Ala Ala Pro Pro Ala Leu Pro Ala Val Tyr Glu Ile Ala His Ser Ile
145                 150                 155                 160

Glu Gly Ala Pro Ser Asn Glu Gln Gly Leu Leu Pro Lys Ile Ser Thr
                165                 170                 175

Val Glu Arg Ser Leu Gly Ile Ile Ser Pro Val Asn Glu Leu Gln His
                180                 185                 190

Pro Glu Val Ile Arg Pro Glu Asn Pro Ser Phe Ser Pro Asn Gly Cys
            195                 200                 205

Ser Leu Asn Glu Ser Arg Arg Phe Ser Lys His Pro Asp Leu Ser Ile
        210                 215                 220

Pro Gln Pro Gly Leu Leu Ser Cys Asp Pro Met Asp Leu Ala Gln Pro
225                 230                 235                 240

Ser Phe Val Glu Pro Pro Asn Val Phe His Gly Phe Pro Ile Arg Lys
                245                 250                 255

Ile Pro Asn Ser Ile Pro Pro Gln Pro Lys Gln Leu Cys Leu Pro Glu
                260                 265                 270

Lys Arg Thr Pro Ser Ser Leu Asp Phe Ser Leu Phe Phe Lys Val Ile
            275                 280                 285

Glu Thr Val Ser Ala Gln Thr Leu Ala Phe Val Arg Tyr His Ser Ala
        290                 295                 300

Met Ser Gln Ser Asp Asn His Gln Arg Ser Leu Pro Gly Leu Ser Ile
305                 310                 315                 320

Thr Glu Ile Asn Gly Leu Leu Ser Gln Glu Gln Lys Gln Asp Val
                325                 330                 335

Leu Ile Tyr Ile Arg Asp Glu Leu Val Arg Phe Asp Gln Tyr Gln Ala
                340                 345                 350

Leu Ala Gln Gln Asn Thr Arg Ala Ala Ala Cys Met Ala Gly Gly Ala
            355                 360                 365

Asp Arg Gly Leu Cys Ser Ser Val Thr Lys Gln Ser Lys Thr His Lys
370                 375                 380

Val Ser Lys Gln Lys Arg Glu Trp His Gly Asp Ser Ala Leu Arg Cys
385                 390                 395                 400

His Ser Cys Asn Arg Ser Glu Thr Pro Glu Trp Arg Arg Gly Pro Asp
                405                 410                 415

Gly Pro Arg Thr Leu Cys Asn Ala Cys Gly Leu His Tyr Ala Lys Leu
            420                 425                 430

Ser Arg Arg Thr Gly Lys Phe Val Ala Leu Asp Asp Ile Gly Ile Arg
            435                 440                 445

Gly Lys Thr
    450

<210> SEQ ID NO 124
<211> LENGTH: 440
<212> TYPE: PRT
<213> ORGANISM: Artificial Sequence
<220> FEATURE:
<223> OTHER INFORMATION: fungal gene

<400> SEQUENCE: 124

Met Thr Ala Pro Ile Thr Asp Val Ser Leu Gly Asp Glu Leu His Leu
1               5                   10                  15
```

```
Asp Gly Glu Asp Val Ala Met Ala His Ala Asp Ala Leu Asp Asp Phe
             20                  25                  30
Asp Leu Asp Met Leu Gly Asp Gly Asp Ser Pro Gly Pro Gly Phe Thr
             35                  40                  45
Pro His Asp Ser Ala Pro Tyr Gly Ala Leu Asp Met Ala Asp Phe Glu
         50                  55                  60
Phe Glu Gln Met Phe Thr Asp Ala Leu Gly Ile Asp Asp Phe Gly Gly
 65                  70                  75                  80
Ile Met Val Leu Leu Lys Lys His Leu Lys Asp Val Asn Arg Glu Asp
                 85                  90                  95
Gln Arg Gln Met Pro Arg Gln Arg Leu Pro Ser Ile Gln Glu Ile Phe
                100                 105                 110
Gly Glu Thr Phe Leu Ala Ile Pro Ser Asn Pro Ser Tyr Ala Leu Pro
            115                 120                 125
Ser His Thr Arg His Ala Ala Pro Pro Ala Leu Pro Ala Val Tyr Glu
130                 135                 140
Ile Ala His Ser Ile Glu Gly Ala Pro Ser Asn Glu Gln Gly Leu Leu
145                 150                 155                 160
Pro Lys Ile Ser Thr Val Glu Arg Ser Leu Gly Ile Ile Ser Pro Val
                165                 170                 175
Asn Glu Leu Gln His Pro Glu Val Ile Arg Pro Glu Asn Pro Ser Phe
            180                 185                 190
Ser Pro Asn Gly Cys Ser Leu Asn Glu Ser Arg Arg Phe Ser Lys His
        195                 200                 205
Pro Asp Leu Ser Ile Pro Gln Pro Gly Leu Leu Ser Cys Asp Pro Met
210                 215                 220
Asp Leu Ala Gln Pro Ser Phe Val Glu Pro Pro Asn Val Phe His Gly
225                 230                 235                 240
Phe Pro Ile Arg Lys Ile Pro Asn Ser Ile Pro Pro Gln Pro Lys Gln
                245                 250                 255
Leu Cys Leu Pro Glu Lys Arg Thr Pro Ser Ser Leu Asp Phe Ser Leu
            260                 265                 270
Phe Phe Lys Val Ile Glu Thr Val Ser Ala Gln Thr Leu Ala Phe Val
        275                 280                 285
Arg Tyr His Ser Ala Met Ser Gln Ser Asp Asn His Gln Arg Ser Leu
    290                 295                 300
Pro Gly Leu Ser Ile Thr Glu Ile Asn Gly Leu Leu Ser Gln Glu Gln
305                 310                 315                 320
Gln Lys Gln Asp Val Leu Ile Tyr Ile Arg Asp Glu Leu Val Arg Phe
                325                 330                 335
Asp Gln Tyr Gln Ala Leu Ala Gln Asn Thr Arg Ala Ala Cys
            340                 345                 350
Met Ala Gly Gly Ala Asp Arg Gly Leu Cys Ser Ser Val Thr Lys Gln
        355                 360                 365
Ser Lys Thr His Lys Val Ser Lys Gln Lys Arg Glu Trp His Gly Asp
    370                 375                 380
Ser Ala Leu Arg Cys His Ser Cys Asn Arg Ser Glu Thr Pro Glu Trp
385                 390                 395                 400
Arg Arg Gly Pro Asp Gly Pro Arg Thr Leu Cys Asn Ala Cys Gly Leu
            405                 410                 415
His Tyr Ala Lys Leu Ser Arg Arg Thr Gly Lys Phe Val Ala Leu Asp
        420                 425                 430
Asp Ile Gly Ile Arg Gly Lys Thr
```

<210> SEQ ID NO 125
<211> LENGTH: 1071
<212> TYPE: DNA
<213> ORGANISM: Artificial Sequence
<220> FEATURE:
<223> OTHER INFORMATION: fungal gene

<400> SEQUENCE: 125

```
atgctcgagt tagtcgatgc tattccgctt cagacccagc cagttcctcc tgctcctgaa    60
gttcaggttc agcccctcc aatcgtggag acggcccatt tcaacccttc atggggatat   120
gatttgaacc ttctttctca tgccgcgagt catgtcgctc ttgagggaca acaagaaagt   180
ctagagactc ttcggaagcc ttcgcaaaac attcaagcgc cgccgccgcc gccgccgctt   240
tctcatatac cagaaagagg gatcactgat aactatggtg ttgagccttc gattctagac   300
cttacagatt taggtgatcc ggttcaggac tttaccgtct tcctagaaag cgtctgtctc   360
tcttcggact gggactccgg catcttctct agtgtagaag agcccttatt gccaactagc   420
ctacccatgg actcgaaacc cccagcccgt gagagttcca ggctgggcat cgatacaagt   480
ttgtacaaaa aagcaggctc acaatgacg gagaaccaca ccccttctac tacgcagccg   540
acgttgcctg cgcctgttgc tgaagccgcg ccgatccaag caaacccggc tccttctgcc   600
tcagtcacgg cgactgctgc cgccgctact gcggcggtga acaacgcccc ctctatgaac   660
ggcgccggtg agcagttgcc ttgccagtgg gttggttgca cggagaagtc ccccactgcc   720
gagtctctat atgagcatgt tgcgagcgt catgttggac gtaaaagcac caacaacctc   780
aacctgacct gccagtgggg cacttgcaac accacaacag tcaagcgtga tcatatcacc   840
tcccacatcc gcgttcatgt gccacttaag ccgcacaaat gcgacttttg tggtaaggct   900
ttcaagcgcc cccaggattt gaagaagcat gtcaagactc atgcggacga ctccgagatc   960
cgctccccg aaccgggcat gaagcaccct gatatgatgt tccccaaaa ccctaagggt  1020
tacgctgctg ccacacatta cttcgaaagc cctatcaacg gcatcaatgg g          1071
```

<210> SEQ ID NO 126
<211> LENGTH: 1035
<212> TYPE: DNA
<213> ORGANISM: Artificial Sequence
<220> FEATURE:
<223> OTHER INFORMATION: fungal gene

<400> SEQUENCE: 126

```
atgctcgagt tagtcgatgc tattccgctt cagacccagc cagttcctcc tgctcctgaa    60
gttcaggttc agcccctcc aatcgtggag acggcccatt tcaacccttc atggggatat   120
gatttgaacc ttctttctca tgccgcgagt catgtcgctc ttgagggaca acaagaaagt   180
ctagagactc ttcggaagcc ttcgcaaaac attcaagcgc cgccgccgcc gccgccgctt   240
tctcatatac cagaaagagg gatcactgat aactatggtg ttgagccttc gattctagac   300
cttacagatt taggtgatcc ggttcaggac tttaccgtct tcctagaaag cgtctgtctc   360
tcttcggact gggactccgg catcttctct agtgtagaag agcccttatt gccaactagc   420
ctacccatgg actcgaaacc cccagcccgt gagagttcca ggctgggcat gacggagaac   480
cacacccctt ctactacgca gccgacgttg cctgcgcctg ttgctgaagc cgcgccgatc   540
caagcaaacc cggctccttc tgcctcagtc acggcgactg ctgccgccgc tactgcggcg   600
gtgaacaacg ccccctctat gaacggcgcc ggtgagcagt tgccttgcca gtgggttggt   660
```

```
tgcacggaga agtcccccac tgccgagtct ctatatgagc atgtttgcga gcgtcatgtt    720
ggacgtaaaa gcaccaacaa cctcaacctg acctgccagt ggggcacttg caacaccaca    780
acagtcaagc gtgatcatat cacctcccac atccgcgttc atgtgccact taagccgcac    840
aaatgcgact tttgtggtaa ggctttcaag cgcccccagg atttgaagaa gcatgtcaag    900
actcatgcgg acgactccga gatccgctcc cccgaaccgg gcatgaagca ccctgatatg    960
atgttccccc aaaaccctaa gggttacgct gctgccacac attacttcga aagccctatc    1020
aacggcatca atggg                                                    1035
```

<210> SEQ ID NO 127
<211> LENGTH: 357
<212> TYPE: PRT
<213> ORGANISM: Artificial Sequence
<220> FEATURE:
<223> OTHER INFORMATION: fungal gene

<400> SEQUENCE: 127

```
Met Leu Glu Leu Val Asp Ala Ile Pro Leu Gln Thr Gln Pro Val Pro
1               5                   10                  15

Pro Ala Pro Glu Val Gln Val Gln Pro Pro Ile Val Glu Thr Ala
            20                  25                  30

His Phe Asn Pro Ser Trp Gly Tyr Asp Leu Asn Leu Leu Ser His Ala
        35                  40                  45

Ala Ser His Val Ala Leu Glu Gly Gln Gln Glu Ser Leu Glu Thr Leu
    50                  55                  60

Arg Lys Pro Ser Gln Asn Ile Gln Ala Pro Pro Pro Pro Pro Leu
65                  70                  75                  80

Ser His Ile Pro Glu Arg Gly Ile Thr Asp Asn Tyr Gly Val Glu Pro
                85                  90                  95

Ser Ile Leu Asp Leu Thr Asp Leu Gly Asp Pro Val Gln Asp Phe Thr
            100                 105                 110

Val Phe Leu Glu Ser Val Cys Leu Ser Ser Asp Trp Asp Ser Gly Ile
        115                 120                 125

Phe Ser Ser Val Glu Glu Pro Leu Leu Pro Thr Ser Leu Pro Met Asp
    130                 135                 140

Ser Lys Pro Pro Ala Arg Glu Ser Ser Arg Leu Gly Ile Asp Thr Ser
145                 150                 155                 160

Leu Tyr Lys Lys Ala Gly Ser Thr Met Thr Glu Asn His Thr Pro Ser
                165                 170                 175

Thr Thr Gln Pro Thr Leu Pro Ala Pro Val Ala Glu Ala Ala Pro Ile
            180                 185                 190

Gln Ala Asn Pro Ala Pro Ser Ala Ser Val Thr Ala Thr Ala Ala Ala
        195                 200                 205

Ala Thr Ala Ala Val Asn Asn Ala Pro Ser Met Asn Gly Ala Gly Glu
    210                 215                 220

Gln Leu Pro Cys Gln Trp Val Gly Cys Thr Glu Lys Ser Pro Thr Ala
225                 230                 235                 240

Glu Ser Leu Tyr Glu His Val Cys Glu Arg His Val Gly Arg Lys Ser
                245                 250                 255

Thr Asn Asn Leu Asn Leu Thr Cys Gln Trp Gly Thr Cys Asn Thr Thr
            260                 265                 270

Thr Val Lys Arg Asp His Ile Thr Ser His Ile Arg Val His Val Pro
        275                 280                 285
```

-continued

```
Leu Lys Pro His Lys Cys Asp Phe Cys Gly Lys Ala Phe Lys Arg Pro
    290             295                 300
Gln Asp Leu Lys Lys His Val Lys Thr His Ala Asp Asp Ser Glu Ile
305                 310                 315                 320
Arg Ser Pro Glu Pro Gly Met Lys His Pro Asp Met Met Phe Pro Gln
                325                 330                 335
Asn Pro Lys Gly Tyr Ala Ala Ala Thr His Tyr Phe Glu Ser Pro Ile
            340                 345                 350
Asn Gly Ile Asn Gly
        355
```

<210> SEQ ID NO 128
<211> LENGTH: 345
<212> TYPE: PRT
<213> ORGANISM: Artificial Sequence
<220> FEATURE:
<223> OTHER INFORMATION: fungal gene

<400> SEQUENCE: 128

```
Met Leu Glu Leu Val Asp Ala Ile Pro Leu Gln Thr Gln Pro Val Pro
1               5                   10                  15
Pro Ala Pro Glu Val Gln Val Gln Pro Pro Ile Val Glu Thr Ala
                20                  25                  30
His Phe Asn Pro Ser Trp Gly Tyr Asp Leu Asn Leu Leu Ser His Ala
            35                  40                  45
Ala Ser His Val Ala Leu Glu Gly Gln Gln Glu Ser Leu Glu Thr Leu
    50                  55                  60
Arg Lys Pro Ser Gln Asn Ile Gln Ala Pro Pro Pro Pro Pro Pro Leu
65                  70                  75                  80
Ser His Ile Pro Glu Arg Gly Ile Thr Asp Asn Tyr Gly Val Glu Pro
                85                  90                  95
Ser Ile Leu Asp Leu Thr Asp Leu Gly Asp Pro Val Gln Asp Phe Thr
            100                 105                 110
Val Phe Leu Glu Ser Val Cys Leu Ser Ser Asp Trp Asp Ser Gly Ile
        115                 120                 125
Phe Ser Ser Val Glu Glu Pro Leu Leu Pro Thr Ser Leu Pro Met Asp
130                 135                 140
Ser Lys Pro Pro Ala Arg Glu Ser Ser Arg Leu Gly Met Thr Glu Asn
145                 150                 155                 160
His Thr Pro Ser Thr Thr Gln Pro Thr Leu Pro Ala Pro Val Ala Glu
                165                 170                 175
Ala Ala Pro Ile Gln Ala Asn Pro Ala Pro Ser Ala Ser Val Thr Ala
            180                 185                 190
Thr Ala Ala Ala Thr Ala Ala Val Asn Asn Ala Pro Ser Met Asn
        195                 200                 205
Gly Ala Gly Glu Gln Leu Pro Cys Gln Trp Val Gly Cys Thr Glu Lys
    210                 215                 220
Ser Pro Thr Ala Glu Ser Leu Tyr Glu His Val Cys Glu Arg His Val
225                 230                 235                 240
Gly Arg Lys Ser Thr Asn Asn Leu Asn Leu Thr Cys Gln Trp Gly Thr
                245                 250                 255
Cys Asn Thr Thr Thr Val Lys Arg Asp His Ile Thr Ser His Ile Arg
            260                 265                 270
Val His Val Pro Leu Lys Pro His Lys Cys Asp Phe Cys Gly Lys Ala
        275                 280                 285
```

```
Phe Lys Arg Pro Gln Asp Leu Lys Lys His Val Lys Thr His Ala Asp
    290                 295                 300
Asp Ser Glu Ile Arg Ser Pro Glu Pro Gly Met Lys His Pro Asp Met
305                 310                 315                 320
Met Phe Pro Gln Asn Pro Lys Gly Tyr Ala Ala Thr His Tyr Phe
                325                 330                 335
Glu Ser Pro Ile Asn Gly Ile Asn Gly
            340                 345
```

<210> SEQ ID NO 129
<211> LENGTH: 1071
<212> TYPE: DNA
<213> ORGANISM: Artificial Sequence
<220> FEATURE:
<223> OTHER INFORMATION: fungal gene

<400> SEQUENCE: 129

| | | | | | |
|---|---|---|---|---|---|
| atgctcgagt | tagtcgatgc | tattccgctt | cagacccagc | cagttcctcc | tgctcctgaa | 60 |
| gttcaggttc | agcccctcc | aatcgtggag | acggcccatt | tcaacccttc | atggggatat | 120 |
| gatttgaacc | ttcttcctca | tgccgcgagt | catgtcgctc | ttgagggaca | caagaaagt | 180 |
| ctagagactc | ttcggaagcc | ttcgcaaaac | attcaagcgc | cgccgccgcc | gccgccgctt | 240 |
| tctcatatac | cagaaagagg | gatcactgat | aactatggtg | ttgagccttc | gattctagac | 300 |
| cttacagatt | taggtgatcc | ggttcaggac | tttaccgtct | tcctagaaag | cgtcgatctc | 360 |
| tcttcggact | gggactccgg | catcttctct | agtgtagaag | agcccttatt | gccaactagc | 420 |
| ctacccatgg | actcgaaacc | cccagcccgt | gagagttcca | ggctgggcat | cgatacaagt | 480 |
| ttgtacaaaa | aagcaggctc | cacaatgacg | agaaccaca | ccccttctac | tacgcagccg | 540 |
| acgttgcctg | cgcctgttgc | tgaagccgcg | ccgatccaag | caaacccggc | tccttctgcc | 600 |
| tcagtcacgg | cgactgctgc | cgccgctact | gcggcggtga | acaacgcccc | ctctatgaac | 660 |
| ggcgccggtg | agcagttgcc | ttgccagtgg | gttggttgca | cggagaagtc | ccccactgcc | 720 |
| gagtctctat | atgagcatgt | tgcgagcgt | catgttggac | gtaaaagcac | caacaacctc | 780 |
| aacctgacct | gccagtgggg | cacttgcaac | accacaacag | tcaagcgtga | tcatatcacc | 840 |
| tcccacatcc | gcgttcatgt | gccacttaag | ccgcacaaat | gcgacttttg | tggtaaggct | 900 |
| ttcaagcgcc | cccaggattt | gaagaagcat | gtcaagactc | atgcggacga | ctccgagatc | 960 |
| cgctcccccg | aaccgggcat | gaagcaccct | gatatgatgt | tccccaaaa | ccctaagggt | 1020 |
| tacgctgctg | ccacacatta | cttcgaaagc | cctatcaacg | gcatcaatgg | g | 1071 |

<210> SEQ ID NO 130
<211> LENGTH: 1035
<212> TYPE: DNA
<213> ORGANISM: Artificial Sequence
<220> FEATURE:
<223> OTHER INFORMATION: fungal gene

<400> SEQUENCE: 130

| | | | | | |
|---|---|---|---|---|---|
| atgctcgagt | tagtcgatgc | tattccgctt | cagacccagc | cagttcctcc | tgctcctgaa | 60 |
| gttcaggttc | agcccctcc | aatcgtggag | acggcccatt | tcaacccttc | atggggatat | 120 |
| gatttgaacc | ttcttcctca | tgccgcgagt | catgtcgctc | ttgagggaca | caagaaagt | 180 |
| ctagagactc | ttcggaagcc | ttcgcaaaac | attcaagcgc | cgccgccgcc | gccgccgctt | 240 |
| tctcatatac | cagaaagagg | gatcactgat | aactatggtg | ttgagccttc | gattctagac | 300 |
| cttacagatt | taggtgatcc | ggttcaggac | tttaccgtct | tcctagaaag | cgtcgatctc | 360 |

-continued

```
tcttcggact gggactccgg catcttctct agtgtagaag agcccttatt gccaactagc    420
ctacccatgg actcgaaacc cccagcccgt gagagttcca ggctgggcat gacggagaac    480
cacacccctt ctactacgca gccgacgttg cctgcgcctg ttgctgaagc cgcgccgatc    540
caagcaaacc cggctccttc tgcctcagtc acggcgactg ctgccgccgc tactgcggcg    600
gtgaacaacg ccccctctat gaacggcgcc ggtgagcagt tgccttgcca gtgggttggt    660
tgcacggaga agtcccccac tgccgagtct ctatatgagc atgtttgcga gcgtcatgtt    720
ggacgtaaaa gcaccaacaa cctcaacctg acctgccagt ggggcacttg caacaccaca    780
acagtcaagc gtgatcatat cacctcccac atccgcgttc atgtgccact taagccgcac    840
aaatgcgact tttgtggtaa ggctttcaag cgcccccagg atttgaagaa gcatgtcaag    900
actcatgcgg acgactccga gatccgctcc cccgaaccgg gcatgaagca ccctgatatg    960
atgttccccc aaaaccctaa gggttacgct gctgccacac attacttcga aagccctatc   1020
aacggcatca atggg                                                    1035
```

<210> SEQ ID NO 131
<211> LENGTH: 357
<212> TYPE: PRT
<213> ORGANISM: Artificial Sequence
<220> FEATURE:
<223> OTHER INFORMATION: fungal gene

<400> SEQUENCE: 131

```
Met Leu Glu Leu Val Asp Ala Ile Pro Leu Gln Thr Gln Pro Val Pro
 1               5                   10                  15

Pro Ala Pro Glu Val Gln Val Gln Pro Pro Ile Val Glu Thr Ala
                20                  25                  30

His Phe Asn Pro Ser Trp Gly Tyr Asp Leu Asn Leu Ser His Ala
            35                  40                  45

Ala Ser His Val Ala Leu Glu Gly Gln Gln Glu Ser Leu Glu Thr Leu
     50                  55                  60

Arg Lys Pro Ser Gln Asn Ile Gln Ala Pro Pro Pro Pro Pro Leu
 65                  70                  75                  80

Ser His Ile Pro Glu Arg Gly Ile Thr Asp Asn Tyr Gly Val Glu Pro
                 85                  90                  95

Ser Ile Leu Asp Leu Thr Asp Leu Gly Asp Pro Val Gln Asp Phe Thr
            100                 105                 110

Val Phe Leu Glu Ser Val Asp Leu Ser Ser Asp Trp Asp Ser Gly Ile
        115                 120                 125

Phe Ser Ser Val Glu Glu Pro Leu Leu Pro Thr Ser Leu Pro Met Asp
    130                 135                 140

Ser Lys Pro Pro Ala Arg Glu Ser Ser Arg Leu Gly Ile Asp Thr Ser
145                 150                 155                 160

Leu Tyr Lys Lys Ala Gly Ser Thr Met Thr Glu Asn His Thr Pro Ser
                165                 170                 175

Thr Thr Gln Pro Thr Leu Pro Ala Pro Val Ala Glu Ala Ala Pro Ile
            180                 185                 190

Gln Ala Asn Pro Ala Pro Ser Ala Ser Val Thr Ala Thr Ala Ala Ala
        195                 200                 205

Ala Thr Ala Ala Val Asn Asn Ala Pro Ser Met Asn Gly Ala Gly Glu
    210                 215                 220

Gln Leu Pro Cys Gln Trp Val Gly Cys Thr Glu Lys Ser Pro Thr Ala
225                 230                 235                 240
```

```
Glu Ser Leu Tyr Glu His Val Cys Glu Arg His Val Gly Arg Lys Ser
            245                 250                 255

Thr Asn Leu Asn Leu Thr Cys Gln Trp Gly Thr Cys Asn Thr Thr
        260                 265                 270

Thr Val Lys Arg Asp His Ile Thr Ser His Ile Arg Val His Val Pro
        275                 280                 285

Leu Lys Pro His Lys Cys Asp Phe Cys Gly Lys Ala Phe Lys Arg Pro
        290                 295                 300

Gln Asp Leu Lys Lys His Val Lys Thr His Ala Asp Ser Glu Ile
305                 310                 315                 320

Arg Ser Pro Glu Pro Gly Met Lys His Pro Asp Met Met Phe Pro Gln
                325                 330                 335

Asn Pro Lys Gly Tyr Ala Ala Thr His Tyr Phe Glu Ser Pro Ile
            340                 345                 350

Asn Gly Ile Asn Gly
        355

<210> SEQ ID NO 132
<211> LENGTH: 345
<212> TYPE: PRT
<213> ORGANISM: Artificial Sequence
<220> FEATURE:
<223> OTHER INFORMATION: fungal gene

<400> SEQUENCE: 132

Met Leu Glu Leu Val Asp Ala Ile Pro Leu Gln Thr Gln Pro Val Pro
1               5                   10                  15

Pro Ala Pro Glu Val Gln Val Gln Pro Pro Ile Val Glu Thr Ala
            20                  25                  30

His Phe Asn Pro Ser Trp Gly Tyr Asp Leu Asn Leu Leu Ser His Ala
        35                  40                  45

Ala Ser His Val Ala Leu Glu Gly Gln Gln Glu Ser Leu Glu Thr Leu
    50                  55                  60

Arg Lys Pro Ser Gln Asn Ile Gln Ala Pro Pro Pro Pro Pro Leu
65                  70                  75                  80

Ser His Ile Pro Glu Arg Gly Ile Thr Asp Asn Tyr Gly Val Glu Pro
                85                  90                  95

Ser Ile Leu Asp Leu Thr Asp Leu Gly Asp Pro Val Gln Asp Phe Thr
            100                 105                 110

Val Phe Leu Glu Ser Val Asp Leu Ser Ser Asp Trp Asp Ser Gly Ile
        115                 120                 125

Phe Ser Ser Val Glu Glu Pro Leu Leu Pro Thr Ser Leu Pro Met Asp
130                 135                 140

Ser Lys Pro Pro Ala Arg Glu Ser Ser Arg Leu Gly Met Thr Glu Asn
145                 150                 155                 160

His Thr Pro Ser Thr Thr Gln Pro Thr Leu Pro Ala Pro Val Ala Glu
                165                 170                 175

Ala Ala Pro Ile Gln Ala Asn Pro Ala Pro Ser Ala Ser Val Thr Ala
            180                 185                 190

Thr Ala Ala Ala Thr Ala Ala Val Asn Asn Ala Pro Ser Met Asn
        195                 200                 205

Gly Ala Gly Glu Gln Leu Pro Cys Gln Trp Val Gly Cys Thr Glu Lys
    210                 215                 220

Ser Pro Thr Ala Glu Ser Leu Tyr Glu His Val Cys Glu Arg His Val
225                 230                 235                 240
```

```
Gly Arg Lys Ser Thr Asn Asn Leu Asn Leu Thr Cys Gln Trp Gly Thr
                245                 250                 255

Cys Asn Thr Thr Thr Val Lys Arg Asp His Ile Thr Ser His Ile Arg
            260                 265                 270

Val His Val Pro Leu Lys Pro His Lys Cys Asp Phe Cys Gly Lys Ala
        275                 280                 285

Phe Lys Arg Pro Gln Asp Leu Lys Lys His Val Lys Thr His Ala Asp
    290                 295                 300

Asp Ser Glu Ile Arg Ser Pro Glu Pro Gly Met Lys His Pro Asp Met
305                 310                 315                 320

Met Phe Pro Gln Asn Pro Lys Gly Tyr Ala Ala Thr His Tyr Phe
                325                 330                 335

Glu Ser Pro Ile Asn Gly Ile Asn Gly
                340                 345

<210> SEQ ID NO 133
<211> LENGTH: 810
<212> TYPE: DNA
<213> ORGANISM: Artificial Sequence
<220> FEATURE:
<223> OTHER INFORMATION: fungal gene

<400> SEQUENCE: 133
atgacggaga accacacccc ttctactacg cagccgacgt tgcctgcgcc tgttgctgaa      60
gccgcgccga tccaagcaaa cccggctcct tctgcctcag tcacggcgac tgctgccgcc     120
gctactgcgg cggtgaacaa cgccccctct atgaacggcg ccggtgagca gttgccttgc     180
cagtgggttg gttgcacgga gaagtccccc actgccgagt ctctatatga gcatgtttgc     240
gagcgtcatg ttggacgtaa aagcaccaac aacctcaacc tgacctgcca gtggggcact     300
tgcaacacca caacagtcaa gcgtgatcat atcacctccc acatccgcgt tcatgtgcca     360
cttaagccgc acaaatgcga cttttgtggt aaggctttca gcgcccccca ggatttgaag     420
aagcatgtca agactcatgc ggacgactcc gagatccgct cccccgaacc gggcatgaag     480
caccctgata tgatgttccc ccaaaaccct aagggttacg ctgctgccac acattacttc     540
gaaagcccta tcaacggcat caatggggga tctaccgccc ccattaccga cgtcagcctg     600
ggggacgagc tccacttaga cggcgaggac gtggcgatgg cgcatgccga cgcgctagac     660
gatttcgatc tggacatgtt ggggacgggg gattccccgg gtccgggatt tacccccca      720 gactccgccc cctacggcgc tctggatatg gccgacttcg agtttgagca gatgtttacc     780
gatgccctgg gcattgacga ctttggggga                                      810

<210> SEQ ID NO 134
<211> LENGTH: 804
<212> TYPE: DNA
<213> ORGANISM: Artificial Sequence
<220> FEATURE:
<223> OTHER INFORMATION: fungal gene

<400> SEQUENCE: 134
atgacggaga accacacccc ttctactacg cagccgacgt tgcctgcgcc tgttgctgaa      60
gccgcgccga tccaagcaaa cccggctcct tctgcctcag tcacggcgac tgctgccgcc     120
gctactgcgg cggtgaacaa cgccccctct atgaacggcg ccggtgagca gttgccttgc     180
cagtgggttg gttgcacgga gaagtccccc actgccgagt ctctatatga gcatgtttgc     240
gagcgtcatg ttggacgtaa aagcaccaac aacctcaacc tgacctgcca gtggggcact     300
```

-continued

```
tgcaacacca caacagtcaa gcgtgatcat atcacctccc acatccgcgt tcatgtgcca      360
cttaagccgc acaaatgcga cttttgtggt aaggctttca agcgccccca ggatttgaag      420
aagcatgtca agactcatgc ggacgactcc gagatccgct ccccgaacc gggcatgaag       480 caccctgata tgatgttccc ccaaaaccct aagggttacg ctgctgccac acattacttc     540
gaaagcccta tcaacggcat caatgggacc gccccatta ccgacgtcag cctgggggac      600
gagctccact tagacggcga ggacgtggcg atggcgcatg ccgacgcgct agacgatttc     660
gatctggaca tgttggggga cggggattcc ccgggtccgg gatttacccc ccacgactcc     720 gcccctacg gcgctctgga tatggccgac ttcgagtttg agcagatgtt taccgatgcc      780
ctgggcattg acgactttgg ggga                                            804
```

<210> SEQ ID NO 135
<211> LENGTH: 270
<212> TYPE: PRT
<213> ORGANISM: Artificial Sequence
<220> FEATURE:
<223> OTHER INFORMATION: fungal gene

<400> SEQUENCE: 135

```
Met Thr Glu Asn His Thr Pro Ser Thr Thr Gln Pro Thr Leu Pro Ala
 1               5                  10                  15

Pro Val Ala Glu Ala Ala Pro Ile Gln Ala Asn Pro Ala Pro Ser Ala
                20                  25                  30

Ser Val Thr Ala Thr Ala Ala Ala Thr Ala Ala Val Asn Asn Ala
            35                  40                  45

Pro Ser Met Asn Gly Ala Gly Glu Gln Leu Pro Cys Gln Trp Val Gly
 50                  55                  60

Cys Thr Glu Lys Ser Pro Thr Ala Glu Ser Leu Tyr Glu His Val Cys
65                  70                  75                  80

Glu Arg His Val Gly Arg Lys Ser Thr Asn Asn Leu Asn Leu Thr Cys
                85                  90                  95

Gln Trp Gly Thr Cys Asn Thr Thr Val Lys Arg Asp His Ile Thr
                100                 105                 110

Ser His Ile Arg Val His Val Pro Leu Lys Pro His Lys Cys Asp Phe
            115                 120                 125

Cys Gly Lys Ala Phe Lys Arg Pro Gln Asp Leu Lys Lys His Val Lys
130                 135                 140

Thr His Ala Asp Asp Ser Glu Ile Arg Ser Pro Glu Pro Gly Met Lys
145                 150                 155                 160

His Pro Asp Met Met Phe Pro Gln Asn Pro Lys Gly Tyr Ala Ala Ala
                165                 170                 175

Thr His Tyr Phe Glu Ser Pro Ile Asn Gly Ile Asn Gly Gly Ser Thr
            180                 185                 190

Ala Pro Ile Thr Asp Val Ser Leu Gly Asp Glu Leu His Leu Asp Gly
        195                 200                 205

Glu Asp Val Ala Met Ala His Ala Asp Ala Leu Asp Asp Phe Asp Leu
    210                 215                 220

Asp Met Leu Gly Asp Gly Asp Ser Pro Gly Pro Gly Phe Thr Pro His
225                 230                 235                 240

Asp Ser Ala Pro Tyr Gly Ala Leu Asp Met Ala Asp Phe Glu Phe Glu
                245                 250                 255

Gln Met Phe Thr Asp Ala Leu Gly Ile Asp Asp Phe Gly Gly
            260                 265                 270
```

-continued

<210> SEQ ID NO 136
<211> LENGTH: 268
<212> TYPE: PRT
<213> ORGANISM: Artificial Sequence
<220> FEATURE:
<223> OTHER INFORMATION: fungal gene

<400> SEQUENCE: 136

```
Met Thr Glu Asn His Thr Pro Ser Thr Thr Gln Pro Thr Leu Pro Ala
  1               5                  10                  15
Pro Val Ala Glu Ala Ala Pro Ile Gln Ala Asn Pro Ala Pro Ser Ala
             20                  25                  30
Ser Val Thr Ala Thr Ala Ala Ala Thr Ala Ala Val Asn Asn Ala
         35                  40                  45
Pro Ser Met Asn Gly Ala Gly Glu Gln Leu Pro Cys Gln Trp Val Gly
     50                  55                  60
Cys Thr Glu Lys Ser Pro Thr Ala Glu Ser Leu Tyr Glu His Val Cys
 65                  70                  75                  80
Glu Arg His Val Gly Arg Lys Ser Thr Asn Asn Leu Asn Leu Thr Cys
                 85                  90                  95
Gln Trp Gly Thr Cys Asn Thr Thr Val Lys Arg Asp His Ile Thr
            100                 105                 110
Ser His Ile Arg Val His Val Pro Leu Lys Pro His Lys Cys Asp Phe
        115                 120                 125
Cys Gly Lys Ala Phe Lys Arg Pro Gln Asp Leu Lys Lys His Val Lys
    130                 135                 140
Thr His Ala Asp Asp Ser Glu Ile Arg Ser Pro Glu Pro Gly Met Lys
145                 150                 155                 160
His Pro Asp Met Met Phe Pro Gln Asn Pro Lys Gly Tyr Ala Ala Ala
                165                 170                 175
Thr His Tyr Phe Glu Ser Pro Ile Asn Gly Ile Asn Gly Thr Ala Pro
            180                 185                 190
Ile Thr Asp Val Ser Leu Gly Asp Glu Leu His Leu Asp Gly Glu Asp
        195                 200                 205
Val Ala Met Ala His Ala Asp Ala Leu Asp Asp Phe Asp Leu Asp Met
    210                 215                 220
Leu Gly Asp Gly Asp Ser Pro Gly Pro Gly Phe Thr Pro His Asp Ser
225                 230                 235                 240
Ala Pro Tyr Gly Ala Leu Asp Met Ala Asp Phe Glu Phe Glu Gln Met
                245                 250                 255
Phe Thr Asp Ala Leu Gly Ile Asp Asp Phe Gly Gly
            260                 265
```

<210> SEQ ID NO 137
<211> LENGTH: 2415
<212> TYPE: DNA
<213> ORGANISM: Artificial Sequence
<220> FEATURE:
<223> OTHER INFORMATION: fungal gene

<400> SEQUENCE: 137

| | | | | |
|---|---|---|---|---|
| atggttaaag agagtattat tgctcttgct gagcatgcgg cctccagagc ctcaagagtt | 60 |
| attcctccag tgaagctagc ctataaaaat atgcttaagg acccttcctc caagtacaag | 120 |
| ccatttaacg ctccaaagct atctaataga aagtggccgg ataaccggat cacgagggct | 180 |
| cctcgttggt tatcaacaga tttgagagat ggtaaccaat ctctgccgga tcccatgtca | 240 |

-continued

```
gtggaacaaa agaaagaata ctttcacaag ctggtcaata ttgggttcaa agaaatcgag      300
gtttccttcc cctctgcatc tcaaacagat ttcgacttca ctagatatgc tgtagaaaac      360
gccccagacg atgttagtat tcaatgtctt gtccaatcta gagaacactt gattaagaga      420
acggtggaag cattaacagg tgctaaaaag gctactatac atacttactt ggcaacaagt      480
gatatgttcc gtgaaattgt ttttaatatg tctagagagg aagctatttc caaggcagta      540
gaggccacca aactagttag gaaactaact aaggatgacc cttcccaaca agccactcgt      600
tggtcctatg agtttttcccc cgaatgtttc agtgatactc caggtgaatt tgctgtagaa      660
atttgcgaag ctgttaagaa ggcttgggaa cctaccgagg aaaatccaat cattttcaac      720
ttacctgcta ccgtagaagt tgcctctcca aatgtttatg ctgatcagat tgaatacttc      780
gctacccata ttactgagcg tgagaaggtt tgcatctcta cacattgtca caatgaccgt      840
ggttgcggtg tcgccgccac agagttaggt atgcttgcag gtgccgaccg tgtagaagga      900
tgtctctttg gtaatggtga acgtacaggt aatgtggact tggttactgt tgctatgaat      960
atgtataccc aagtgtttc tcctaatttg gatttctctg acttgacctc tgtcctagat     1020
gtggttgagc gttgtaataa gatcccagta tcgcaaagag caccatacgg cggtgacttg     1080
gtcgtttgtg ccttttccgg ttctcaccaa gacgccatta agaagggttt caacttacaa     1140
aacaagaagc gtgctcaagg tgaaactcaa tggagaatcc catacttgcc attggatcca     1200
aaggacattg gccgtgatta cgaagctgtc atcagagtca actctcagtc tggtaaaggt     1260
ggtgccgctt gggttatttt gagatctttg ggtttggatc taccaagaaa catgcaaatc     1320
gaattttcta cgccgttca agaccatgct gactccttgg gtagagaact aaaatcagat     1380
gagatttcca agttattcaa agaggcttac aactacaatg acgaacagta ccaagctatt     1440
agtttagtca attataatgt tgaaaaattc ggcactgaac gtagagtgtt cactggtcaa     1500
gtcaaagtag gcgaccagat cctctacgcc ggacgcatcg tggccggcat caccggcgcc     1560
acaggtgcgg ttgctggcgc ctatatcgcc gacatcaccg atgggaaga tcgggctcgc     1620
cacttcgggc tcatgagcgc ttgtttcggc gtgggtatgg tggcaggccc cgtgccgggg     1680
ggactgttgg gcgccatctc cttgcatgca ccattccttg cggcggcggt gctcaacggc     1740
ctcaacctac tactgggctg cttcctaatg caggagtcgc ataagggaga gcgtcgaccg     1800
atgcccttga gagccttcaa cccagtcagc tccttccggt gggcgcgggg catgactatc     1860
gtcgccgcac ttatgactgt cttctttatc atgcaactcg taggacaggt gccggcagcg     1920
ctctgggtca ttttcggcga ggaccgcttt cgctggagcg cgacgatgat cggcctgtcg     1980
cttgcggtat tcggaatctt gcacgccctc gctcaagcct tcgtcactgg tcccgccacc     2040
aaacgtttcg gcgagaagca ggccattatc gccggcatgg cggccgacgc gctgggctac     2100
gtcttgctgg cgttcgcgac gcgaggctgg atggccttcc ccattatgat tcttctcgct     2160
tccggcggca tcgggatgcc cgcgttgcag gccatgctgt ccaggcaggt agatgacgac     2220
catcagggac agcttcaagg atcgctcgcg gctcttacca gcctaacttc gatcactgga     2280
ccgctgatcg tcacggcgat ttatgccgcc tcggcgagca catggaacgg gttggcatgg     2340
attgtaggcg ccgccctata ccttgtctgc ctccccgcgt tgcgtcgcgg tgcatggagc     2400
cgggccacct cgacc                                                      2415
```

<210> SEQ ID NO 138
<211> LENGTH: 805
<212> TYPE: PRT

```
<213> ORGANISM: Artificial Sequence
<220> FEATURE:
<223> OTHER INFORMATION: fungal gene

<400> SEQUENCE: 138
```

| | | | | | | | | | | | | | | |
|---|---|---|---|---|---|---|---|---|---|---|---|---|---|---|
| Met | Val | Lys | Glu | Ser | Ile | Ile | Ala | Leu | Ala | Glu | His | Ala | Ala | Ser | Arg |
| 1 | | | | 5 | | | | | 10 | | | | | 15 | |
| Ala | Ser | Arg | Val | Ile | Pro | Pro | Val | Lys | Leu | Ala | Tyr | Lys | Asn | Met | Leu |
| | | | 20 | | | | | 25 | | | | | 30 | | |
| Lys | Asp | Pro | Ser | Ser | Lys | Tyr | Lys | Pro | Phe | Asn | Ala | Pro | Lys | Leu | Ser |
| | | | 35 | | | | 40 | | | | | 45 | | | |
| Asn | Arg | Lys | Trp | Pro | Asp | Asn | Arg | Ile | Thr | Arg | Ala | Pro | Arg | Trp | Leu |
| | 50 | | | | | 55 | | | | | 60 | | | | |
| Ser | Thr | Asp | Leu | Arg | Asp | Gly | Asn | Gln | Ser | Leu | Pro | Asp | Pro | Met | Ser |
| 65 | | | | | 70 | | | | | 75 | | | | | 80 |
| Val | Glu | Gln | Lys | Lys | Glu | Tyr | Phe | His | Lys | Leu | Val | Asn | Ile | Gly | Phe |
| | | | | 85 | | | | | 90 | | | | | 95 | |
| Lys | Glu | Ile | Glu | Val | Ser | Phe | Pro | Ser | Ala | Ser | Gln | Thr | Asp | Phe | Asp |
| | | | | 100 | | | | | 105 | | | | | 110 | |
| Phe | Thr | Arg | Tyr | Ala | Val | Glu | Asn | Ala | Pro | Asp | Asp | Val | Ser | Ile | Gln |
| | | | 115 | | | | | 120 | | | | | 125 | | |
| Cys | Leu | Val | Gln | Ser | Arg | Glu | His | Leu | Ile | Lys | Arg | Thr | Val | Glu | Ala |
| | 130 | | | | | 135 | | | | | 140 | | | | |
| Leu | Thr | Gly | Ala | Lys | Lys | Ala | Thr | Ile | His | Thr | Tyr | Leu | Ala | Thr | Ser |
| 145 | | | | | 150 | | | | | 155 | | | | | 160 |
| Asp | Met | Phe | Arg | Glu | Ile | Val | Phe | Asn | Met | Ser | Arg | Glu | Glu | Ala | Ile |
| | | | | 165 | | | | | 170 | | | | | 175 | |
| Ser | Lys | Ala | Val | Glu | Ala | Thr | Lys | Leu | Val | Arg | Lys | Leu | Thr | Lys | Asp |
| | | | 180 | | | | | 185 | | | | | 190 | | |
| Asp | Pro | Ser | Gln | Gln | Ala | Thr | Arg | Trp | Ser | Tyr | Glu | Phe | Ser | Pro | Glu |
| | | | 195 | | | | | 200 | | | | | 205 | | |
| Cys | Phe | Ser | Asp | Thr | Pro | Gly | Glu | Phe | Ala | Val | Glu | Ile | Cys | Glu | Ala |
| | 210 | | | | | 215 | | | | | 220 | | | | |
| Val | Lys | Lys | Ala | Trp | Glu | Pro | Thr | Glu | Glu | Asn | Pro | Ile | Ile | Phe | Asn |
| 225 | | | | | 230 | | | | | 235 | | | | | 240 |
| Leu | Pro | Ala | Thr | Val | Glu | Val | Ala | Ser | Pro | Asn | Val | Tyr | Ala | Asp | Gln |
| | | | | 245 | | | | | 250 | | | | | 255 | |
| Ile | Glu | Tyr | Phe | Ala | Thr | His | Ile | Thr | Glu | Arg | Glu | Lys | Val | Cys | Ile |
| | | | 260 | | | | | 265 | | | | | 270 | | |
| Ser | Thr | His | Cys | His | Asn | Asp | Arg | Gly | Cys | Gly | Val | Ala | Ala | Thr | Glu |
| | | | 275 | | | | | 280 | | | | | 285 | | |
| Leu | Gly | Met | Leu | Ala | Gly | Ala | Asp | Arg | Val | Glu | Gly | Cys | Leu | Phe | Gly |
| | | | 290 | | | | | 295 | | | | | 300 | | |
| Asn | Gly | Glu | Arg | Thr | Gly | Asn | Val | Asp | Leu | Val | Thr | Val | Ala | Met | Asn |
| 305 | | | | | 310 | | | | | 315 | | | | | 320 |
| Met | Tyr | Thr | Gln | Gly | Val | Ser | Pro | Asn | Leu | Asp | Phe | Ser | Asp | Leu | Thr |
| | | | | 325 | | | | | 330 | | | | | 335 | |
| Ser | Val | Leu | Asp | Val | Glu | Arg | Cys | Asn | Lys | Ile | Pro | Val | Ser | Gln |
| | | | 340 | | | | | 345 | | | | | 350 | | |
| Arg | Ala | Pro | Tyr | Gly | Gly | Asp | Leu | Val | Val | Cys | Ala | Phe | Ser | Gly | Ser |
| | | | 355 | | | | | 360 | | | | | 365 | | |
| His | Gln | Asp | Ala | Ile | Lys | Lys | Gly | Phe | Asn | Leu | Gln | Asn | Lys | Lys | Arg |
| | | | 370 | | | | | 375 | | | | | 380 | | |

-continued

```
Ala Gln Gly Glu Thr Gln Trp Arg Ile Pro Tyr Leu Pro Leu Asp Pro
385                 390                 395                 400

Lys Asp Ile Gly Arg Asp Tyr Glu Ala Val Ile Arg Val Asn Ser Gln
            405                 410                 415

Ser Gly Lys Gly Gly Ala Ala Trp Val Ile Leu Arg Ser Leu Gly Leu
            420                 425                 430

Asp Leu Pro Arg Asn Met Gln Ile Glu Phe Ser Ser Ala Val Gln Asp
            435                 440                 445

His Ala Asp Ser Leu Gly Arg Glu Leu Lys Ser Asp Glu Ile Ser Lys
    450                 455                 460

Leu Phe Lys Glu Ala Tyr Asn Tyr Asn Asp Glu Gln Tyr Gln Ala Ile
465                 470                 475                 480

Ser Leu Val Asn Tyr Asn Val Glu Lys Phe Gly Thr Glu Arg Arg Val
            485                 490                 495

Phe Thr Gly Gln Val Lys Val Gly Asp Gln Ile Leu Tyr Ala Gly Arg
            500                 505                 510

Ile Val Ala Gly Ile Thr Gly Ala Thr Gly Ala Val Ala Gly Ala Tyr
            515                 520                 525

Ile Ala Asp Ile Thr Asp Gly Glu Asp Arg Ala Arg His Phe Gly Leu
530                 535                 540

Met Ser Ala Cys Phe Gly Val Gly Met Val Ala Gly Pro Val Ala Gly
545                 550                 555                 560

Gly Leu Leu Gly Ala Ile Ser Leu His Ala Pro Phe Leu Ala Ala Ala
            565                 570                 575

Val Leu Asn Gly Leu Asn Leu Leu Gly Cys Phe Leu Met Gln Glu
            580                 585                 590

Ser His Lys Gly Glu Arg Arg Pro Met Pro Leu Arg Ala Phe Asn Pro
    595                 600                 605

Val Ser Ser Phe Arg Trp Ala Arg Gly Met Thr Ile Val Ala Ala Leu
    610                 615                 620

Met Thr Val Phe Phe Ile Met Gln Leu Val Gly Gln Val Pro Ala Ala
625                 630                 635                 640

Leu Trp Val Ile Phe Gly Glu Asp Arg Phe Arg Trp Ser Ala Thr Met
            645                 650                 655

Ile Gly Leu Ser Leu Ala Val Phe Gly Ile Leu His Ala Leu Ala Gln
            660                 665                 670

Ala Phe Val Thr Gly Pro Ala Thr Lys Arg Phe Gly Glu Lys Gln Ala
    675                 680                 685

Ile Ile Ala Gly Met Ala Ala Asp Ala Leu Gly Tyr Val Leu Leu Ala
    690                 695                 700

Phe Ala Thr Arg Gly Trp Met Ala Phe Pro Ile Met Ile Leu Leu Ala
705                 710                 715                 720

Ser Gly Gly Ile Gly Met Pro Ala Leu Gln Ala Met Leu Ser Arg Gln
            725                 730                 735

Val Asp Asp Asp His Gln Gly Gln Leu Gln Gly Ser Leu Ala Ala Leu
            740                 745                 750

Thr Ser Leu Thr Ser Ile Thr Gly Pro Leu Ile Val Thr Ala Ile Tyr
    755                 760                 765

Ala Ala Ser Ala Ser Thr Trp Asn Gly Leu Ala Trp Ile Val Gly Ala
770                 775                 780
```

```
Ala Leu Tyr Leu Val Cys Leu Pro Ala Leu Arg Arg Gly Ala Trp Ser
785                 790             795                 800

Arg Ala Thr Ser Thr
                805
```

ISOLATED NUCLEIC ACID MOLECULE ENCODING A REGULATOR OF FUNGAL GENE EXPRESSION

This is a continuation-in-part of provisional application Serial No. 60/257,431, filed 22 Dec. 2000.

FIELD OF THE INVENTION

The invention relates to regulators of fungal gene expression and their use in commercial and medical applications. More particularly, the invention relates to regulators of fungal genes involved in production of enzymes, secondary metabolites and other useful products, as well as to regulators of genes involved in fungal invasion.

SUMMARY OF THE RELATED ART

Fungi are among the most common natural sources of useful substances for commercial and medical applications. Many of these useful substances are secondary metabolites.

Secondary metabolite production by various fungi has been an extremely important source of a variety of therapeutically significant pharmaceuticals. β-lactam antibacterials such as penicillin and cephalosporin are produced by *Penicillium chrysogenum* and *Acremonium chrysogenum*, respectively, and these compounds are by far the most frequently used antibacterials (reviewed in Luengo and Penalva, Prog. Ind. Microbiol. 29: 603–38 (1994); Jensen and Demain, Biotechnology 28: 239–68 (1995); Brakhage, Microbiol. Mol. Biol. Rev. 62: 547–85 (1998)). Cyclosporin A, a member of a class of cyclic undecapeptides, is produced by *Tolypocladium inflatum*. Cyclosporin A dramatically reduces morbidity and increases survival rates in transplant patients (Borel, Prog. Allergy 38: 9–18 (1986)). In addition, several fungal secondary metabolites are cholesterol-lowering drugs, including lovastatin that is made by *Aspergillus terreus* and several other fungi (Alberts et al., Proc. Natl. Acad. Sci. USA 77: 3957–3961 (1980)). These and many other fungal secondary metabolites have contributed greatly to health care throughout the world (see Demain, Ciba Found Symp 171: 3–16 (1992); Bentley, Crit. Rev. Biotechnol. 19: 1–40 (1999)).

Unfortunately, many challenges are encountered between the detection of a secondary metabolite activity and production of significant quantities of pure drug. Thus, efforts have been made to improve the production of secondary metabolites by fungi. Recently, strains have been improved by manipulating genes encoding the biosynthetic enzymes that catalyze the reactions required for production of secondary metabolites. Penalva et al., Trends Biotechnol. 16: 483–489 (1998) discloses that production strains of *P. chrysogenum* have increased copy number of the penicillin synthesis structural genes. Other studies have modulated expression of other biosynthetic enzyme-encoding genes, thereby affecting overall metabolism in the fungus. Mingo et al., J. Biol. Chem. 21: 14545–14550 (1999), demonstrate that disruption of the gene encoding phacA, an enzyme in *A. nidulans* that catalyzes phenylacetate 2-hydroxylation, leads to increased penicillin production, probably by elimination of competition for the substrate phenylacetate. Similarly, disruption of the gene encoding aminoadipate reductase in *P. chrysogenum* increased penicillin production, presumably by eliminating competition for the substrate alpha-aminoadipate (Casquiero et al., J. Bacteriol. 181: 1181–1188 (1999)).

Thus, genetic manipulation holds promise for improving production of secondary metabolites. Genetic manipulation to increase the activity of biosynthetic enzymes for secondary metabolite production or to decrease the activity of competing biosynthetic pathways has proven effective for improving production. Maximum benefit might be achieved by combining several strategies of manipulation. For example, modulating the expression of genes that regulate the biosynthetic enzyme-encoding genes or altering concentrations of metabolic precursors might improve production. In addition, genetic manipulation could be used to impact upon the challenges that are encountered in the fermenter run or downstream processing (e.g. energy cost, specific production of desired metabolite, maximal recovery of metabolite, cost of processing waste from fermentations). There is, therefore, a need for regulator genes that can improve secondary metabolite production in a fungus.

Enzymes are another commercially important fungal product. Recently, efforts have been made to improve fungal enzyme production through genetic manipulation. Noel et al., Molecular Microbiology 27: 131–142 (1998), teaches that xlnR, a ZBC protein, induces expression of xylanolytic extracellular enzymes in *Aspergillus niger*. Hasper et al., Molecular Microbiology 36: 193–200 (2000) teaches that xlnR also regulates D-xylose reductase gene expression in *Aspergillus niger*. Given the many useful enzymes produced by fungi, there remains a need for regulator genes that can improve the production of these enzymes.

There is also a need for regulator identifying genes relevant to fungal invasion. Fungal invasion is required for fungal pathogenesis and its regulation is likely related to secondary metabolite and enzyme production. Fungal infections have become a serious health concern, especially in immunocompromised patients. Ha and White, Antimicrobial Agents and Chemotherapy 43: 763–768 (1999) teach that candidiasis, which is caused by the pathogenic yeast *Candida albicans*, is the most frequent fungal infection associated with AIDS and other immunocompromised states. Weig et al., Trends in Microbiology 6: 468–470 (1998) discloses that the frequency of Candida infections has increased in recent years and has been accompanied by a significant rise in morbidity and mortality. Many of these infections take place in the hospital setting. Baillie and Douglas, Methods in Enzymology 310: 644–656 (1999) teach that a majority of nosocomial septicemias caused by Candida species derive from biofilm formation on catheters and shunts. Little is known about the genes necessary for invasion or biofilm formation. There is, therefore, a need for the identification of new fungal invasion regulatory genes to act as targets for the development of antifungal drugs.

BRIEF SUMMARY OF THE INVENTION

The invention provides novel fungal regulator genes and methods for using regulator genes in commercial and medical applications.

In a first aspect, the invention provides novel isolated or recombinant genes that have been demonstrated to encode proteins that regulate fungal genes that are involved in secondary metabolite production, enzyme production, or fungal invasion. In certain preferred embodiments, the invention further provides homologs of such genes. These genes and their homologs are useful for improving secondary metabolite or enzyme production, or as targets for discovering new antifungal drugs.

In a second aspect, the invention provides isolated or recombinant nucleic acids that are specifically complementary to genes that have been demonstrated to encode proteins that regulate fungal genes that are involved in secondary metabolite production, enzyme production, or fungal invasion.

In a third aspect, the invention provides purified proteins that have been demonstrated to regulate fungal genes that are involved in secondary metabolite production, enzyme production, or fungal invasion. In certain embodiments, the invention further provides homologs of such proteins.

In a fourth aspect, the invention provides novel binding agents that specifically bind to proteins that have been demonstrated to regulate fungal genes that are involved in secondary metabolite production, enzyme production, or fungal invasion.

In a fifth aspect, the invention provides novel recombinant genes that are direct or indirect regulators of expression of FLO11, a fungal gene that is required for fungal invasion and whose expression is believed to be regulated by factors that also modulate secondary metabolite production. In certain embodiments, the invention further provides homologs of such genes. These genes are useful as targets for the development of antifungal drugs, and are expected to be useful for improving the production of secondary metabolites or fungal enzymes.

In a sixth aspect, the invention provides novel recombinant genes that are direct or indirect regulators of expression of lovF, a fungal gene involved in the production of the secondary metabolite lovastatin. In certain embodiments, the invention further provides homologs of such genes. These genes are expected to be useful for improving the production of secondary metabolites or fungal enzymes.

In a seventh aspect, the invention provides novel recombinant genes that are direct or indirect regulators of expression of lovE, a fungal gene involved in the production of the secondary metabolite lovastatin. In certain embodiments, the invention further provides homologs of such genes. These genes are expected to be useful for improving the production of secondary metabolites or fungal enzymes.

In an eighth aspect, the invention provides novel recombinant genes that are direct or indirect regulators of expression of acvA, a fungal gene involved in the production of the secondary metabolite penicillin. In certain embodiments, the invention further provides homologs of such genes. These genes are expected to be useful for improving the production of secondary metabolites or fungal enzymes.

In a ninth aspect, the invention provides methods for modulating production of a secondary metabolite or enzyme, the method comprising expressing in the fungus a novel fungal regulator gene.

In a tenth aspect, the invention provides novel chimeric fungal regulator genes.

In an eleventh aspect, the invention provides methods for modulating production of a secondary metabolite or extracellular enzyme, the method comprising expressing in the fungus a novel chimeric fungal regulator gene.

DETAILED DESCRIPTION OF THE PREFERRED EMBODIMENTS

The invention relates to regulators of fungal gene expression and their use in commercial and medical applications. More particularly, the invention relates to regulators of fungal genes involved in production of enzymes, secondary metabolites and other useful products, as well as to regulators of genes involved in fungal invasion. The patents and publications cited herein reflect the level of knowledge in this field and are hereby incorporated by reference in their entirety. In the case of conflict between the teaching of a cited reference and the present specification, the latter shall prevail.

The invention provides novel regulators of fungal gene expression, and methods for using regulator genes in commercial and medical applications.

In a first aspect, the invention provides novel isolated or recombinant genes that have been demonstrated to encode proteins that regulate fungal genes that are involved in secondary metabolite production, enzyme production, or fungal invasion. In certain preferred embodiments, the invention further provides homologs of such genes. These genes and their homologs are useful for improving secondary metabolite or enzyme production, or as targets for discovering new antifungal drugs.

As used herein, a "recombinant gene" is a nucleic acid sequence which encodes a protein, wherein the recombinant gene may be in the form of linear DNA or RNA, covalently closed circular DNA or RNA, or as part of a chromosome, provided however that it cannot be a single copy at the native chromosomal locus in which the gene normally resides in nature. Thus, this aspect of the invention includes genetically modified organisms containing such recombinant genes.

As used herein, a "homolog" of a gene is a gene that, when compared to the reference gene, has a lower E-value, or has a higher percent identity value in the region of homology than that listed in Table I. Table I shows a listing of reference genes, their E-values, and where applicable, their percent identity. In cases where regions of identity exist between the reference gene and a sequence from a public gene database, the region of identity is indicated. In such instances, position 1 is defined as the first nucleotide of the reference gene shown in the Sequence Listing.

In certain preferred embodiments, the homolog is a dominant mutation of the novel reference gene. A "dominant mutation" is an allele of a gene that encodes a protein capable of changing a phenotype of an organism more than a non-mutated form of the gene. Dominant mutations include, without limitation, mutations that encode a protein capable of changing a phenotype of an organism even when a non-mutant form of this gene (or its homologs) is resident in the organism. Preferred dominant mutations include dominant negative mutations, dominant positive mutations, and dominant neomorphic mutations. A "dominant negative mutation" is a dominant mutation that achieves its phenotypic effect by interfering with some function of the gene or gene product from which it was derived, or from a homolog thereof. A "dominant positive mutation" is a dominant mutation that achieves its phenotypic effect by activating some function of the gene or gene product from which it was derived, or from a homolog thereof. A "dominant neomorphic mutation" is a dominant mutation that achieves the phenotypic effect of providing a novel or different function to the gene or gene product from which it was derived, or from a homolog thereof.

TABLE I

Novel regulator genes

| | Gene | E-score for coding sequence | Percent Identity (only for E <1e − 25) | Starting Nucleotide | Ending Nucleotide |
|---|---|---|---|---|---|
| 1 | An10 | 6.00E − 16 | n/a | | |
| 2 | An1000 | 1.00E − 05 | n/a | | |
| 3 | At01-1 | 1.00E − 05 | n/a | | |
| 4 | At01-2 | 7.00E − 10 | n/a | | |
| 5 | At03 | 7.00E − 12 | n/a | | |

TABLE I-continued

Novel regulator genes

| | Gene | E-score for coding sequence | Percent Identity (only for E <1e − 25) | Starting Nucleotide | Ending Nucleotide |
|---|---|---|---|---|---|
| 6 | At05 | 1.00E − 05 | n/a | | |
| 7 | At07 | 2.00E − 06 | n/a | | |
| 8 | At08 | 1.00E − 57 | 81 | 1 | 428 |
| 9 | At11 | 8.00E − 22 | n/a | | |
| 10 | At14 | 1.00E − 05 | n/a | | |
| 11 | At16 | 7.00E − 24 | n/a | | |
| 12 | At167 | 0 | 87 | 5 | 1514 |
| 13 | At18 | 1.00E − 05 | n/a | | |
| 14 | At19 | 1.00E − 05 | n/a | | |
| 15 | At20 | 1.00E − 05 | n/a | | |
| 16 | At22 | 3.00E − 52 | n/a | | |
| 17 | At221 | 9.00E − 17 | n/a | | |
| 18 | At233 | 9.00E − 25 | n/a | | |
| 19 | At239 | 6.00E − 30 | 84 | 763 | 939 |
| 20 | At24 | 5.00E − 07 | n/a | | |
| 21 | At240 | 7.00E − 29 | n/a | | |
| 22 | At27 | 1.00E − 05 | n/a | | |
| 23 | At274 | 1.00E − 05 | n/a | | |
| 24 | At279 | 1.00E − 05 | n/a | | |
| 25 | At286 | 1.00E − 05 | n/a | | |
| 26 | At291 | 1.00E − 05 | n/a | | |
| 27 | At32 | 1.00E − 12 | n/a | | |
| 28 | At320 | 4.00E − 15 | n/a | | |
| 29 | At322 | 1.00E − 05 | n/a | | |
| 30 | At501 | 3.00E − 21 | n/a | | |
| 31 | At574 | 2.00E − 25 | n/a | | |
| 32 | Pc05 | 1.00E − 05 | n/a | | |
| 33 | Pc06 | 1.00E − 05 | n/a | | |
| 34 | Pc07 | 1.00E − 05 | n/a | | |
| 35 | Pc08 | 1.00E − 05 | n/a | | |
| 36 | Pc09 | 6.00E − 16 | n/a | | |
| 37 | Pc10 | 1.00E − 05 | n/a | | |
| 38 | Pc1000 | 2.00E − 25 | n/a | | |
| 39 | Pc1001 | 1.00E − 05 | n/a | | |
| 40 | Pc18 | 4.00E − 12 | n/a | | |
| 41 | Pc23 | 1.00E − 05 | n/a | | |
| 42 | Pc24 | 5.00E − 18 | n/a | | |
| 43 | Pc25 | 1.00E − 05 | n/a | | |
| 44 | Pc33 | 4.00E − 07 | n/a | | |
| 45 | Pc34 | 6.00E − 30 | 87 | 1042 | 1178 |
| 46 | Pc804 | 1.00E − 05 | n/a | | |

Data shown in Table I are derived by comparing the novel reference genes with available genetic databases. The present inventors utilized the BLAST (Basic Local Alignment Search Tool) tool, which is publicly available at http://www.ncbi.nlm.nih.gov/blast/. This is a set of similarity search programs designed to explore sequence databases. The current version of NCBI BLAST, BLAST 2.1.2 was accessed directly from the NCBI web site. One of the outputs of the BLAST program is an Expect (E) value, which is a parameter that describes the number of "hits" one can expect to see by chance when searching a database of a particular size.

To determine E-values for the nucleotide coding sequences of the novel regulator genes according to the invention, the blastn program was used. This program compares a nucleotide query (reference) sequence against a nucleotide sequence database. The following databases available at the NCBI BLAST site were used: nr, which includes all GenBank, EMBL, DDBJ and PDB sequences; yeast (*Saccharomyces cerevisiae*) genomic nucleotide sequences; patents; and non-human/mouse EST (expressed sequence tag) sequences. BLAST analysis was also performed using the *Neurospora crassa* partial genome sequence available at http://www.mips.biochem.mpg.dc/cgi-bin/blast/blast page?genus=neurospora. Table I reflects the lowest E-value for these five databases.

For a gapped alignment analysis, the blastn algorithm default settings were used. These are: −G, cost to open a gap, default=5; −E, cost to extend a gap, default=2; −q, penalty for a mismatch, default=−3; −r, reward for a match, default= 1; −e, expectation value, default=10.0; and −W, word size, default=11.

For novel reference genes having no related sequences in the databases, E-values were "floored" to 1e-5 as a way of defining a reasonable E-value for a hypothetical related gene. For genes having non-identical but related sequences in the databases, the E-value is that of the closest "relative" gene. For genes having extensive regions of homology to a gene in the database, a percent identity value provided by the algorithm is included in Table I, along with the region of identity.

Table II shows novel regulator genes according to the invention for which a portion of the gene sequence is in a database, but for which the present inventors now provide more complete sequence.

TABLE II

Novel regulator genes partially publicly disclosed

| | Gene Name | Nucleotide Coding Sequence | | Amino Acid Sequence | | E score from BlastP of Microbia |
|---|---|---|---|---|---|---|
| | | Microbia | Public | Microbia | Public | Proprietary AA |
| 1 | An01 | 506–649 | 1–505, 650–939 | 170–216 | 1–169, 217–313 | 1.00E − 05 |
| 2 | An05 | 1–1131 | 1132–1512 | 1–377 | 378–504 | 2.00E − 13 |
| 3 | An09 | 1–946 | 947–1557 | 1–315 | 316–519 | 1.00E − 05 |
| 4 | An13 | 532–823 | 1–531, 824–933 | 178–274 | 1–177, 275–311 | 1.00E − 05 |
| 5 | An17 | 1–457 | 458–660 | 1–152 | 153–220 | 1.00E − 05 |
| 6 | An20 | 28–90, 186–249 | 1–27, 91–185, 250–684 | 10–30, 62–83 | 1–9, 31–62, 84–228 | 1.00E − 05 |
| 7 | An28 | 521–572 | 1–520, 573–906 | 175–190 | 1–174, 191–302 | 1.00E − 05 |
| 8 | An34 | 1–119 533–810 | 120–532 | 1–39 179–270 | 40–178 | 1.00E − 05 1.00E − 05 |

Preferred genes according to this aspect of the invention are selected from the group consisting of Pc804 (SEQ ID NO.1), An01 (SEQ ID NO. 3), An05 (SEQ ID NO. 5), An09 (SEQ ID NO 7), An10 (SEQ ID NO. 9), An13 (SEQ ID NO. 11), An17 (SEQ ID NO. 13), An20 (SEQ ID NO. 15), An28 (SEQ ID NO. 17), An34 (SEQ ID NO. 19), At01-1 (SEQ ID NO. 21), At01-2 (SEQ ID NO. 23), At03 (SEQ ID NO. 25), At05 (SEQ ID NO. 27), At07 (SEQ ID NO. 29), At08 (SEQ ID NO. 31), At11 (SEQ ID NO. 33), At14 (SEQ ID NO. 35), At16 (SEQ ID NO. 37), At18 (SEQ ID NO. 39), At19 (SEQ ID NO. 41), At20 (SEQ ID NO. 43), At22 (SEQ ID NO. 45), At24 (SEQ ID NO. 47), At27 (SEQ ID NO. 49), At32 (SEQ ID NO. 51), Pc05 (SEQ ID NO. 53), Pc06 (SEQ ID NO. 55), Pc07 (SEQ ID NO. 57), Pc08 (SEQ ID NO. 59), Pc09 (SEQ ID NO. 61), Pc10 (SEQ ID NO. 63), Pc18 (SEQ ID NO. 65), Pc24 (SEQ ID NO. 69), Pc25 (SEQ ID NO. 71), Pc33 (SEQ ID NO. 73), Pc34 (SEQ ID NO. 75), At501 (SEQ ID NO. 77), At574 (SEQ ID NO. 79), At279 (SEQ ID NO. 81), At286 (SEQ ID NO. 83), At291 (SEQ ID NO. 85), At320 (SEQ ID NO. 87), At322 (SEQ ID NO. 89), An1000 (SEQ ID NO. 91), At167 (SEQ ID NO. 93), At221 (SEQ ID NO. 95), At233 (SEQ ID NO. 97), At239 (SEQ ID NO. 99), At240 (SEQ ID NO. 101), At274 (SEQ ID NO. 103), Pc1000 (SEQ ID NO. 105), Pc1001 (SEQ ID NO.107).

In a second aspect, the invention provides isolated or recombinant nucleic acids that are specifically complementary to genes that have been demonstrated to encode proteins that regulate fungal genes that are involved in secondary metabolite production, enzyme production, or fungal invasion. The term "recombinant" is as used previously.

A sequence is "specifically complementary" to another sequence if it is sufficiently homologous to specifically hybridize to the sequence. A sequence "specifically hybridizes" to another sequence if it hybridizes to form Watson-Crick or Hoogsteen base pairs either in vivo or under conditions which approximate physiological conditions with respect to ionic strength, e.g., 140 mM NaCl, 5 mM $MgCl_2$. Preferably, such specific hybridization is maintained under stringent conditions, e.g., 0.2× SSC at 68° C.

In a third aspect, the invention provides purified proteins that have been demonstrated to regulate fungal genes that are involved in secondary metabolite production, enzyme production, or fungal invasion. In certain embodiments, the invention further provides homologs of such proteins. As used herein, a "homolog" of a protein is a protein that, when compared to the reference protein, has a lower E-value or has a higher percent positive value in the region of similarity than that listed in Table III. Table III shows a listing of reference proteins, their E-values, and where applicable, their percent positives. In cases where regions of identity exist between the reference protein and a sequence from a protein sequence database, the positive region is indicated. In such instances, position 1 is defined as the first amino acid of the reference protein shown in the Sequence Listing. The percent positive score is defined by the BLAST 2.1.2 algorithm.

TABLE III

Novel regulator proteins

| | Gene | E Score for Protein Sequence | Percent positive (only for E < 1e − 25) | Starting AA | Ending AA |
|---|---|---|---|---|---|
| 1 | An10 | 1.00E − 166 | 85 | 7 | 372 |
| 2 | An1000 | 1.00E − 122 | 50 | 17 | 700 |
| 3 | At01-1 | 1.00E − 26 | 44 | 1 | 371 |
| 4 | At01-2 | 1.00E − 120 | 69 | 70 | 455 |
| 5 | At03 | 2.00E − 71 | 69 | 482 | 691 |
| 6 | At05 | 4.00E − 08 | n/a | | |
| 7 | At07 | 1.00E − 11 | n/a | | |
| 8 | At08 | 0 | 78 | 1 | 430 |
| 9 | At11 | 3.00E − 95 | 46 | 488 | 1043 |
| 10 | At14 | 5.00E − 09 | n/a | | |
| 11 | At16 | 1.00E − 10 | n/a | | |
| 12 | At167 | 0 | 97 | 1 | 510 |
| 13 | At18 | 2.00E − 08 | n/a | | |
| 14 | At19 | 1.00E − 166 | 85 | 32 | 385 |
| 15 | At20 | 2.00E − 78 | 62 | 129 | 437 |
| 16 | At22 | 0 | 84 | 1 | 506 |
| 17 | At221 | 0 | 78 | 13 | 850 |
| 18 | At233 | 6.00E − 71 | 90 | 18 | 161 |
| 19 | At239 | 1.00E − 43 | 94 | 231 | 328 |
| 20 | At24 | 3.00E − 39 | 42 | 6 | 346 |
| 21 | At240 | 0 | 82 | 1 | 571 |
| 22 | At27 | 3.00E − 24 | n/a | | |
| 23 | At274 | 1.00E − 05 | n/a | | |
| 24 | At279 | 1.00E − 95 | 55 | 1 | 496 |
| 25 | At286 | 1.00E − 156 | 81 | 71 | 412 |
| 26 | At291 | 4.00E − 10 | n/a | | |
| 27 | At32 | 0 | 72 | 4 | 796 |
| 28 | At320 | 2.00E − 47 | 76 | 1 | 126 |
| 29 | At322 | 1.00E − 05 | n/a | | |
| 30 | At501 | 1.00E − 116 | 60 | 1 | 398 |
| 31 | At574 | 1.00E − 127 | 60 | 1 | 463 |
| 32 | Pc05 | 8.00E − 77 | 66 | 127 | 413 |
| 33 | Pc06 | 7.00E − 12 | n/a | | |
| 34 | Pc07 | 1.00E − 05 | n/a | | |
| 35 | Pc08 | 2.00E − 56 | 81 | 48 | 181 |
| 36 | Pc09 | 4.00E − 22 | n/a | | |
| 37 | Pc10 | 3.00E − 31 | 68 | 76 | 189 |
| 38 | Pc1000 | 1.00E − 124 | 56 | 1 | 491 |
| 39 | Pc1001 | 0 | 78 | 20 | 858 |
| 40 | Pc18 | 7.00E − 78 | 81 | 2 | 212 |
| 41 | Pc23 | 3.00E − 21 | n/a | | |
| 42 | Pc24 | 1.00E − 10 | n/a | | |
| 43 | Pc25 | 5.00E − 24 | n/a | | |
| 44 | Pc33 | 2.00E − 72 | 38 | 43 | 852 |
| 45 | Pc34 | 2.00E − 65 | 87 | 241 | 395 |
| 46 | Pc804 | 1.00E − 05 | n/a | | |

To obtain the values shown in Table III, a blastp alignment was performed against the respective nr, yeast and patent databases. This algorithm compares an amino acid query (reference) sequence against a protein sequence database. For this analysis, the following default settings were used for the blastp algorithm: −G, cost to open a gap, default=11; −E, cost to extend a gap, default=1; −e, expectation value, default=10.0; and −W, word size, default=3. In addition, the default substitution matrix, BLOSUM-62 was used to assign a score for aligning any possible pair of amino acid residues. The relevant settings for this matrix were gap existence cost=11, per residue gap cost=1, and lambda ratio=0.85. In cases where E-value was below 1e-25, a percent positive value is shown, along with the region over which this value occurs. In addition, coding sequence data is shown in Table II for proteins for which only a partial sequence has previously been known. Preferred proteins according to this aspect of the invention are selected from the group consisting of Pc804 (SEQ ID NO. 2), An01 (SEQ ID NO. 4), An05 (SEQ ID NO. 6), An09 (SEQ ID NO8), An10 (SEQ ID NO. 10), An13 (SEQ ID NO. 12), An17 (SEQ ID NO. 14), An20 (SEQ ID NO. 16), An28 (SEQ ID NO. 18), An34 (SEQ ID NO. 20), At01-1 (SEQ ID NO. 22), At01-2 (SEQ ID NO.

24), At03 (SEQ ID NO. 26), At05 (SEQ ID NO. 28), At07 (SEQ ID NO. 30), At08 (SEQ ID NO. 32), At11 (SEQ ID NO. 34), At14 (SEQ ID NO. 36), At16 (SEQ ID NO. 38), At18 (SEQ ID NO. 40), At19 (SEQ ID NO. 42), At20 (SEQ ID NO. 44), At22 (SEQ ID NO. 46), At24 (SEQ ID NO. 48), At27 (SEQ ID NO. 50), At32 (SEQ ID NO. 52), Pc05 (SEQ ID NO. 54), Pc06 (SEQ ID NO. 56), Pc07 (SEQ ID NO. 58), Pc08 (SEQ ID NO. 60), Pc09 (SEQ ID NO. 62), Pc10 (SEQ ID NO. 64), Pc18 (SEQ ID NO. 66), Pc23 (SEQ ID NO. 68), Pc24 (SEQ ID NO. 70), Pc25 (SEQ ID NO. 72), Pc33 (SEQ ID NO. 74), Pc34 (SEQ ID NO. 76), At501(SEQ ID NO. 78), At574 (SEQ ID NO. 80), At279 (SEQ ID NO. 82), At286 (SEQ ID NO. 84), At291 (SEQ ID NO. 86), At320 (SEQ ID NO. 88), At322 (SEQ ID NO. 90), An1000 (SEQ ID NO. 92), At167 (SEQ ID NO. 94), At221 (SEQ ID NO. 96), At233 (SEQ ID NO. 98), At239 (SEQ ID NO. 100), At240 (SEQ ID NO. 102), At274 (SEQ ID NO. 104), Pc1000 (SEQ ID NO. 106), Pc1001 (SEQ ID NO.108).

"Purified", as used herein means having less than about 25% by weight, and preferably less than about 10% by weight contamination with other proteins. Such purified proteins may be obtained from natural sources, from recombinant expression, or by chemical synthesis. "Protein", as used herein is intended to encompass any polypeptide having at least 10 amino acid residues.

In a fourth aspect, the invention provides novel binding agents that specifically bind to proteins that have been demonstrated to regulate fungal genes that are involved in secondary metabolite production, enzyme production, or fungal invasion. Numerous methods familiar to those skilled in the art can be used to isolate novel binding agents. A binding agent "specifically binds" to a protein if it binds to that protein with greater affinity than to other unrelated proteins. Preferably, binding affinity of the molecule is at least 5-fold greater than affinity for unrelated proteins, more preferably at least 10-fold greater, still more preferably at least 50-fold greater, and most preferably at least 100-fold greater. In certain preferred embodiments, such binding agents decrease the biological function of a protein. In other preferred embodiments, binding agents increase the biological function of a protein. In other preferred embodiments, binding agents confer a novel or different biological function to a protein encoded by a fungal regulator gene. These effects may be achieved by increasing or decreasing protein activity through changes in secondary or tertiary structure, creating a new protein activity through changes in secondary or tertiary structure; increasing or decreasing transcription, increasing or decreasing translation, increasing or decreasing post-translational modification, altering intracellular localization, increasing or decreasing translocation from one cellular location to another, increasing or decreasing protein activity by interaction of the protein with another molecule, or creating a new protein activity by interaction of the protein with another molecule.

In a fifth aspect, the invention provides novel isolated or recombinant genes and their encoded proteins that are direct or indirect regulators of expression of FLO11, a fungal gene that is required for fungal invasion and whose expression is believed to be regulated by factors that also modulate secondary metabolite production. In certain embodiments, the invention further provides homologs of such genes or proteins. The term "homolog" is as defined previously. These genes are useful as targets for the development of antifungal drugs, and are expected to be useful for improving the production of secondary metabolites or fungal enzymes. They are also useful as tools to study the role of FLO11 in fungal metabolism.

Preferred genes according to this aspect of the invention are selected from the group consisting of An01 (SEQ ID NO. 3), An05 (SEQ ID NO. 5), An09 (SEQ ID NO 7), An10 (SEQ ID NO. 9), An13 (SEQ ID NO. 11), An17 (SEQ ID NO. 13), An20 (SEQ ID NO. 15), An28 (SEQ ID NO. 17), An34 (SEQ ID NO. 19), At01-1 (SEQ ID NO. 21), At01-2 (SEQ ID NO. 23), At03 (SEQ ID NO. 25), At05 (SEQ ID NO. 27), At07 (SEQ ID NO. 29), At08 (SEQ ID NO. 31), At11 (SEQ ID NO. 33), At14 (SEQ ID NO. 35), At16 (SEQ ID NO. 37), At18 (SEQ ID NO. 39), At19 (SEQ ID NO. 41), At20 (SEQ ID NO. 43), At22 (SEQ ID NO. 45), At24 (SEQ ID NO. 47), At27 (SEQ ID NO. 49), At32 (SEQ ID NO. 51), Pc05 (SEQ ID NO. 53), Pc06 (SEQ ID NO. 55), Pc07 (SEQ ID NO. 57), Pc08 (SEQ ID NO. 59), Pc09 (SEQ ID NO. 61), Pc10 (SEQ ID NO. 63), Pc18 (SEQ ID NO. 65), Pc23 (SEQ ID NO. 67), Pc24 (SEQ ID NO. 69), Pc25 (SEQ ID NO. 71), Pc33 (SEQ ID NO. 73), Pc34 (SEQ ID NO. 75).

Preferred proteins according to this aspect of the invention are selected from the group consisting of An01 (SEQ ID NO. 4), An05 (SEQ ID NO. 6), An09 (SEQ ID NO. 8), An10 (SEQ ID NO. 10), An13 (SEQ ID NO. 12), An17 (SEQ ID NO. 14), An20 (SEQ ID NO. 16), An28 (SEQ ID NO. 18), An34 (SEQ ID NO. 20), At01-1 (SEQ ID NO. 22), At01-2 (SEQ ID NO. 24), At03 (SEQ ID NO. 26), At05 (SEQ ID NO. 28), At07 (SEQ ID NO. 30), At08 (SEQ ID NO. 32), At11 (SEQ ID NO. 34), At14 (SEQ ID NO. 36), At16 (SEQ ID NO. 38), At18 (SEQ ID NO. 40), At19 (SEQ ID NO. 42), At20 (SEQ ID NO. 44), At22 (SEQ ID NO. 46), At24 (SEQ ID NO. 48), At27 (SEQ ID NO. 50), At32 (SEQ ID NO. 52), Pc05 (SEQ ID NO. 54), Pc06 (SEQ ID NO. 56), Pc07 (SEQ ID NO. 58), Pc08 (SEQ ID NO. 60), Pc09 (SEQ ID NO. 62), Pc10 (SEQ ID NO. 64), Pc18 (SEQ ID NO. 66), Pc23 (SEQ ID NO. 68), Pc24 (SEQ ID NO. 70), Pc25 (SEQ ID NO. 72), Pc33 (SEQ ID NO. 74), and Pc34 (SEQ ID NO. 76).

In a sixth aspect, the invention provides novel recombinant genes and their encoded proteins that are direct or indirect regulators of expression of lovF, a fungal gene believed to be involved in the production of the secondary metabolite lovastatin. In certain embodiments, the invention further provides homologs of such genes or proteins. The term "homolog" is as defined previously. These genes are expected to be useful for improving the production of secondary metabolites or fungal enzymes. They may also be useful as tools to study the role of lovF in fungal metabolism.

Preferred genes according to this aspect of the invention are selected from the group consisting of At279 (SEQ ID NO. 81), At286 (SEQ ID NO. 83), At291 (SEQ ID NO. 85), At320 (SEQ ID NO. 87), At322 (SEQ ID NO. 89), An1000 (SEQ ID NO. 91), At167 (SEQ ID NO. 93), At221 (SEQ ID NO. 95), At233 (SEQ ID NO. 97), At239 (SEQ ID NO. 99), At240 (SEQ ID NO. 101), At274 (SEQ ID NO. 103), Pc1000 (SEQ ID NO. 105), Pc1001 (SEQ ID NO.107).

Preferred proteins according to this aspect of the invention are selected from the group consisting of At279 (SEQ ID NO. 82), At286 (SEQ ID NO. 84), At291 (SEQ ID NO. 86), At320 (SEQ ID NO. 88), At322 (SEQ ID NO. 90), An1000 (SEQ ID NO. 92), At167 (SEQ ID NO. 94), At221 (SEQ ID NO. 96), At233 (SEQ ID NO. 98), At239 (SEQ ID NO. 100), At240 (SEQ ID NO. 102), At274 (SEQ ID NO. 104), Pc1000 (SEQ ID NO. 106), and Pc1001 (SEQ ID NO.108).

In a seventh aspect, the invention provides novel recombinant genes and their encoded proteins that are direct or indirect regulators of expression of lovE, a fungal gene believed to be involved in the production of the secondary metabolite lovastatin. In certain embodiments, the invention further provides homologs of such genes or proteins. The term "homolog" is as defined previously. These genes are expected to be useful for improving the production of secondary metabolites or fungal enzymes. They may also be useful as tools to study the role of lovE in fungal metabolism.

Preferred genes according to this aspect of the invention are selected from the group consisting of At501(SEQ ID NO. 77), At574 (SEQ ID NO. 79).

Preferred proteins according to this aspect of the invention are selected from the group consisting of At501 (SEQ ID NO. 78), At574 (SEQ ID NO. 80).

In an eighth aspect, the invention provides novel recombinant genes and their encoded proteins that are direct or indirect regulators of expression of acvA, a fungal gene involved in the production of the secondary metabolite penicillin. In certain embodiments, the invention further provides homologs of such genes. The term "homolog" is as defined previously. These genes are expected to be useful for improving the production of secondary metabolites or fungal enzymes. They may also be useful as tools to study the role of acvA in fungal metabolism.

A preferred gene according to this aspect of the invention is Pc804 (SEQ ID NO. 1). A preferred protein according to this aspect of the invention is Pc804 (SEQ ID NO. 2).

In a ninth aspect, the invention provides methods for modulating production of a secondary metabolite or extracellular enzyme, the method comprising expressing in the fungus a novel fungal regulator gene. Such expression may be achieved and/or modulated by expression of another gene, interaction with a drug or small molecule, or genetic transformation, e.g., as described in the Examples. In addition it may include expression of an entire gene or of a biologically active portion or fragment of the gene, or a fusion product of the gene or a portion or fragment of the gene. In certain preferred embodiments, combinations of more than one novel regulator gene according to the invention may be expressed simultaneously or sequentially.

As used herein, the term "modulatinging production of a secondary metabolite or extracellular enzyme" means to positively impact upon one or more of the variables that affect the process of production of secondary metabolites or extracellular enzyme in a fungal fermentation. These variables include, without limitation, amount of secondary metabolite or extracellular enzyme being produced (in absolute terms or in quantity per unit volume of fermentation broth or per unit mass of solid substrate), the volume required for production of sufficient quantities, the cost of raw materials and energy, the time of fermenter or culture run, the amount of waste that must be processed after a fermenter run, the specific production of the desired metabolite or extracellular enzyme (both in total amounts and as a fraction of all secondary metabolites and side products made by the fungus), the percent of produced final secondary metabolite or extracellular enzyme that can be recovered from the fermentation broth or culture, and the resistance of an organism producing a secondary metabolite or extracellular enzyme to possible deleterious effects of contact with the secondary metabolite or extracellular enzyme. Also, the term "secondary metabolite" means a compound, derived from primary metabolites, that is produced by an organism, is not a primary metabolite, is not ethanol or a fusel alcohol, and is not required for growth under standard conditions. Secondary metabolites are derived from intermediates of many pathways of primary metabolism. These pathways include, without limitation, pathways for biosynthesis of amino acids, the shikimic acid pathway for biosynthesis of aromatic amino acids, the polyketide biosynthetic pathway from acetyl coenzyme A (CoA), the mevalonic acid pathway from acetyl CoA, and pathways for biosynthesis of polysaccharides and peptidopolysaccharides. Collectively, secondary metabolism involves all primary pathways of carbon metabolism (Fungal Physiology, Chapter 9 pp 246–274 ed D H Griffin (1994)). "Secondary metabolites" also include intermediate compounds in the biosynthetic pathway for a secondary metabolite that are dedicated to the pathway for synthesis of the secondary metabolite. "Dedicated to the pathway for synthesis of the secondary metabolite" means that once the intermediate is synthesized by the cell, the cell will not convert the intermediate to a primary metabolite. "Intermediate compounds" also include secondary metabolite intermediate compounds which can be converted to useful compounds by subsequent chemical conversion or subsequent biotransformation. As such, providing improved availability of such intermediate compounds would still lead to improved production of the ultimate useful compound, which itself may be referred to herein as a secondary metabolite. The yeast Saccharomyces cerevisiae is not known to produce secondary metabolites. The term "primary metabolite" means a natural product that has an obvious role in the functioning of almost all organisms. Primary metabolites include, without limitation, compounds involved in the biosynthesis of lipids, carbohydrates, proteins, and nucleic acids. The term "increasing the yield of the secondary metabolite" means increasing the quantity of the secondary metabolite present in the total fermentation broth per unit volume of fermentation broth or unit mass of solid media. An "extracellular enzyme" is an enzyme that is secreted by a fungus into its surrounding media.

In a tenth aspect, the invention provides novel chimeric fungal regulator genes. For purposes of the invention, a "chimeric fungal regulator gene" is a fungal regulator gene, or a portion thereof, fused to a nucleic acid sequence to which it is not fused in nature. Preferred nucleic acids for such fusion purposes include, without limitation, fungal regulator genes, or portions thereof, as well as regulatory regions from a gene.

A non-limiting example of some preferred chimeric fungal regulator genes is shown in Table 4 below, and in the Sequence listing as SEQ ID NOS.

TABLE IV

Novel chimeric regulator proteins

| | Chimera | species A* | species B** | n-terminal fusion (nt) | filler (nt) | c-terminal fusion (nt) |
|---|---|---|---|---|---|---|
| 1 | amdA-pacC(DBD) | A. nidulans | P. chrysogenum | 1–468 | 469–504 | 505–1074 |
| 2 | VP16-An09 | Herpes simplex virus | A. nidulans | 1–243 | 244–276 | 277–1833 |

TABLE IV-continued

Novel chimeric regulator proteins

| | Chimera | species A* | species B** | n-terminal fusion (nt) | filler (nt) | c-terminal fusion (nt) |
|---|---|---|---|---|---|---|
| 3 | VP16-Pc23 | Herpes simplex virus | P. chrysogenum | 1–243 | 244–276 | 277–1353 |
| 4 | amdAG229C-pacC(DBD) | A. nidulans | P. chrysogenum | 1–468 | 469–504 | 505–1074 |
| 5 | amdAG229D-pacC(DBD) | A. nidulans | P. chrysogenum | 1–468 | 469–504 | 505–1074 |
| 6 | pacC(DBD)-VP16 | P. chrysogenum | Herpes simplex virus | 1–567 | 568–573 | 574–810 |
| 7 | leu4-tet | S. cerevisiae | E. coli | 1–1515 | n/a | 1516–2415 |

In an eleventh aspect, the invention provides methods for modulating production of a secondary metabolite or extracellular enzyme, the method comprising expressing in the fungus a novel chimeric fungal regulator gene. Such expression may be achieved and/or modulated by expression of another gene, interaction with a drug or small molecule, or genetic transformation, e.g., as described in the Examples. In certain preferred embodiments, combinations of more than one novel regulator gene and/or chimeric reggene according to the invention may be expressed simultaneously or sequentially.

As used herein, the term "modulating production of a secondary metabolite or extracellular enzyme" means to positively impact upon one or more of the variables that affect the process of production of secondary metabolites or extracellular enzyme in a fungal fermentation. These variables include, without limitation, amount of secondary metabolite or extracellular enzyme being produced (in absolute terms or in quantity per unit volume of fermentation broth or per unit mass of solid substrate), the volume required for production of sufficient quantities, the cost of raw materials and energy, the time of fermenter or culture run, the amount of waste that must be processed after a fermenter run, the specific production of the desired metabolite or extracellular enzyme (both in total amounts and as a fraction of all secondary metabolites and side products made by the fungus), the percent of produced final secondary metabolite or extracellular enzyme that can be recovered from the fermentation broth or culture, and the resistance of an organism producing a secondary metabolite or extracellular enzyme to possible deleterious effects of contact with the secondary metabolite or extracellular enzyme. Also, the term "secondary metabolite" means a compound, derived from primary metabolites, that is produced by an organism, is not a primary metabolite, is not ethanol or a fusel alcohol, and is not required for growth under standard conditions. Secondary metabolites are derived from intermediates of many pathways of primary metabolism. These pathways include, without limitation, pathways for biosynthesis of amino acids, the shikimic acid pathway for biosynthesis of aromatic amino acids, the polyketide biosynthetic pathway from acetyl coenzyme A (CoA), the mevalonic acid pathway from acetyl CoA, and pathways for biosynthesis of polysaccharides and peptidopolysaccharides. Collectively, secondary metabolism involves all primary pathways of carbon metabolism (Fungal Physiology, Chapter 9 pp 246–274 ed D H Griffin (1994)). "Secondary metabolites" also include intermediate compounds in the biosynthetic pathway for a secondary metabolite that are dedicated to the pathway for synthesis of the secondary metabolite. "Dedicated to the pathway for synthesis of the secondary metabolite" means that once the intermediate is synthesized by the cell, the cell will not convert the intermediate to a primary metabolite. "Intermediate compounds" also include secondary metabolite intermediate compounds which can be converted to useful compounds by subsequent chemical conversion or subsequent biotransformation. As such, providing improved availability of such intermediate compounds would still lead to improved production of the ultimate useful compound, which itself may be referred to herein as a secondary metabolite. The yeast *Saccharomyces cerevisiae* is not known to produce secondary metabolites. The term "primary metabolite" means a natural product that has an obvious role in the functioning of almost all organisms. Primary metabolites include, without limitation, compounds involved in the biosynthesis of lipids, carbohydrates, proteins, and nucleic acids. The term "increasing the yield of the secondary metabolite" means increasing the quantity of the secondary metabolite present in the total fermentation broth per unit volume of fermentation broth or unit mass of solid media. An "extracellular enzyme" is an enzyme that is secreted by a fungus into its surrounding media.

The following examples are intended to further illustrate certain particularly preferred embodiments of the invention and are not intended to limit the scope of the invention.

EXAMPLE 1

Transformation of Filamentous Fungi

Protoplasts were generated as follows. Rich media was inoculated with spores and spores were allowed to germinate for about 20 hrs or until germ tubes were between 5 and 10 spore lengths. If a fungus does not sporulate (some taxol producing fungi do not sporulate), hyphae can be sonicated into small fragments and these small hyphal fragments can be used as inoculums. Another alternative is to find a medium where the fungus will sporulate. For example, sporulation of a taxol producing fungus can be induced by growth on water agar plates that contain gamma-irradiated carnations leaves. In addition, high salt medium can promote sporulation in late sporulating *P. chrysogenum* strains. The germlings were centrifuged and washed twice with sterile distilled water and once with 1M magnesium sulfate. Germlings were then resuspended in 1M magnesium sulfate containing approximately 2 mg/ml of Novozyme. Tubes were then incubated at 30° C. shaking at 80 rpm for about 2 hrs or until most of the hyphae were digested and protoplasts were abundant. Protoplasts were filtered through one layer of Miracloth. At least one volume of STC was added and protoplasts were spun down. Protoplasts were washed twice with STC. Protoplasts then were resuspended in 1 ml STC and counted in a hemocytometer. A final concentration of approximately $5 \times 10^7$ protoplasts/ml were frozen in a 9:1:0.1 solution of STC, SPTC and DMSO in a Nalgene Cryo cooler at $-80°$ C. (cools $-1°$ C./min).

Solutions for transformation were as follows: STC (0.8M Sorbitol, 25 mM Tris-HCl pH 7.5, 25 mM $CaCl_2$) and SPTC (0.8M Sorbitol, 40% PEG 4000, 25 mM Tris-HCl pH 8, 50 mM $CaCl_2$).

1–5 µg of DNA comprising a novel regulator gene according to the invention in a fungal expression vector was placed in a 50 mL Falcon tube. 100 µl of previously frozen protoplasts were added to the DNA, gently mixed, and then incubated on ice for 30 min. 15 µl of SPTC was added, followed by mixing by tapping and incubation at RT for 15 min. 500 µl SPTC was added and mixed well by tapping and rolling, then incubated at RT for 15 min. 25 mls of regeneration minimal medium was added, mixed well and poured on plates containing 25 mls of regeneration minimal medium with 2× the concentration of selection drug. Transformation plates were incubated at 26° C. for 5–6 days or until colonies started to appear. Regeneration minimal medium contains trace elements, salts, 25 mM sodium nitrate, 0.8M Sucrose, and 1% agarose at pH 6.5. The selection drug that was used successfully with *P. chrysogenum* and *A. terreus* is phleomycin, a broad-spectrum glycopeptide antibiotic. Transformants were picked onto new plates with a toothpick (if fungus was sporulating) or with sterile forceps (if fungus did not sporulate). Purification plates contained minimal medium (same as regeneration minimal medium but containing 2% instead of 0.8M sucrose) and 1× drug concentration. Picked transformants were incubated at 26° C. for 5–6 days.

EXAMPLE 2

Growing Transformants in Production Media

For *P. chrysogenum* and penicillin production, a plug containing spores and mycelia was used as the inoculum. The medium used was the published P2 production media which contains, 30% lactose, 5× pharmamedia cotton seed flour, ammonium sulfate, calcium carbonate, potassium phosphate, potassium sulfate, and phenoxyacetic acid pH 7. Flasks were incubated at 26° C. with shaking at 225 rpm.

For *A. terreus* and lovastatin production, spores were used as the inoculum. Spores were obtained from the purification plate by using a wooden inoculation stick. The medium was RPM containing corn steep liquor, sodium nitrate, potassium phosphate, magnesium sulfate, sodium chloride, P2000 (Dow chemical), trace elements and lactose or glucose as carbon source. The medium was pH 6.5. Flasks were incubated at 26° C. with shaking at 225 rpm. For static 96-well cultures, the same medium was used and the spores were obtained from the purification plate with a wooden toothpick. 96-well plates were incubated, without shaking at 26° C.

Sampling was done after 6 days of incubation for penicillin, after 5 days for lovastatin, and after 21 days for taxol. For shake flask experiments 1–1.5 mls of supernatant was placed into 96-well plates, which were centrifuged and supernatants transferred to new 96-well plates. Samples were frozen at $-80°$ C. for storage or for later assays.

Cultures that were grown standing in a 96-well plate were centrifuged and the supernatant was transferred to a new 96 well plate. Samples were frozen at $-80°$ C.

The assay kit from Hawaii Biotechnology Group has a taxol detection limit of 0.5 ng/mL. Assuming a fungus which produces taxol at a level of 25 ng/L, a 20–25-fold concentration step of the taxol-producing culture should be within the standard curve achievable with the kit (>0.625 ng/mL). In order to have enough of each sample for duplicate testing, we will need a minimum culture volume of 15 mL. Samples will be taken after 21 days of incubation.

EXAMPLE 3

Determination of Penicillin Concentration

Solutions of phenoxymethylpenicillin (sodium salt) in 10 mM potassium phosphate (pH 7.0) were prepared at 0, 25, 50, 100, 200, 300, 400 and 500 µg/mL. Imidazole reagent was prepared as follows. 8.25 g of imidazole was dissolved in 60 mL of water, 10 mL of 5 M HCl was added and then 10 mL of a solution of mercuric chloride (0.27 g dissolved in 100 mL of water) was added. The pH was adjusted to 6.80+/–0.05 with 5 M HCl and the solution was diluted to 100 mL with water.

The fermentation broth was clarified by centrifugation for 10 min at 4000 g. 40 µL of clarified fermentation broth and penicillin standard solutions were pipetted into individual wells of a 96-well UV, collection plate. 200 µL of imidazole reagent was pipetted into a 96-well filter plate (0.45 micron). The derivatization reaction of penicillin was initiated by vacuum filtration of imidazole reagent into a collection plate containing the aliquoted samples and standards. The collection plate was placed into the 96-well plate reader at 45° C. while an increase at 325 nm was monitored over 20 minutes. A Molecular Devices 96-well UV/Vis plate reader was used for all spectrophotometric detection. This is a conventional assay, described, e.g., in Bundgaard and Ilver, Journal of Pharm Pharmac 24: 790–794 (1972).

EXAMPLE 4

Determination of Lovastatin Concentration

10 µL of sample was removed and diluted 1:100 in $H_2O$. 10 µl of this diluted broth was assayed in a reaction (200 µL total) containing 1 mM HMGCoA, 1 mM NADPH, 0.005 mM DTT and 5 µL $(His)_6$HMGR. The disappearance of absorbance at 340 nm was observed over time. This represents the disappearance of NADPH, and lovastatin inhibits this reaction. The initial velocities were calculated for the reactions containing samples, adjusted for dilution, and compared to reactions containing lovastatin standards to determine levels of metabolite produced. $(His)_6$HMGR was expressed in *Saccharomyces cerevisiae* and purified with a nickel column.

EXAMPLE 5

Determination of Taxol Concentration

Assay 1: From a resting culture of at least 15 mL, the broth will be neutralized to pH 7 (taxol is unstable in non-neutral conditions), frozen using liquid nitrogen and the entire sample lyophilized to dryness (cell mass and broth together) overnight. The dry material will be pulverized using glass beads and vigorous shaking. 10 mL of methylene chloride will be used to extract each sample (estimated at 1 g of dry material). After 6 hours, the methylene chloride extract will be passed through a cotton plug and lyophilized to dryness overnight. 50 µL of methanol will be added to every sample and once in solution, 450 µL of appropriate buffer or water will be added and tested by immunoassay. If we assume that there was 15 mL of starting sample from a fungus that produced approximately 25 ng/L, then the final concentration is expected to be approximately 0.75 ng/mL.

Assay 2: From a resting culture of at least 15 mL, the broth will be neutralized to pH 7 and filtered through four layers of cheesecloth. The broth will be extracted with 15 mL of methylene chloride, twice and the organic layers combined. The biomass will be macerated and extracted three times with 10 mL each of chloroform/methanol (1:1). The extracts of macerated mycelia will be combined with the extracted broths, and the 60 mL of organic extract per sample will be lyophilized to dryness overnight. 50 µL of methanol will be added to every sample and once in solution, 450 µL of appropriate buffer or water will be added and tested by immunoassay. If we assume that there were 15 mLs of starting sample from a fungus that produced approximately 25 ng/L, then the final concentration is expected to be approximately 0.75 ng/mL.

The assay kit includes a taxol-protein antigen that is detected by an anti-taxane antibody. The presence of taxol in a tested isolate competitively inhibits detection of the taxol-protein antigen. The immunoassay requires 100 μL samples and follows the protocol in the kit. It will be done in a 96-well plate and will take approximately 8–9 hours.

What is claimed is:

1. An isolated nucleic acid molecule comprising a nucleic acid sequence encoding the amino acid sequence of SEQ ID NO:8.

2. The isolated nucleic acid molecule of claim 1 wherein the isolated nucleic acid molecule comprises the nucleotide sequence of SEQ ID NO:7.

3. A vector comprising the isolated nucleic acid molecule of claim 1.

4. A vector the isolated nucleic acid molecule of claim 2.

5. The vector of claim 3 wherein the vector is a fungal expression vector.

6. The vector of claim 4 wherein the vector is a fungal expression vector.

7. An isolated cell harboring the isolated nucleic acid molecule of claim 1.

8. An isolated cell harboring the isolated nucleic acid molecule of claim 2.

9. The isolated cell of claim 7 wherein the cell is a fungal cell.

10. The isolated cell of claim 8 wherein the cell is a fungal cell.

* * * * *

UNITED STATES PATENT AND TRADEMARK OFFICE
CERTIFICATE OF CORRECTION

PATENT NO. : 6,806,082 B2
DATED : October 19, 2004
INVENTOR(S) : Cali et al.

It is certified that error appears in the above-identified patent and that said Letters Patent is hereby corrected as shown below:

Column 289,
Line 20, after "vector" insert -- comprising --.

Signed and Sealed this

Twenty-seventh Day of December, 2005

JON W. DUDAS
*Director of the United States Patent and Trademark Office*